(12) United States Patent
Berman et al.

(10) Patent No.: US 10,201,603 B2
(45) Date of Patent: Feb. 12, 2019

(54) THERAPEUTIC COMPOSITIONS AND METHODS FOR TREATING HIV INCLUDING IDENTIFICATION AND MANIPULATION OF PARTICULAR DOMAINS ASSOCIATED WITH IMMUNOGENICITY

(71) Applicant: The Regents of the University of California, Oakland, CA (US)

(72) Inventors: Phillip Berman, Santa Cruz, CA (US); Sara O'Rourke, Santa Cruz, CA (US); William Scott, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/694,388

(22) Filed: Sep. 1, 2017

(65) Prior Publication Data

US 2018/0099041 A1    Apr. 12, 2018

Related U.S. Application Data

(63) Continuation of application No. 13/079,472, filed on Apr. 4, 2011, now Pat. No. 9,782,472, which is a continuation-in-part of application No. PCT/US2010/055747, filed on Nov. 5, 2010, said application No. 13/079,472 is a continuation-in-part of application No. PCT/US2010/053637, filed on Oct. 22, 2010, said application No. 13/079,472 is a continuation-in-part of application No. PCT/US2009/059583, filed on Oct. 5, 2009.

(60) Provisional application No. 61/258,833, filed on Nov. 6, 2009, provisional application No. 61/253,858, filed on Oct. 22, 2009, provisional application No. 61/195,112, filed on Oct. 4, 2008.

(51) Int. Cl.
| | |
|---|---|
| C07K 14/005 | (2006.01) |
| C07K 14/16 | (2006.01) |
| A61K 39/21 | (2006.01) |
| C07K 14/00 | (2006.01) |
| A61K 38/00 | (2006.01) |
| A61K 38/16 | (2006.01) |
| G01N 33/569 | (2006.01) |
| A61K 39/12 | (2006.01) |

(52) U.S. Cl.
CPC ............ *A61K 39/21* (2013.01); *A61K 38/162* (2013.01); *A61K 39/12* (2013.01); *C07K 14/005* (2013.01); *G01N 33/56988* (2013.01); *C12N 2740/15022* (2013.01); *C12N 2740/16122* (2013.01); *C12N 2740/16134* (2013.01); *G01N 2333/162* (2013.01); *G01N 2500/02* (2013.01)

(58) Field of Classification Search
CPC ........ C12N 2740/16122; C07K 14/005; A61K 39/00; A61K 38/00; A61K 38/162
See application file for complete search history.

(56) References Cited

U.S. PATENT DOCUMENTS 5,585,250 A    12/1996    Garrity et al.

FOREIGN PATENT DOCUMENTS

WO    WO 2001/064013    9/2001

OTHER PUBLICATIONS

Ataman-Onal Y., Cheynet V., Verrier B., "Mutations and transcriptional alterations associated with the downregulation of HIV-envelope glycoprotein expression following acute cytopathic effect", 2001, submitted to the INSDC.UMR 2142 CNRS/BioMerieux, pdf pp. 1-2.
Howard, et al.; "Antibodies in the Future: Challenges and Opportunities, Chapter 15"; Making and Using Antibodies: A Practical Handbook; 8 pages (2007).
Olivia, et al, "Structural investigation of the HIV-1 envelope glycoprotein gp160 cleavage site", Chemistry, 2002, 8(6):1467-1473.
Stephens, et al.; "A chink in HIV's armour";1990, Nature, 343:219.
Yang, et al.; "Selective modification of variable loops alters tropism and enhances immunogenecity of human immunodeficiency virus type 1 envelope"; 2004, Journal of Virology, 78(8):4029-4036.

*Primary Examiner* — Barry A Chestnut
(74) *Attorney, Agent, or Firm* — Bozicevic, Field & Francis LLP; Shweta Chandra

(57) ABSTRACT

Selection of HIV vaccine antigens by use of intrapatient sequence variation to identify mutations in the HIV envelope glycoprotein that affect the binding of broadly neutralizing antibodies and polypeptides identified by these methods.

10 Claims, 29 Drawing Sheets

Specification includes a Sequence Listing.

FIG. 1
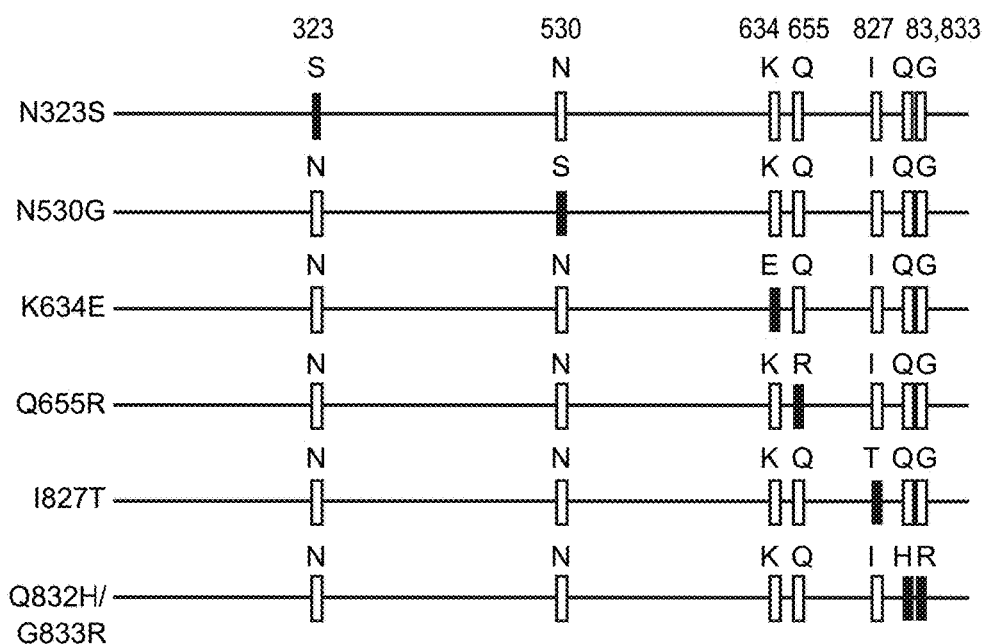
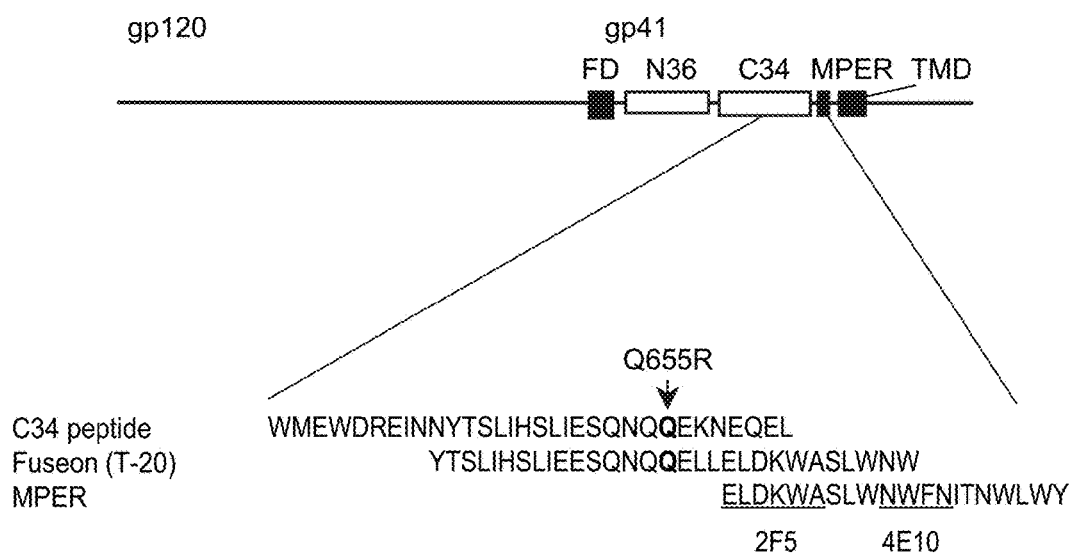

*a=6kD, b=5kD, and c=4kD

FIG. 13

```
                45/L
MN      TEKLWVTVYYGVPVWKEATTTLFCASDAKAYDTEAHNVWATHACVPTDPNPQEVELV
HXB2    TEKLWVTVYYGVPVWKEATTTLFCASDAKAYDTEAHNVWATHACVPTDPNPQEVVLV
A1.KE   VENLWVTVYYGVPVWRDADTTLFCASDAKAYETEKHNVWATHACVPTDPNPQEIHLD
A1.UG   AENLWVTVIYYGVPIWKDANTTLFCASDAKAYDTEVHNVWATHACVPTDPNPQELKME
C.ET    MGNLWVTVYYGVPVWKDASPTLFCASDAKAYDTEVHNVWGTFACVPTDPSPQELGLE
C.IN    GGNLWVTVYYGVPVWKEAKTTLLCASDAKAYEREVHNVWATHACVPTDPNPQEIVLG
D.TZ    AEQLWVTIYYGVPVWREANTTLFCASDAKAYDTEAHNIWATHACVPTDPNPQEMDLV
D.UG    TGKSWVTVYYGVPVWKEATTTLFCASDAKSFDTEAHNIWATHACVPTDPNPQEIKLE
AE.T93  SDNLWVTVYYGVPVWKDADTTLFCASDAKAYKAEAHNIWATHACVPTDPNPQEIHLE
AE.T90  SDNLWVTVYYGVPVWRDADTTLFCASDAKAHETEVHNVWATYACVPTDPNPQEIHLE
CPZ05   EENWVTVYYGVPVWRDVETTLFCASDAKTTLFCASDAKSYSTEAHNIWATQACVPTDPTPQEVLLP
CPZ85   LSSLWATVYYGVPVWRDVETTLFCASDAKYQEAHNIWATQACVPTDPNPQEVHLP
SIV51   YCTQYVTVFYGVPAWRNATIPLFCA----TKNRDTWGTTQCLPDNGDYSELAL-
SIV39   YCTLYVTVFYGVPAWRNATIPLFCA----TKNRDTWGTTQCLPDNGDYSEVAL-

96/L
MN      NVTENFNMWKNNMVEQMHEDIISLWDQSLKPCVKLTPLCVTLNCTDLR-------
HXB2    NVTENFNMWKNNMVEQMHEDIISLWDQSLKPCVKLTPLCVSLKCTDLK-------
A1.KE   NVTEKFNMWKNNMVEQMHEDIISLWDQSLKPCVKLTPLCVSLKCTDLK-------
A1.UG   NVTEEFNMWKINNMVEQMHTDIISLWDQSLKPCVQLTPLCVTLHCTN--------
C.ET    NVTEEFNMWKNNMVEQMHQDIISLWDQSLKPCVKLTPLCVTLDCSYNITN-----
C.IN    NVTENFNMWKNDMVEQMHEDIISLWDGSLKPCVKLTPLCVTLNCNAIK-------
D.TZ    NVTENFNMWKNDMVDQMHEDVISLWDQSLKPCVKLTPLCVTLECRNVS-------
D.UG    NVSENFNMWKNNMVEQMHEDIISLWEESLKPCVKLTPLCVTLHCSDANTT-----
AE.T93  NVTENFNMWKNNMVEQMHEDIISLWDQSLKPCVKLTPLCVTLHCTNWV-------
AE.T90  NVTENFNMWKNNMVEQMQEDVISLWDQSLKPCVQLTPLCVTLHCTNANLK-----
CPZ05   NVTEEFNMWKNYMVEQMQEDVISLWEQSLKPCVKLTPLCVTLHCTNANLT-----
CPZ85   NVTEKFDMWENINMVDQMQEDIISLWEQSLKPCVKLTPLCVTLTCNNP-------
SIV51   NVTESFDAWENMAEQMQEDIISLWEQSLKPCIKLSPLCIKLSPLCITMCLNPD------

SIV51   NVTESFDAWENTVTEQAIEDVWQLFETSIKPCVKLSPLCITMRCNKSETDRWGLTKS
SIV39   NVTESFDAWNNTVTEQAIEDVWQLFETSIKPCVKLSPLCITMRCNKSETDRWGLTKS
```

FIG. 13 (Cont.)

```
MN       ----NTTNTNNSTDNNN------------------------------SKSEGTIKGGEMKNCSFNITTSIGDKMQ
HXB2     ----NDTNTNSSS----------------------------------GRMIMEKGEIKNCSFNISTSIRGKVQ
A1.KE    -------VTSVNTT---------------------------------GDREGLKNCSFNMTTELRDKRQ
A1.UG    ----NITNSITNS----------------------------SVNMREEIKNCSFNMTTELRDKNR
C.ET     ----NNTKVTNNS------------------------------INSANDEMKNCSFNITTELRDKKR
C.IN     ----RNVSSYNTY------------------------------NGSVEEIKNCSFNATPEVRDRKQ
D.TZ     -----NSGNGTNTT---------------------------------------DPRLIEKGEMKNCSFNITTEIRDKRK
D.UG     ----TDTTNTT------------------------------------------------------DPRLIEKGEMKNCSFNITTEIRDKKK
AE.T93   ---ANLTNVNNT---------------------------TNVGNITEEVRNCSFNMTTELRDRQQ
AE.T90   ---NGSSKTNVS---------------------------NIIGNITDEVRNCTFNMTTELTDKKQ
CPZ05    ----TNTSCTNST----------------------------DDRLGDMRNCSFNVTTELRDKKR
CPZ285   ----SNSSAVNTT----------------------------DIMRNCSFNITTELRDKKK
SIV51    STTITTAAPTSAPVSEKIDMVNETSSCIAQNNCTGLEQEQMISCKFTMTGLKRDKTK
SIV39    IT--TTASTTSTTASAKVDMVNETSSCIAQDNCTGLEQEQMISCKFNMTGLKRDKKK
```

```
              181/D 183/L                          197/L        208/S     215/D
MN       KEYALFYKLDIEPIDNDS----------TSYRLISCNTSVITQACPKISFEPIPIHYCAPAG
HXB2     KEYAFFYKLDIIPIDNDT----------TSYKLTSCNTSVITQACPKVSFEPIPIHYCAPAG
A1.KE    KVYSLFYKLDVVKINDSDN-----SEYRLINCNTSAITQACPKVSFEPIPIHYCAPAG
A1.UG    KVVSLFYKLDVVQINNGNSS----NLYRLINCNTSALTQACPKVTFEPIPIHYCAPAG
C.ET     KAYALFYKLDIVPLNNGS------TDYRLINCNTSTITQACPKVSLDPIPIHYCAPAG
C.IN     RMYALFYGLDIVPLNKKNSSENS SEYRLINCNTSAITQACPKVSFEPIPIHYCAPAG
D.TZ     QVQALFYKLDIVPIDKKNN-----NSYTLMHCNTSAIKQACPKMTFEPIPIHYCAPAG
D.UG     QVQALFYKLDVVPIDKKNN-----TSYRLINCNTSAITQACPKISFEDPIPIHYCAPAG
AE.T93   KVYALFYKLDLVQMGNNNNSNNY SEYRLINCNTSVIKQACPKISFDDPIPIHYCTPAG
AE.T90   KVHALFYKLDIVQIEDKKTS----STYRLINCNTSVIKQACPKISFDPIPIHYCTPAG
CPZ05    QVYSLFYVEDITAIGNN-------NTYRLINCNTTAITQACPKTSFEPIPIHYCAPAG
CPZ285   QVYSLFYVDDLAHINN--------SRCYMNHCNTSVIQESCDKHYWDTIRFRYCAPPG
SIV51    EYNETWYSTDLVCEQGNSTDNE--SRCYMNHCNTSVIQESCDKHYWDTIRFRYCAPPG
SIV39    EYNETWYSADLVCEQGNNTGNE--SRCYMNHCNTSVIQESCDKHYWDAIRFRYCAPPG
```

FIG. 13 (Cont.)

```
                    261/S                              274/D
MN      FAILKCNDKKFSGKGS-CKNVSTVQCTHGIRPVVSTQLLLNGSLAEEEVVIRSEDFT
HXB2    FAILKCNNKTFNGTGP-CTNVSTVQCTHGIRPVVSTQLLLNGSLAEEEVIRSVNFT
A1.KE   FAILKCKDEGFNGTGL-CKNVSTVQCTHGIKPVVSTQLLLNGSLAEKNITIRSENIT
A1.UG   YAILKCNDKEFNGTGL-CKNVSTVQCTHGIKPVVSTQLLLNGSLAEGKVMIRSENIT
C.ET    YAILKCRDKTFTGTGP-CHNVSTVQCTHGIKPVVSTQLLLNGSIAEGETIIRFENLT
C.IN    YAILKCNNKTFNGTGP-CNNVSTVQCTHGIKPVVSTQLLLNGSLAEGEIIIRSENLT
D.TZ    FAILKCKDKKFNGTGP-CKKVSTVQCTHGIKPVVSTQLLLNGSLAGEEIIIRSENLT
D.UG    FAILKCNEKKFNGTGP-CKNVSTVQCTHGIKPVVSTQLLLNGSLAEEEIIIRSENLT
AE.T93  YAILKCNDKNFNGTGP-CKNVSTVQCTHGIKPVVSTQLLLNGSLAEEEIIIRSENLT
AE.T90  YAILKCNDKNFNGTGP-CKNVSSVQCTHGIKPVVSTQLLLNGSLAEEEIIIRSEDLT
CPZ05   FALLKCNDIDYKGNET-CKNVSTVHCTHGIKPVATTQLIINGSTADNQTVARIDPSE
CPZ85   FAILKCNEKDFKGKGE-CKNVSTVQCTHGIKPVVTTQLIINGSLATKNVTVRSKNFA
SIV51   YALLRCNDTNYSGFMPKCSKVVVSSCTRMMETQTSTWFGFNGTRAENRTYIYWHGRD
SIV39   YALLRCNDTNYSGFMPKCSKVVVSSCTRMMETQTSTWFGFNGTRAENRTYIYWHGRD

322/S          327/L
MN      DNAKTIIVHLKE--SVQINCTRPNYNKRKRIHI--GPGRAFYTTKNIKGTIRQAHCI
HXB2    DNAKTIIVQLNT--SVEINCTRPNNNTRKRIRIQRGPGPGRAFVTIGK-IGNMRQAHCN
A1.KE   NNVKNIIVQLVQ--PVTIKCIRPNNNTRKSIRI--GPGPGRAFVTIGK-IIGDIIRQAHCN
A1.UG   NNVKNIIVQLNE--SVTINCTRPNNNTRRSVRI--GPGQTFYATGDIIGDIRQAHCN
C.ET    NNAKIIIVQLNE--SVEINCTRPSNNTRESIRI--GPGQTFYATGDIIGDIRQAHCN
C.IN    NNVKTIIIVHLNQ--SVEIVCTRPNNNTRKSIRI--GPGQTFYATGDIIGDIRQAHCN
D.TZ    NNVKTIIVQLNE--TVKINCTRPNNNTRKGIRI--GPGQTFF-TAEVTGDIRKAYCN
D.UG    NNAKIIIVQLNE--SVPINCIRPYNNNTRQSTRI--GPGQALFTT-KVIGDIRQAHCN
AE.T93  NNAKIIIVHLNK--SVEINCTRPSNNIRTSIRI--GPGRVFYKTGAITGDIRKAYCE
AE.T90  NNAKTIIVHLNK--SVEINCTRPSNNTRTSITI--GPGRVFYRTGDIIGNIRKAYCE
CPZ05   N---LAIIQLKD--PVKITCRRPGNNITVGNVQL--GPAMTFYNIENVGDTRKAYCE
CPZ85   D---IILVQFSE--GVNMTCIRPGNNTVGNVQL--GPGMTFYNIPKIVGDVREAHCN
SIV51   NRT----IISLNKYYNLTMKCRRPGNKTVLPVTI--PINDRPKQAWCW
SIV39   NRT----IISLNKYYNLTMKCRRPGNKTVLPVTI--PINDRPKQAWCW
```

```
                                                    471/L                   482/L    487/L 489/L
MN      GQIRCSSNITGLLLT-------------RDGGEDTDT--NDTEIFR PGGGDMRDNWR SELYK YK
HXB2    GQIRCSSNITGLLLT-------------RDGGNS-N---NESEIFR PGGGDMRDNWR SELYK YK
A1.KE   GVIKCESNITGLLLT-------------RDGGKD-N---NVNETFR PGGGDMRDNWR SELYK YK
A1.UG   GVIKCESNITGLILT-------------RDGGVN-S---SDSETFR PGGGDMRDNWR SELYK YK
C.ET    GIIMCRSNITGLLLT-------------RDGAKEPH---STKEIFR PEGGDMRDNWR SELYK YK
C.IN    GNITCTSNITGLLLV-------------HDGGIKENDTENKTEIFR PGGGDMRDNWR SELYK YK
D.TZ    GLIRCTSNITGLLLT-------------RDGGNVNN---SREEIFR PGGGDMRDNWR SELYK YK
D.UG    GFINCSSNITGLLLT-------------RDGGAINS---SQNETFR PGGGDMRNNWR SELYK YK
AE.T93  GRINCVSNITGILLT-------------RDGGAN-N---TQNETFR PGGGNIKDNWR SELYK YK
AE.T90  GRINCVSNITGILLT-------------RDGGVN-N---TDNETFR PGGGNIKDNWR SELYK YK
CPZ05   GNITCTSNITGMLLEIHKNREDQGED-Q--DQNNTYVCLTGGNMKDIWR SELYK YK
CPZ85   GVLSCNSNITGMILD-------------ISISAVNND--SRNITVM PTGGDMTALWKNELHK YK
SIV51   GDLTCNSTVTSLIAN-------------IDWT------DGNQTSI TMSAEVAELYR LELGDYK
SIV39   GDLTCNSTVTSLIAN-------------IDWI------DGNQTNI TMSAEVAELYR LELGDYK

MN      VVTIEPLGVAPTKAKRRVVQRE----
HXB2    VVKIEPLGVAPTKAKRRVVQREKR
A1.KE   VVEIEPLGVAPTRAKRRVVQRV----
A1.UG   VVKIEPLGVAPTKARRRVV-------
C.ET    VVEIKPLGVAPTKPKRRVV-------
C.IN    VVEIKPLGVAPTAAKRRVV-------
D.TZ    VVRIEPIGVAPTRAKRRVV-------
D.UG    VVKLEPIGLAPTAAKRRVV-------
AE.T93  VVQIEPIGIAPTRAKRRVV-------
AE.T90  VVQIEPLGIAPTRAKRRVV-------
CPZ05   IVEIQPLGVAPTKSRRYAV-------
CPZ285  VVSIEPIGVAPGKAKRHTV-------
SIV51   LVEITPIGLAPTDVKRYTTGGT----
SIV39   LVEITPIGLAPTDVKRYTTGGT----
```

>p 1.10848_c2 Resistant
MRAREIRMNYQNLWRWGTLLFGILMICSTAENLWVTVYYG
VPVWREATTTLFCASDAKSYETEVHNVWATHACVPTDPNP
QEILLENVTEDFNIWTNNMVEQMHEDIISLWDQSLKPCVK
LTPLCVTLNCTDLKNATNITNSEGGMREGGEIKNCSFNIT
TSLRDRVQKEYALFYKLDVEPIDDDKNSTDNNSTNYTNYR
LISCNTSVITQACPKVSFEPIPIHYCVPAGYALLQCNNKT
FSGKGQCKNVSTVQCTHGIRPVVSTQLLLNGSLAEEEVVI
RSENFTDNAKTIIVQLNETVEINCTRPNNNTRRSISIGPG
RAFYATGDIIGDIRQAHCNLSEAKWNRTLELVVEKLRDQF
KNKTIVFNHSSGGDPEIVMFSFNCGGEFFYCDSTKLFNST
WNGTEDDSGKNRTITLPCRIKQFINMWQEVGKAMYAPPIK
GQISCLSNITGLLLTRDGGNNVSNTTEVFRPGGGNMRDNW
RSELYKYKVVEIEPLGLAPTKAKRRVVQREKRAVGIGALF
LGFLGAAGSTMGAASMTLTVQARQLLSGIVQQQNNLLRAI
EAQQHLLQLTVWGIKQLQARVLAMERYLKDQQLLGIWGCS
GKLICTTTVPWNTSWSHNRSLNEIWDNMTWMQWDKEINNY
TDLIYNLLGEAQNQQEKNEQELLELDKWASLWNWFSITNW
LWYIKIFIIVAGLVGLRIVFTVFSLVNRVRQGYSPLSFQ
THLPAPRGPDRPEGTEERGGEQDRDRSGHLVDGLLTIIWV
DLRSLFLFSYHRLRDLLLILARIVELLGRRGWEILKYWWN
LLLFWSQELKNSAVSLLNTIAIVVAEGTDWVIAGLQRLFR
AFLHIPRRIRQGFERALL

```
>pl.10848_cl1 Sensitive
MRAREIRMNYQNLWRWGTLLFGILMICSTAENLWVTVYYG
VPVWREATTTLFCASDAKSYETEVHNVWATHACVPTDPNP
QEILLENVTEDFNIWTNNMVEQMHEDIISLWDQSLKPCVK
LTPLCVTLNCTDLKNATNITNSEGGMREGGEIKNCSFNIT
TSLRDRVQKEYALFYKLDVEPIDDDKNSTDNNSTNYTNYR
LISCNTSVITQACPKVSFEPIPIHYCVPAGYALLRCNNKT
FSGKGQCKNVSTVQCTHGIRPVVSTQLLLNGSLAEEEVVI
RSENFTDNAKTIIVQLNETVEINCTRPNNNTRRSISIGPG
RAFYATGDIIGDIRQAHCNLSEAKWNRTLELVVEKLRDQF
KNKTIVFNHSSGGDPEIVMFSFNCGGEFFYCDSTKLFNST
WNGTEDDSGKNRTITLPCRIKQFINMWQEVGKAMYAPPIK
GQISCLSNITGLLLTRDGGNNVSNTTEVFRPGGGNMRDNW
RSELYKYKVVEIEPLGLAPTKAKRRVVQREKRAVGIGALF
LGFLGAAGSTMGAASMTLTVQARQLLSGIVQQQNNLLRAI
EAQQHLLQLTVWGIKQLQARVLAMERYLKDQQLLGIWGCS
GKLICTTTVPWNTSWSHNRSLNEIWDNMTWMQWDKEINNY
TDLIYNLLEEAQNQQEKNEQELLELDKWASLWNWFSITNW
LWYIKIFIIIVAGLVGLRIVFTVFSLVNRVRQGYSPLSFQ
THLPAPRGPDRPEGTEERGGEQDRDRSGHLVDGLLTIIWV
DLRSLFLFSYHRLRDLLLILARIVELLGRRGWEILKYWWN
LLLFWSQELKNSAVSLLNTIAIVVAEGTDWVIAGLQRLFR
AFLHIPRRIRQGFERALL
```

```
>108051 c6 Sensitive
MRVKGIRRNYQHLWRGATLLLGILMICSVAGNLWVTVYYG
VPVWKEATTTLFCASDAKAYDTEVHNVWATHACVPTDPNP
QELALENVTENFNMWENDMVEQMHEDIISLWDQSLKPCVK
LTPLCVTLNCTDAEVTRKTNTTSGDWEKVKKGEIKNCSFD
AINTKNKVQKQYALFDTLNVVSIDDDNNSNNNSNNNNNTN
YSDFRLTKCDTSVIRQACPKVSFEPIPIHYCAPAGFAILK
CNETDFNGTGLCNNVSTVQCTHGIRPVVSTQLLLNGSLAE
KGVVLRSKDFKENTKIIIVQLNKAVNITCTRPNNNTRKGV
HMGPGGALFATDVIGDIRKAHCNITREEWNNTLKQIVLKL
KEKFENKTKIVFTNSSGGDPEVTMHTFNCGGEFFYCNTTE
LFSSTWNITGDSIGNITGESLNITLPCRIKQIINMWQGVG
KAMYAPPISGQIRCISNITGLLLTRDGGDNNTENDNNTEI
FRPWGGDMRDNWRSELYKYKVVEPLGLAPTKAKRRVVQ
REKRAIGVGAMFLGFLGAAGSTMGAASLTLTVQARQLLSG
IVQQQNNLLRAIEAQQHLLQLTVWGIKQLQARVLAVERYL
KDQQLLGIWGCSGKLICTTTVPWNDSWGYSWSNRTNKSLE
EIWDNLTWREWEREIDNYTDLIYNLIEKSQNQQEKNEQEL
LALDKWANLWNWFDITNWLWYIRIFIMIVGGLIGLRIVFA
VLSIVRRVRQGYSPLSFQTLLPVPRGPDRPEGIEEEGGEQ
DRGRSVRLVDGFLALFWDDLRSLCLFLYHRLRDLLLIVTR
IVGVLGHRGWEILKYWWSLIQYWSQELKNSAVSLLNATAI
TVAEGTDRVIEIRQRVFRGVLHIPRRIRQGLERALL
```

```
>pl.108051_c5  Resistant
MRVKGIRRNYQHLWRGVTLLLGILMICSVAGNLWVTVYYG
VPVWKEATTTLFCASDAKAYDTEVHNVWATHACVPTDPNP
QELALENVTENFNMWENDMVEQMHEDIISLWDQSLKPCVK
LTPLCVTLNCTDAEVTGKTNTTIGEWEKVKEGEMKNCSFD
AINTKNKVQKQYALFDTLDVVPIDDDNNSNSNYSDFRLTK
CDTSVIRQACPKVSFEPIPIHYCAPAGFAILKCNETDFNG
TGLCNNVSTVQCTHGIRPVVSTQLLLNGSLAEEGVVLRSK
DFKENTKIIIVQLNKAVNITCTRPNNNTRKGVHMGPGGAL
FATDVIGDIRKAHCNITREEWNNTLKQIVLKLKEKFENKT
KIVFTNSSGGDPEVTMHTFNCGGEFFYCNTTELFSSTWNI
TGDSIGNITGEYTLNITLPCRIKQIINMWQGVGKAMYAPP
ISGQIRCISNITGLLLTRDGGGNNTENDNNTEIFRPWGGD
MRDNWRSELYKYKVVKLEPLGLAPTKAKRRVVQREKRAIG
VGAMFLGFLGAAGSTMGAASLTLTVQARQLLSGIVQQQNN
LLRAIEAQQHLLQLTVWGIKQLQARVLAVERYLKDQQLLG
IWGCSGKLICTTTVPWNDSWGYSWSNRTNKSLEEIWDNLT
WREWEREIDNYTDLIYNLIEKSQNQQEKNEQELLALDKWA
NLWNWFDITNWLWYIRIFIMIVGGLIGLRIVFAVLSIVRR
VRQGYSPLSFQTLLPVPRGPDRPEGTEKEGGEQDRGRSVR
LVDGFLALFWDDLRSLCLFLYHRLRDLLLIVTRIVGVLGH
RGWEILKYWWSLIQYWSQELKNSAVSLLNATAITVAEGTD
RVIEIVRRVFRGVLHIPRRIRQGLERALL
```

```
>pl. 108060_c22 Resistant
MKVKGIKKSCQHLWKWGILLLGMLMICSAAEKMWVTVYYG
VPVWKEATTTLFCASDAKSYDTEVHNVWATHACVPTDPNP
QEVVLGNVTENFNMWKNNMVEQMHEDVISLWDQSLKPCVK
LTPLCVTLNCTDKLRNDAFGVNNTMEGEMKNCSFNTTTSL
RDKIQKEYALFYKLDVVQIKNNNNSNYTSYRLINCNTSVI
TQACPKVTFEPIPIHYCTPAGFAILKCNNKTFSGKGTCTN
VSTVQCTHGIRPVVSTQLLLNGSLAEEDVVIRSDNFSQNA
KIIVQLNEAVVINCTRPGNNTRKSIPIGPGRAFYATGDI
IGNIRQAHCNVSSTKWNNTLQKIVEKLREQFGNKTIKFTS
PSPGGDPEIVMHSFNCGGEFFYCDTTQLFNSTWDNTSTWN
NSNTQNKNDRNITLQCRIKQIINMWQEVGKAMYAPPIMGQ
IRCVSNITGLLLTRDGGNGSEAKNDTEIFRPGGGDMRDNW
RSELYKYKVVKIEPLGVAPTKAKRRVVQREKRAVGTIGAM
FLGFLGAAGNTMGAASLTLTVQARQLLSGIVQQQNNLLRA
IQAQQHLLQLTVWGIKQLQARVLAVERYLRDQQLLGIWGC
SGKLICTTAVPWNASWSNKSYTDIWDNMTWMQWEKEIENY
TSLIYTLIEDSQNQQEKNEQELLELDKWASLWNWFDITSW
LWYIKIFIMIVGGLIGLRIVFAVLSIVNRVRQGYSPLSLQ
TRLPAPGGPDRPGGIEEEGGEQGRGRSVRLVDGFLALIWD
DLRNLCLFIYHRLRDLLWIVGLLGRRGWEILKYWWNILQY
WSQELKNSAVSLLNTIAIAVAEGTDRIIELAQGICRAILH
IPRRIRQGFERALL
```

>pl.108060_c24 Sensitive
MKVKGIKKSCQHLWKWGILLLGMLMICSAAEKMWVTVYYG
VPVWKEATTTLFCASDAKSYDTEVHNVWATHACVPTDPNP
QEVVLGNVTENFNMWKNNMVEQMHEDVISLWDQSLKPCVK
LTPLCVTLNCTDKLRNDAFGVNNTMEGEMKNCSFNTTTSL
RDKIQKEYALFYKLDVVQIKNNNNSNYTSYRLINCNTSVI
TQACPKVTFEPIPIHYCTPAGFAILKCNNKTFSGKGTCTN
VSTVQCTHGIRPVVSTQLLLNGSLAEEDVVIRSDNFSQNA
KIIVQLNEAVVINCTRPGNNTRKSIPIGPGRAFYATGDI
IGSIRQAHCNVSSTKWNNTLQKIVEKLREQFGNKTIKFTS
PSPGGDPEIVMHSFNCGGEFYCDTTQLFNSTWDNTSTWN
NSNTQNKNDRNITLQCRIKQIINMWQEVGKAMYAPPIMGQ
IRCVSNITGLLLTRDGGNGSEAKNDTEIFRPGGGDMRDNW
RSELYKYKVVKIEPLGVAPTKAKRRVVQREKRAVGTIGAM
FLGFLGAAGSTMGAASLTLTVQARQLLSGIVQQQNNLLRA
IQAQQHLLQLTVWGIKQLQARVLAVERYLRDQQLLGIWGC
SGKLICTTAVPWNASWSNKSYTDIWDNMTWMQWEEEIENY
TSLIYTLIEDSQNQREKNEQELLELDKWASLWNWFDITSW
LWYIKIFIMIVGGLIGLRIVFAVLSIVNRVRQGYSPLSLQ
TRLPAPGGPDRPGGIEEEGGEQGRGRSVRLVDGFLALIWD
DLRNLCLFIYHRLRDLLWIVGLLGRRGWEILKYWWNILQY
WSQELKNSAVSLLNTIAIAVAEGTDRTIELAHRICRAILH
IPRRIRQGFERALL

SEQUENCE LISTING

<160> NUMBER OF SEQ ID NOS: 48

<210> SEQ ID NO 1
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (16)..(16)
<223> OTHER INFORMATION: Xaa may be any amino acid except for Gln or
      Asn.

<400> SEQUENCE: 1

Tyr Thr Ser Leu Ile His Ser Leu Ile Glu Glu Ser Gln Asn Gln Xaa
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 2
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (16)..(16)
<223> OTHER INFORMATION: Xaa may be any amino acid except for Gln or
      Asn.

<400> SEQUENCE: 2

Tyr Thr Asn Thr Ile Tyr Thr Leu Leu Glu Glu Ser Gln Asn Gln Xaa
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 3

```
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (16)..(16)
<223> OTHER INFORMATION: Xaa may be any amino acid except for Gln or
      Asn.

<400> SEQUENCE: 3

Tyr Thr Gly Ile Ile Tyr Asn Leu Leu Glu Glu Ser Gln Asn Gln Xaa
1               5                   10                  15

Glu Lys Asn Glu Gln Glu Leu Leu Glu Leu Asp Lys Trp Ala Asn Leu
            20                  25                  30

Trp Asn Trp Phe
        35

<210> SEQ ID NO 4
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (16)..(16)
<223> OTHER INFORMATION: Xaa may be any amino acid except for Gln or
      Asn.

<400> SEQUENCE: 4

Tyr Thr Ser Leu Ile Tyr Ser Leu Leu Glu Lys Ser Gln Ile Gln Xaa
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 5
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (16)..(16)
<223> OTHER INFORMATION: Xaa may be any amino acid except for Gln or
      Asn.

<400> SEQUENCE: 5

Leu Glu Ala Asn Ile Ser Lys Ser Leu Glu Gln Ala Gln Ile Gln Xaa
1               5                   10                  15

Glu Lys Asn Met Tyr Glu Leu Gln Lys Leu Asn Ser Trp Asp Ile Phe
            20                  25                  30

Gly Asn Trp Phe
        35

<210> SEQ ID NO 6
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
```

```
<222> LOCATION: (16)..(16)
<223> OTHER INFORMATION: Xaa may be any amino acid except for Gln or
      Asn.

<400> SEQUENCE: 6

Leu Glu Ala Asn Ile Ser Gln Ser Leu Glu Gln Ala Gln Ile Gln Xaa
1               5                   10                  15

Glu Lys Asn Met Tyr Glu Leu Gln Lys Leu Asn Ser Trp Asp Val Phe
            20                  25                  30

Thr Asn Trp Leu
        35

<210> SEQ ID NO 7
<211> LENGTH: 5
<212> TYPE: PRT
<213> ORGANISM: Human immunodeficiency virus 1

<400> SEQUENCE: 7

Gly Thr Ile Arg Gln
1               5

<210> SEQ ID NO 8
<211> LENGTH: 4
<212> TYPE: PRT
<213> ORGANISM: Human immunodeficiency virus 1

<400> SEQUENCE: 8

Lys Ala Met Tyr
1

<210> SEQ ID NO 9
<211> LENGTH: 4
<212> TYPE: PRT
<213> ORGANISM: Human immunodeficiency virus 1

<400> SEQUENCE: 9

Ala Pro Pro Ile
1

<210> SEQ ID NO 10
<211> LENGTH: 4
<212> TYPE: PRT
<213> ORGANISM: Human immunodeficiency virus 1

<400> SEQUENCE: 10

Ala Cys Pro Lys
1

<210> SEQ ID NO 11
<211> LENGTH: 4
<212> TYPE: PRT
<213> ORGANISM: Human immunodeficiency virus 1

<400> SEQUENCE: 11

Thr Gln Leu Leu
1

<210> SEQ ID NO 12
<211> LENGTH: 4
<212> TYPE: PRT
<213> ORGANISM: Human immunodeficiency virus 1

<400> SEQUENCE: 12

Thr Lys Asn Ile
```

-continued

```
<210> SEQ ID NO 13
<211> LENGTH: 4
<212> TYPE: PRT
<213> ORGANISM: Human immunodeficiency virus 1

<400> SEQUENCE: 13

Tyr Lys Leu Asp
1

<210> SEQ ID NO 14
<211> LENGTH: 5
<212> TYPE: PRT
<213> ORGANISM: Human immunodeficiency virus 1

<400> SEQUENCE: 14

Val Val Ile Arg Ser
1               5

<210> SEQ ID NO 15
<211> LENGTH: 4
<212> TYPE: PRT
<213> ORGANISM: Human immunodeficiency virus 1

<400> SEQUENCE: 15

Lys Tyr Ala Leu
1

<210> SEQ ID NO 16
<211> LENGTH: 854
<212> TYPE: PRT
<213> ORGANISM: Artificial sequence
<220> FEATURE:
<223> OTHER INFORMATION: Synthetic polypeptide

<400> SEQUENCE: 16

Met Lys Val Lys Gly Ile Lys Lys Ser Cys Gln His Leu Trp Lys Trp
1               5                   10                  15

Gly Ile Leu Leu Leu Gly Met Leu Met Ile Cys Ser Ala Ala Glu Lys
                20                  25                  30

Met Trp Val Thr Val Tyr Tyr Gly Val Pro Val Trp Lys Glu Ala Thr
            35                  40                  45

Thr Thr Leu Phe Cys Ala Ser Asp Ala Lys Ser Tyr Asp Thr Glu Val
        50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asn Met Val Glu Gln Met His Glu Asp Val Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Lys Leu Arg Asn Asp Ala Phe Gly Val Asn Asn Thr
        130                 135                 140

Met Glu Gly Glu Met Lys Asn Cys Ser Phe Asn Thr Thr Thr Ser Leu
145                 150                 155                 160

Arg Asp Lys Ile Gln Lys Glu Tyr Ala Leu Phe Tyr Lys Leu Asp Val
                165                 170                 175

Val Gln Ile Lys Asn Asn Asn Asn Ser Asn Tyr Thr Ser Tyr Arg Leu
```

-continued

```
                180                 185                 190
Ile Asn Cys Asn Thr Ser Val Ile Thr Gln Ala Cys Pro Lys Val Thr
            195                 200                 205
Phe Glu Pro Ile Pro Ile His Tyr Cys Thr Pro Ala Gly Phe Ala Ile
        210                 215                 220
Leu Lys Cys Asn Asn Lys Thr Phe Ser Gly Lys Gly Thr Cys Thr Asn
225                 230                 235                 240
Val Ser Thr Val Gln Cys Thr His Gly Ile Arg Pro Val Val Ser Thr
                245                 250                 255
Gln Leu Leu Asn Gly Ser Leu Ala Glu Glu Asp Val Val Ile Arg
            260                 265                 270
Ser Asp Asn Phe Ser Gln Asn Ala Lys Ile Ile Val Gln Leu Asn
        275                 280                 285
Glu Ala Val Val Ile Asn Cys Thr Arg Pro Gly Asn Asn Thr Arg Lys
        290                 295                 300
Ser Ile Pro Ile Gly Pro Gly Arg Ala Phe Tyr Ala Thr Gly Asp Ile
305                 310                 315                 320
Ile Gly Asn Ile Arg Gln Ala His Cys Asn Val Ser Ser Thr Lys Trp
                325                 330                 335
Asn Asn Thr Leu Gln Lys Ile Val Glu Lys Leu Arg Glu Gln Phe Gly
            340                 345                 350
Asn Lys Thr Ile Lys Phe Thr Ser Pro Ser Gly Gly Asp Pro Glu
        355                 360                 365
Ile Val Met His Ser Phe Asn Cys Gly Gly Glu Phe Phe Tyr Cys Asp
        370                 375                 380
Thr Thr Gln Leu Phe Asn Ser Thr Trp Asp Asn Thr Ser Thr Trp Asn
385                 390                 395                 400
Asn Ser Asn Thr Gln Asn Lys Asn Asp Arg Asn Ile Thr Leu Gln Cys
                405                 410                 415
Arg Ile Lys Gln Ile Ile Asn Met Trp Gln Glu Val Gly Lys Ala Met
            420                 425                 430
Tyr Ala Pro Pro Ile Met Gly Gln Ile Arg Cys Val Ser Asn Ile Thr
        435                 440                 445
Gly Leu Leu Leu Thr Arg Asp Gly Gly Asn Gly Ser Glu Ala Lys Asn
        450                 455                 460
Asp Thr Glu Ile Phe Arg Pro Gly Gly Gly Asp Met Arg Asp Asn Trp
465                 470                 475                 480
Arg Ser Glu Leu Tyr Lys Tyr Lys Val Val Lys Ile Glu Pro Leu Gly
                485                 490                 495
Val Ala Pro Thr Lys Ala Lys Arg Arg Val Val Gln Arg Glu Lys Arg
            500                 505                 510
Ala Val Gly Thr Ile Gly Ala Met Phe Leu Gly Phe Leu Gly Ala Ala
        515                 520                 525
Gly Asn Thr Met Gly Ala Ala Ser Leu Thr Leu Thr Val Gln Ala Arg
        530                 535                 540
Gln Leu Leu Ser Gly Ile Val Gln Gln Asn Asn Leu Leu Arg Ala
545                 550                 555                 560
Ile Gln Ala Gln Gln His Leu Leu Gln Leu Thr Val Trp Gly Ile Lys
                565                 570                 575
Gln Leu Gln Ala Arg Val Leu Ala Val Glu Arg Tyr Leu Arg Asp Gln
            580                 585                 590
Gln Leu Leu Gly Ile Trp Gly Cys Ser Gly Lys Leu Ile Cys Thr Thr
        595                 600                 605
```

Ala Val Pro Trp Asn Ala Ser Trp Ser Asn Lys Ser Tyr Thr Asp Ile
            610                 615                 620

Trp Asp Asn Met Thr Trp Met Gln Trp Glu Lys Glu Ile Glu Asn Tyr
625                 630                 635                 640

Thr Ser Leu Ile Tyr Thr Leu Ile Glu Asp Ser Gln Asn Gln Arg Glu
                645                 650                 655

Lys Asn Glu Gln Glu Leu Leu Glu Leu Asp Lys Trp Ala Ser Leu Trp
            660                 665                 670

Asn Trp Phe Asp Ile Thr Ser Trp Leu Trp Tyr Ile Lys Ile Phe Ile
        675                 680                 685

Met Ile Val Gly Gly Leu Ile Gly Leu Arg Ile Val Phe Ala Val Leu
    690                 695                 700

Ser Ile Val Asn Arg Val Arg Gln Gly Tyr Ser Pro Leu Ser Leu Gln
705                 710                 715                 720

Thr Arg Leu Pro Ala Pro Gly Gly Pro Asp Arg Pro Gly Gly Ile Glu
                725                 730                 735

Glu Glu Gly Gly Glu Gln Gly Arg Gly Arg Ser Val Arg Leu Val Asp
            740                 745                 750

Gly Phe Leu Ala Leu Ile Trp Asp Asp Leu Arg Asn Leu Cys Leu Phe
        755                 760                 765

Ile Tyr His Arg Leu Arg Asp Leu Leu Trp Ile Val Gly Leu Leu Gly
    770                 775                 780

Arg Arg Gly Trp Glu Ile Leu Lys Tyr Trp Trp Asn Ile Leu Gln Tyr
785                 790                 795                 800

Trp Ser Gln Glu Leu Lys Asn Ser Ala Val Ser Leu Leu Asn Thr Ile
                805                 810                 815

Ala Ile Ala Val Ala Glu Gly Thr Asp Arg Ile Ile Glu Leu Ala Gln
            820                 825                 830

Gly Ile Cys Arg Ala Ile Leu His Ile Pro Arg Arg Ile Arg Gln Gly
        835                 840                 845

Phe Glu Arg Ala Leu Leu
    850

<210> SEQ ID NO 17
<211> LENGTH: 685
<212> TYPE: PRT
<213> ORGANISM: Artificial sequence
<220> FEATURE:
<223> OTHER INFORMATION: Synthetic polypeptide

<400> SEQUENCE: 17

Met Lys Val Lys Gly Ile Lys Lys Ser Cys Gln His Leu Trp Lys Trp
1               5                   10                  15

Gly Ile Leu Leu Leu Gly Met Leu Met Ile Cys Ser Ala Ala Glu Lys
            20                  25                  30

Met Trp Val Thr Val Tyr Tyr Gly Val Pro Val Trp Lys Glu Ala Thr
        35                  40                  45

Thr Thr Leu Phe Cys Ala Ser Asp Ala Lys Ser Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asn Met Val Glu Gln Met His Glu Asp Val Ile Ser Leu Trp Asp
            100                 105                 110

```
Gln Ser Leu Lys Pro Cys Val Lys Leu Thr Pro Leu Cys Val Thr Leu
    115                 120                 125

Asn Cys Thr Asp Lys Leu Arg Asn Asp Ala Phe Gly Val Asn Asn Thr
130                 135                 140

Met Glu Gly Glu Met Lys Asn Cys Ser Phe Asn Thr Thr Thr Ser Leu
145                 150                 155                 160

Arg Asp Lys Ile Gln Lys Glu Tyr Ala Leu Phe Tyr Lys Leu Asp Val
                165                 170                 175

Val Gln Ile Lys Asn Asn Asn Ser Asn Tyr Thr Ser Tyr Arg Leu
                180                 185                 190

Ile Asn Cys Asn Thr Ser Val Ile Thr Gln Ala Cys Pro Lys Val Thr
            195                 200                 205

Phe Glu Pro Ile Pro Ile His Tyr Cys Thr Pro Ala Gly Phe Ala Ile
210                 215                 220

Leu Lys Cys Asn Asn Lys Thr Phe Ser Gly Lys Gly Thr Cys Thr Asn
225                 230                 235                 240

Val Ser Thr Val Gln Cys Thr His Gly Ile Arg Pro Val Val Ser Thr
                245                 250                 255

Gln Leu Leu Leu Asn Gly Ser Leu Ala Glu Glu Asp Val Val Ile Arg
        260                 265                 270

Ser Asp Asn Phe Ser Gln Asn Ala Lys Ile Ile Ile Val Gln Leu Asn
    275                 280                 285

Glu Ala Val Val Ile Asn Cys Thr Arg Pro Gly Asn Asn Thr Arg Lys
290                 295                 300

Ser Ile Pro Ile Gly Pro Gly Arg Ala Phe Tyr Ala Thr Gly Asp Ile
305                 310                 315                 320

Ile Gly Asn Ile Arg Gln Ala His Cys Asn Val Ser Ser Thr Lys Trp
                325                 330                 335

Asn Asn Thr Leu Gln Lys Ile Val Glu Lys Leu Arg Glu Gln Phe Gly
            340                 345                 350

Asn Lys Thr Ile Lys Phe Thr Ser Pro Ser Pro Gly Gly Asp Pro Glu
        355                 360                 365

Ile Val Met His Ser Phe Asn Cys Gly Gly Glu Phe Phe Tyr Cys Asp
    370                 375                 380

Thr Thr Gln Leu Phe Asn Ser Thr Trp Asp Asn Thr Ser Thr Trp Asn
385                 390                 395                 400

Asn Ser Asn Thr Gln Asn Lys Asn Asp Arg Asn Ile Thr Leu Gln Cys
                405                 410                 415

Arg Ile Lys Gln Ile Ile Asn Met Trp Gln Glu Val Gly Lys Ala Met
            420                 425                 430

Tyr Ala Pro Pro Ile Met Gly Gln Ile Arg Cys Val Ser Asn Ile Thr
        435                 440                 445

Gly Leu Leu Leu Thr Arg Asp Gly Gly Asn Gly Ser Glu Ala Lys Asn
    450                 455                 460

Asp Thr Glu Ile Phe Arg Pro Gly Gly Gly Asp Met Arg Asp Asn Trp
465                 470                 475                 480

Arg Ser Glu Leu Tyr Lys Tyr Lys Val Val Lys Ile Glu Pro Leu Gly
                485                 490                 495

Val Ala Pro Thr Lys Ala Lys Arg Arg Val Val Gln Arg Glu Lys Arg
            500                 505                 510

Ala Val Gly Thr Ile Gly Ala Met Phe Leu Gly Phe Leu Gly Ala Ala
        515                 520                 525
```

```
Gly Asn Thr Met Gly Ala Ala Ser Leu Thr Leu Thr Val Gln Ala Arg
            530                 535                 540

Gln Leu Leu Ser Gly Ile Val Gln Gln Asn Asn Leu Leu Arg Ala
545                 550                 555                 560

Ile Gln Ala Gln Gln His Leu Leu Gln Leu Thr Val Trp Gly Ile Lys
                    565                 570                 575

Gln Leu Gln Ala Arg Val Leu Ala Val Glu Arg Tyr Leu Arg Asp Gln
            580                 585                 590

Gln Leu Leu Gly Ile Trp Gly Cys Ser Gly Lys Leu Ile Cys Thr Thr
                595                 600                 605

Ala Val Pro Trp Asn Ala Ser Trp Ser Asn Lys Ser Tyr Thr Asp Ile
            610                 615                 620

Trp Asp Asn Met Thr Trp Met Gln Trp Glu Lys Glu Ile Glu Asn Tyr
625                 630                 635                 640

Thr Ser Leu Ile Tyr Thr Leu Ile Glu Asp Ser Gln Asn Gln Arg Glu
                    645                 650                 655

Lys Asn Glu Gln Glu Leu Leu Glu Leu Asp Lys Trp Ala Ser Leu Trp
            660                 665                 670

Asn Trp Phe Asp Ile Thr Ser Trp Leu Trp Tyr Ile Lys
                675                 680                 685

<210> SEQ ID NO 18
<211> LENGTH: 645
<212> TYPE: PRT
<213> ORGANISM: Artificial sequence
<220> FEATURE:
<223> OTHER INFORMATION: Synthetic polypeptide

<400> SEQUENCE: 18

Val Pro Val Trp Lys Glu Ala Thr Thr Thr Leu Phe Cys Ala Ser Asp
1               5                   10                  15

Ala Lys Ser Tyr Asp Thr Glu Val His Asn Val Trp Ala Thr His Ala
            20                  25                  30

Cys Val Pro Thr Asp Pro Asn Pro Gln Glu Val Val Leu Gly Asn Val
        35                  40                  45

Thr Glu Asn Phe Asn Met Trp Lys Asn Asn Met Val Glu Gln Met His
    50                  55                  60

Glu Asp Val Ile Ser Leu Trp Asp Gln Ser Leu Lys Pro Cys Val Lys
65                  70                  75                  80

Leu Thr Pro Leu Cys Val Thr Leu Asn Cys Thr Asp Lys Leu Arg Asn
                85                  90                  95

Asp Ala Phe Gly Val Asn Asn Thr Met Glu Gly Glu Met Lys Asn Cys
            100                 105                 110

Ser Phe Asn Thr Thr Thr Ser Leu Arg Asp Lys Ile Gln Lys Glu Tyr
        115                 120                 125

Ala Leu Phe Tyr Lys Leu Asp Val Val Gln Ile Lys Asn Asn Asn Asn
    130                 135                 140

Ser Asn Tyr Thr Ser Tyr Arg Leu Ile Asn Cys Asn Thr Ser Val Ile
145                 150                 155                 160

Thr Gln Ala Cys Pro Lys Val Thr Phe Glu Pro Ile Pro Ile His Tyr
                165                 170                 175

Cys Thr Pro Ala Gly Phe Ala Ile Leu Lys Cys Asn Asn Lys Thr Phe
            180                 185                 190

Ser Gly Lys Gly Thr Cys Thr Asn Val Ser Thr Val Gln Cys Thr His
        195                 200                 205
```

-continued

Gly Ile Arg Pro Val Val Ser Thr Gln Leu Leu Asn Gly Ser Leu
210                 215                 220

Ala Glu Asp Val Val Ile Arg Ser Asp Asn Phe Ser Gln Asn Ala
225                 230                 235                 240

Lys Ile Ile Ile Val Gln Leu Asn Glu Ala Val Val Ile Asn Cys Thr
                245                 250                 255

Arg Pro Gly Asn Asn Thr Arg Lys Ser Ile Pro Ile Gly Pro Gly Arg
            260                 265                 270

Ala Phe Tyr Ala Thr Gly Asp Ile Ile Gly Asn Ile Arg Gln Ala His
            275                 280                 285

Cys Asn Val Ser Ser Thr Lys Trp Asn Asn Thr Leu Gln Lys Ile Val
290                 295                 300

Glu Lys Leu Arg Glu Gln Phe Gly Asn Lys Thr Ile Lys Phe Thr Ser
305                 310                 315                 320

Pro Ser Pro Gly Gly Asp Pro Glu Ile Val Met His Ser Phe Asn Cys
                325                 330                 335

Gly Gly Glu Phe Phe Tyr Cys Asp Thr Thr Gln Leu Phe Asn Ser Thr
            340                 345                 350

Trp Asp Asn Thr Ser Thr Trp Asn Asn Ser Asn Thr Gln Asn Lys Asn
            355                 360                 365

Asp Arg Asn Ile Thr Leu Gln Cys Arg Ile Lys Gln Ile Ile Asn Met
370                 375                 380

Trp Gln Glu Val Gly Lys Ala Met Tyr Ala Pro Pro Ile Met Gly Gln
385                 390                 395                 400

Ile Arg Cys Val Ser Asn Ile Thr Gly Leu Leu Leu Thr Arg Asp Gly
                405                 410                 415

Gly Asn Gly Ser Glu Ala Lys Asn Asp Thr Glu Ile Phe Arg Pro Gly
            420                 425                 430

Gly Gly Asp Met Arg Asp Asn Trp Arg Ser Glu Leu Tyr Lys Tyr Lys
            435                 440                 445

Val Val Lys Ile Glu Pro Leu Gly Val Ala Pro Thr Lys Ala Lys Arg
450                 455                 460

Arg Val Val Gln Arg Glu Lys Arg Ala Val Gly Thr Ile Gly Ala Met
465                 470                 475                 480

Phe Leu Gly Phe Leu Gly Ala Ala Gly Asn Thr Met Gly Ala Ala Ser
                485                 490                 495

Leu Thr Leu Thr Val Gln Ala Arg Gln Leu Leu Ser Gly Ile Val Gln
            500                 505                 510

Gln Gln Asn Asn Leu Leu Arg Ala Ile Gln Ala Gln Gln His Leu Leu
            515                 520                 525

Gln Leu Thr Val Trp Gly Ile Lys Gln Leu Gln Ala Arg Val Leu Ala
530                 535                 540

Val Glu Arg Tyr Leu Arg Asp Gln Gln Leu Leu Gly Ile Trp Gly Cys
545                 550                 555                 560

Ser Gly Lys Leu Ile Cys Thr Thr Ala Val Pro Trp Asn Ala Ser Trp
                565                 570                 575

Ser Asn Lys Ser Tyr Thr Asp Ile Trp Asp Asn Met Thr Trp Met Gln
            580                 585                 590

Trp Glu Lys Glu Ile Glu Asn Tyr Thr Ser Leu Ile Tyr Thr Leu Ile
            595                 600                 605

Glu Asp Ser Gln Asn Gln Arg Glu Lys Asn Glu Gln Glu Leu Leu Glu
610                 615                 620

Leu Asp Lys Trp Ala Ser Leu Trp Asn Trp Phe Asp Ile Thr Ser Trp

```
                625                 630                 635                 640

Leu Trp Tyr Ile Lys
                645

<210> SEQ ID NO 19
<211> LENGTH: 645
<212> TYPE: PRT
<213> ORGANISM: Artificial sequence
<220> FEATURE:
<223> OTHER INFORMATION: Synthetic polypeptide

<400> SEQUENCE: 19

Val Pro Val Trp Lys Glu Ala Thr Thr Thr Leu Phe Cys Ala Ser Asp
1               5                  10                  15

Ala Lys Ser Tyr Asp Thr Glu Val His Asn Val Trp Ala Thr His Ala
            20                  25                  30

Cys Val Pro Thr Asp Pro Asn Pro Gln Glu Val Val Leu Gly Asn Val
        35                  40                  45

Thr Glu Asn Phe Asn Met Trp Lys Asn Asn Met Val Glu Gln Met His
    50                  55                  60

Glu Asp Val Ile Ser Leu Trp Asp Gln Ser Leu Lys Pro Cys Val Lys
65                  70                  75                  80

Leu Thr Pro Leu Cys Val Thr Leu Asn Cys Thr Asp Lys Leu Arg Asn
                85                  90                  95

Asp Ala Phe Gly Val Asn Asn Thr Met Glu Gly Glu Met Lys Asn Cys
            100                 105                 110

Ser Phe Asn Thr Thr Thr Ser Leu Arg Asp Lys Ile Gln Lys Glu Tyr
        115                 120                 125

Ala Leu Phe Tyr Lys Leu Asp Val Val Gln Ile Lys Asn Asn Asn Asn
    130                 135                 140

Ser Asn Tyr Thr Ser Tyr Arg Leu Ile Asn Cys Asn Thr Ser Val Ile
145                 150                 155                 160

Thr Gln Ala Cys Pro Lys Val Thr Phe Glu Pro Ile Pro Ile His Tyr
                165                 170                 175

Cys Thr Pro Ala Gly Phe Ala Ile Leu Lys Cys Asn Asn Lys Thr Phe
            180                 185                 190

Ser Gly Lys Gly Thr Cys Thr Asn Val Ser Thr Val Gln Cys Thr His
        195                 200                 205

Gly Ile Arg Pro Val Val Ser Thr Gln Leu Leu Asn Gly Ser Leu
    210                 215                 220

Ala Glu Glu Asp Val Val Ile Arg Ser Asp Asn Phe Ser Gln Asn Ala
225                 230                 235                 240

Lys Ile Ile Ile Val Gln Leu Asn Glu Ala Val Val Ile Asn Cys Thr
                245                 250                 255

Arg Pro Gly Asn Asn Thr Arg Lys Ser Ile Pro Ile Gly Pro Gly Arg
            260                 265                 270

Ala Phe Tyr Ala Thr Gly Asp Ile Ile Gly Asn Ile Arg Gln Ala His
        275                 280                 285

Cys Asn Val Ser Ser Thr Lys Trp Asn Asn Thr Leu Gln Lys Ile Val
    290                 295                 300

Glu Lys Leu Arg Glu Gln Phe Gly Asn Lys Thr Ile Lys Phe Thr Ser
305                 310                 315                 320

Pro Ser Pro Gly Gly Asp Pro Glu Ile Val Met His Ser Phe Asn Cys
                325                 330                 335

Gly Gly Glu Phe Phe Tyr Cys Asp Thr Thr Gln Leu Phe Asn Ser Thr
```

```
                340                 345                 350
Trp Asp Asn Thr Ser Thr Trp Asn Asn Ser Asn Thr Gln Asn Lys Asn
            355                 360                 365
Asp Arg Asn Ile Thr Leu Gln Cys Arg Ile Lys Gln Ile Ile Asn Met
370                 375                 380
Trp Gln Glu Val Gly Lys Ala Met Tyr Ala Pro Pro Ile Met Gly Gln
385                 390                 395                 400
Ile Arg Cys Val Ser Asn Ile Thr Gly Leu Leu Leu Thr Arg Asp Gly
                405                 410                 415
Gly Asn Gly Ser Glu Ala Lys Asn Asp Thr Glu Ile Phe Arg Pro Gly
            420                 425                 430
Gly Gly Asp Met Arg Asp Asn Trp Arg Ser Glu Leu Tyr Lys Tyr Lys
            435                 440                 445
Val Val Lys Ile Glu Pro Leu Gly Val Ala Pro Thr Lys Ala Lys Arg
450                 455                 460
Arg Val Val Gln Gly Glu Gly Gly Ala Val Gly Thr Ile Gly Ala Met
465                 470                 475                 480
Phe Leu Gly Phe Leu Gly Ala Ala Gly Asn Thr Met Gly Ala Ala Ser
                485                 490                 495
Leu Thr Leu Thr Val Gln Ala Arg Gln Leu Leu Ser Gly Ile Val Gln
            500                 505                 510
Gln Gln Asn Asn Leu Leu Arg Ala Ile Gln Ala Gln Gln His Leu Leu
            515                 520                 525
Gln Leu Thr Val Trp Gly Ile Lys Gln Leu Gln Ala Arg Val Leu Ala
            530                 535                 540
Val Glu Arg Tyr Leu Arg Asp Gln Gln Leu Leu Gly Ile Trp Gly Cys
545                 550                 555                 560
Ser Gly Lys Leu Ile Cys Thr Thr Ala Val Pro Trp Asn Ala Ser Trp
                565                 570                 575
Ser Asn Lys Ser Tyr Thr Asp Ile Trp Asp Asn Met Thr Trp Met Gln
            580                 585                 590
Trp Glu Lys Glu Ile Glu Asn Tyr Thr Ser Leu Ile Tyr Thr Leu Ile
            595                 600                 605
Glu Asp Ser Gln Asn Gln Arg Glu Lys Asn Glu Gln Glu Leu Leu Glu
            610                 615                 620
Leu Asp Lys Trp Ala Ser Leu Trp Asn Trp Phe Asp Ile Thr Ser Trp
625                 630                 635                 640
Leu Trp Tyr Ile Lys
                645

<210> SEQ ID NO 20
<211> LENGTH: 645
<212> TYPE: PRT
<213> ORGANISM: Artificial sequence
<220> FEATURE:
<223> OTHER INFORMATION: Synthetic polypeptide

<400> SEQUENCE: 20

Val Pro Val Trp Lys Glu Ala Thr Thr Thr Leu Phe Cys Ala Ser Asp
1               5                   10                  15
Ala Lys Ser Tyr Asp Thr Glu Val His Asn Val Trp Ala Thr His Ala
                20                  25                  30
Cys Val Pro Thr Asp Pro Asn Pro Gln Glu Val Leu Gly Asn Val
            35                  40                  45
Thr Glu Asn Phe Asn Met Trp Lys Asn Asn Met Val Glu Gln Met His
```

-continued

```
                50                  55                  60
Glu Asp Val Ile Ser Leu Trp Asp Gln Ser Leu Lys Pro Cys Val Lys
 65                  70                  75                  80

Leu Thr Pro Leu Cys Val Thr Leu Asn Cys Thr Asp Lys Leu Arg Asn
                 85                  90                  95

Asp Ala Phe Gly Val Asn Asn Thr Met Glu Gly Glu Met Lys Asn Cys
            100                 105                 110

Ser Phe Asn Thr Thr Thr Ser Leu Arg Asp Lys Ile Gln Lys Glu Tyr
        115                 120                 125

Ala Leu Phe Tyr Lys Leu Asp Val Val Gln Ile Lys Asn Asn Asn Asn
    130                 135                 140

Ser Asn Tyr Thr Ser Tyr Arg Leu Ile Asn Cys Asn Thr Ser Val Ile
145                 150                 155                 160

Thr Gln Ala Cys Pro Lys Val Thr Phe Glu Pro Ile Pro Ile His Tyr
                165                 170                 175

Cys Thr Pro Ala Gly Phe Ala Ile Leu Lys Cys Asn Asn Lys Thr Phe
            180                 185                 190

Ser Gly Lys Gly Thr Cys Thr Asn Val Ser Thr Val Gln Cys Thr His
        195                 200                 205

Gly Ile Arg Pro Val Val Ser Thr Gln Leu Leu Asn Gly Ser Leu
    210                 215                 220

Ala Glu Glu Asp Val Val Ile Arg Ser Asp Asn Phe Ser Gln Asn Ala
225                 230                 235                 240

Lys Ile Ile Ile Val Gln Leu Asn Glu Ala Val Val Ile Asn Cys Thr
                245                 250                 255

Arg Pro Gly Asn Asn Thr Arg Lys Ser Ile Pro Ile Gly Pro Gly Arg
            260                 265                 270

Ala Phe Tyr Ala Thr Gly Asp Ile Ile Gly Asn Ile Arg Gln Ala His
        275                 280                 285

Cys Asn Val Ser Ser Thr Lys Trp Asn Asn Thr Leu Gln Lys Ile Val
    290                 295                 300

Glu Lys Leu Arg Glu Gln Phe Gly Asn Lys Thr Ile Lys Phe Thr Ser
305                 310                 315                 320

Pro Ser Pro Gly Gly Asp Pro Glu Ile Val Met His Ser Phe Asn Cys
                325                 330                 335

Gly Gly Glu Phe Phe Tyr Cys Asp Thr Thr Gln Leu Phe Asn Ser Thr
            340                 345                 350

Trp Asp Asn Thr Ser Thr Trp Asn Asn Ser Asn Thr Gln Asn Lys Asn
        355                 360                 365

Asp Arg Asn Ile Thr Leu Gln Cys Arg Ile Lys Gln Ile Ile Asn Met
    370                 375                 380

Trp Gln Glu Val Gly Lys Ala Met Tyr Ala Pro Pro Ile Met Gly Gln
385                 390                 395                 400

Ile Arg Cys Val Ser Asn Ile Thr Gly Leu Leu Leu Thr Arg Asp Gly
                405                 410                 415

Gly Asn Gly Ser Glu Ala Lys Asn Asp Thr Glu Ile Phe Arg Pro Gly
            420                 425                 430

Gly Gly Asp Met Arg Asp Asn Trp Arg Ser Glu Leu Tyr Lys Tyr Lys
        435                 440                 445

Val Val Lys Ile Glu Pro Leu Gly Val Ala Pro Thr Lys Ala Lys Arg
    450                 455                 460

Arg Val Val Gln Arg Glu Lys Arg Ala Val Gly Thr Ile Gly Ala Met
465                 470                 475                 480
```

```
Phe Leu Gly Phe Leu Gly Ala Ala Gly Asn Thr Met Gly Ala Ala Ser
                485                 490                 495

Leu Thr Leu Thr Val Gln Ala Arg Gln Leu Leu Ser Gly Ile Val Gln
            500                 505                 510

Gln Gln Asn Asn Leu Leu Arg Ala Ile Gln Ala Gln Gln His Leu Leu
        515                 520                 525

Gln Leu Thr Val Trp Gly Ile Lys Gln Leu Gln Ala Arg Val Leu Ala
    530                 535                 540

Val Glu Arg Tyr Leu Arg Asp Gln Gln Leu Leu Gly Ile Trp Gly Cys
545                 550                 555                 560

Ser Gly Lys Leu Ile Cys Thr Thr Ala Val Pro Trp Asn Ala Ser Trp
                565                 570                 575

Ser Asn Lys Ser Tyr Thr Asp Ile Trp Asp Asn Met Thr Trp Met Gln
            580                 585                 590

Trp Glu Lys Glu Ile Glu Asn Tyr Thr Ser Leu Ile Tyr Thr Leu Ile
        595                 600                 605

Glu Asp Ser Gln Asn Gln Arg Glu Lys Asn Glu Gln Glu Leu Leu Glu
    610                 615                 620

Leu Asp Lys Trp Ala Ser Leu Trp Asn Trp Phe Asp Ile Thr Ser Trp
625                 630                 635                 640

Leu Trp Tyr Ile Lys
                645

<210> SEQ ID NO 21
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 21

Val Pro Val Trp Lys Glu Ala
1               5

<210> SEQ ID NO 22
<211> LENGTH: 507
<212> TYPE: PRT
<213> ORGANISM: Human immunodeficiency virus 1

<400> SEQUENCE: 22

Gly Ile Arg Arg Asn Tyr Gln His Trp Trp Gly Arg Gly Thr Met Leu
1               5                   10                  15

Leu Gly Leu Leu Met Ile Cys Ser Ala Thr Glu Lys Leu Trp Val Thr
            20                  25                  30

Val Tyr Tyr Gly Val Pro Val Trp Lys Glu Ala Thr Thr Thr Leu Phe
        35                  40                  45

Cys Ala Ser Asp Ala Lys Ala Tyr Asp Thr Glu Ala His Asn Val Trp
    50                  55                  60

Ala Thr His Ala Cys Val Pro Thr Asp Pro Asn Pro Gln Glu Val Glu
65                  70                  75                  80

Leu Val Asn Val Thr Glu Asn Phe Asn Met Trp Lys Asn Asn Met Val
                85                  90                  95

Glu Gln Met His Glu Asp Ile Ile Ser Leu Trp Asp Gln Ser Leu Lys
            100                 105                 110

Pro Cys Val Lys Leu Thr Pro Leu Cys Val Thr Leu Asn Cys Thr Asp
        115                 120                 125
```

```
Leu Arg Asn Thr Thr Asn Thr Asn Asn Ser Thr Asp Asn Asn Asn Ser
130                 135                 140

Lys Ser Glu Gly Thr Ile Lys Gly Gly Glu Met Lys Asn Cys Ser Phe
145                 150                 155                 160

Asn Ile Thr Thr Ser Ile Gly Asp Lys Met Gln Lys Glu Tyr Ala Leu
                165                 170                 175

Leu Tyr Lys Leu Asp Ile Glu Pro Ile Asp Asn Asp Ser Thr Ser Tyr
            180                 185                 190

Arg Leu Ile Ser Cys Asn Thr Ser Val Ile Thr Gln Ala Cys Pro Lys
        195                 200                 205

Ile Ser Phe Glu Pro Ile Pro Ile His Tyr Cys Ala Pro Ala Gly Phe
    210                 215                 220

Ala Ile Leu Lys Cys Asn Asp Lys Lys Phe Ser Gly Lys Gly Ser Cys
225                 230                 235                 240

Lys Asn Val Ser Thr Val Gln Cys Thr His Gly Ile Arg Pro Val Val
                245                 250                 255

Ser Thr Gln Leu Leu Leu Asn Gly Ser Leu Ala Glu Glu Glu Val Val
            260                 265                 270

Ile Arg Ser Glu Asp Phe Thr Asp Asn Ala Lys Thr Ile Ile Val His
        275                 280                 285

Leu Lys Glu Ser Val Gln Ile Asn Cys Thr Arg Pro Asn Tyr Asn Lys
    290                 295                 300

Arg Lys Arg Ile His Ile Gly Pro Gly Arg Ala Phe Tyr Thr Thr Lys
305                 310                 315                 320

Asn Ile Lys Gly Thr Ile Arg Gln Ala His Cys Ile Ile Ser Arg Ala
                325                 330                 335

Lys Trp Asn Asp Thr Leu Arg Gln Ile Val Ser Lys Leu Lys Glu Gln
            340                 345                 350

Phe Lys Asn Lys Thr Ile Val Phe Asn Pro Ser Ser Gly Gly Asp Pro
        355                 360                 365

Glu Ile Val Met His Ser Phe Asn Cys Gly Gly Glu Phe Phe Tyr Cys
    370                 375                 380

Asn Thr Ser Pro Leu Phe Asn Ser Ile Trp Asn Gly Asn Asn Thr Trp
385                 390                 395                 400

Asn Asn Thr Thr Gly Ser Asn Asn Ile Thr Leu Gln Cys Lys Ile
                405                 410                 415

Lys Gln Ile Ile Asn Met Trp Gln Lys Val Gly Lys Ala Met Tyr Ala
            420                 425                 430

Pro Pro Ile Glu Gly Gln Ile Arg Cys Ser Ser Asn Ile Thr Gly Leu
        435                 440                 445

Leu Leu Thr Arg Asp Gly Gly Glu Asp Thr Asp Thr Asn Asp Thr Glu
450                 455                 460

Ile Phe Arg Pro Gly Gly Gly Asp Met Arg Asp Asn Trp Arg Ser Glu
465                 470                 475                 480

Leu Tyr Lys Tyr Lys Val Val Thr Ile Glu Pro Leu Gly Val Ala Pro
                485                 490                 495

Thr Lys Ala Lys Arg Arg Val Val Gln Arg Glu
            500                 505
```

<210> SEQ ID NO 23
<211> LENGTH: 507
<212> TYPE: PRT
<213> ORGANISM: Human immunodeficiency virus 1

<400> SEQUENCE: 23

```
Glu Lys Tyr Gln His Leu Trp Arg Trp Gly Trp Gly Thr Met
  1               5                  10                 15

Leu Leu Gly Met Leu Met Ile Cys Ser Ala Thr Glu Lys Leu Trp Val
             20                  25                  30

Thr Val Tyr Tyr Gly Val Pro Val Trp Lys Glu Ala Thr Thr Thr Leu
             35                  40                  45

Phe Cys Ala Ser Asp Ala Lys Ala Tyr Asp Thr Glu Val His Asn Val
     50                  55                  60

Trp Ala Thr His Ala Cys Val Pro Thr Asp Pro Asn Pro Gln Glu Val
 65              70                  75                  80

Val Leu Val Asn Val Thr Glu Asn Phe Asn Met Trp Lys Asn Asp Met
             85                  90                  95

Val Glu Gln Met His Glu Asp Ile Ile Ser Leu Trp Asp Gln Ser Leu
            100                 105                 110

Lys Pro Cys Val Lys Leu Thr Pro Leu Cys Val Ser Leu Lys Cys Thr
            115                 120                 125

Asp Leu Lys Asn Asp Thr Asn Thr Asn Ser Ser Ser Gly Arg Met Ile
    130                 135                 140

Met Glu Lys Gly Glu Ile Lys Asn Cys Ser Phe Asn Ile Ser Thr Ser
145                 150                 155                 160

Ile Arg Gly Lys Val Gln Lys Glu Tyr Ala Phe Phe Tyr Lys Leu Asp
            165                 170                 175

Ile Ile Pro Ile Asp Asn Asp Thr Thr Ser Tyr Lys Leu Thr Ser Cys
            180                 185                 190

Asn Thr Ser Val Ile Thr Gln Ala Cys Pro Lys Val Ser Phe Glu Pro
        195                 200                 205

Ile Pro Ile His Tyr Cys Ala Pro Ala Gly Phe Ala Ile Leu Lys Cys
    210                 215                 220

Asn Asn Lys Thr Phe Asn Gly Thr Gly Pro Cys Thr Asn Val Ser Thr
225                 230                 235                 240

Val Gln Cys Thr His Gly Ile Arg Pro Val Val Ser Thr Gln Leu Leu
            245                 250                 255

Leu Asn Gly Ser Leu Ala Glu Glu Val Val Ile Arg Ser Val Asn
        260                 265                 270

Phe Thr Asp Asn Ala Lys Thr Ile Ile Val Gln Leu Asn Thr Ser Val
    275                 280                 285

Glu Ile Asn Cys Thr Arg Pro Asn Asn Asn Thr Arg Lys Arg Ile Arg
    290                 295                 300

Ile Gln Arg Gly Pro Gly Arg Ala Phe Val Thr Ile Gly Lys Ile Gly
305                 310                 315                 320

Asn Met Arg Gln Ala His Cys Asn Ile Ser Arg Ala Lys Trp Asn Asn
            325                 330                 335

Thr Leu Lys Gln Ile Ala Ser Lys Leu Arg Glu Gln Phe Gly Asn Asn
            340                 345                 350

Lys Thr Ile Ile Phe Lys Gln Ser Ser Gly Gly Asp Pro Glu Ile Val
            355                 360                 365

Thr His Ser Phe Asn Cys Gly Gly Glu Phe Phe Tyr Cys Asn Ser Thr
        370                 375                 380

Gln Leu Phe Asn Ser Thr Trp Phe Asn Ser Thr Trp Ser Thr Glu Gly
385                 390                 395                 400

Ser Asn Asn Thr Glu Gly Ser Asp Thr Ile Thr Leu Pro Cys Arg Ile
            405                 410                 415
```

```
Lys Gln Ile Ile Asn Met Trp Gln Lys Val Gly Lys Ala Met Tyr Ala
            420                 425                 430

Pro Pro Ile Ser Gly Gln Ile Arg Cys Ser Ser Asn Ile Thr Gly Leu
            435                 440                 445

Leu Leu Thr Arg Asp Gly Gly Asn Ser Asn Asn Glu Ser Glu Ile Phe
            450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Lys
                    485                 490                 495

Ala Lys Arg Arg Val Val Gln Arg Glu Lys Arg
            500                 505

<210> SEQ ID NO 24
<211> LENGTH: 492
<212> TYPE: PRT
<213> ORGANISM: Human immunodeficiency virus 1

<400> SEQUENCE: 24

Gly Ile Gln Arg Asn Cys Gln His Leu Leu Thr Trp Gly Ile Met Ile
1               5                   10                  15

Leu Gly Thr Ile Ile Phe Cys Ser Ala Val Glu Asn Leu Trp Val Thr
                20                  25                  30

Val Tyr Tyr Gly Val Pro Val Trp Arg Asp Ala Asp Thr Thr Leu Phe
            35                  40                  45

Cys Ala Ser Asp Ala Lys Ala Tyr Glu Thr Glu Lys His Asn Val Trp
    50                  55                  60

Ala Thr His Ala Cys Val Pro Thr Asp Pro Asn Pro Gln Glu Ile His
65                  70                  75                  80

Leu Asp Asn Val Thr Glu Lys Phe Asn Met Trp Lys Asn Asn Met Val
                85                  90                  95

Glu Gln Met His Thr Asp Ile Ile Ser Leu Trp Asp Gln Ser Leu Lys
            100                 105                 110

Pro Cys Val Lys Leu Thr Pro Leu Cys Val Thr Leu His Cys Thr Asn
        115                 120                 125

Val Thr Ser Val Asn Thr Thr Gly Asp Arg Glu Gly Leu Lys Asn Cys
    130                 135                 140

Ser Phe Asn Met Thr Thr Glu Leu Arg Asp Lys Arg Gln Lys Val Tyr
145                 150                 155                 160

Ser Leu Phe Tyr Arg Leu Asp Ile Val Pro Ile Asn Glu Asn Gln Gly
                165                 170                 175

Ser Glu Tyr Arg Leu Ile Asn Cys Asn Thr Ser Ala Ile Thr Gln Ala
            180                 185                 190

Cys Pro Lys Val Ser Phe Glu Pro Ile Pro Ile His Tyr Cys Thr Pro
        195                 200                 205

Ala Gly Phe Ala Ile Leu Lys Cys Lys Asp Glu Gly Phe Asn Gly Thr
    210                 215                 220

Gly Leu Cys Lys Asn Val Ser Thr Val Gln Cys Thr His Gly Ile Lys
225                 230                 235                 240

Pro Val Val Ser Thr Gln Leu Leu Leu Asn Gly Ser Leu Ala Glu Lys
                245                 250                 255

Asn Ile Thr Ile Arg Ser Glu Asn Ile Thr Asn Asn Ala Lys Ile Ile
            260                 265                 270

Ile Val Gln Leu Val Gln Pro Val Thr Ile Lys Cys Ile Arg Pro Asn
        275                 280                 285
```

Asn Asn Thr Arg Lys Ser Ile Arg Ile Gly Pro Gly Gln Ala Phe Tyr
            290                 295                 300

Ala Thr Gly Asp Ile Ile Gly Asp Ile Arg Gln Ala His Cys Asn Val
305                 310                 315                 320

Thr Arg Ser Arg Trp Asn Lys Thr Leu Gln Glu Val Ala Glu Lys Leu
                325                 330                 335

Arg Thr Tyr Phe Gly Asn Lys Thr Ile Ile Phe Ala Asn Ser Ser Gly
            340                 345                 350

Gly Asp Leu Glu Ile Thr Thr His Ser Phe Asn Cys Gly Gly Glu Phe
            355                 360                 365

Phe Tyr Cys Asn Thr Ser Gly Leu Phe Asn Ser Thr Trp Tyr Val Asn
            370                 375                 380

Ser Thr Trp Asn Asp Thr Asp Ser Thr Gln Glu Ser Asn Asp Thr Ile
385                 390                 395                 400

Thr Leu Pro Cys Arg Ile Lys Gln Ile Ile Asn Met Trp Gln Arg Ala
                405                 410                 415

Gly Gln Ala Met Tyr Ala Pro Pro Ile Pro Gly Val Ile Lys Cys Glu
            420                 425                 430

Ser Asn Ile Thr Gly Leu Leu Leu Thr Arg Asp Gly Gly Lys Asp Asn
            435                 440                 445

Asn Val Asn Glu Thr Phe Arg Pro Gly Gly Gly Asp Met Arg Asp Asn
450                 455                 460

Trp Arg Ser Glu Leu Tyr Lys Tyr Lys Val Val Glu Ile Glu Pro Leu
465                 470                 475                 480

Gly Val Ala Pro Thr Arg Ala Lys Arg Arg Val Val
            485                 490

<210> SEQ ID NO 25
<211> LENGTH: 496
<212> TYPE: PRT
<213> ORGANISM: Human immunodeficiency virus 1

<400> SEQUENCE: 25

Gly Ile Glu Arg Asn Tyr Pro Cys Trp Trp Thr Trp Gly Ile Met Ile
1               5                   10                  15

Leu Gly Met Ile Ile Cys Asn Thr Ala Glu Asn Leu Trp Val Thr
            20                  25                  30

Val Tyr Tyr Gly Val Pro Ile Trp Lys Asp Ala Asn Thr Thr Leu Phe
            35                  40                  45

Cys Ala Ser Asp Ala Lys Ala Tyr Asp Thr Glu Val His Asn Val Trp
50                  55                  60

Ala Thr His Ala Cys Val Pro Thr Asp Pro Ser Pro Gln Glu Leu Lys
65                  70                  75                  80

Met Glu Asn Val Thr Glu Glu Phe Asn Met Trp Lys Asn Asn Met Val
                85                  90                  95

Glu Gln Met His Thr Asp Ile Ile Ser Leu Trp Asp Gln Ser Leu Lys
            100                 105                 110

Pro Cys Val Gln Leu Thr Pro Leu Cys Val Thr Leu Asp Cys Ser Tyr
            115                 120                 125

Asn Ile Thr Asn Asn Ile Thr Asn Ser Ile Thr Asn Ser Ser Val Asn
            130                 135                 140

Met Arg Glu Glu Ile Lys Asn Cys Ser Phe Asn Met Thr Thr Glu Leu
145                 150                 155                 160

Arg Asp Lys Asn Arg Lys Val Tyr Ser Leu Phe Tyr Lys Leu Asp Val

```
            165                 170                 175
Val Gln Ile Asn Asn Gly Asn Asn Ser Ser Asn Leu Tyr Arg Leu Ile
            180                 185                 190

Asn Cys Asn Thr Ser Ala Leu Thr Gln Ala Cys Pro Lys Val Thr Phe
        195                 200                 205

Glu Pro Ile Pro Ile His Tyr Cys Ala Pro Ala Gly Tyr Ala Ile Leu
    210                 215                 220

Lys Cys Asn Asp Lys Glu Phe Asn Gly Thr Gly Leu Cys Lys Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Gly Lys Val Met Ile Arg Ser
            260                 265                 270

Glu Asn Ile Thr Asn Asn Val Lys Asn Ile Ile Val Gln Leu Asn Glu
        275                 280                 285

Ser Val Thr Ile Asn Cys Thr Arg Pro Asn Asn Asn Thr Arg Arg Ser
    290                 295                 300

Val Arg Ile Gly Pro Gly Gln Thr Phe Tyr Ala Thr Gly Asp Ile Ile
305                 310                 315                 320

Gly Asp Ile Arg Gln Ala His Cys Asn Val Ser Gly Ser Gln Trp Asn
                325                 330                 335

Lys Thr Leu His Gln Val Val Glu Gln Leu Arg Lys Tyr Trp Asn Asn
            340                 345                 350

Asn Thr Ile Ile Phe Asn Ser Ser Gly Gly Asp Leu Glu Ile Thr
        355                 360                 365

Thr His Ser Phe Asn Cys Ala Gly Glu Phe Phe Tyr Cys Asn Thr Ser
    370                 375                 380

Gly Leu Phe Asn Ser Thr Trp Val Asn Gly Thr Thr Ser Ser Met Ser
385                 390                 395                 400

Asn Gly Thr Ile Thr Leu Pro Cys Arg Ile Lys Gln Ile Ile Asn Met
                405                 410                 415

Trp Gln Arg Val Gly Gln Ala Met Tyr Ala Pro Pro Ile Gln Gly Val
            420                 425                 430

Ile Lys Cys Glu Ser Asn Ile Thr Gly Leu Ile Leu Thr Arg Asp Gly
        435                 440                 445

Gly Val Asn Ser Ser Asp Ser Glu Thr Phe Arg Pro Gly Gly Gly Asp
    450                 455                 460

Met Arg Asp Asn Trp Arg Ser Glu Leu Tyr Lys Tyr Lys Val Val Lys
465                 470                 475                 480

Ile Glu Pro Leu Gly Val Ala Pro Thr Lys Ala Arg Arg Arg Val Val
                485                 490                 495
```

<210> SEQ ID NO 26
<211> LENGTH: 491
<212> TYPE: PRT
<213> ORGANISM: Human immunodeficiency virus 1

<400> SEQUENCE: 26

```
Gly Ile Gln Arg Asn Cys Gln Gln Trp Trp Ile Trp Gly Ile Leu Gly
1               5                   10                  15

Phe Trp Met Leu Met Ile Cys Asn Gly Met Gly Asn Leu Trp Val Thr
            20                  25                  30

Val Tyr Tyr Gly Val Pro Val Trp Lys Asp Ala Ser Pro Thr Leu Phe
        35                  40                  45
```

-continued

```
Cys Ala Ser Asp Ala Lys Ala Tyr Asp Thr Glu Val His Asn Val Trp
    50              55                  60
Gly Thr Phe Ala Cys Val Pro Thr Asp Pro Ser Pro Gln Glu Leu Gly
 65              70                  75                      80
Leu Glu Asn Val Thr Glu Asn Phe Asn Met Trp Lys Asn Asp Met Val
                 85                  90                  95
Glu Gln Met His Gln Asp Ile Ile Ser Leu Trp Asp Gln Gly Leu Lys
                100                 105                 110
Pro Cys Val Lys Leu Thr Pro Leu Cys Val Thr Leu Asn Cys Asn Ala
                115                 120                 125
Ile Lys Asn Asn Thr Lys Val Thr Asn Asn Ser Ile Asn Ser Ala Asn
    130                 135                 140
Asp Glu Met Lys Asn Cys Ser Phe Asn Ile Thr Thr Glu Leu Arg Asp
145                 150                 155                 160
Lys Lys Arg Lys Ala Tyr Ala Leu Phe Tyr Lys Leu Asp Ile Val Pro
                    165                 170                 175
Leu Asn Asn Gly Ser Thr Asp Tyr Arg Leu Ile Asn Cys Asn Thr Ser
                180                 185                 190
Thr Ile Thr Gln Ala Cys Pro Lys Val Ser Leu Asp Pro Ile Pro Ile
            195                 200                 205
His Tyr Cys Ala Pro Ala Gly Tyr Ala Ile Leu Lys Cys Arg Asp Lys
        210                 215                 220
Thr Phe Thr Gly Thr Gly Pro Cys His Asn Val Ser Thr Val Gln Cys
225                 230                 235                 240
Thr His Gly Ile Lys Pro Val Val Ser Thr Gln Leu Leu Leu Asn Gly
                    245                 250                 255
Ser Ile Ala Glu Gly Glu Thr Ile Ile Arg Phe Glu Asn Leu Thr Asn
                260                 265                 270
Asn Ala Lys Ile Ile Ile Val Gln Leu Asn Glu Ser Val Glu Ile Thr
            275                 280                 285
Cys Thr Arg Pro Ser Asn Asn Thr Arg Glu Ser Ile Arg Ile Gly Pro
        290                 295                 300
Gly Gln Thr Phe Tyr Ala Thr Gly Asp Ile Ile Gly Asp Ile Arg Gln
305                 310                 315                 320
Ala His Cys Asn Ile Ser Glu Glu Lys Trp Asn Lys Thr Leu Gln Lys
                    325                 330                 335
Val Lys Glu Lys Leu Gln Lys His Phe Pro Asn Lys Thr Ile Glu Phe
                340                 345                 350
Lys Pro Ser Ser Gly Gly Asp Leu Glu Ile Thr Thr His Ser Phe Asn
            355                 360                 365
Cys Gly Gly Glu Phe Phe Tyr Cys Asn Thr Ser Asn Leu Phe Asn Ser
        370                 375                 380
Thr Lys Leu Glu Leu Phe Asn Ser Ser Thr Asn Leu Asn Ile Thr Leu
385                 390                 395                 400
Gln Cys Arg Ile Lys Gln Ile Ile Asn Met Trp Gln Gly Val Gly Arg
                    405                 410                 415
Ala Met Tyr Ala Pro Pro Ile Glu Gly Ile Ile Met Cys Arg Ser Asn
                420                 425                 430
Ile Thr Gly Leu Leu Leu Thr Arg Asp Gly Ala Lys Glu Pro His Ser
            435                 440                 445
Thr Lys Glu Ile Phe Arg Pro Glu Gly Gly Asp Met Arg Asp Asn Trp
        450                 455                 460
Arg Ser Glu Leu Tyr Lys Tyr Lys Val Val Glu Ile Lys Pro Leu Gly
```

```
                465                 470                 475                 480
Val Ala Pro Thr Lys Pro Lys Arg Arg Val Val
                485                 490

<210> SEQ ID NO 27
<211> LENGTH: 503
<212> TYPE: PRT
<213> ORGANISM: Human immunodeficiency virus 1

<400> SEQUENCE: 27

Gly Thr Leu Arg Asn Tyr Gln Gln Trp Trp Ile Trp Gly Val Leu Gly
1               5                   10                  15

Phe Trp Met Leu Met Ile Cys Asn Gly Gly Asn Leu Trp Val Thr
            20                  25                  30

Val Tyr Tyr Gly Val Pro Val Trp Lys Glu Ala Lys Thr Thr Leu Leu
        35                  40                  45

Cys Ala Ser Asp Ala Lys Ala Tyr Glu Arg Glu Val His Asn Val Trp
    50                  55                  60

Ala Thr His Ala Cys Val Pro Thr Asp Pro Asn Pro Gln Glu Ile Val
65                  70                  75                  80

Leu Gly Asn Val Thr Glu Asn Phe Asn Met Trp Lys Asn Asp Met Val
                85                  90                  95

Asp Gln Met His Glu Asp Val Ile Ser Leu Trp Asp Gln Ser Leu Lys
            100                 105                 110

Pro Cys Val Lys Leu Thr Pro Leu Cys Val Thr Leu Glu Cys Arg Asn
        115                 120                 125

Val Ser Arg Asn Val Ser Ser Tyr Asn Thr Tyr Asn Gly Ser Val Glu
    130                 135                 140

Glu Ile Lys Asn Cys Ser Phe Asn Ala Thr Pro Glu Val Arg Asp Arg
145                 150                 155                 160

Lys Gln Arg Met Tyr Ala Leu Phe Tyr Gly Leu Asp Ile Val Pro Leu
                165                 170                 175

Asn Lys Lys Asn Ser Ser Glu Asn Ser Ser Glu Tyr Arg Leu Ile Asn
            180                 185                 190

Cys Asn Thr Ser Ala Ile Thr Gln Ala Cys Pro Lys Val Thr Phe Asp
        195                 200                 205

Pro Ile Pro Ile His Tyr Cys Ala Pro Ala Gly Tyr Ala Ile Leu Lys
    210                 215                 220

Cys Asn Asn Lys Thr Phe Asn Gly Thr Gly Pro Cys Asn Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Gly Glu Ile Ile Ile Arg Ser Glu
            260                 265                 270

Asn Leu Thr Asn Asn Val Lys Thr Ile Ile Val His Leu Asn Gln Ser
        275                 280                 285

Val Glu Ile Val Cys Thr Arg Pro Asn Asn Asn Thr Arg Lys Ser Ile
    290                 295                 300

Arg Ile Gly Pro Gly Gln Thr Phe Tyr Ala Thr Gly Asp Ile Ile Gly
305                 310                 315                 320

Asp Ile Arg Gln Ala His Cys Asn Ile Ser Arg Asp Lys Trp Asn Glu
                325                 330                 335

Thr Leu Gln Arg Val Gly Lys Lys Leu Ala Glu His Phe His Asn Lys
            340                 345                 350
```

```
Thr Ile Lys Phe Ala Ser Ser Gly Gly Asp Leu Glu Ile Thr Thr
            355                 360                 365

His Ser Phe Asn Cys Arg Gly Glu Phe Phe Tyr Cys Asn Thr Ser Gly
    370                 375                 380

Leu Phe Asn Gly Thr Tyr Met Pro Thr Tyr Met Pro Asn Gly Thr Glu
385                 390                 395                 400

Ser Asn Ser Asn Ser Thr Ile Thr Ile Pro Cys Arg Ile Lys Gln Ile
                405                 410                 415

Ile Asn Met Trp Gln Glu Val Gly Arg Ala Met Tyr Ala Pro Pro Ile
                420                 425                 430

Ala Gly Asn Ile Thr Cys Thr Ser Asn Ile Thr Gly Leu Leu Leu Val
            435                 440                 445

His Asp Gly Gly Ile Lys Glu Asn Asp Thr Glu Asn Lys Thr Glu Ile
    450                 455                 460

Phe Arg Pro Gly Gly Gly Asp Met Arg Asp Asn Trp Arg Ser Glu Leu
465                 470                 475                 480

Tyr Lys Tyr Lys Val Val Glu Ile Lys Pro Leu Gly Val Ala Pro Thr
                485                 490                 495

Ala Ala Lys Arg Arg Val Val
            500

<210> SEQ ID NO 28
<211> LENGTH: 498
<212> TYPE: PRT
<213> ORGANISM: Human immunodeficiency virus 1

<400> SEQUENCE: 28

Glu Thr Gln Arg Asn Tyr Gln His Leu Trp Arg Trp Gly Ile Met Leu
1               5                   10                  15

Leu Gly Met Trp Met Thr Tyr Ser Val Ala Glu Gln Leu Trp Val Thr
                20                  25                  30

Ile Tyr Tyr Gly Val Pro Val Trp Arg Glu Ala Asn Thr Thr Leu Phe
            35                  40                  45

Cys Ala Ser Asp Ala Lys Ser Phe Asp Thr Glu Ala His Asn Ile Trp
    50                  55                  60

Ala Thr His Ala Cys Val Pro Thr Asp Pro Asn Pro Gln Glu Met Asp
65                  70                  75                  80

Leu Val Asn Val Ser Glu Asn Phe Asn Met Trp Lys Asn Asn Met Val
                85                  90                  95

Glu Gln Met His Glu Asp Ile Ile Ser Leu Trp Glu Glu Ser Leu Lys
                100                 105                 110

Pro Cys Val Lys Leu Thr Pro Leu Cys Val Thr Leu His Cys Ser Asp
            115                 120                 125

Ala Asn Thr Thr Asn Ser Gly Asn Gly Thr Asn Thr Thr Asp Pro Arg
    130                 135                 140

Leu Ile Glu Lys Gly Glu Met Lys Asn Cys Ser Phe Asn Ile Thr Thr
145                 150                 155                 160

Glu Ile Arg Asp Lys Arg Lys Gln Val Gln Ala Leu Phe Tyr Lys Leu
                165                 170                 175

Asp Val Val Pro Ile Asp Lys Lys Asn Asn Ser Tyr Thr Leu Met
                180                 185                 190

His Cys Asn Thr Ser Ala Ile Lys Gln Ala Cys Pro Lys Val Ser Phe
            195                 200                 205

Glu Pro Ile Pro Ile His Tyr Cys Ala Pro Ala Gly Phe Ala Ile Leu
    210                 215                 220
```

```
Lys Cys Lys Asp Lys Lys Phe Asn Gly Thr Gly Pro Cys Lys Val
225                 230                 235                 240

Ser Thr Val Gln Cys Thr His Gly Ile Arg Pro Val Val Ser Thr Gln
            245                 250                 255

Leu Leu Leu Asn Gly Ser Leu Ala Gly Glu Glu Ile Ile Ile Arg Ser
            260                 265                 270

Glu Asn Leu Thr Asn Asn Val Lys Thr Ile Ile Val Gln Leu Asn Glu
        275                 280                 285

Thr Val Lys Ile Asn Cys Thr Arg Pro Asn Asn Asn Thr Arg Lys Gly
    290                 295                 300

Ile Arg Ile Gly Pro Gly Gln Thr Phe Phe Thr Ala Glu Val Thr Gly
305                 310                 315                 320

Asp Ile Arg Lys Ala Tyr Cys Asn Ile Ser Gly Ala Glu Trp Asp Lys
                325                 330                 335

Thr Leu Gln Gln Val Ala Thr Lys Leu Gly Asp Leu Leu Asn Lys Thr
            340                 345                 350

Ile Ile Asn Phe Ser Pro Ser Gly Gly Asp Pro Glu Ile Thr Thr
        355                 360                 365

His Ser Phe Asn Cys Gly Gly Glu Phe Phe Tyr Cys Asn Thr Ser Leu
    370                 375                 380

Leu Phe Asn Thr Thr Trp Ile Lys Gly Thr Gln Asn Asn Thr Glu Thr
385                 390                 395                 400

Asn Asn Ser Thr Ile Thr Ile Pro Cys Arg Ile Lys Gln Ile Ile Asn
                405                 410                 415

Met Trp Gln Gly Val Gly Lys Ala Met Tyr Ala Pro Pro Ile Ala Gly
            420                 425                 430

Leu Ile Arg Cys Thr Ser Asn Ile Thr Gly Leu Leu Leu Thr Arg Asp
        435                 440                 445

Gly Gly Asn Val Asn Asn Ser Arg Glu Glu Ile Phe Arg Pro Gly Gly
    450                 455                 460

Gly Asp Met Arg Asp Asn Trp Arg Ser Glu Leu Tyr Lys Tyr Lys Val
465                 470                 475                 480

Val Arg Ile Glu Pro Ile Gly Val Ala Pro Thr Arg Ala Lys Arg Arg
                485                 490                 495

Val Val

<210> SEQ ID NO 29
<211> LENGTH: 490
<212> TYPE: PRT
<213> ORGANISM: Human immunodeficiency virus 1

<400> SEQUENCE: 29

Glu Thr Lys Arg Asn Tyr Gln His Leu Trp Lys Trp Gly Thr Met Leu
1               5                   10                  15

Leu Gly Met Leu Met Ile Cys Ser Val Thr Gly Lys Ser Trp Val Thr
            20                  25                  30

Val Tyr Tyr Gly Val Pro Val Trp Lys Glu Ala Thr Thr Thr Leu Phe
        35                  40                  45

Cys Ala Ser Asp Ala Lys Ala Tyr Lys Ala Glu Ala His Asn Ile Trp
    50                  55                  60

Ala Thr His Ala Cys Val Pro Thr Asp Pro Asn Pro Gln Glu Ile Lys
65                  70                  75                  80

Leu Glu Asn Val Thr Glu Asn Phe Asn Met Trp Lys Asn Asn Met Val
                85                  90                  95
```

```
Glu Gln Met His Glu Asp Ile Ile Ser Leu Trp Asp Gln Ser Leu Lys
            100                 105                 110

Pro Cys Val Lys Leu Thr Pro Leu Cys Val Thr Leu Asn Cys Thr Asn
            115                 120                 125

Trp Val Thr Asp Thr Thr Asn Thr Thr Gly Met Ala Asn Cys Ser Phe
130                 135                 140

Asn Ile Thr Thr Glu Ile Arg Asp Lys Lys Lys Gln Val Gln Ala Leu
145                 150                 155                 160

Phe Tyr Lys Leu Asp Val Val Lys Ile Asn Asp Asp Ser Asp Asn
            165                 170                 175

Thr Ser Tyr Arg Leu Ile Asn Cys Asn Thr Ser Ala Ile Thr Gln Ala
            180                 185                 190

Cys Pro Lys Met Thr Phe Glu Pro Ile Pro Ile His Tyr Cys Ala Pro
            195                 200                 205

Ala Gly Phe Ala Ile Leu Lys Cys Asn Glu Lys Lys Phe Asn Gly Thr
            210                 215                 220

Gly Pro Cys Lys Asn Val Ser Thr Val Gln Cys Thr His Gly Ile Lys
225                 230                 235                 240

Pro Val Val Ser Thr Gln Leu Leu Leu Asn Gly Ser Leu Ala Glu Glu
            245                 250                 255

Glu Ile Ile Ile Arg Ser Glu Asn Leu Thr Asn Asn Ala Lys Ile Ile
            260                 265                 270

Ile Val Gln Leu Asn Glu Ser Val Pro Ile Asn Cys Ile Arg Pro Tyr
            275                 280                 285

Asn Asn Thr Arg Gln Ser Thr Arg Ile Gly Pro Gly Gln Ala Leu Phe
            290                 295                 300

Thr Thr Lys Val Ile Gly Asp Ile Arg Gln Ala His Cys Asn Ile Ser
305                 310                 315                 320

Gly Ala Gly Trp Asn Lys Thr Leu Gln Gln Val Ala Glu Lys Leu Gly
            325                 330                 335

Asn Leu Leu Asn Gln Thr Thr Ile Ile Phe Lys Pro Ser Ser Gly Gly
            340                 345                 350

Asp Pro Glu Ile Thr Thr His Ser Phe Asn Cys Gly Gly Glu Phe Phe
            355                 360                 365

Tyr Cys Asn Thr Thr Arg Leu Phe Asn Ser Thr Trp Lys Arg Asn Asn
370                 375                 380

Ser Glu Trp Arg Ser Asp Asn Thr Pro Asp Glu Thr Ile Thr Leu Gln
385                 390                 395                 400

Cys Arg Ile Lys Gln Ile Ile Asn Met Trp Gln Glu Val Gly Lys Ala
            405                 410                 415

Met Tyr Ala Pro Pro Ile Glu Gly Phe Ile Asn Cys Ser Ser Asn Ile
            420                 425                 430

Thr Gly Leu Leu Leu Thr Arg Asp Gly Gly Ala Ile Asn Ser Ser Gln
            435                 440                 445

Asn Glu Thr Phe Arg Pro Gly Gly Asp Met Arg Asn Asn Trp Arg
            450                 455                 460

Ser Glu Leu Tyr Lys Tyr Lys Val Val Lys Leu Glu Pro Ile Gly Leu
465                 470                 475                 480

Ala Pro Thr Ala Ala Lys Arg Arg Val Val
            485                 490

<210> SEQ ID NO 30
<211> LENGTH: 499
```

<212> TYPE: PRT
<213> ORGANISM: Human immunodeficiency virus 1

<400> SEQUENCE: 30

```
Glu Thr Gln Met Asn Trp Pro Asn Leu Trp Lys Trp Gly Thr Leu Ile
1               5                   10                  15

Leu Gly Leu Val Ile Ile Cys Ser Ala Ser Asp Asn Leu Trp Val Thr
            20                  25                  30

Val Tyr Tyr Gly Val Pro Val Trp Lys Asp Ala Asp Thr Thr Leu Phe
        35                  40                  45

Cys Ala Ser Asp Ala Lys Ala His Glu Thr Glu Val His Asn Val Trp
    50                  55                  60

Ala Thr Tyr Ala Cys Val Pro Thr Asp Pro Asn Pro Gln Glu Ile His
65                  70                  75                  80

Leu Glu Asn Val Thr Glu Asn Phe Asn Met Trp Lys Asn Asn Met Val
                85                  90                  95

Glu Gln Met Gln Glu Asp Val Ile Ser Leu Trp Glu Gln Ser Leu Lys
            100                 105                 110

Pro Cys Val Gln Leu Thr Pro Leu Cys Val Thr Leu His Cys Thr Asn
        115                 120                 125

Ala Asn Leu Lys Ala Asn Leu Thr Asn Val Asn Asn Thr Thr Asn Val
    130                 135                 140

Gly Asn Ile Thr Glu Glu Val Arg Asn Cys Ser Phe Asn Met Thr Thr
145                 150                 155                 160

Glu Leu Arg Asp Arg Gln Gln Lys Val Tyr Ala Leu Phe Tyr Lys Leu
                165                 170                 175

Asp Leu Val Gln Met Gly Asn Asn Asn Ser Asn Asn Tyr Ser Glu
            180                 185                 190

Tyr Arg Leu Ile Asn Cys Asn Thr Ser Val Ile Lys Gln Ala Cys Pro
        195                 200                 205

Lys Ile Ser Phe Asp Pro Ile Pro Ile His Tyr Cys Thr Pro Ala Gly
    210                 215                 220

Tyr Ala Ile Leu Lys Cys Asn Asp Lys Asn Phe Asn Gly Thr Gly Pro
225                 230                 235                 240

Cys Lys Asn Val Ser Ser Val Gln Cys Thr His Gly Ile Lys Pro Val
                245                 250                 255

Val Ser Thr Gln Leu Leu Leu Asn Gly Ser Leu Ala Glu Glu Ile
            260                 265                 270

Ile Ile Arg Ser Glu Asn Leu Thr Asn Asn Ala Lys Thr Ile Ile Val
        275                 280                 285

His Leu Asn Lys Ser Val Glu Ile Asn Cys Thr Arg Pro Ser Asn Asn
    290                 295                 300

Ile Arg Thr Ser Ile Arg Ile Gly Pro Gly Arg Val Phe Tyr Lys Thr
305                 310                 315                 320

Gly Ala Ile Thr Gly Asp Ile Arg Lys Ala Tyr Cys Glu Val Asn Gly
                325                 330                 335

Thr Lys Trp Asn Glu Ala Leu Lys Gln Val Ala Gly Lys Leu Lys Glu
            340                 345                 350

His Phe Asn Asn Thr Ile Val Phe Gln Pro Pro Ser Gly Gly Asp Leu
        355                 360                 365

Glu Ile Thr Met His His Phe Asn Cys Arg Gly Glu Phe Phe Tyr Cys
    370                 375                 380

Asn Thr Thr Gln Leu Phe Asn Ser Thr Trp Thr Arg Asn Glu Thr Met
385                 390                 395                 400
```

-continued

```
Gly Gly Arg Asn Gly Thr Ile Thr Leu Pro Cys Arg Ile Lys Gln Ile
                405                 410                 415

Ile Asn Met Trp Gln Gly Val Gly Gln Ala Met Tyr Ala Pro Pro Ile
            420                 425                 430

Ser Gly Arg Ile Asn Cys Val Ser Asn Ile Thr Gly Ile Leu Leu Thr
        435                 440                 445

Arg Asp Gly Gly Ala Asn Asn Thr Gln Asn Glu Thr Phe Arg Pro Gly
    450                 455                 460

Gly Gly Asn Ile Lys Asp Asn Trp Arg Ser Glu Leu Tyr Lys Tyr Lys
465                 470                 475                 480

Val Val Gln Ile Glu Pro Leu Gly Ile Ala Pro Thr Arg Ala Lys Arg
                485                 490                 495

Arg Val Val

<210> SEQ ID NO 31
<211> LENGTH: 496
<212> TYPE: PRT
<213> ORGANISM: Human immunodeficiency virus 1

<400> SEQUENCE: 31

Glu Thr Gln Met Asn Trp Pro Asn Leu Trp Lys Trp Gly Thr Leu Ile
1               5                   10                  15

Leu Gly Leu Val Ile Ile Cys Ser Ala Ser Asp Asn Leu Trp Val Thr
            20                  25                  30

Val Tyr Tyr Gly Val Pro Val Trp Arg Asp Ala Asp Thr Thr Leu Phe
        35                  40                  45

Cys Ala Ser Asp Ala Lys Ala His Glu Thr Glu Val His Asn Val Trp
    50                  55                  60

Ala Thr His Ala Cys Val Pro Thr Asp Pro Asn Pro Gln Glu Ile His
65                  70                  75                  80

Leu Glu Asn Val Thr Glu Asn Phe Asn Met Trp Lys Asn Asn Met Val
                85                  90                  95

Glu Gln Met Gln Glu Asp Val Ile Ser Leu Trp Asp Gln Ser Leu Lys
            100                 105                 110

Pro Cys Val Lys Leu Thr Pro Leu Cys Val Thr Leu Asn Cys Thr Asn
        115                 120                 125

Ala Asn Leu Thr Asn Gly Ser Ser Lys Thr Asn Val Ser Asn Ile Ile
    130                 135                 140

Gly Asn Ile Thr Asp Glu Val Arg Asn Cys Thr Phe Asn Met Thr Thr
145                 150                 155                 160

Glu Leu Thr Asp Lys Lys Gln Lys Val His Ala Leu Phe Tyr Lys Leu
                165                 170                 175

Asp Ile Val Gln Ile Glu Asp Lys Lys Thr Ser Ser Glu Tyr Arg Leu
            180                 185                 190

Ile Asn Cys Asn Thr Ser Val Ile Lys Gln Ala Cys Pro Lys Ile Ser
        195                 200                 205

Phe Asp Pro Ile Pro Ile His Tyr Cys Thr Pro Ala Gly Tyr Ala Ile
    210                 215                 220

Leu Lys Cys Asn Asp Lys Asn Phe Asn Gly Thr Gly Pro Cys Lys Asn
225                 230                 235                 240

Val Ser Ser Val Gln Cys Thr His Gly Ile Lys Pro Val Val Ser Thr
                245                 250                 255

Gln Leu Leu Leu Asn Gly Ser Leu Ala Glu Glu Ile Ile Ile Arg
            260                 265                 270
```

```
Ser Glu Asp Leu Thr Asn Asn Ala Lys Thr Ile Ile Val His Leu Asn
            275                 280                 285

Lys Ser Val Glu Ile Asn Cys Thr Arg Pro Ser Asn Asn Thr Arg Thr
        290                 295                 300

Ser Ile Thr Ile Gly Pro Gly Arg Val Phe Tyr Arg Thr Gly Asp Ile
305                 310                 315                 320

Ile Gly Asn Ile Arg Lys Ala Tyr Cys Glu Ile Asn Gly Thr Lys Trp
                325                 330                 335

Asn Lys Val Leu Lys Gln Val Thr Glu Lys Leu Lys Glu His Phe Asn
            340                 345                 350

Lys Thr Ile Ile Phe Gln Pro Pro Ser Gly Gly Asp Leu Glu Ile Thr
        355                 360                 365

Met His His Phe Asn Cys Arg Gly Glu Phe Phe Tyr Cys Asn Thr Thr
    370                 375                 380

Lys Leu Phe Asn Asn Thr Cys Leu Gly Asn Glu Thr Met Ala Gly Cys
385                 390                 395                 400

Asn Asp Thr Ile Thr Leu Pro Cys Lys Ile Lys Gln Ile Ile Asn Met
                405                 410                 415

Trp Gln Gly Ala Gly Gln Ala Met Tyr Ala Pro Pro Ile Ser Gly Arg
            420                 425                 430

Ile Asn Cys Val Ser Asn Ile Thr Gly Ile Leu Leu Thr Arg Asp Gly
        435                 440                 445

Gly Val Asn Asn Thr Asp Asn Glu Thr Phe Arg Pro Gly Gly Gly Asn
    450                 455                 460

Ile Lys Asp Asn Trp Arg Ser Glu Leu Tyr Lys Tyr Lys Val Val Gln
465                 470                 475                 480

Ile Glu Pro Leu Gly Ile Ala Pro Thr Arg Ala Lys Arg Arg Val Val
                485                 490                 495

<210> SEQ ID NO 32
<211> LENGTH: 485
<212> TYPE: PRT
<213> ORGANISM: Simian immunodeficiency virus

<400> SEQUENCE: 32

Gly Met Lys Arg Asn Ser Cys Arg Ser Ile Ser Ile Lys Leu Ile Leu
1               5                   10                  15

Ile Gly Trp Ile Ala Ser Cys Phe Gly Glu Glu Asn Trp Trp Val Thr
                20                  25                  30

Val Tyr Tyr Gly Val Pro Val Trp Arg Glu Ala Lys Thr Thr Leu Phe
            35                  40                  45

Cys Ala Ser Asp Ala Lys Ser Tyr Ser Thr Glu Ala His Asn Ile Trp
        50                  55                  60

Ala Thr Gln Ala Cys Val Pro Thr Asp Pro Thr Pro Gln Glu Val Leu
65                  70                  75                  80

Leu Pro Asn Val Thr Glu Glu Phe Asn Met Trp Glu Asn Tyr Met Val
                85                  90                  95

Asp Gln Met Gln Glu Asp Ile Ile Ser Leu Trp Glu Gln Ser Leu Lys
            100                 105                 110

Pro Cys Val Lys Leu Thr Pro Leu Cys Val Thr Leu Thr Cys Asn Asn
        115                 120                 125

Pro Thr Asn Thr Ser Cys Thr Asn Ser Thr Asp Asp Arg Leu Gly Asp
    130                 135                 140

Met Arg Asn Cys Ser Phe Asn Val Thr Thr Glu Leu Arg Asp Lys Lys
```

145 150 155 160

Arg Gln Val Tyr Ser Leu Phe Tyr Val Glu Asp Ile Thr Ala Ile Gly
165 170 175

Asn Asn Ser Thr Tyr Arg Leu Ile Asn Cys Asn Thr Thr Ala Ile Thr
180 185 190

Gln Ala Cys Pro Lys Thr Ser Phe Glu Pro Ile Pro Ile His Tyr Cys
195 200 205

Ala Pro Ala Gly Phe Ala Leu Leu Lys Cys Asn Asp Ile Asp Tyr Lys
210 215 220

Gly Asn Glu Thr Cys Lys Asn Val Ser Thr Val His Cys Thr His Gly
225 230 235 240

Ile Lys Pro Val Ala Thr Thr Gln Leu Ile Leu Asn Gly Ser Thr Ala
245 250 255

Asp Asn Gln Thr Val Ala Arg Ile Asp Pro Ser Glu Asn Leu Ala Ile
260 265 270

Ile Gln Leu Lys Asp Pro Val Lys Ile Thr Cys Arg Arg Pro Gly Asn
275 280 285

Asn Thr Arg Gly Gln Ile Gln Ile Gly Pro Ala Met Thr Phe Tyr Asn
290 295 300

Ile Glu Asn Val Val Gly Asp Thr Arg Lys Ala Tyr Cys Glu Ile Asn
305 310 315 320

Gly Thr Gln Trp Ala Lys Ala Leu Asn Glu Thr Lys Glu Val Leu Arg
325 330 335

Asn Ile Leu Arg Lys Asn Ile Ser Phe Met Val Pro Ser Gly Gly Asp
340 345 350

Pro Glu Val Thr Asn His His Phe Asn Cys Gly Gly Glu Phe Phe Tyr
355 360 365

Cys Asn Thr Ser Glu Ile Ile Asn Ile Thr Lys Ile Asn Lys Thr Glu
370 375 380

Asn Met Thr Ile Ile Pro Cys Arg Ile Arg Gln Ile Val Asn Ser Trp
385 390 395 400

Met Arg Val Gly Lys Gly Ile Phe Ala Pro Pro Ile Arg Gly Asn Ile
405 410 415

Thr Cys Thr Ser Asn Ile Thr Gly Met Leu Leu Glu Ile His Lys Asn
420 425 430

Arg Glu Asp Gln Gly Glu Asp Gln Asp Gln Asn Asn Thr Tyr Val Cys
435 440 445

Leu Thr Gly Gly Asn Met Lys Asp Ile Trp Arg Ser Glu Leu Tyr Lys
450 455 460

Tyr Lys Ile Val Glu Ile Gln Pro Leu Gly Val Ala Pro Thr Lys Ser
465 470 475 480

Arg Arg Tyr Ala Val
485

<210> SEQ ID NO 33
<211> LENGTH: 473
<212> TYPE: PRT
<213> ORGANISM: Simian immunodeficiency virus

<400> SEQUENCE: 33

Glu Lys Lys Lys Arg Leu Trp Leu Ser Tyr Cys Leu Leu Ser Ser Leu
1 5 10 15

Ile Ile Pro Gly Leu Ser Ser Leu Trp Ala Thr Val Tyr Tyr Gly Val
20 25 30

-continued

```
Pro Val Trp Arg Asp Val Glu Thr Thr Leu Phe Cys Ala Ser Asp Ala
             35                  40                  45

Lys Ala Tyr Lys Gln Glu Ala His Asn Ile Trp Ala Thr Gln Ala Cys
 50                  55                  60

Val Pro Thr Asp Pro Asn Pro Gln Glu Val His Leu Pro Asn Val Thr
 65                  70                  75                  80

Glu Lys Phe Asp Met Trp Glu Asn Asn Met Ala Glu Gln Met Gln Glu
                 85                  90                  95

Asp Ile Ile Ser Leu Trp Asp Gln Ser Leu Lys Pro Cys Ile Lys Leu
                100                 105                 110

Thr Pro Leu Cys Val Thr Met Thr Cys Leu Asn Pro Asp Ser Asn Ser
            115                 120                 125

Ser Ala Val Asn Thr Thr Asp Ile Met Arg Asn Cys Ser Phe Asn Ile
130                 135                 140

Thr Thr Glu Leu Arg Asp Lys Lys Gln Val Tyr Ser Leu Phe Tyr
145                 150                 155                 160

Val Asp Asp Leu Ala His Ile Asn Asn Asn Thr Tyr Arg Leu Ile Asn
                165                 170                 175

Cys Asn Thr Thr Ala Ile Thr Gln Ala Cys Pro Lys Thr Ser Phe Glu
            180                 185                 190

Pro Ile Pro Ile His Tyr Cys Ala Pro Pro Gly Phe Ala Ile Leu Lys
        195                 200                 205

Cys Asn Glu Lys Asp Phe Lys Gly Lys Gly Glu Cys Lys Asn Val Ser
        210                 215                 220

Thr Val Gln Cys Thr His Gly Ile Lys Pro Val Val Thr Thr Gln Leu
225                 230                 235                 240

Ile Ile Asn Gly Ser Leu Ala Thr Lys Asn Val Thr Val Arg Ser Lys
                245                 250                 255

Asn Phe Ala Asp Ile Ile Leu Val Gln Phe Ser Glu Gly Val Asn Met
                260                 265                 270

Thr Cys Ile Arg Pro Gly Asn Asn Thr Val Gly Asn Val Gln Leu Gly
            275                 280                 285

Pro Gly Met Thr Phe Tyr Asn Ile Pro Lys Ile Val Gly Asp Val Arg
        290                 295                 300

Glu Ala His Cys Asn Ile Ser Lys Leu Thr Trp Glu Lys Gln Arg Lys
305                 310                 315                 320

Tyr Thr Leu Glu Ile Ile Lys Lys Glu Ala Asn Leu Thr Lys Val Glu
                325                 330                 335

Leu Ile Pro Asn Ala Gly Gly Asp Pro Glu Val Val Asn Met Met Leu
            340                 345                 350

Asn Cys Gly Gly Glu Phe Phe Tyr Cys Asn Thr Ile Pro Leu Phe Asn
        355                 360                 365

Met Thr Tyr Asn Asn Thr Asp Asn Thr Thr Ile Thr Leu Lys Cys Arg
        370                 375                 380

Ile Arg Gln Ile Val Asn Gln Trp Met Arg Val Gly Lys Gly Ile Phe
385                 390                 395                 400

Ala Pro Pro Ile Lys Gly Val Leu Ser Cys Asn Ser Asn Ile Thr Gly
            405                 410                 415

Met Ile Leu Asp Ile Ser Ile Ser Ala Val Asn Asn Asp Ser Arg Asn
            420                 425                 430

Ile Thr Val Met Pro Thr Gly Gly Asp Met Thr Ala Leu Trp Lys Asn
            435                 440                 445

Glu Leu His Lys Tyr Lys Val Val Ser Ile Glu Pro Ile Gly Val Ala
```

Pro Gly Lys Ala Lys Arg His Thr Val
465                 470

<210> SEQ ID NO 34
<211> LENGTH: 518
<212> T

```
Lys Glu Val Lys Gln Thr Ile Val Lys His Pro Arg Tyr Thr Gly Thr
            355                 360                 365

Asn Asn Thr Asp Lys Ile Asn Leu Thr Ala Pro Gly Gly Gly Asp Pro
    370                 375                 380

Glu Val Thr Phe Met Trp Thr Asn Cys Arg Gly Glu Phe Leu Tyr Cys
385                 390                 395                 400

Lys Met Asn Trp Phe Leu Asn Trp Val Glu Asp Arg Asp Val Thr Thr
                405                 410                 415

Gln Arg Pro Lys Glu Arg His Arg Arg Asn Tyr Val Pro Cys His Ile
            420                 425                 430

Arg Gln Ile Ile Asn Thr Trp His Lys Val Gly Lys Asn Val Tyr Leu
        435                 440                 445

Pro Pro Arg Glu Gly Asp Leu Thr Cys Asn Ser Thr Val Thr Ser Leu
    450                 455                 460

Ile Ala Asn Ile Asp Trp Thr Asp Gly Asn Gln Thr Ser Ile Thr Met
465                 470                 475                 480

Ser Ala Glu Val Ala Glu Leu Tyr Arg Leu Glu Leu Gly Asp Tyr Lys
                485                 490                 495

Leu Val Glu Ile Thr Pro Ile Gly Leu Ala Pro Thr Asp Val Lys Arg
            500                 505                 510

Tyr Thr Thr Gly Gly Thr
        515

<210> SEQ ID NO 35
<211> LENGTH: 516
<212> TYPE: PRT
<213> ORGANISM: Simian immunodeficiency virus

<400> SEQUENCE: 35

Gly Asn Gln Leu Leu Ile Ala Ile Leu Leu Leu Ser Val Tyr Gly Ile
1               5                   10                  15

Tyr Cys Thr Leu Tyr Val Thr Val Phe Tyr Gly Val Pro Ala Trp Arg
            20                  25                  30

Asn Ala Thr Ile Pro Leu Phe Cys Ala Thr Lys Asn Arg Asp Thr Trp
        35                  40                  45

Gly Thr Thr Gln Cys Leu Pro Asp Asn Gly Asp Tyr Ser Glu Val Ala
    50                  55                  60

Leu Asn Val Thr Glu Ser Phe Asp Ala Trp Asn Asn Thr Val Thr Glu
65                  70                  75                  80

Gln Ala Ile Glu Asp Val Trp Gln Leu Phe Glu Thr Ser Ile Lys Pro
                85                  90                  95

Cys Val Lys Leu Ser Pro Leu Cys Ile Thr Met Arg Cys Asn Lys Ser
            100                 105                 110

Glu Thr Asp Arg Trp Gly Leu Thr Lys Ser Ile Thr Thr Thr Ala Ser
        115                 120                 125

Thr Thr Ser Thr Thr Ala Ser Ala Lys Val Asp Met Val Asn Glu Thr
    130                 135                 140

Ser Ser Cys Ile Ala Gln Asp Asn Cys Thr Gly Leu Glu Gln Glu Gln
145                 150                 155                 160

Met Ile Ser Cys Lys Phe Asn Met Thr Gly Leu Lys Arg Asp Lys Lys
                165                 170                 175

Lys Glu Tyr Asn Glu Thr Trp Tyr Ser Ala Asp Leu Val Cys Glu Gln
            180                 185                 190

Gly Asn Asn Thr Gly Asn Glu Ser Arg Cys Tyr Met Asn His Cys Asn
        195                 200                 205
```

```
Thr Ser Val Ile Gln Glu Ser Cys Asp Lys His Tyr Trp Asp Ala Ile
    210                 215                 220

Arg Phe Arg Tyr Cys Ala Pro Pro Gly Tyr Ala Leu Leu Arg Cys Asn
225                 230                 235                 240

Asp Thr Asn Tyr Ser Gly Phe Met Pro Lys Cys Ser Lys Val Val Val
                245                 250                 255

Ser Ser Cys Thr Arg Met Met Glu Thr Gln Thr Ser Thr Trp Phe Gly
            260                 265                 270

Phe Asn Gly Thr Arg Ala Glu Asn Arg Thr Tyr Ile Tyr Trp His Gly
        275                 280                 285

Arg Asp Asn Arg Thr Ile Ile Ser Leu Asn Lys Tyr Tyr Asn Leu Thr
290                 295                 300

Met Lys Cys Arg Arg Pro Gly Asn Lys Thr Val Leu Pro Val Thr Ile
305                 310                 315                 320

Met Ser Gly Leu Val Phe His Ser Gln Pro Ile Asn Asp Arg Pro Lys
                325                 330                 335

Gln Ala Trp Cys Trp Phe Gly Gly Lys Trp Lys Asp Ala Ile Lys Glu
            340                 345                 350

Val Lys Gln Thr Ile Val Lys His Pro Arg Tyr Thr Gly Thr Asn Asn
        355                 360                 365

Thr Asp Lys Ile Asn Leu Thr Ala Pro Gly Gly Gly Asp Pro Glu Val
370                 375                 380

Thr Phe Met Trp Thr Asn Cys Arg Gly Glu Phe Leu Tyr Cys Lys Met
385                 390                 395                 400

Asn Trp Phe Leu Asn Trp Val Glu Asp Arg Asn Thr Ala Asn Gln Lys
                405                 410                 415

Pro Lys Glu Gln His Lys Arg Asn Tyr Val Pro Cys His Ile Arg Gln
            420                 425                 430

Ile Ile Asn Thr Trp His Lys Val Gly Lys Asn Val Tyr Leu Pro Pro
        435                 440                 445

Arg Glu Gly Asp Leu Thr Cys Asn Ser Thr Val Thr Ser Leu Ile Ala
450                 455                 460

Asn Ile Asp Trp Ile Asp Gly Asn Gln Thr Asn Ile Thr Met Ser Ala
465                 470                 475                 480

Glu Val Ala Glu Leu Tyr Arg Leu Glu Leu Gly Asp Tyr Lys Leu Val
                485                 490                 495

Glu Ile Thr Pro Ile Gly Leu Ala Pro Thr Asp Val Lys Arg Tyr Thr
            500                 505                 510

Thr Gly Gly Thr
        515

<210> SEQ ID NO 36
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 36

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu
```

<210> SEQ ID NO 37
<211> LENGTH: 35
<212> TYPE: PRT
<213> ORGANISM: Artificial sequence
<220> FEATURE:
<223> OTHER INFORMATION: Synthetic polypeptide

<400> SEQUENCE: 37

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp
        35

<210> SEQ ID NO 38
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 38

Glu Leu Asp Lys Trp Ala Ser Leu Trp Asn Trp Phe Asn Ile Thr Asn
1               5                   10                  15

Trp Leu Trp Tyr
            20

<210> SEQ ID NO 39
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 39

Ser Trp Leu Trp Tyr Ile Lys
1               5

<210> SEQ ID NO 40
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 40

Gly Pro Gly Arg Ala Phe
1               5

<210> SEQ ID NO 41
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 41

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu
        35

<210> SEQ ID NO 42
<211> LENGTH: 36
<212> TYPE: PRT
<213> ORGANISM: Artificial sequence
<220> FEATURE:
<223> OTHER INFORMATION: Synthetic polypeptide

<400> SEQUENCE: 42

His Ser Leu Ile Glu Glu Ser Gln Asn Gln Gln Glu Lys Asn Glu Gln
1               5                   10                  15

Glu Leu Leu Glu Leu Asp Lys Trp Ala Ser Leu Trp Asn Trp Phe Asn
            20                  25                  30

Ile Thr Asn Trp
        35

<210> SEQ ID NO 43
<211> LENGTH: 858
<212> TYPE: PRT
<213> ORGANISM: Human immunodeficiency virus 1

<400> SEQUENCE: 43

Met Arg Ala Arg Glu Ile Arg Met Asn Tyr Gln Asn Leu Trp Arg Trp
1               5                   10                  15

Gly Thr Leu Leu Phe Gly Ile Leu Met Ile Cys Ser Thr Ala Glu Asn
            20                  25                  30

Leu Trp Val Thr Val Tyr Tyr Gly Val Pro Val Trp Arg Glu Ala Thr
        35                  40                  45

Thr Thr Leu Phe Cys Ala Ser Asp Ala Lys Ser Tyr Glu Thr Glu Val
    50                  55                  60

His Asn Val Trp Ala Thr His Ala Cys Val Pro Thr Asp Pro Asn Pro
65                  70                  75                  80

Gln Glu Ile Leu Leu Glu Asn Val Thr Glu Asp Phe Asn Ile Trp Thr
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Lys Asn Ala Thr Asn Ile Thr Asn Ser Glu Gly
    130                 135                 140

Gly Met Arg Glu Gly Gly Glu Ile Lys Asn Cys Ser Phe Asn Ile Thr
145                 150                 155                 160

Thr Ser Leu Arg Asp Arg Val Gln Lys Glu Tyr Ala Leu Phe Tyr Lys
                165                 170                 175

Leu Asp Val Glu Pro Ile Asp Asp Lys Asn Ser Thr Asp Asn Asn
            180                 185                 190

Ser Thr Asn Tyr Thr Asn Tyr Arg Leu Ile Ser Cys Asn Thr Ser Val
        195                 200                 205

Ile Thr Gln Ala Cys Pro Lys Val Ser Phe Glu Pro Ile Pro Ile His
    210                 215                 220

Tyr Cys Val Pro Ala Gly Tyr Ala Leu Leu Gln Cys Asn Asn Lys Thr
225                 230                 235                 240

Phe Ser Gly Lys Gly Gln Cys Lys Asn Val Ser Thr Val Gln Cys Thr
                245                 250                 255

His Gly Ile Arg Pro Val Val Ser Thr Gln Leu Leu Leu Asn Gly Ser
            260                 265                 270

```
Leu Ala Glu Glu Val Val Ile Arg Ser Glu Asn Phe Thr Asp Asn
            275                 280                 285

Ala Lys Thr Ile Ile Val Gln Leu Asn Glu Thr Val Glu Ile Asn Cys
290                 295                 300

Thr Arg Pro Asn Asn Asn Thr Arg Arg Ser Ile Ser Ile Gly Pro Gly
305                 310                 315                 320

Arg Ala Phe Tyr Ala Thr Gly Asp Ile Ile Gly Asp Ile Arg Gln Ala
                325                 330                 335

His Cys Asn Leu Ser Glu Ala Lys Trp Asn Arg Thr Leu Glu Leu Val
            340                 345                 350

Val Glu Lys Leu Arg Asp Gln Phe Lys Asn Lys Thr Ile Val Phe Asn
        355                 360                 365

His Ser Ser Gly Gly Asp Pro Glu Ile Val Met Phe Ser Phe Asn Cys
    370                 375                 380

Gly Gly Glu Phe Phe Tyr Cys Asp Ser Thr Lys Leu Phe Asn Ser Thr
385                 390                 395                 400

Trp Asn Gly Thr Glu Asp Asp Ser Gly Lys Asn Arg Thr Ile Thr Leu
                405                 410                 415

Pro Cys Arg Ile Lys Gln Phe Ile Asn Met Trp Gln Glu Val Gly Lys
            420                 425                 430

Ala Met Tyr Ala Pro Pro Ile Lys Gly Gln Ile Ser Cys Leu Ser Asn
        435                 440                 445

Ile Thr Gly Leu Leu Leu Thr Arg Asp Gly Gly Asn Asn Val Ser Asn
    450                 455                 460

Thr Thr Glu Val Phe Arg Pro Gly Gly Gly Asn Met Arg Asp Asn Trp
465                 470                 475                 480

Arg Ser Glu Leu Tyr Lys Tyr Lys Val Val Glu Ile Glu Pro Leu Gly
                485                 490                 495

Leu Ala Pro Thr Lys Ala Lys Arg Arg Val Val Gln Arg Glu Lys Arg
            500                 505                 510

Ala Val Gly Ile Gly Ala Leu Phe Leu Gly Phe Leu Gly Ala Ala Gly
        515                 520                 525

Ser Thr Met Gly Ala Ala Ser Met Thr Leu Thr Val Gln Ala Arg Gln
    530                 535                 540

Leu Leu Ser Gly Ile Val Gln Gln Asn Asn Leu Leu Arg Ala Ile
545                 550                 555                 560

Glu Ala Gln Gln His Leu Leu Gln Leu Thr Val Trp Gly Ile Lys Gln
                565                 570                 575

Leu Gln Ala Arg Val Leu Ala Met Glu Arg Tyr Leu Lys Asp Gln Gln
            580                 585                 590

Leu Leu Gly Ile Trp Gly Cys Ser Gly Lys Leu Ile Cys Thr Thr Thr
        595                 600                 605

Val Pro Trp Asn Thr Ser Trp Ser His Asn Arg Ser Leu Asn Glu Ile
    610                 615                 620

Trp Asp Asn Met Thr Trp Met Gln Trp Asp Lys Glu Ile Asn Asn Tyr
625                 630                 635                 640

Thr Asp Leu Ile Tyr Asn Leu Leu Gly Glu Ala Gln Asn Gln Gln Glu
                645                 650                 655

Lys Asn Glu Gln Glu Leu Leu Glu Leu Asp Lys Trp Ala Ser Leu Trp
            660                 665                 670

Asn Trp Phe Ser Ile Thr Asn Trp Leu Trp Tyr Ile Lys Ile Phe Ile
        675                 680                 685

Ile Ile Val Ala Gly Leu Val Gly Leu Arg Ile Val Phe Thr Val Phe
```

```
            690             695             700
Ser Leu Val Asn Arg Val Arg Gln Gly Tyr Ser Pro Leu Ser Phe Gln
705                 710                 715                 720

Thr His Leu Pro Ala Pro Arg Gly Pro Asp Arg Pro Glu Gly Thr Glu
                725                 730                 735

Glu Arg Gly Gly Glu Gln Asp Arg Asp Arg Ser Gly His Leu Val Asp
            740                 745                 750

Gly Leu Leu Thr Ile Ile Trp Val Asp Leu Arg Ser Leu Phe Leu Phe
            755                 760                 765

Ser Tyr His Arg Leu Arg Asp Leu Leu Leu Ile Leu Ala Arg Ile Val
        770                 775                 780

Glu Leu Leu Gly Arg Arg Gly Trp Glu Ile Leu Lys Tyr Trp Trp Asn
785                 790                 795                 800

Leu Leu Leu Phe Trp Ser Gln Glu Leu Lys Asn Ser Ala Val Ser Leu
                805                 810                 815

Leu Asn Thr Ile Ala Ile Val Val Ala Glu Gly Thr Asp Trp Val Ile
                820                 825                 830

Ala Gly Leu Gln Arg Leu Phe Arg Ala Phe Leu His Ile Pro Arg Arg
            835                 840                 845

Ile Arg Gln Gly Phe Glu Arg Ala Leu Leu
        850                 855
```

<210> SEQ ID NO 44
<211> LENGTH: 858
<212> TYPE: PRT
<213> ORGANISM: Human immunodeficiency virus 1

<400> SEQUENCE: 44

```
Met Arg Ala Arg Glu Ile Arg Met Asn Tyr Gln Asn Leu Trp Arg Trp
1               5                   10                  15

Gly Thr Leu Leu Phe Gly Ile Leu Met Ile Cys Ser Thr Ala Glu Asn
                20                  25                  30

Leu Trp Val Thr Val Tyr Tyr Gly Val Pro Val Trp Arg Glu Ala Thr
            35                  40                  45

Thr Thr Leu Phe Cys Ala Ser Asp Ala Lys Ser Tyr Glu Thr Glu Val
        50                  55                  60

His Asn Val Trp Ala Thr His Ala Cys Val Pro Thr Asp Pro Asn Pro
65                  70                  75                  80

Gln Glu Ile Leu Leu Glu Asn Val Thr Glu Asp Phe Asn Ile Trp Thr
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Leu Lys Asn Ala Thr Asn Ile Thr Asn Ser Glu Gly
        130                 135                 140

Gly Met Arg Glu Gly Gly Glu Ile Lys Asn Cys Ser Phe Asn Ile Thr
145                 150                 155                 160

Thr Ser Leu Arg Asp Arg Val Gln Lys Glu Tyr Ala Leu Phe Tyr Lys
                165                 170                 175

Leu Asp Val Glu Pro Ile Asp Asp Lys Asn Ser Thr Asp Asn Asn
            180                 185                 190

Ser Thr Asn Tyr Thr Asn Tyr Arg Leu Ile Ser Cys Asn Thr Ser Val
            195                 200                 205
```

-continued

```
Ile Thr Gln Ala Cys Pro Lys Val Ser Phe Glu Pro Ile Pro Ile His
    210                 215                 220
Tyr Cys Val Pro Ala Gly Tyr Ala Leu Leu Arg Cys Asn Asn Lys Thr
225                 230                 235                 240
Phe Ser Gly Lys Gly Gln Cys Lys Asn Val Ser Thr Val Gln Cys Thr
                245                 250                 255
His Gly Ile Arg Pro Val Val Ser Thr Gln Leu Leu Leu Asn Gly Ser
                260                 265                 270
Leu Ala Glu Glu Val Val Ile Arg Ser Glu Asn Phe Thr Asp Asn
    275                 280                 285
Ala Lys Thr Ile Ile Val Gln Leu Asn Glu Thr Val Glu Ile Asn Cys
290                 295                 300
Thr Arg Pro Asn Asn Asn Thr Arg Arg Ser Ile Ser Ile Gly Pro Gly
305                 310                 315                 320
Arg Ala Phe Tyr Ala Thr Gly Asp Ile Ile Gly Asp Ile Arg Gln Ala
                325                 330                 335
His Cys Asn Leu Ser Glu Ala Lys Trp Asn Arg Thr Leu Glu Leu Val
                340                 345                 350
Val Glu Lys Leu Arg Asp Gln Phe Lys Asn Lys Thr Ile Val Phe Asn
    355                 360                 365
His Ser Ser Gly Gly Asp Pro Glu Ile Val Met Phe Ser Phe Asn Cys
370                 375                 380
Gly Gly Glu Phe Phe Tyr Cys Asp Ser Thr Lys Leu Phe Asn Ser Thr
385                 390                 395                 400
Trp Asn Gly Thr Glu Asp Asp Ser Gly Lys Asn Arg Thr Ile Thr Leu
                405                 410                 415
Pro Cys Arg Ile Lys Gln Phe Ile Asn Met Trp Gln Glu Val Gly Lys
                420                 425                 430
Ala Met Tyr Ala Pro Pro Ile Lys Gly Gln Ile Ser Cys Leu Ser Asn
            435                 440                 445
Ile Thr Gly Leu Leu Leu Thr Arg Asp Gly Gly Asn Asn Val Ser Asn
    450                 455                 460
Thr Thr Glu Val Phe Arg Pro Gly Gly Gly Asn Met Arg Asp Asn Trp
465                 470                 475                 480
Arg Ser Glu Leu Tyr Lys Tyr Lys Val Val Glu Ile Glu Pro Leu Gly
                485                 490                 495
Leu Ala Pro Thr Lys Ala Lys Arg Arg Val Val Gln Arg Glu Lys Arg
            500                 505                 510
Ala Val Gly Ile Gly Ala Leu Phe Leu Gly Phe Leu Gly Ala Ala Gly
            515                 520                 525
Ser Thr Met Gly Ala Ala Ser Met Thr Leu Thr Val Gln Ala Arg Gln
    530                 535                 540
Leu Leu Ser Gly Ile Val Gln Gln Asn Asn Leu Leu Arg Ala Ile
545                 550                 555                 560
Glu Ala Gln Gln His Leu Leu Gln Leu Thr Val Trp Gly Ile Lys Gln
                565                 570                 575
Leu Gln Ala Arg Val Leu Ala Met Glu Arg Tyr Leu Lys Asp Gln Gln
            580                 585                 590
Leu Leu Gly Ile Trp Gly Cys Ser Gly Lys Leu Ile Cys Thr Thr Thr
            595                 600                 605
Val Pro Trp Asn Thr Ser Trp Ser His Asn Arg Ser Leu Asn Glu Ile
610                 615                 620
Trp Asp Asn Met Thr Trp Met Gln Trp Asp Lys Glu Ile Asn Asn Tyr
```

```
                625                 630                 635                 640
            Thr Asp Leu Ile Tyr Asn Leu Leu Glu Glu Ala Gln Asn Gln Gln Glu
                            645                 650                 655
            Lys Asn Glu Gln Glu Leu Leu Glu Leu Asp Lys Trp Ala Ser Leu Trp
                            660                 665                 670
            Asn Trp Phe Ser Ile Thr Asn Trp Leu Trp Tyr Ile Lys Ile Phe Ile
                            675                 680                 685
            Ile Ile Val Ala Gly Leu Val Gly Leu Arg Ile Val Phe Thr Val Phe
                            690                 695                 700
            Ser Leu Val Asn Arg Val Arg Gln Gly Tyr Ser Pro Leu Ser Phe Gln
            705                 710                 715                 720
            Thr His Leu Pro Ala Pro Arg Gly Pro Asp Arg Pro Glu Gly Thr Glu
                            725                 730                 735
            Glu Arg Gly Gly Glu Gln Asp Arg Asp Arg Ser Gly His Leu Val Asp
                            740                 745                 750
            Gly Leu Leu Thr Ile Ile Trp Val Asp Leu Arg Ser Leu Phe Leu Phe
                            755                 760                 765
            Ser Tyr His Arg Leu Arg Asp Leu Leu Leu Ile Leu Ala Arg Ile Val
            770                 775                 780
            Glu Leu Leu Gly Arg Arg Gly Trp Glu Ile Leu Lys Tyr Trp Trp Asn
            785                 790                 795                 800
            Leu Leu Leu Phe Trp Ser Gln Glu Leu Lys Asn Ser Ala Val Ser Leu
                            805                 810                 815
            Leu Asn Thr Ile Ala Ile Val Val Ala Glu Gly Thr Asp Trp Val Ile
                            820                 825                 830
            Ala Gly Leu Gln Arg Leu Phe Arg Ala Phe Leu His Ile Pro Arg Arg
                            835                 840                 845
            Ile Arg Gln Gly Phe Glu Arg Ala Leu Leu
                            850                 855

<210> SEQ ID NO 45
<211> LENGTH: 876
<212> TYPE: PRT
<213> ORGANISM: Human immunodeficiency virus 1

<400> SEQUENCE: 45

Met Arg Val Lys Gly Ile Arg Arg Asn Tyr Gln His Leu Trp Arg Gly
            1                   5                   10                  15
            Ala Thr Leu Leu Leu Gly Ile Leu Met Ile Cys Ser Val Ala Gly Asn
                            20                  25                  30
            Leu Trp Val Thr Val Tyr Tyr Gly Val Pro Val Trp Lys Glu Ala Thr
                            35                  40                  45
            Thr Thr Leu Phe Cys Ala Ser Asp Ala Lys Ala Tyr Asp Thr Glu Val
                            50                  55                  60
            His Asn Val Trp Ala Thr His Ala Cys Val Pro Thr Asp Pro Asn Pro
            65                  70                  75                  80
            Gln Glu Leu Ala Leu Glu Asn Val Thr Glu Asn Phe Asn Met Trp Glu
                            85                  90                  95
            Asn Asp Met Val Glu Gln Met His Glu Asp Ile Ile Ser Leu Trp Asp
                            100                 105                 110
            Gln Ser Leu Lys Pro Cys Val Lys Leu Thr Pro Leu Cys Val Thr Leu
                            115                 120                 125
            Asn Cys Thr Asp Ala Glu Val Thr Arg Lys Thr Asn Thr Thr Ser Gly
                            130                 135                 140
```

-continued

Asp Trp Glu Lys Val Lys Lys Gly Glu Ile Lys Asn Cys Ser Phe Asp
145                 150                 155                 160

Ala Ile Asn Thr Lys Asn Lys Val Gln Lys Gln Tyr Ala Leu Phe Asp
            165                 170                 175

Thr Leu Asn Val Val Ser Ile Asp Asp Asn Asn Ser Asn Asn Asn
                180                 185                 190

Ser Asn Asn Asn Asn Asn Thr Asn Tyr Ser Asp Phe Arg Leu Thr Lys
        195                 200                 205

Cys Asp Thr Ser Val Ile Arg Gln Ala Cys Pro Lys Val Ser Phe Glu
    210                 215                 220

Pro Ile Pro Ile His Tyr Cys Ala Pro Ala Gly Phe Ala Ile Leu Lys
225                 230                 235                 240

Cys Asn Glu Thr Asp Phe Asn Gly Thr Gly Leu Cys Asn Asn Val Ser
            245                 250                 255

Thr Val Gln Cys Thr His Gly Ile Arg Pro Val Val Ser Thr Gln Leu
                260                 265                 270

Leu Leu Asn Gly Ser Leu Ala Glu Lys Gly Val Val Leu Arg Ser Lys
        275                 280                 285

Asp Phe Lys Glu Asn Thr Lys Ile Ile Ile Val Gln Leu Asn Lys Ala
    290                 295                 300

Val Asn Ile Thr Cys Thr Arg Pro Asn Asn Asn Thr Arg Lys Gly Val
305                 310                 315                 320

His Met Gly Pro Gly Gly Ala Leu Phe Ala Thr Asp Val Ile Gly Asp
            325                 330                 335

Ile Arg Lys Ala His Cys Asn Ile Thr Arg Glu Glu Trp Asn Asn Thr
                340                 345                 350

Leu Lys Gln Ile Val Leu Lys Leu Lys Glu Lys Phe Glu Asn Lys Thr
        355                 360                 365

Lys Ile Val Phe Thr Asn Ser Ser Gly Gly Asp Pro Glu Val Thr Met
    370                 375                 380

His Thr Phe Asn Cys Gly Gly Glu Phe Phe Tyr Cys Asn Thr Thr Glu
385                 390                 395                 400

Leu Phe Ser Ser Thr Trp Asn Ile Thr Gly Asp Ser Ile Gly Asn Ile
            405                 410                 415

Thr Gly Glu Ser Leu Asn Ile Thr Leu Pro Cys Arg Ile Lys Gln Ile
                420                 425                 430

Ile Asn Met Trp Gln Gly Val Gly Lys Ala Met Tyr Ala Pro Pro Ile
        435                 440                 445

Ser Gly Gln Ile Arg Cys Ile Ser Asn Ile Thr Gly Leu Leu Leu Thr
    450                 455                 460

Arg Asp Gly Gly Asp Asn Asn Thr Glu Asn Asp Asn Asn Thr Glu Ile
465                 470                 475                 480

Phe Arg Pro Trp Gly Gly Asp Met Arg Asp Asn Trp Arg Ser Glu Leu
            485                 490                 495

Tyr Lys Tyr Lys Val Val Lys Leu Glu Pro Leu Gly Leu Ala Pro Thr
                500                 505                 510

Lys Ala Lys Arg Arg Val Val Gln Arg Glu Lys Arg Ala Ile Gly Val
        515                 520                 525

Gly Ala Met Phe Leu Gly Phe Leu Gly Ala Ala Gly Ser Thr Met Gly
    530                 535                 540

Ala Ala Ser Leu Thr Leu Thr Val Gln Ala Arg Gln Leu Leu Ser Gly
545                 550                 555                 560

Ile Val Gln Gln Gln Asn Asn Leu Leu Arg Ala Ile Glu Ala Gln Gln

```
                565                 570                 575
His Leu Gln Leu Thr Val Trp Gly Ile Lys Gln Leu Gln Ala Arg
            580                 585                 590
Val Leu Ala Val Glu Arg Tyr Leu Lys Asp Gln Gln Leu Leu Gly Ile
            595                 600                 605
Trp Gly Cys Ser Gly Lys Leu Ile Cys Thr Thr Thr Val Pro Trp Asn
610                 615                 620
Asp Ser Trp Gly Tyr Ser Trp Ser Asn Arg Thr Asn Lys Ser Leu Glu
625                 630                 635                 640
Glu Ile Trp Asp Asn Leu Thr Trp Arg Glu Trp Glu Arg Glu Ile Asp
            645                 650                 655
Asn Tyr Thr Asp Leu Ile Tyr Asn Leu Ile Glu Lys Ser Gln Asn Gln
            660                 665                 670
Gln Glu Lys Asn Glu Gln Glu Leu Leu Ala Leu Asp Lys Trp Ala Asn
            675                 680                 685
Leu Trp Asn Trp Phe Asp Ile Thr Asn Trp Leu Trp Tyr Ile Arg Ile
            690                 695                 700
Phe Ile Met Ile Val Gly Gly Leu Ile Gly Leu Arg Ile Val Phe Ala
705                 710                 715                 720
Val Leu Ser Ile Val Arg Arg Val Arg Gln Gly Tyr Ser Pro Leu Ser
            725                 730                 735
Phe Gln Thr Leu Leu Pro Val Pro Arg Gly Pro Asp Arg Pro Glu Gly
            740                 745                 750
Ile Glu Glu Glu Gly Gly Glu Gln Asp Arg Gly Arg Ser Val Arg Leu
            755                 760                 765
Val Asp Gly Phe Leu Ala Leu Phe Trp Asp Asp Leu Arg Ser Leu Cys
770                 775                 780
Leu Phe Leu Tyr His Arg Leu Arg Asp Leu Leu Leu Ile Val Thr Arg
785                 790                 795                 800
Ile Val Gly Val Leu Gly His Arg Gly Trp Glu Ile Leu Lys Tyr Trp
            805                 810                 815
Trp Ser Leu Ile Gln Tyr Trp Ser Gln Glu Leu Lys Asn Ser Ala Val
            820                 825                 830
Ser Leu Leu Asn Ala Thr Ala Ile Thr Val Ala Glu Gly Thr Asp Arg
            835                 840                 845
Val Ile Glu Ile Arg Gln Arg Val Phe Arg Gly Val Leu His Ile Pro
            850                 855                 860
Arg Arg Ile Arg Gln Gly Leu Glu Arg Ala Leu Leu
865                 870                 875

<210> SEQ ID NO 46
<211> LENGTH: 869
<212> TYPE: PRT
<213> ORGANISM: Human immunodeficiency virus 1

<400> SEQUENCE: 46

Met Arg Val Lys Gly Ile Arg Arg Asn Tyr Gln His Leu Trp Arg Gly
1               5                   10                  15
Val Thr Leu Leu Leu Gly Ile Leu Met Ile Cys Ser Val Ala Gly Asn
            20                  25                  30
Leu Trp Val Thr Val Tyr Tyr Gly Val Pro Val Trp Lys Glu Ala Thr
            35                  40                  45
Thr Thr Leu Phe Cys Ala Ser Asp Ala Lys Ala Tyr Asp Thr Glu Val
        50                  55                  60
```

```
His Asn Val Trp Ala Thr His Ala Cys Val Pro Thr Asp Pro Asn Pro
 65                  70                  75                  80

Gln Glu Leu Ala Leu Glu Asn Val Thr Glu Asn Phe Asn Met Trp Glu
                 85                  90                  95

Asn Asp Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Ala Glu Val Thr Gly Lys Thr Asn Thr Thr Ile Gly
    130                 135                 140

Glu Trp Glu Lys Val Lys Glu Gly Glu Met Lys Asn Cys Ser Phe Asp
145                 150                 155                 160

Ala Ile Asn Thr Lys Asn Lys Val Gln Lys Gln Tyr Ala Leu Phe Asp
                165                 170                 175

Thr Leu Asp Val Val Pro Ile Asp Asp Asn Asn Ser Asn Ser Asn
            180                 185                 190

Tyr Ser Asp Phe Arg Leu Thr Lys Cys Asp Thr Ser Val Ile Arg Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Glu Thr Asp Phe Asn Gly
225                 230                 235                 240

Thr Gly Leu Cys Asn Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Gly Val Val Leu Arg Ser Lys Asp Phe Lys Glu Asn Thr Lys Ile
        275                 280                 285

Ile Ile Val Gln Leu Asn Lys Ala Val Asn Ile Thr Cys Thr Arg Pro
    290                 295                 300

Asn Asn Asn Thr Arg Lys Gly Val His Met Gly Pro Gly Gly Ala Leu
305                 310                 315                 320

Phe Ala Thr Asp Val Ile Gly Asp Ile Arg Lys Ala His Cys Asn Ile
                325                 330                 335

Thr Arg Glu Glu Trp Asn Asn Thr Leu Lys Gln Ile Val Leu Lys Leu
            340                 345                 350

Lys Glu Lys Phe Glu Asn Lys Thr Lys Ile Val Phe Thr Asn Ser Ser
        355                 360                 365

Gly Gly Asp Pro Glu Val Thr Met His Thr Phe Asn Cys Gly Gly Glu
    370                 375                 380

Phe Phe Tyr Cys Asn Thr Thr Glu Leu Phe Ser Ser Thr Trp Asn Ile
385                 390                 395                 400

Thr Gly Asp Ser Ile Gly Asn Ile Thr Gly Glu Tyr Thr Leu Asn Ile
                405                 410                 415

Thr Leu Pro Cys Arg Ile Lys Gln Ile Ile Asn Met Trp Gln Gly Val
            420                 425                 430

Gly Lys Ala Met Tyr Ala Pro Pro Ile Ser Gly Gln Ile Arg Cys Ile
        435                 440                 445

Ser Asn Ile Thr Gly Leu Leu Leu Thr Arg Asp Gly Gly Asn Asn
    450                 455                 460

Thr Glu Asn Asp Asn Asn Thr Glu Ile Phe Arg Pro Trp Gly Gly Asp
465                 470                 475                 480

Met Arg Asp Asn Trp Arg Ser Glu Leu Tyr Lys Tyr Lys Val Val Lys
```

485                 490                 495

Leu Glu Pro Leu Gly Leu Ala Pro Thr Lys Ala Lys Arg Val Val
                500                 505                 510

Gln Arg Glu Lys Arg Ala Ile Gly Val Gly Ala Met Phe Leu Gly Phe
                515                 520                 525

Leu Gly Ala Ala Gly Ser Thr Met Gly Ala Ala Ser Leu Thr Leu Thr
                530                 535                 540

Val Gln Ala Arg Gln Leu Leu Ser Gly Ile Val Gln Gln Gln Asn Asn
545                 550                 555                 560

Leu Leu Arg Ala Ile Glu Ala Gln Gln His Leu Leu Gln Leu Thr Val
                565                 570                 575

Trp Gly Ile Lys Gln Leu Gln Ala Arg Val Leu Ala Val Glu Arg Tyr
                580                 585                 590

Leu Lys Asp Gln Gln Leu Leu Gly Ile Trp Gly Cys Ser Gly Lys Leu
                595                 600                 605

Ile Cys Thr Thr Thr Val Pro Trp Asn Asp Ser Trp Gly Tyr Ser Trp
                610                 615                 620

Ser Asn Arg Thr Asn Lys Ser Leu Glu Glu Ile Trp Asp Asn Leu Thr
625                 630                 635                 640

Trp Arg Glu Trp Glu Arg Glu Ile Asp Asn Tyr Thr Asp Leu Ile Tyr
                645                 650                 655

Asn Leu Ile Glu Lys Ser Gln Asn Gln Gln Glu Lys Asn Glu Gln Glu
                660                 665                 670

Leu Leu Ala Leu Asp Lys Trp Ala Asn Leu Trp Asn Trp Phe Asp Ile
                675                 680                 685

Thr Asn Trp Leu Trp Tyr Ile Arg Ile Phe Ile Met Ile Val Gly Gly
                690                 695                 700

Leu Ile Gly Leu Arg Ile Val Phe Ala Val Leu Ser Ile Val Arg Arg
705                 710                 715                 720

Val Arg Gln Gly Tyr Ser Pro Leu Ser Phe Gln Thr Leu Leu Pro Val
                725                 730                 735

Pro Arg Gly Pro Asp Arg Pro Glu Gly Thr Glu Lys Glu Gly Gly Glu
                740                 745                 750

Gln Asp Arg Gly Arg Ser Val Arg Leu Val Asp Gly Phe Leu Ala Leu
                755                 760                 765

Phe Trp Asp Asp Leu Arg Ser Leu Cys Leu Phe Leu Tyr His Arg Leu
                770                 775                 780

Arg Asp Leu Leu Leu Ile Val Thr Arg Ile Val Gly Val Leu Gly His
785                 790                 795                 800

Arg Gly Trp Glu Ile Leu Lys Tyr Trp Trp Ser Leu Ile Gln Tyr Trp
                805                 810                 815

Ser Gln Glu Leu Lys Asn Ser Ala Val Ser Leu Leu Asn Ala Thr Ala
                820                 825                 830

Ile Thr Val Ala Glu Gly Thr Asp Arg Val Ile Glu Ile Val Arg Arg
                835                 840                 845

Val Phe Arg Gly Val Leu His Ile Pro Arg Arg Ile Arg Gln Gly Leu
                850                 855                 860

Glu Arg Ala Leu Leu
865

<210> SEQ ID NO 47
<211> LENGTH: 854
<212> TYPE: PRT
<213> ORGANISM: Human immunodeficiency virus 1

<400> SEQUENCE: 47

```
Met Lys Val Lys Gly Ile Lys Lys Ser Cys Gln His Leu Trp Lys Trp
1               5                   10                  15
Gly Ile Leu Leu Leu Gly Met Leu Met Ile Cys Ser Ala Ala Glu Lys
                20                  25                  30
Met Trp Val Thr Val Tyr Tyr Gly Val Pro Val Trp Lys Glu Ala Thr
                35                  40                  45
Thr Thr Leu Phe Cys Ala Ser Asp Ala Lys Ser Tyr Asp Thr Glu Val
        50                  55                  60
His Asn Val Trp Ala Thr His Ala Cys Val Pro Thr Asp Pro Asn Pro
65                  70                  75                  80
Gln Glu Val Val Leu Gly Asn Val Thr Glu Asn Phe Asn Met Trp Lys
                85                  90                  95
Asn Asn Met Val Glu Gln Met His Glu Asp Val Ile Ser Leu Trp Asp
                100                 105                 110
Gln Ser Leu Lys Pro Cys Val Lys Leu Thr Pro Leu Cys Val Thr Leu
            115                 120                 125
Asn Cys Thr Asp Lys Leu Arg Asn Asp Ala Phe Gly Val Asn Asn Thr
130                 135                 140
Met Glu Gly Glu Met Lys Asn Cys Ser Phe Asn Thr Thr Thr Ser Leu
145                 150                 155                 160
Arg Asp Lys Ile Gln Lys Glu Tyr Ala Leu Phe Tyr Lys Leu Asp Val
                165                 170                 175
Val Gln Ile Lys Asn Asn Asn Ser Asn Tyr Thr Ser Tyr Arg Leu
                180                 185                 190
Ile Asn Cys Asn Thr Ser Val Ile Thr Gln Ala Cys Pro Lys Val Thr
            195                 200                 205
Phe Glu Pro Ile Pro Ile His Tyr Cys Thr Pro Ala Gly Phe Ala Ile
210                 215                 220
Leu Lys Cys Asn Asn Lys Thr Phe Ser Gly Lys Gly Thr Cys Thr Asn
225                 230                 235                 240
Val Ser Thr Val Gln Cys Thr His Gly Ile Arg Pro Val Val Ser Thr
                245                 250                 255
Gln Leu Leu Leu Asn Gly Ser Leu Ala Glu Glu Asp Val Val Ile Arg
            260                 265                 270
Ser Asp Asn Phe Ser Gln Asn Ala Lys Ile Ile Ile Val Gln Leu Asn
            275                 280                 285
Glu Ala Val Val Ile Asn Cys Thr Arg Pro Gly Asn Asn Thr Arg Lys
        290                 295                 300
Ser Ile Pro Ile Gly Pro Gly Arg Ala Phe Tyr Ala Thr Gly Asp Ile
305                 310                 315                 320
Ile Gly Asn Ile Arg Gln Ala His Cys Asn Val Ser Ser Thr Lys Trp
                325                 330                 335
Asn Asn Thr Leu Gln Lys Ile Val Glu Lys Leu Arg Glu Gln Phe Gly
            340                 345                 350
Asn Lys Thr Ile Lys Phe Thr Ser Pro Ser Gly Gly Asp Pro Glu
        355                 360                 365
Ile Val Met His Ser Phe Asn Cys Gly Gly Glu Phe Phe Tyr Cys Asp
        370                 375                 380
Thr Thr Gln Leu Phe Asn Ser Thr Trp Asp Asn Thr Ser Thr Trp Asn
385                 390                 395                 400
Asn Ser Asn Thr Gln Asn Lys Asn Asp Arg Asn Ile Thr Leu Gln Cys
```

```
                405                 410                 415
Arg Ile Lys Gln Ile Ile Asn Met Trp Gln Glu Val Gly Lys Ala Met
                420                 425                 430

Tyr Ala Pro Pro Ile Met Gly Gln Ile Arg Cys Val Ser Asn Ile Thr
            435                 440                 445

Gly Leu Leu Leu Thr Arg Asp Gly Gly Asn Gly Ser Glu Ala Lys Asn
        450                 455                 460

Asp Thr Glu Ile Phe Arg Pro Gly Gly Gly Asp Met Arg Asp Asn Trp
465                 470                 475                 480

Arg Ser Glu Leu Tyr Lys Tyr Lys Val Val Lys Ile Glu Pro Leu Gly
                485                 490                 495

Val Ala Pro Thr Lys Ala Lys Arg Arg Val Val Gln Arg Glu Lys Arg
            500                 505                 510

Ala Val Gly Thr Ile Gly Ala Met Phe Leu Gly Phe Leu Gly Ala Ala
        515                 520                 525

Gly Asn Thr Met Gly Ala Ala Ser Leu Thr Leu Thr Val Gln Ala Arg
    530                 535                 540

Gln Leu Leu Ser Gly Ile Val Gln Gln Asn Asn Leu Leu Arg Ala
545                 550                 555                 560

Ile Gln Ala Gln Gln His Leu Leu Gln Leu Thr Val Trp Gly Ile Lys
                565                 570                 575

Gln Leu Gln Ala Arg Val Leu Ala Val Glu Arg Tyr Leu Arg Asp Gln
            580                 585                 590

Gln Leu Leu Gly Ile Trp Gly Cys Ser Gly Lys Leu Ile Cys Thr Thr
        595                 600                 605

Ala Val Pro Trp Asn Ala Ser Trp Ser Asn Lys Ser Tyr Thr Asp Ile
    610                 615                 620

Trp Asp Asn Met Thr Trp Met Gln Trp Glu Lys Glu Ile Glu Asn Tyr
625                 630                 635                 640

Thr Ser Leu Ile Tyr Thr Leu Ile Glu Asp Ser Gln Asn Gln Gln Glu
                645                 650                 655

Lys Asn Glu Gln Glu Leu Leu Glu Leu Asp Lys Trp Ala Ser Leu Trp
            660                 665                 670

Asn Trp Phe Asp Ile Thr Ser Trp Leu Trp Tyr Ile Lys Ile Phe Ile
        675                 680                 685

Met Ile Val Gly Gly Leu Ile Gly Leu Arg Ile Val Phe Ala Val Leu
    690                 695                 700

Ser Ile Val Asn Arg Val Arg Gln Gly Tyr Ser Pro Leu Ser Leu Gln
705                 710                 715                 720

Thr Arg Leu Pro Ala Pro Gly Gly Pro Asp Arg Pro Gly Gly Ile Glu
                725                 730                 735

Glu Glu Gly Gly Glu Gln Gly Arg Gly Arg Ser Val Arg Leu Val Asp
            740                 745                 750

Gly Phe Leu Ala Leu Ile Trp Asp Asp Leu Arg Asn Leu Cys Leu Phe
        755                 760                 765

Ile Tyr His Arg Leu Arg Asp Leu Leu Trp Ile Val Gly Leu Leu Gly
    770                 775                 780

Arg Arg Gly Trp Glu Ile Leu Lys Tyr Trp Trp Asn Ile Leu Gln Tyr
785                 790                 795                 800

Trp Ser Gln Glu Leu Lys Asn Ser Ala Val Ser Leu Leu Asn Thr Ile
                805                 810                 815

Ala Ile Ala Val Ala Glu Gly Thr Asp Arg Ile Ile Glu Leu Ala Gln
            820                 825                 830
```

Gly Ile Cys Arg Ala Ile Leu His Ile Pro Arg Arg Ile Arg Gln Gly
            835                 840                 845

Phe Glu Arg Ala Leu Leu
    850

<210> SEQ ID NO 48
<211> LENGTH: 854
<212> TYPE: PRT
<213> ORGANISM: Human immunodeficiency virus 1

<400> SEQUENCE: 48

Met Lys Val Lys Gly Ile Lys Lys Ser Cys Gln His Leu Trp Lys Trp
1               5                   10                  15

Gly Ile Leu Leu Leu Gly Met Leu Met Ile Cys Ser Ala Ala Glu Lys
                20                  25                  30

Met Trp Val Thr Val Tyr Tyr Gly Val Pro Val Trp Lys Glu Ala Thr
            35                  40                  45

Thr Thr Leu Phe Cys Ala Ser Asp Ala Lys Ser Tyr Asp Thr Glu Val
        50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asn Met Val Glu Gln Met His Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Lys Leu Arg Asn Asp Ala Phe Gly Val Asn Asn Thr
    130                 135                 140

Met Glu Gly Glu Met Lys Asn Cys Ser Phe Asn Thr Thr Thr Ser Leu
145                 150                 155                 160

Arg Asp Lys Ile Gln Lys Glu Tyr Ala Leu Phe Tyr Lys Leu Asp Val
                165                 170                 175

Val Gln Ile Lys Asn Asn Asn Ser Asn Tyr Thr Ser Tyr Arg Leu
            180                 185                 190

Ile Asn Cys Asn Thr Ser Val Ile Thr Gln Ala Cys Pro Lys Val Thr
        195                 200                 205

Phe Glu Pro Ile Pro Ile His Tyr Cys Thr Pro Ala Gly Phe Ala Ile
    210                 215                 220

Leu Lys Cys Asn Asn Lys Thr Phe Ser Gly Lys Gly Thr Cys Thr Asn
225                 230                 235                 240

Val Ser Thr Val Gln Cys Thr His Gly Ile Arg Pro Val Val Ser Thr
                245                 250                 255

Gln Leu Leu Leu Asn Gly Ser Leu Ala Glu Glu Asp Val Val Ile Arg
            260                 265                 270

Ser Asp Asn Phe Ser Gln Asn Ala Lys Ile Ile Val Gln Leu Asn
        275                 280                 285

Glu Ala Val Val Ile Asn Cys Thr Arg Pro Gly Asn Asn Thr Arg Lys
    290                 295                 300

Ser Ile Pro Ile Gly Pro Gly Arg Ala Phe Tyr Ala Thr Gly Asp Ile
305                 310                 315                 320

Ile Gly Ser Ile Arg Gln Ala His Cys Asn Val Ser Ser Thr Lys Trp
                325                 330                 335

Asn Asn Thr Leu Gln Lys Ile Val Glu Lys Leu Arg Glu Gln Phe Gly

-continued

```
                340                 345                 350
Asn Lys Thr Ile Lys Phe Thr Ser Pro Ser Pro Gly Gly Asp Pro Glu
            355                 360                 365
Ile Val Met His Ser Phe Asn Cys Gly Gly Glu Phe Phe Tyr Cys Asp
            370                 375                 380
Thr Thr Gln Leu Phe Asn Ser Thr Trp Asp Asn Thr Ser Thr Trp Asn
385                 390                 395                 400
Asn Ser Asn Thr Gln Asn Lys Asn Asp Arg Asn Ile Thr Leu Gln Cys
                405                 410                 415
Arg Ile Lys Gln Ile Ile Asn Met Trp Gln Glu Val Gly Lys Ala Met
            420                 425                 430
Tyr Ala Pro Pro Ile Met Gly Gln Ile Arg Cys Val Ser Asn Ile Thr
            435                 440                 445
Gly Leu Leu Leu Thr Arg Asp Gly Gly Asn Gly Ser Glu Ala Lys Asn
            450                 455                 460
Asp Thr Glu Ile Phe Arg Pro Gly Gly Gly Asp Met Arg Asp Asn Trp
465                 470                 475                 480
Arg Ser Glu Leu Tyr Lys Tyr Lys Val Val Lys Ile Glu Pro Leu Gly
                485                 490                 495
Val Ala Pro Thr Lys Ala Lys Arg Arg Val Val Gln Arg Glu Lys Arg
            500                 505                 510
Ala Val Gly Thr Ile Gly Ala Met Phe Leu Gly Phe Leu Gly Ala Ala
            515                 520                 525
Gly Ser Thr Met Gly Ala Ala Ser Leu Thr Leu Thr Val Gln Ala Arg
            530                 535                 540
Gln Leu Leu Ser Gly Ile Val Gln Gln Gln Asn Asn Leu Leu Arg Ala
545                 550                 555                 560
Ile Gln Ala Gln Gln His Leu Leu Gln Leu Thr Val Trp Gly Ile Lys
                565                 570                 575
Gln Leu Gln Ala Arg Val Leu Ala Val Glu Arg Tyr Leu Arg Asp Gln
            580                 585                 590
Gln Leu Leu Gly Ile Trp Gly Cys Ser Gly Lys Leu Ile Cys Thr Thr
            595                 600                 605
Ala Val Pro Trp Asn Ala Ser Trp Ser Asn Lys Ser Tyr Thr Asp Ile
            610                 615                 620
Trp Asp Asn Met Thr Trp Met Gln Trp Glu Glu Ile Glu Asn Tyr
625                 630                 635                 640
Thr Ser Leu Ile Tyr Thr Leu Ile Glu Asp Ser Gln Asn Gln Arg Glu
                645                 650                 655
Lys Asn Glu Gln Glu Leu Leu Glu Leu Asp Lys Trp Ala Ser Leu Trp
            660                 665                 670
Asn Trp Phe Asp Ile Thr Ser Trp Leu Trp Tyr Ile Lys Ile Phe Ile
            675                 680                 685
Met Ile Val Gly Gly Leu Ile Gly Leu Arg Ile Val Phe Ala Val Leu
            690                 695                 700
Ser Ile Val Asn Arg Val Arg Gln Gly Tyr Ser Pro Leu Ser Leu Gln
705                 710                 715                 720
Thr Arg Leu Pro Ala Pro Gly Gly Pro Asp Arg Pro Gly Gly Ile Glu
                725                 730                 735
Glu Glu Gly Gly Glu Gln Gly Arg Gly Arg Ser Val Arg Leu Val Asp
            740                 745                 750
Gly Phe Leu Ala Leu Ile Trp Asp Asp Leu Arg Asn Leu Cys Leu Phe
            755                 760                 765
```

```
Ile Tyr His Arg Leu Arg Asp Leu Leu Trp Ile Val Gly Leu Leu Gly
    770             775             780

Arg Arg Gly Trp Glu Ile Leu Lys Tyr Trp Trp Asn Ile Leu Gln Tyr
785             790              795                     800

Trp Ser Gln Glu Leu Lys Asn Ser Ala Val Ser Leu Leu Asn Thr Ile
                805             810              815

Ala Ile Ala Val Ala Glu Gly Thr Asp Arg Thr Ile Glu Leu Ala His
            820             825              830

Arg Ile Cys Arg Ala Ile Leu His Ile Pro Arg Arg Ile Arg Gln Gly
        835             840              845

Phe Glu Arg Ala Leu Leu
    850
```

THERAPEUTIC COMPOSITIONS AND METHODS FOR TREATING HIV INCLUDING IDENTIFICATION AND MANIPULATION OF PARTICULAR DOMAINS ASSOCIATED WITH IMMUNOGENICITY

RELATIONSHIP TO OTHER APPLICATIONS

This application is a continuation of U.S. application Ser. No. 13/079,472 filed on Apr. 4, 2011, now issued as U.S. Pat. No. 9,782,472, which application is a continuation in part of: (i) PCT/US2010/055747 filed on Nov. 5, 2010, which claims priority benefit of U.S. provisional application Ser. No. 61/258,833 filed on Nov. 6, 2009; (ii) PCT/US2010/053637 filed on Oct. 22, 2010, which claims priority benefit of U.S. provisional application Ser. No. 61/253,858 filed on Oct. 22, 2009; and (iii) PCT/US2009/059583 filed on Oct. 5, 2009, which claims priority benefit of U.S. provisional application Ser. No. 61/195,112 filed on Oct. 4, 2008. The disclosures of these earlier filed priority applications are incorporated herein by reference.

STATEMENT OF SUPPORT

This invention was made with support of the Bill and Melinda Gates Foundation and the University of California, Santa Cruz start-up fund.

SEQUENCE LISTING

The information recorded in electronic form (if any) submitted (under Rule 13ter if appropriate) with this application is identical to the sequence listing as contained in the application as filed.

FIELD OF THE INVENTION

The Invention (SC2009-449) relates to therapeutic compositions and methods for treating HIV and other viral diseases and to vaccines for preventing HIV and other viral diseases. Specifically the invention relates to therapeutic applications against HIV infections and to methods for creation, screening and identification of viral epitopes of HIV that have therapeutic value.

Additionally the invention (UCSC2008-776) relates to methods use of intrapatient sequence variation data to identify mutations in the HIV envelope glycoprotein that affect the binding of broadly neutralizing antibodies. Additionally the invention (SC2010-117) relates to methods for improving the immunogenicity of HIV antigens by mutation of protease cleavage sites in regions important for receptor binding and the binding of neutralizing antibodies; and therapeutic compositions and vaccines.

BACKGROUND

A major goal in HIV vaccine research is the identification of antigens able to elicit the production of broadly neutralizing antibodies (bNAbs) effective against primary isolates of HIV. The applicant has investigated the molecular features of the HIV-1 envelope glycoproteins, gp160, gp120 and gp41, that confer sensitivity and resistance of viruses to neutralization.

BRIEF DESCRIPTION OF THE INVENTION

Disclosed are therapeutic compositions and methods for treating HIV and other viral diseases and vaccines for preventing HIV and other viral diseases. These therapeutic compositions contain species and compositions that have been identified by a novel method for identifying mutations in envelope proteins, which mutations provide enhanced sensitivity to neutralization of an virus by anti-viral antisera; in particular neutralization of an HIV virus by anti-HIV antisera. This novel method is disclosed in U.S. provisional application 61/195,112 filed 4 Oct. 2008 and also in related International application No. PCT/US09/59583 filed 5 Oct. 2009, both of which are incorporated by reference in their entirety and which disclose novel methods comprising analyzing intra-patient HIV-1 virus variation to identify specific amino acid residues of the HIV-1 envelope glycoproteins, gp160, gp120, and gp41 that affect sensitivity or resistance to broadly neutralizing HIV-1 antibodies. Also provided are proteins identified by these methods, the nucleic acids encoding the proteins, and vaccines comprising the proteins and nucleic acids.

Identification of the determinants of sensitivity and resistance to broadly neutralizing antibodies is a high priority for HIV research. Analysis of the swarm of closely related envelope protein variants in HIV infected individuals revealed a mutation that markedly affected sensitivity to neutralization by antibodies and antiviral entry inhibitors targeting both gp41 and gp120. This mutation mapped to the C34 helix of gp41 and disrupted an overlooked structural feature consisting of a ring of hydrogen bonds in the gp41 trimer. This mutation affects the assembly of the 6 helix bundle required for virus fusion, and alters the conformational equilibrium so as to favor the pre-hairpin intermediate conformation required for the binding of the HIV-1 env membrane proximal external region (MPER) specific neutralizing antibodies, 2F5 and 4E10, and the antiviral drug, FUZEON. Targeting cooperative interactions that stabilize conformational transitions provides new approach to the design of vaccine antigens and antiviral compounds. Methods for measuring the integrity of the pre-hairpin intermediate conformation include those described by Yang Xu et al., "Development of a FRET Assay for Monitoring of HIV gp41 Core Disruption" J. Org. Chem. 2007, 72, 6700-6707.

The invention encompasses the use of various compounds used for therapeutic purposes. These compounds may be contacted with a virus, such as an HIV virus, and interact with and/or bind to one or more regions on the viral envelope (env) protein or other viral protein or glycoprotein. This interaction thereby (i) exposes one or more previously unexposed epitopes which epitope can bind specifically with a neutralizing antibody and/or (ii) limits, inhibits or prevents fusion of a viral membrane with a cell membrane, thereby inhibiting infection of a cell by a virus. Such compounds may be therapeutic compositions, drugs, small molecules or antibodies.

Also disclosed are therapeutic methods that employ compositions such as drugs and small molecules or antibodies that interact with specific antigens or epitopes or regions of the glycoproteins or polypeptides described, thereby (i) exposing a previously unexposed epitope which epitope can bind specifically with a neutralizing antibody and/or (ii) limiting, inhibiting or preventing fusion of a viral membrane with a cell membrane, thereby inhibiting infection of a call by a virus. Also disclosed are the therapeutic compositions, drugs, small molecules or antibodies used in the above method.

Also disclosed are generic and specific sequences, mutations, antigens and epitopes that may be used therapeutically for the treatment and/or prevention of viral infection such as HIV infection, and vectors, pseudo-viruses and other constructs that comprise specific polynucleotide sequences and mutations that encode antigens and epitopes of the invention.

Also disclosed are therapeutic methods that comprise delivering a vaccine to a subject wherein the vaccine may comprise one or more antibodies or antigens or epitopes of the invention, or polynucleotide sequences or vectors encoding antigens and epitopes of the invention.

Also disclosed are therapeutic methods and therapeutic compositions comprising drugs such as small molecules that target a specific antigens or epitopes of the invention, thereby limiting, inhibition or preventing fusion of a viral membrane with a cell membrane, thereby inhibiting infection of a call by a virus.

One particular embodiment is a method for inhibiting the fusion of an HIV virus to a host cell, the method comprising exposing the HIV virus to a drug compound that disrupts the hydrogen-bonded ring structure between the N36 and C34 helices of gp41.

Another embodiment is a method for increasing the immunogenicity of HIV envelope proteins the method comprising exposing the HIV virus to a drug compound that disrupts the hydrogen bonded ring structure between the N36 and C34 helices of gp41. Methods for measuring the integrity of the hydrogen-bonded ring structure are known in the art and include those described by Yang Xu et al., "Development of a FRET Assay for Monitoring of HIV gp41 Core Disruption" J. Org. Chem. 2007, 72, 6700-6707. The drugs used in these methods may be, for example, antibodies, small molecules or peptidomimetics, including, for example, FUZEON, 4E10, 2F5, Q665R, Q655K and Q655E. In some of the methods the drug compound interacts with the gp120 fragment of the HIV envelope protein. In some of the methods, the drug compound is an inhibitor of HIV fusion binding and becomes a more effective inhibitor in the presence of a molecule that disrupts the disulfide bonded ring structure of gp41.

An important element of the invention is the mechanism by which the drug works to prevent viral fusion and/or to expose previously hidden epitopes. In various methods the drug compound disrupts the hydrogen bonded ring structure between the N36 and C34 helices of gp41 and thereby exposes neutralizing epitopes which are recognized by endogenous or exogenous antibodies which then are able to neutralize the virus. The invention encompasses methods for screening for a drug that prevents or attenuates intracellular membrane fusion, the method comprising exposing the multimeric coiled coil bundle of the activated fusion complex to a drug candidate, wherein disruption of one or more hydrogen bonds of the fusion complex is associated with prevention or attenuation of intracellular membrane fusion. The fusion complex may comprise a cellular hairpin membrane fusion protein. The cellular hairpin membrane fusion protein may be a cellular SNARE protein. The multimeric coiled coil bundle may be a 4 helix bundle. The intracellular membrane fusion may be associated with secretion of a hormone, cytokine or neurotransmitter.

The invention also includes a method of treating, attenuating or preventing HIV infection, the method comprising administering to a patient a drug compound which disrupts one or more intra-molecular or inter-molecular hydrogen bonds of the hydrogen-bonded ring structure of gp41 trimer, wherein disruption of the hydrogen-bonded ring structure is associated with attenuation or prevention of HIV infection.

The invention also encompasses a synthetic helical peptide wherein the peptide sequence binds specifically to at least a fragment of the N-36 helix of gp41, wherein the fragment includes the residue Q655 and wherein binding of the synthetic helical peptide to the N-36 helix disrupts hydrogen bonded ring structure between the N36 and C34 helices of gp41.

The invention also encompasses a peptidomimetic drug that binds specifically to helical sequences adjacent to the Q655 or Q553 residues of gp41, and disrupts or prevents the formation of a hydrogen bonded ring structure involving Q655 from the C34 helix and Q553 from the N36 helix. The peptide or peptidomimetic binds to or interacts with the N36 or C34 helices of gp41 and thereby disrupts one or more intra-molecular or inter-molecular hydrogen bonds of the hydrogen-bonded ring structure of gp41 trimer, wherein disruption of the hydrogen-bonded ring structure is associated with attenuation or prevention of HIV infection. The peptide or peptidomimetic may disrupt one or more of the intra-molecular or inter-molecular hydrogen bonds stabilizing the multimeric coiled coil bundle in the activated fusion complex required for the fusion and release of synaptic vesicles. It may also disrupt one or more of the intra-molecular or inter-molecular hydrogen bonds stabilizing the multimeric coiled coil bundle structurally homologous to the N36 or C34 helix of HIV in the activated fusion complex required for the fusion and release of vesicles or granules containing pro-inflammatory proteins, cytokines, hormones, or vasoactive substances.

The invention also encompasses a method of attenuating or preventing HIV-1 infection comprising administering to a patient an effective amount of an agent which disrupts one or more intra-molecular or inter-molecular hydrogen bonds of the hydrogen-bonded ring structure of gp41 trimer, wherein disruption of the hydrogen-bonded ring structure makes HIV-1 susceptible to neutralization by the patient's antibodies which thereby attenuate or prevent HIV infection. The agent may comprise a peptide or peptidomimetic compound.

The invention also encompasses a peptide having a formula selected from the group consisting of:

```
                                         (SEQ ID NO: 1)
X-YTSLIHSLIEESQNQ[*]EKNEQELLELDKWASLWNWF-Z (SEQ ID NO: 2)
X-YTNTIYTLLEESQNQ[*]EKNEQELLELDKWASLWNWF-Z (SEQ ID NO: 3)
X-YTGIIYNLLEESQNQ[*]EKNEQELLELDKWANLWNWF-Z (SEQ ID NO: 4)
X-YTSLIYSLLEKSQIQ[*]EKNEQELLELDKWASLWNWF-Z (SEQ ID NO: 5)
X-LEANISKSLEQAQIQ[*]EKNMYELQKLNSWDIFGNWF-Z
and (SEQ ID NO: 6)
X-LEANISQSLEQAQIQ[*]EKNMYELQKLNSWDVFTNWL-Z
```

For the above listed peptides, amino acid residues are presented by the single-letter code; X comprises an amino group, an acetyl group, a 9-fluorenylmethoxy-carbonyl group, a hydrophobic group, or a macromolecule carrier group; Z comprises a carboxyl group, or an amido group, or a hydrophobic group, or a macromolecular carrier group; and [*] represents any amino acid other than Q or N. In some embodiments [*] represents R, K, S, or E.

Another discovery of potential relevance to the understanding of the determinants of neutralization sensitivity and resistance of HIV-1 is disclosed in J. Virol. doi:10.1128/JVI.00790-10, 'Mutation at a single position in the V2 domain of the HIV-1 envelope protein confers neutralization sensitivity to a highly neutralization resistant virus' by Sara M. O'Rourke, Becky Schweighardt, Pham Phung, Dora P. A. J. Fonseca, Karianne Terry, Terri Wrin, Faruk Sinangil, and Phillip W. Berman, hereby incorporated by reference. In this work the authors made use of the swarm of closely related envelope protein variants (quasispecies) from an extremely neutralization resistant clinical isolate in order to identify mutations that conferred neutralization sensitivity to antibodies in serum from HIV-1 infected individuals. The authors describe a virus with a rare mutation at position 179 in the V2 domain of gp120, where replacement of aspartic acid (D) by asparagine (N) converts a virus that is highly resistant to neutralization by multiple polyclonal and monoclonal antibodies, as well as antiviral entry inhibitors, to one that is sensitive to neutralization. Although the V2 domain sequence is highly variable, D at position 179 is highly conserved in HIV-1 and SIV and is located within the LDI/V recognition motif of the recently described alpha-4B7 receptor binding site. Our results suggest that the D179N mutation induces a conformational change that exposes epitopes in both the gp120 and gp41 portions of the envelope protein such as the CD4 binding site and the MPER that are normally concealed by conformational masking. These results suggest that D179 plays a central role in maintaining the conformation and infectivity of HIV-1 as well as mediating binding to alpha-4-beta-7 ($\alpha 4\beta 7$).

Additionally, the inventors have discovered (SC2009-117) certain protease cleavage sites in HIV glycoproteins occur in regions important for receptor binding and the binding of neutralizing antibodies. The inventors believe that HIV has developed a mechanism of immune escape involving incorporation of protease cleavage sites in regions of the molecule important for the formation and binding of neutralizing antibodies. It is believed that these sites cause critical epitopes to "self destruct" before they can stimulate effective immune responses. The inventors disclose methods that use inhibition of proteolysis at one or more of these cleavage sites to enhance the immunogenicity of HIV antigens. This is believed to be an entirely novel approach to treating and preventing HIV infection.

For the sake of ease of reference during prosecution, the applicant herein sets out a number of defined inventions in claim-like format, taken from the priority applications. These are not claims, although they have a claim format. The claims appear, as usual, at the end of the application.

Claims from SC2009-449

1. A method for screening drug candidates to identify a drug that prevents or attenuates the ability of HIV gp41 to mediate cell fusion with a CD4+ cell, the method comprising the following steps:
   a) providing a putative drug candidate
   b) providing a membrane-bound trimeric HIV gp41 trimer
   c) measuring the integrity of the hydrogen-bonded ring structure of the HIV gp41 trimer
   d) contacting the membrane-bound trimeric HIV gp41 with the putative drug candidate
   e) re-measuring the integrity of the hydrogen-bonded ring structure of the HIV gp41 trimer
   f) whereby degree of integrity of the hydrogen-bonded ring structure of the HIV gp41 trimer is proportional to the ability of HIV gp41 to mediate cell fusion with a CD4+ cell, and wherein the ability of the membrane-bound trimeric HIV gp41 to mediate cell fusion is reduced by disruption of the hydrogen-bonded ring structure of the HIV gp41 trimer.

2. The method of claim 1 wherein the membrane-bound trimeric HIV 41 is bound in the membrane of a virus, a pseudovirus, or a transfected cell.

3. The method of claim 1 wherein disruption of the hydrogen-bonded ring structure results in exposure of previously hidden epitopes which bind specifically with broadly neutralizing antibodies.

4. The method of claim 1 wherein the drug candidate is an antibody that binds specifically with an epitope of gp41 or a neutralizing antibody that targets gp120.

5. A method for increasing the immunogenicity of HIV envelope proteins the method comprising exposing the HIV virus to a drug compound that disrupts the hydrogen bonded ring structure between the N36 and C34 helices of gp41.

6. The method of claims 1 of 5 wherein the drug compound is a small molecule.

7. The method of claims 1 of 5 wherein the drug compound is an antibody.

8. The method of claims 1 of 5 wherein the drug compound is an inhibitor of CD4 binding selected from the group consisting of: 4E10, 2F5, Q665R, Q655K and Q655E.

9. The method of claim 1 or 5 wherein the drug compound is an inhibitor of HIV fusion binding and becomes a more effective inhibitor in the presence of a molecule that disrupts the disulfide bonded ring structure of gp41.

10. The method of claim 1 or 5 wherein the drug compound disrupts the hydrogen bonded ring structure between the N36 and C34 helices of gp41 and thereby exposes neutralizing epitopes which are recognized by endogenous or exogenous antibodies which then are able to neutralize the virus.

11. A method for screening for a drug that prevents or attenuates intracellular membrane fusion, the method comprising exposing the multimeric coiled coil bundle of the activated fusion complex to a drug candidate, wherein the fusion complex comprises a cellular hairpin membrane fusion protein, wherein disruption of one or more hydrogen bonds of the fusion complex is associated with prevention or attenuation of intracellular membrane fusion.

12. The method of claim 11 wherein the intracellular membrane fusion is associated with secretion of a hormone, cytokine or neurotransmitter.

13. A method of treating, attenuating or preventing HIV infection, the method comprising administering to a patient a drug compound which disrupts one or more intra-molecular or inter-molecular hydrogen bonds of the hydrogen-bonded ring structure of gp41 trimer, wherein disruption of the hydrogen-bonded ring structure is associated with attenuation or prevention of HIV infection.

14. A synthetic helical peptide wherein the peptide sequence binds specifically to at least a fragment of the N-36 helix of gp41, wherein the fragment includes the residue Q655 and wherein binding of the synthetic helical peptide to the N-36 helix disrupts hydrogen bonded ring structure between the N36 and C34 helices of gp41.

15. A peptidomimetic drug that binds specifically to helical sequences adjacent to the Q655 or Q553 residues of gp41, and disrupts of prevents the formation of a hydrogen bonded ring structure involving Q655 from the C34 helix and Q553 from the N36 helix.

16. The peptide or peptidomimetic compound of claim 14 wherein the compound binds to or interacts with the N36 or C34 helices of gp41 and thereby disrupts one or more intra-molecular or inter-molecular hydrogen bonds of the hydrogen-bonded ring structure of gp41 trimer, wherein disruption of the hydrogen-bonded ring structure is associated with attenuation or prevention of HIV infection.

17. The peptide or peptidomimetic compound of claim 14 wherein the compound disrupts one or more of the intra-molecular or inter-molecular hydrogen bonds stabilizing the multimeric coiled coil bundle in the activated fusion complex required for the fusion and release of synaptic vesicles.

18. The peptide or peptidomimetic compound of claim 14 wherein the compound disrupts one or more of the intra-molecular or inter-molecular hydrogen bonds stabilizing the multimeric coiled coil bundle structurally homologous to the N36 or C34 helix of HIV in the activated fusion complex required for the fusion and release of vesicles or granules containing pro-inflammatory proteins, cytokines, hormones, or vasoactive substances.

19. A method of attenuating or preventing HIV-1 infection comprising administering to a patient an effective amount of an agent which disrupts one or more intra-molecular or inter-molecular hydrogen bonds of the hydrogen-bonded ring structure of gp41 trimer, wherein disruption of the hydrogen-bonded ring structure makes HIV-1 susceptible to neutralization by the patient's antibodies which thereby attenuate or prevent HIV infection.

20. The method of claim 19 wherein the agent comprises a peptide or peptidomimetic compound.

21. A peptide having a formula selected from the group consisting of:

```
                                              (SEQ ID NO: 1)
X-YTSLIHSLIEESQNQ[*]EKNEQELLELDKWASLWNWF-Z (SEQ ID NO: 2)
X-YTNTIYTLLEESQNQ[*]EKNEQELLELDKWASLWNWF-Z (SEQ ID NO: 3)
X-YTGIIYNLLEESQNQ[*]EKNEQELLELDKWANLWNWF-Z (SEQ ID NO: 4)
X-YTSLIYSLLEKSQIQ[*]EKNEQELLELDKWASLWNWF-Z (SEQ ID NO: 5)
X-LEANISKSLEQAQIQ[*]EKNMYELQKLNSWDIFGNWF-Z,
and (SEQ ID NO: 6)
X-LEANISQSLEQAQIQ[*]EKNMYELQKLNSWDVFTNWL-Z
``` in which:
amino acid residues are presented by the single-letter code;
X comprises an amino group, an acetyl group, a 9-fluorenylmethoxy-carbonyl group, a hydrophobic group, or a macromolecule carrier group;
Z comprises a carboxyl group, an amido group, a hydrophobic group, or a macromolecular carrier group.
[*] represents any amino acid other than Q or N.

22. The peptide of claim 21 wherein [*] represents R, K, S, or E.

Claims from UCSC 2010-117

1. A vaccine formulation comprising an HIV envelope glycoprotein and a protease inhibitor.

2. The vaccine formulation of claim 1 wherein the protease inhibitor is a cathepsin.

3. The vaccine formulation of claim 2 wherein the cathepsin is human cathepsin L, S or D.

4. The vaccine formulation of claim 1 formulated with an excipient, carrier or adjuvant for use as a vaccine.

5. A vaccine formulation comprising an HIV envelope glycoprotein wherein one or more conserved cleavage sites of the HIV envelope glycoprotein is protected from protease cleavage by in vitro mutagenesis, and wherein the one or more conserved cleavage sites is selected from the cathepsin cleavage sites of MN-rgp120 and variants thereof.

6. The vaccine formulation of claim 5 wherein said vitro mutagenesis results in deletion, mutation, methylation or acetylation at a conserved cleavage site.

7. The vaccine formulation of claim 5 wherein the cathepsin cleavage sites are selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14 and SEQ ID NO:15.

8. A method for treatment or prevention of a viral infection, the method comprising administering to a subject the vaccine formulation comprising an HIV envelope glycoprotein wherein one or more conserved cleavage sites of the HIV envelope glycoprotein is protected from protease cleavage by in vitro mutagenesis resulting in deletion, mutation, methylation or acetylation, and wherein the one or more conserved cleavage sites is selected from the cathepsin cleavage sites of MN-rgp120 and variants thereof.

9. The method of claim 8 wherein the cathepsin cleavage sites are selected from the group consisting of SEQ ID NO:7, SEQ ID NO:8, SEQ ID NO:9, SEQ ID NO:10, SEQ ID NO:11, SEQ ID NO:12, SEQ ID NO:13, SEQ ID NO:14 and SEQ ID NO:15.

10. The method of claim 8 further comprising contemporaneously administering to a subject a protease inhibitor.

11. The method of claim 10 wherein the protease inhibitor is an inhibitor of a cathepsin.

12. The method of claim 11 wherein the protease inhibitor inhibits cleavage at the cathepsin cleavage sites of MN-rgp120.

13. A method for provoking an immune response in a mammal, the method comprising administering to said mammal an HIV envelope glycoprotein wherein one or more conserved cleavage sites of the HIV envelope glycoprotein is protected from protease cleavage by in vitro mutagenesis, and wherein the one or more conserved cleavage sites is selected from the cathepsin cleavage sites of MN-rgp120 as shown in Table 1, and variants and/or homologues thereof.

14. An isolated HIV polynucleotide encoding a protected virus envelope protein wherein one or more conserved cleavage sites of the HIV envelope glycoprotein is protected from protease cleavage by in vitro mutagenesis, and wherein the one or more conserved cleavage sites is selected from the cathepsin cleavage sites of MN-rgp120 and variants thereof.

15. The isolated polynucleotide of claim 14 wherein the conserved protease cleavage sites serve to inactivate epitopes recognized by neutralizing antibodies and are responsible for the lack of protective immune responses when used as a vaccine antigen.

16. The isolated polynucleotide of claim 14 wherein conserved cleavage sites that are recognized by serum or cellular proteases are deleted or inactivated by in vitro mutagenesis.

17. The isolated polynucleotide of claim 14 wherein in vitro mutagenesis of conserved cleavage sites protects the neutralizing epitopes from proteolytic degradation after parenteral injection.

18. The isolated polynucleotide of claim 14 wherein conserved protease cleavage sites located within epitopes recognized by neutralizing antibodies are deleted or inactivated by in vitro mutagenesis in such a way as to preserve the ability to bind neutralizing antibodies.

19. The isolated polynucleotide of claim 14 wherein the protease cleavage sites are specific for the antigen processing enzymes: cathepsin L, cathepsin S, or cathepsin D.

20. The isolated polynucleotide of claim 14 wherein the protease cleavage sites are specific for the serum protease thrombin, or the cell associated protease, tryptase, or the inflammation associated proteases such as elastase.

21. The isolated polynucleotide of claim 14 wherein the protease cleavage sites are specific for cathepsin B, K, or N.

22. The isolated polynucleotide of claim 14 wherein the protein consists of monomeric or oligomeric fragments of the HIV envelope protein gp160 such as gp120, gp140, or gp41.

23. The isolated polynucleotide of claim 14 wherein the protein consists of monomeric or oligomeric fragments of the influenza virus haemagglutinin (HA1/HA2) of any strain of influenza (e.g. H1N1).

24. The isolated polynucleotide of claim 14 wherein the protein consists of monomeric or oligomeric fragments of glycoprotein D from Herpes Simplex virus type 1 or 2.

25. The isolated polynucleotide of claim 14 wherein the protein consists of monomeric or oligomeric fragments of any virus envelope protein for cellular receptor binding.

Claims from UCSC2008-776

1. A method of analyzing intra-patient HIV virus variation to identify specific amino acid residues of the HIV envelope glycoproteins that affect sensitivity or resistance to broadly neutralizing antibodies, the method comprising the steps of:

i) providing a plurality of individual subjects who are seropositive for HIV antibodies and taking a biological sample from each subject, wherein the sample contains a multiplicity of HIV viruses with closely related genomes, wherein all subjects had been infected with HIV no more than one year before, and no less than one month before sample collection, ii) amplifying the env genes of the multiplicity of viruses to produce a library of different env genes, iii) cloning the amplified env genes into a plasmid shuttle vector that allows the plasmid to replicate in both bacteria and mammalian cells, iv) transforming bacterial cells with the shuttle vector and plating out the transformed bacterial cells onto a selective medium so that bacteria containing the shuttle vector plasmid containing the cloned envelope gene are selectable, v) selecting individual colonies at random and preparing plasmid DNA from each colony selected and analyzing the plasmid DNA by restriction digestion so as to identify plasmids containing the full length HIV envelope gene, which plasmids are used to produce pseudoviruses, vi) co-transfecting mammalian cells with the env-containing vector and simultaneously with a plasmid containing a defective HIV provirus plasmid where the coding sequence of the env gene has been replaced with the coding sequence of a marker gene, and culturing the co-transfected mammalian cells in a culture medium, to produce pseudovirions containing the amplified env genes, which pseudovirions are released into the cell culture medium, vii) harvesting the supernatant from the cell culture medium, wherein the supernatant contains pseudoviruses from the transfected cells, and wherein each supernatant contains a stock of pseudovirus resulting from a single purified expression plasmid, viii) testing the pseudovirion from the selected colonies to determine infectivity by culturing the pseudovirions with cells capable of being infected by HIV, wherein infectivity is measured by the degree of expression of the marker gene, ix) selecting pseudovirions that exhibit high infectivity, and testing the selected pseudovirions for sensitivity or resistance to neutralization by one or more broadly neutralizing antibodies, x) selecting pairs of plasmids from the same individual wherein each pair contains at least one neutralization resistant and at least one neutralization sensitive pseudovirus, xi) sequencing the envelope genes identified from sensitive and resistant pseudovirus pairs, xii) comparing the nucleotide sequences of the envelope genes of the neutralization sensitive and resistant pairs thereby identifying specific amino acid differences between the pairs and identifying polymorphisms that may affect sensitivity or resistance to neutralization by broadly neutralizing antibodies, xiii) at each amino acid residue that differs between the neutralization sensitive and neutralization resistant envelope genes, site-by-site replacement of amino acids from the is performed, substituting one amino acid at a time from neutralization sensitive sequence into the neutralization resistant sequence, xiv) each new construct is used to create a pseudotype virus which is tested for neutralization sensitivity so as to identify specific amino acid residues of the HIV envelope glycoproteins that affect sensitivity or resistance to broadly neutralizing antibodies.

2. The method of claim 1 wherein all subjects had been infected with HIV 109 days+/−58 days before specimen collection.

3. A vaccine composition comprising an HIV envelope glycoprotein wherein a glutamine residue at a site identifiable as being homologous to position 655 of SEQ ID NO:16 is replaced by a substitute amino acid such that the amino acid substitution disrupts an inter-molecular hydrogen-bonded ring structure between the N36 and C34 helices of the gp41 trimer.

4. The vaccine composition of claim 3 wherein possession of the HIV envelope glycoprotein confers greater neutralization sensitivity upon an HIV virus when it is exposed to 2F5 or 4E10 monoclonal antibodies, Enfuvirtide or CD4-IgG, than would be provided by another HIV envelope glycoprotein identical in all respects except for the substitution of the glutamine residue.

5. The vaccine composition of claim 3 or 4 wherein the substitute amino acid is arginine.

6. The vaccine composition of claim 3 or 4 wherein the substitute amino acid is Lysine, Serine or Glutamic acid.

7. The vaccine composition of claim 3, 4, 5 or 6 wherein the HIV envelope glycoprotein has at least 60% sequence identity to SEQ ID NO:16.

8. The composition of claim 3, 4, 5 or 6 wherein the HIV envelope glycoprotein comprises a fusion protein that includes a non-HIV signal sequence and a flag epitope.

9. The vaccine composition of claim 3, 4, 5 or 6 wherein the HIV envelope glycoprotein has had a furin cleavage site deleted.

10. The vaccine composition of claim 3 or 4 wherein the HIV envelope glycoprotein comprises a full length gp160 wherein a glutamine residue at a site identifiable as being homologous to position 655 of SEQ ID NO:16 is replaced by arginine.

11. The vaccine composition of claim 3, 4, 5 or 6 wherein the polypeptide comprises a truncated form of the envelope protein lacking the gp41 transmembrane domain and cytoplasmic tail.

12. A polynucleotide encoding an HIV envelope glycoprotein wherein a glutamine residue at a site identifiable as being homologous to position 655 of SEQ ID NO:16 is replaced by a substitute amino acid such that the amino acid substitution disrupts an inter-molecular ring structure between the N36 and C34 helices of the gp41 trimer.

13. The polynucleotide of claim 14 formulated in an vector as a DNA vaccine.

14. A method for inhibiting the fusion of an HIV virus to a host cell, the method comprising exposing the HIV virus to a compound that disrupts the hydrogen-bonded ring structure between the N36 and C34 helices of gp41.

15. A method for increasing the immunogenicity of HIV envelope proteins the method comprising exposing the HIV virus to a compound that disrupts the hydrogen bonded ring structure between the N36 and C34 helices of gp41.

16. The method of claim 14 or 15 wherein the compound is a small molecule.

17. The method of claim 14 or 15 wherein the compound is an antibody.

BRIEF DESCRIPTION OF THE FIGURES
(SC2009-449)

FIG. 1. Mutation of neutralization resistant clone 022 from subject 108060. Top Panel. Amino acids from neutralization-resistant clone 022 are shown as open rectangles. Amino acids from neutralization-sensitive clone 024 were inserted by in vitro mutagenesis, and are shown as shaded rectangles. Bottom Panel Schematic showing the position of the Q655R mutation in relation to the entry inhibitor Fuseon (or T-20 peptide), the MPER, and peptides recognized by the broadly neutralizing monoclonal antibodies 2F5 and 4E10. The locations of gp41 structural elements are shown as follows: shaded boxes for the hydrophobic fusion domain (FD), the transmembrane domain (TMD), and the MPER. Sequences defining the C34 and N36 helices are shown as open rectangles (Sequences are as follows: C34 peptide, SEQ ID NO:36; Fuseon (T-20), SEQ ID NO:37; and MPER, SEQ ID NO:38).

BRIEF DESCRIPTION OF THE FIGURES (SC 2010-117)

Figure 7:
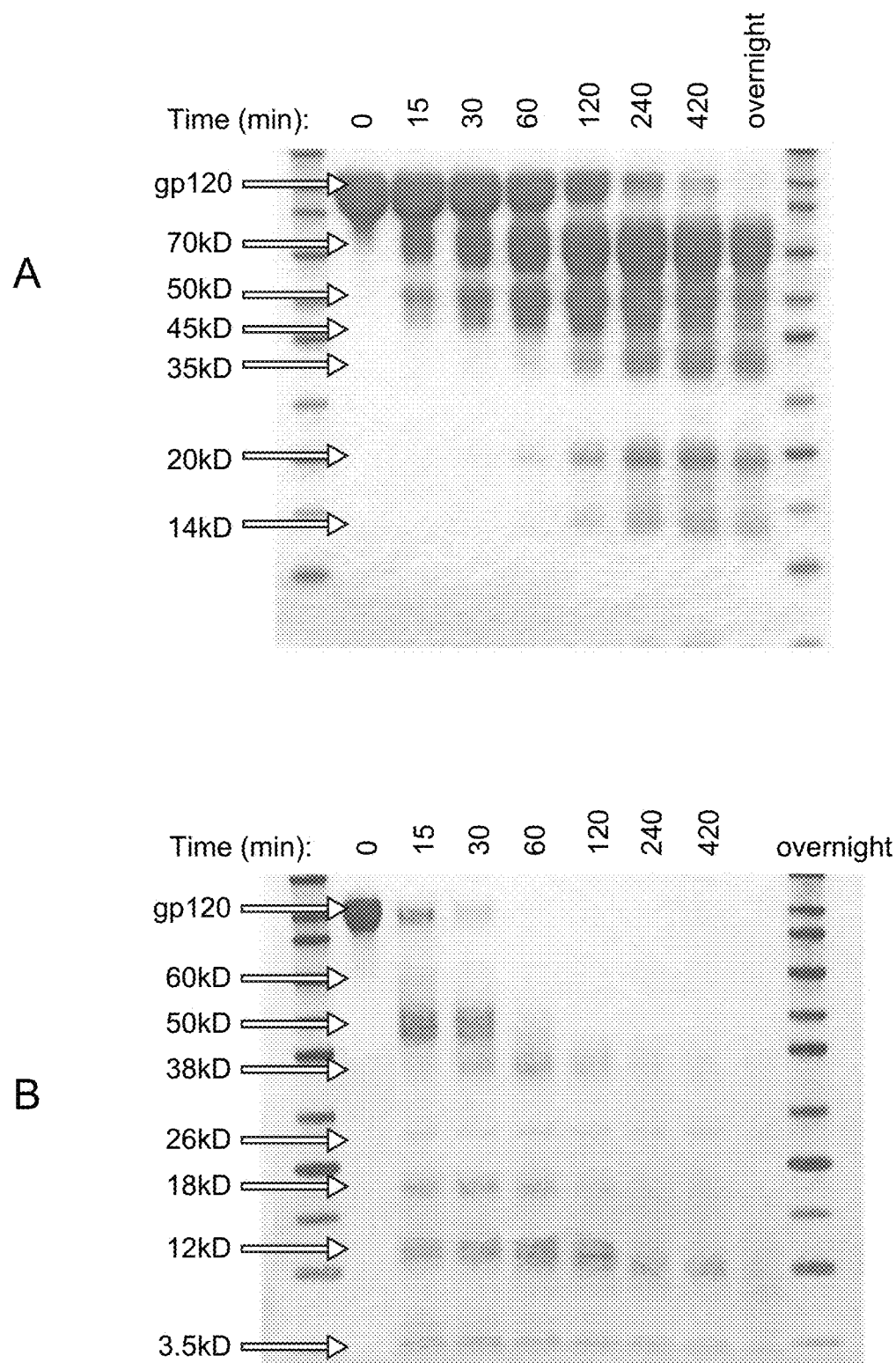
Figure 7:
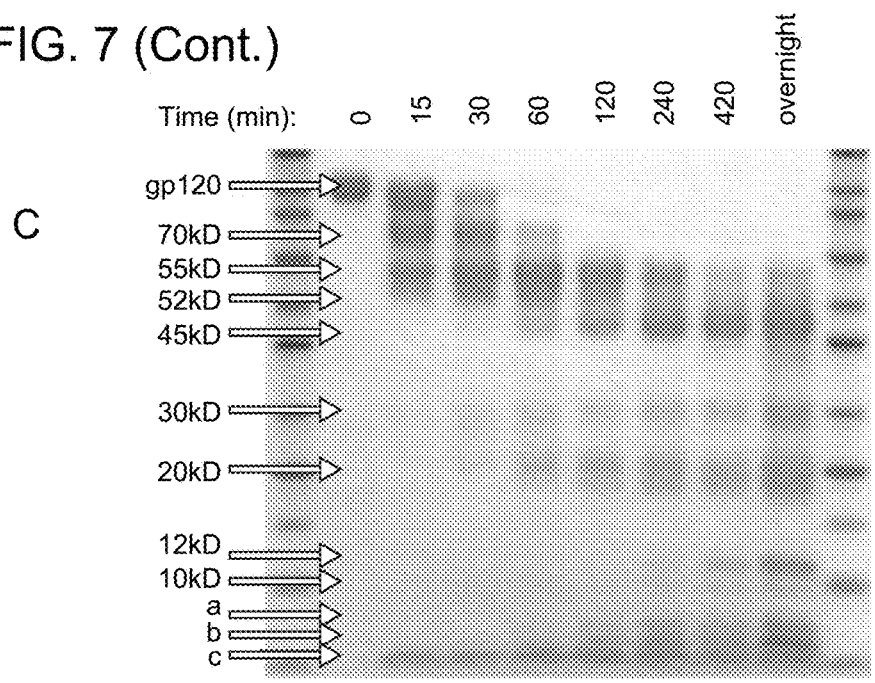

FIG. 7. Cathepsin digestion of MN-rgp120. MN-rgp120 was digested with either cathepsin L (panel A), cathepsin S (panel B), or cathepsin D (panel C). At the indicated times, samples were removed, the digestion was stopped by the addition of liquid nitrogen, and prepared for SDS-PAGE analysis. Bands were visualized by Coomassie blue staining. The mobilities of the fragments identified are shown in the outside lanes.

Figure 8:
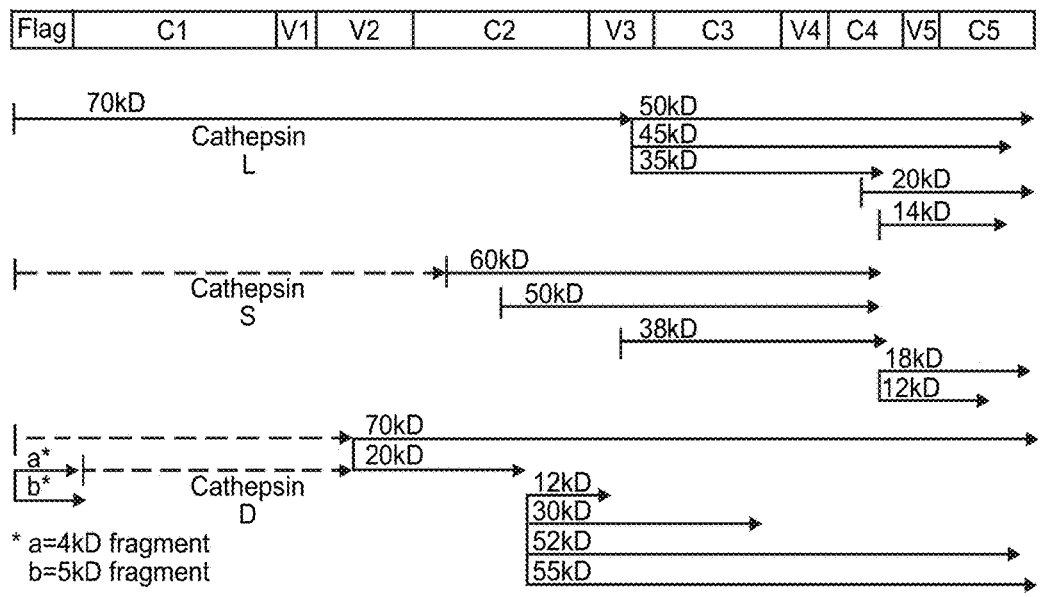

FIG. 8. Diagram of MN-rgp120 fragments generated by cathepsin digestion. MN10-rgp120 was digested with cathepsin L, S, or D and the resulting fragments were purified and analyzed by Edmund sequence degradation. Solid lines indicate peptides that were resolved by polyacrylmide gel electrophoresis and characterized by N-terminal sequence analysis. Dashed lines indicate the location of peptides deduced from mobility and sequence analysis, but not recovered.

Figure 9:
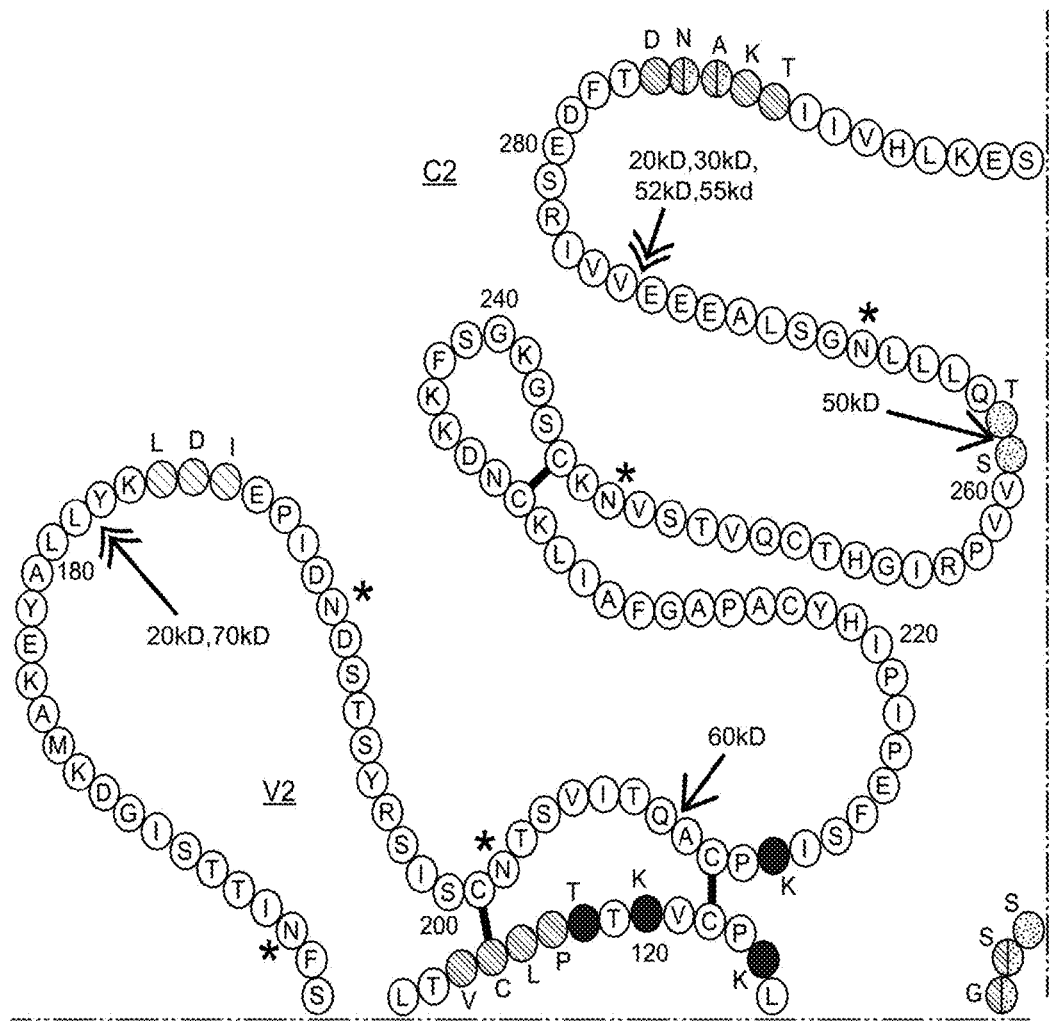
Figure 9:
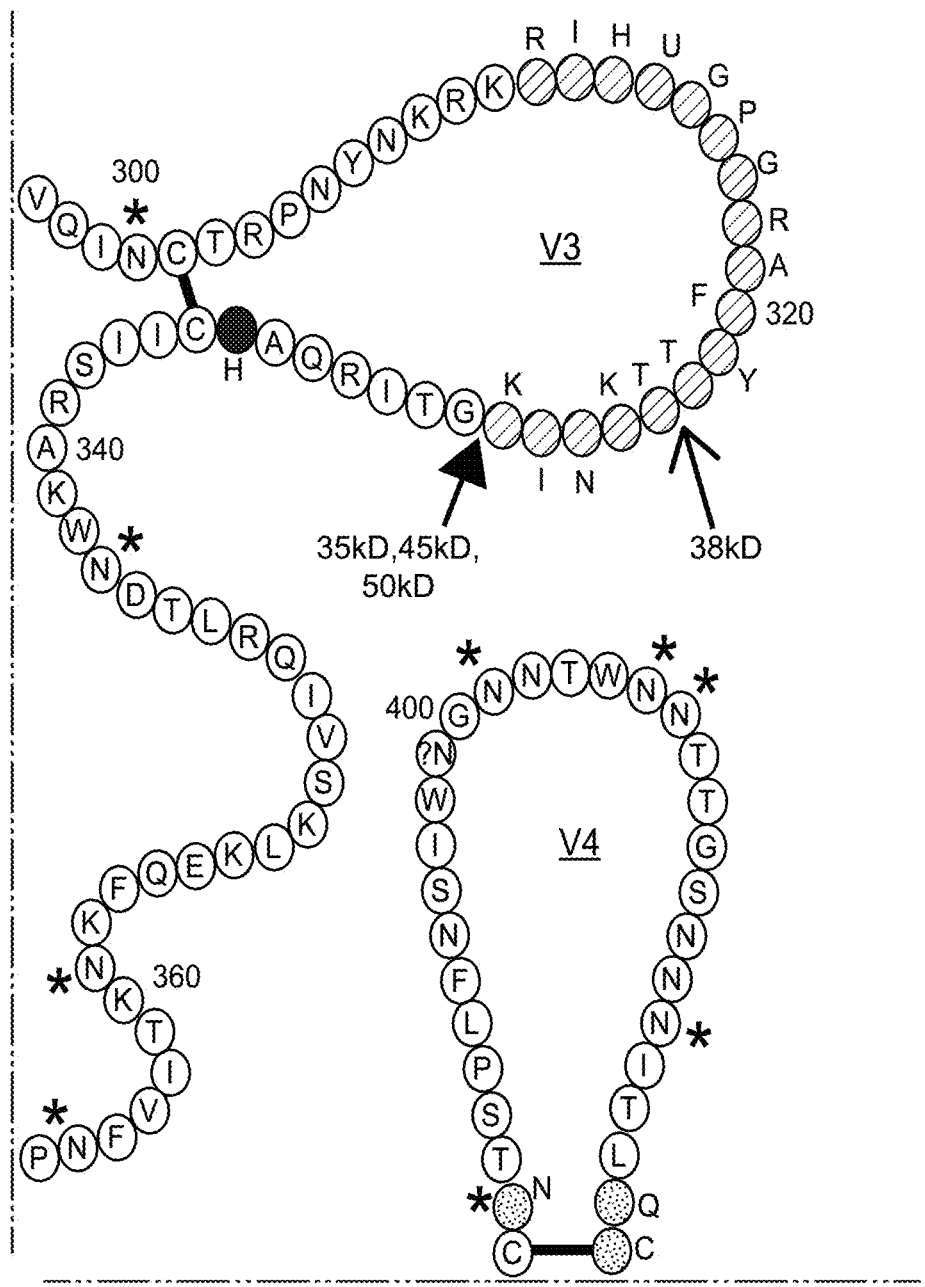
Figure 9:
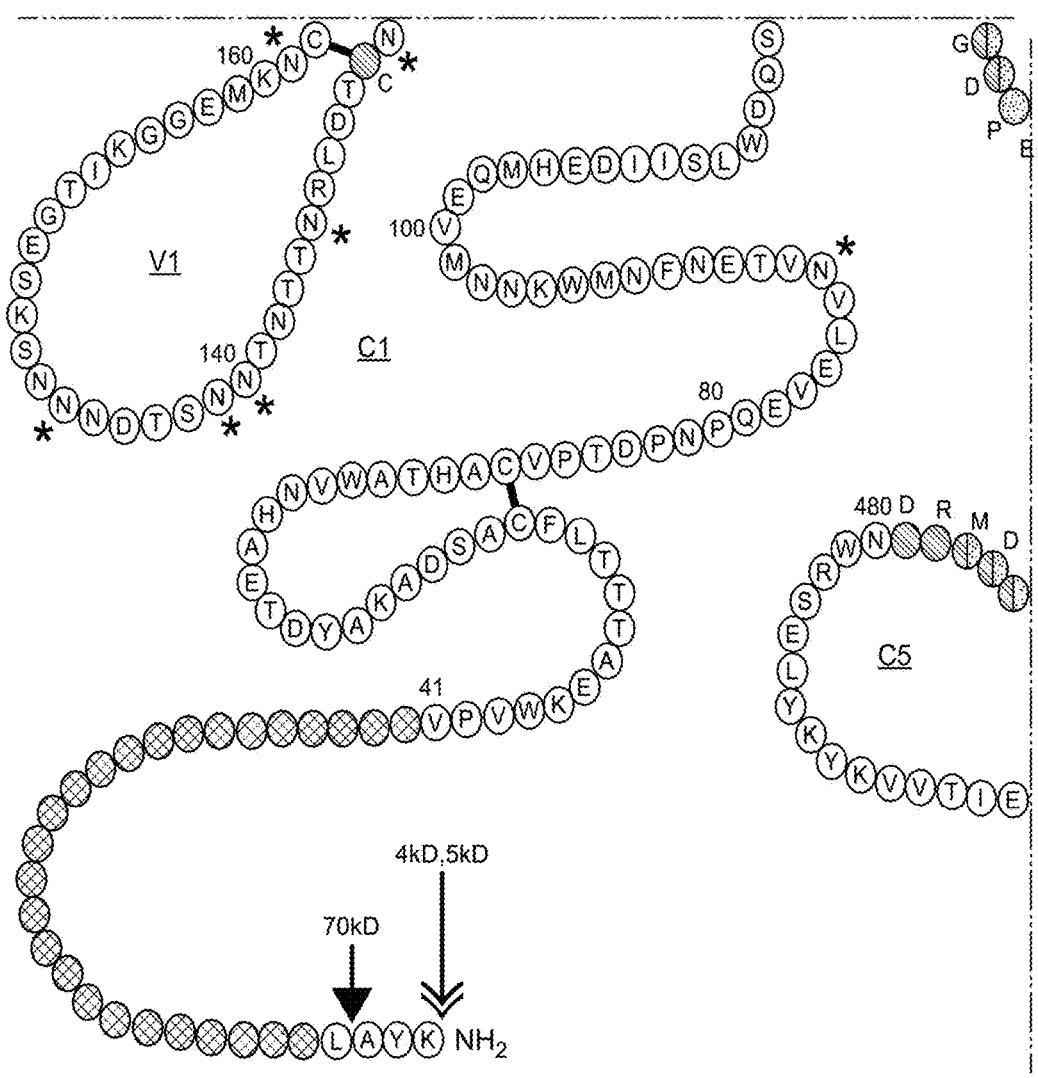
Figure 9:
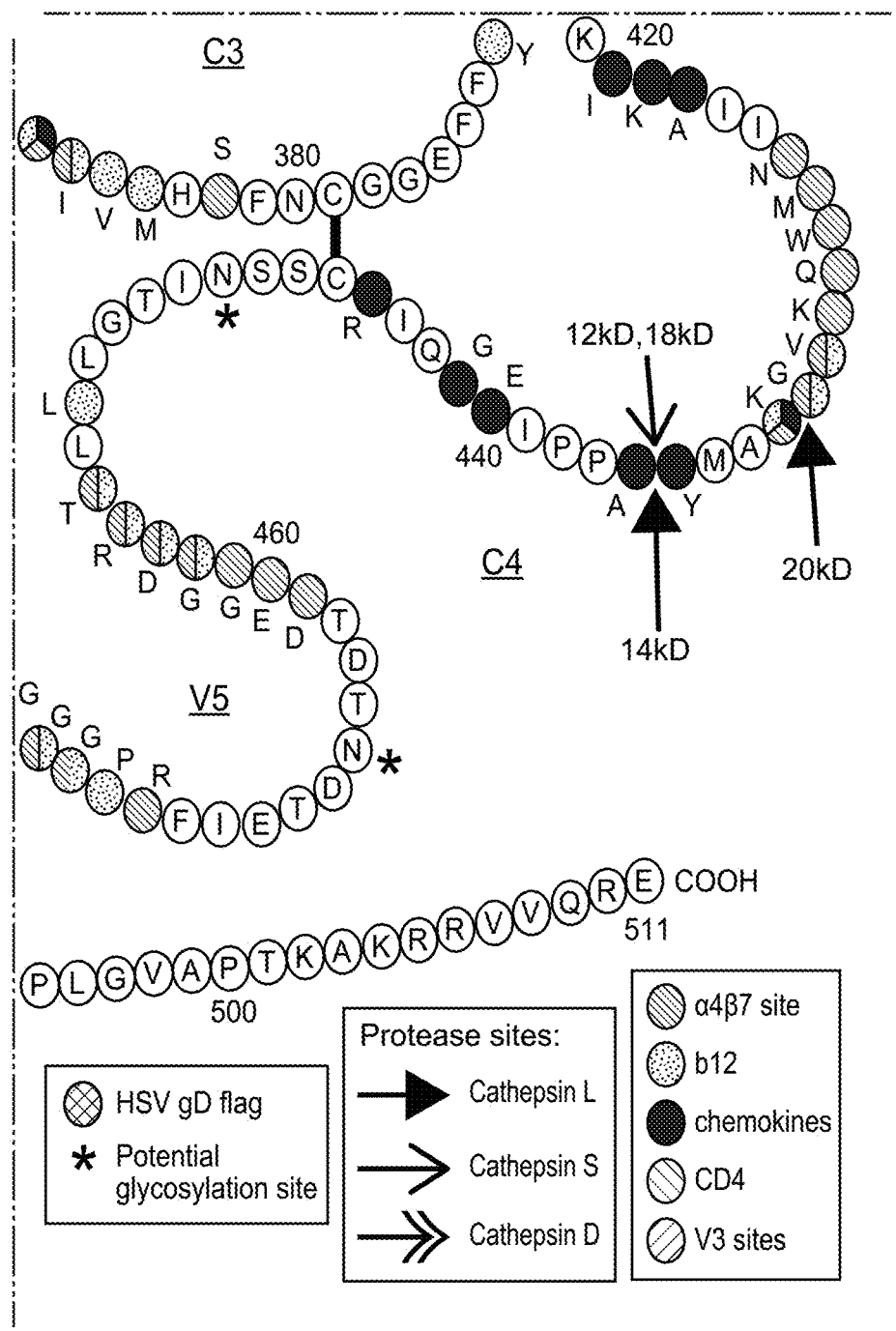

FIG. 9. Location of cathepsin L, S, and D cleavage sites on MN-rgp120 disulfide bonded schematic. Cathepsin L, S and D cleavage sites in MN-rgp120 were identified by Edman sequence degradation and located onto the disulfide bonded structure of gp120 determined by Leonard et al. 1990 (50). Cathepsin L sites are indicated by a closed arrow, cathepsin S sites are indicated by a line arrow, and cathepsin D sites are indicated by an open arrow. The location of amino acid residues reported to be important for the binding of CD4, chemokine receptors, and the α4β integrin are indicated by residues shaded red, dark blue, and light blue, respectively. The location of amino acids known to be important for the binding of the broadly neutralizing antibody, b12, and neutralizing antibodies to the V3 domain are indicated by amino acids shaded green and purple, respectively. Residues with two or more colors indicate amino acids involved in the binding of two or more receptors of neutralizing monoclonal antibodies. The figure was created based on results from Kwong et al.; Zhou et al., Rizzuto et al.; Decker et al. and Arthos et al. (2). The numbering provided is based on the sequence of gp120 from the MNGNE isolate of HIV (SEQ ID NO:22).

Figure 10:
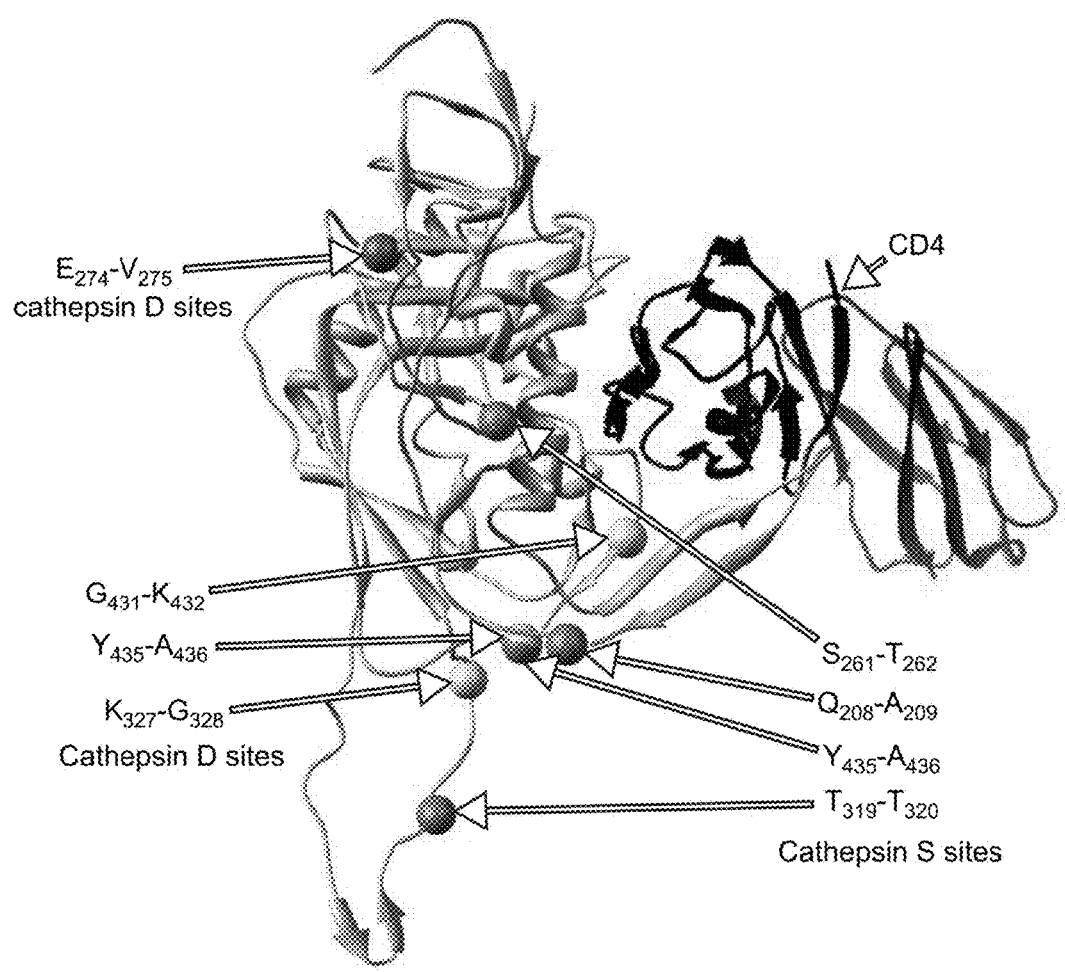

FIG. 10. Location of cathepsin L, S and D cleavage sites on 3-D structure of gp120 bound to CD4. The locations of cathepsin cleavage sites were located on the 3-dimensional structure of gp120 based on the structure of a gp120 fragment complexed with CD4 described by Huang et al. 2005. Cathepsin L sites are indicated in green; cathepsin S sites in red; and cathepsin D sites in blue. The structure of CD4 is shown in yellow. Numbering is based on the sequence of MN-rgp120.

Figure 11:
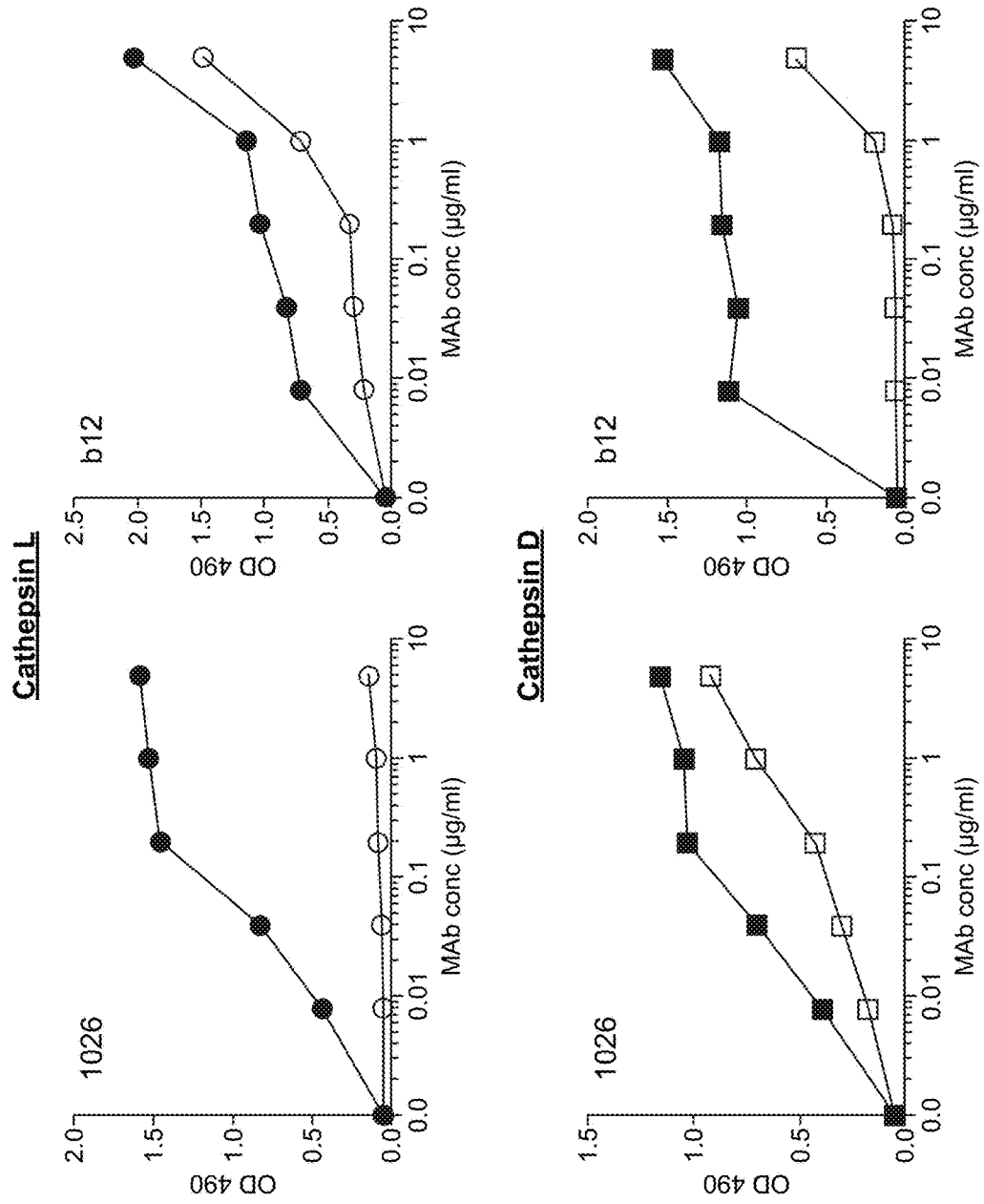
Figure 11:
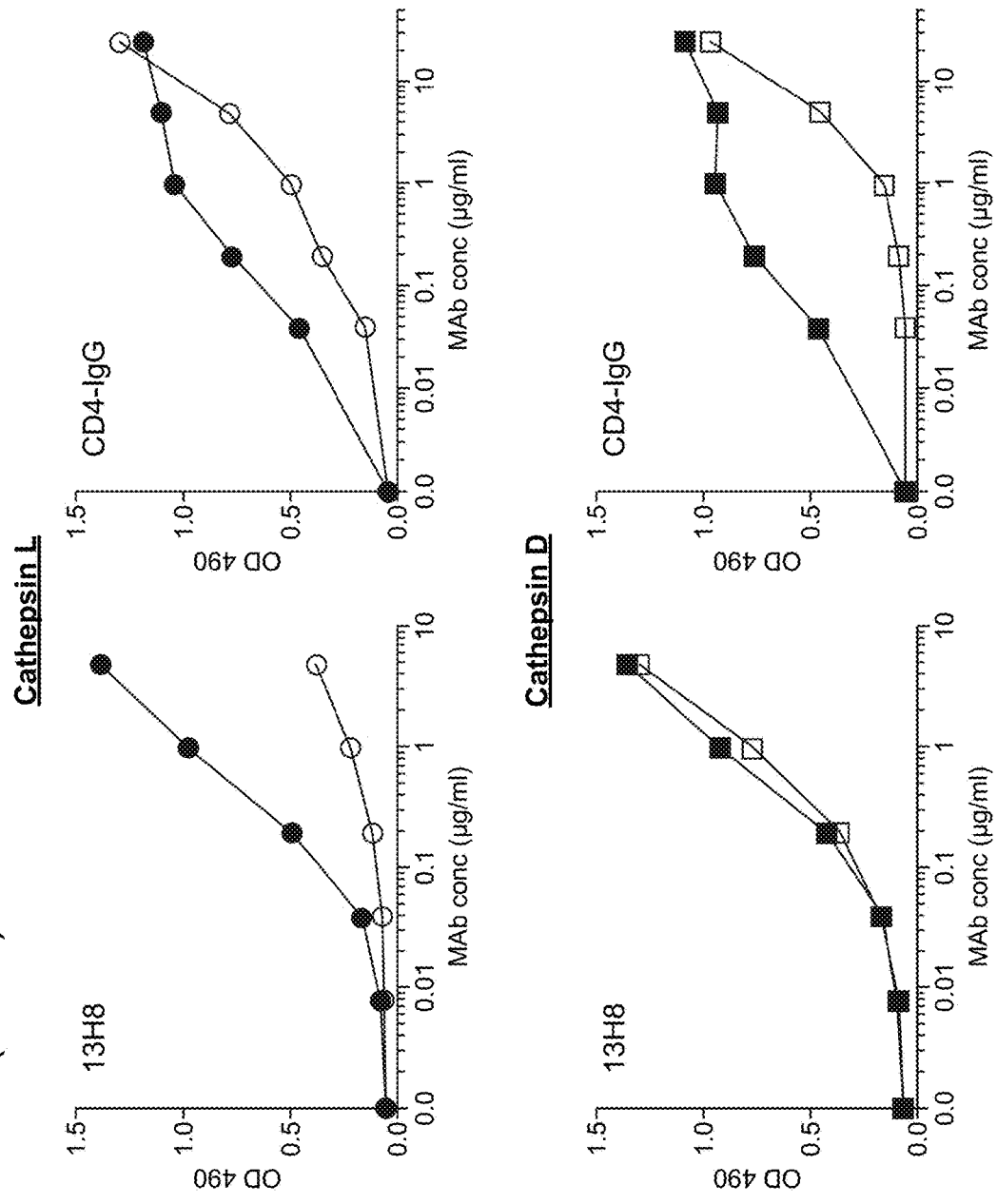

FIG. 11. Antibody binding to cathepsin L and D treated gp120. Purified MN17 rgp120 was treated with either cathepsin L or cathepsin D and captured onto the sur18 face of microtiter plates coated with a polyclonal antibody, D7324, directed to the C ter19 minus of gp120. Monoclonal antibodies were incubated with the gp120 coated microtiter plates and binding was determined by ELISA. Closed symbols indicate the binding to untreated gp120; open circles represent binding to cathepsin-L treated gp120; open squares indicate binding to cathepsin-D treated gp120.

Figure 12:
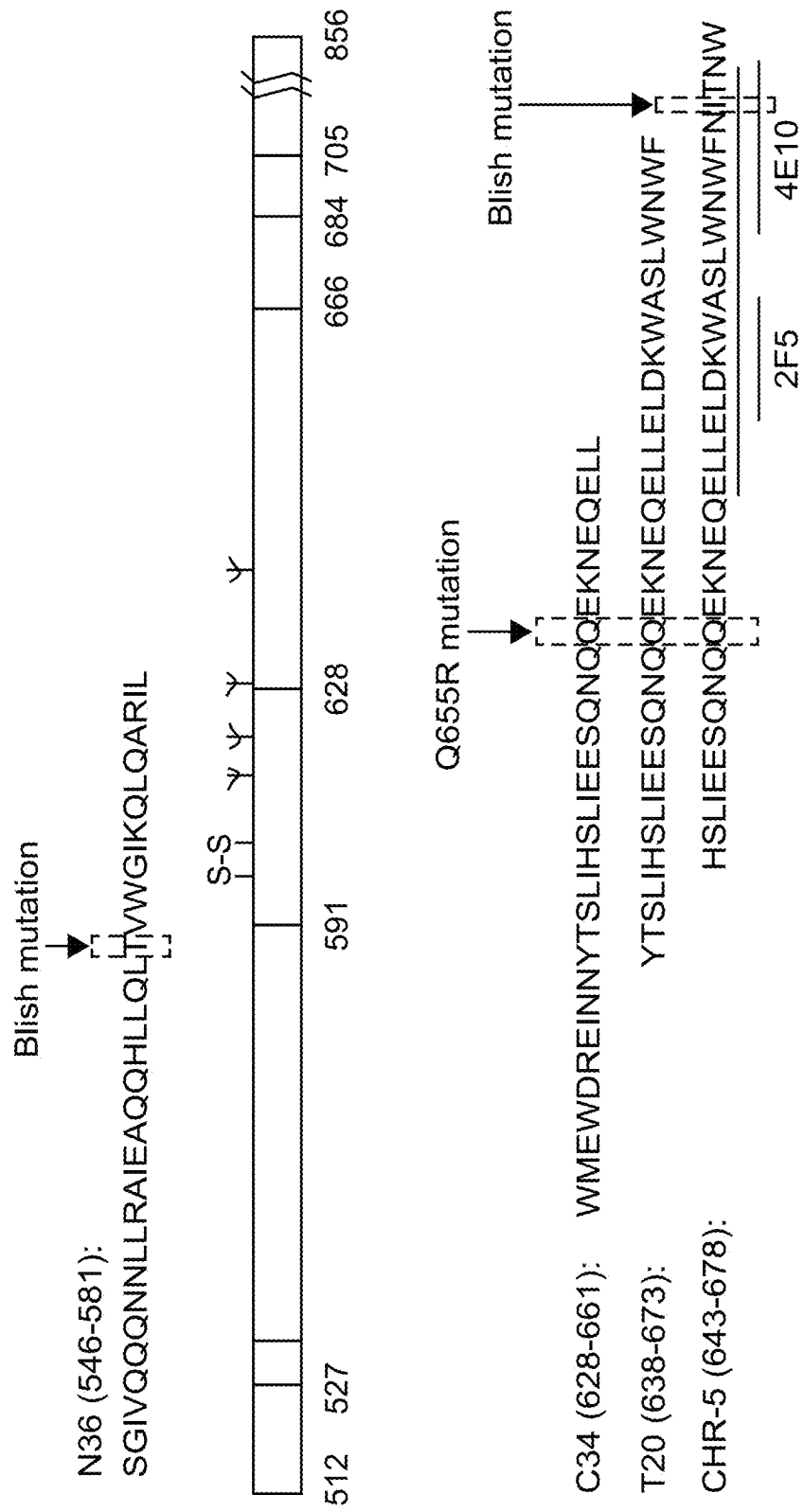

FIG. 12. (from SC-2008-776): Gp41 Functional Domains and Comparison of Sequences of Functionally Significant Regions of the N36 and C34 Helices (Sequences are as follows: N36 (546-581), SEQ ID NO:41; C34 (628-661), SEQ ID NO:36; T-20 (638-673), SEQ ID NO:1; and CHR-5 (643-678), SEQ ID NO:42).

FIG. 13. Alignment of predicted and observed cathepsin L, S and D cleavage sites. Reference sequences for gp120 were obtained from the Losa Alamos HIV database. Env sequences from clades A, C, D and E (crf A/E) as well as reference sequences for chimpanzee isolates of HIV and SIV were aligned with the sequences of prototypic Glade B MN and HXB2 strains of HIV using the MAFFT sequence alignment program. Numbering is provided with reference to the MN strain. Sequences shown begin with the mature amino terminus of gp120. Predicted and observed cathepsin L cleavage sites are indicated by open bars and closed bars respectively. Cathepsin L cleavage sites are indicated in green, cathepsin S sites in red, and cathepsin D sites in blue. The full names of the aligned sequences are: MN (MN-rgp120, the sequence corresponds to residue 26 to 507 of SEQ ID NO:22); HXB2 (the sequence corresponds to residue 27 to 507 of SEQ ID NO:23); A1.KE (A1.KE.94.Q23_17, the sequence corresponds to residue 26 to 492 of SEQ ID NO:24); A1.UG (A1.UG.92.92UG037, the sequence corresponds to residue 26 to 496 of SEQ ID NO:25); C.ET (CET.86.ETH2220, the sequence corresponds to residue 26 to 491 of SEQ ID NO:26); C.IN (C.IN.93.93IN101, the sequence corresponds to residue 26 to 503 of SEQ ID NO:27); D.TZ (D.TZ.01.A208, the sequence corresponds to residue 26 to 498 of SEQ ID NO:28); D.UG (D.UG.94.94UG114, the sequence corresponds to residue 26 to 490 of SEQ ID NO:29); AE.T93 (AE.TH.93.93.TH051, the sequence corresponds to residue 26 to 499 of SEQ ID NO:30); AE.T90 (AE.TH.90.CM240, the sequence corresponds to residue 26 to 496 of SEQ ID NO:31); CPZ.05 (CPZ.CM.05.SIVcpzMT145, the sequence corresponds to residue 26 to 485 of SEQ ID NO:32): CPZ85 (CPZ.US.85.CPZUS, the sequence corresponds to residue 21 to 473 of SEQ ID NO:33); SVV51 (SIV.US.MAC251, the sequence corresponds to residue 17 to 518 of SEQ ID NO:34); SIV39.US.MAC239, the sequence corresponds to residue 17 to 516 of SEQ ID NO:35).

FIG. 14 shows three pairs of sequences from neutralization sensitive and neutralization resistant viruses. The sequences shown are envelope sequences from: subject 108060 (Panel A: p1.10848_c2 Resistant, SEQ ID NO: 43; Panel B: p1.10848_c11 Sensitive, SEQ ID NO: 44); subject 108051 (Panel C: 108051_c6 Sensitive, SEQ ID NO: 45; Panel D: p1. 108051_c5 Resistant, SEQ ID NO: 46); and subject 108060 (Panel E: p1. 108060_c22 Resistant, SEQ ID NO: 47; Panel F: p1. 108060_c24 Sensitive, SEQ ID NO:48).

GENERAL REPRESENTATIONS CONCERNING THE DISCLOSURE

This specification incorporates by reference all documents referred to herein and all documents filed concurrently with this specification or filed previously in connection with this application, including but not limited to such documents which are open to public inspection with this specification.

Definitions

The terms "amino acid" and "amino acid sequence" refer to an oligopeptide, peptide, polypeptide, or protein sequence, or a fragment of any of these.

"Amplification" relates to the production of additional copies of a nucleic acid sequence e.g., using polymerase chain reaction (PCR).

The term "antibody" refers to intact immunoglobulin molecules as well as to fragments thereof, such as Fab, F(ab')$_2$, and Fv fragments, which are capable of binding an epitopic determinant.

The term "similarity" refers to a degree of complementarily. There may be partial similarity or complete similarity. The word "identity" may substitute for the word "similarity." A partially complementary sequence that at least partially inhibits an identical sequence from hybridizing to a target nucleic acid is referred to as "substantially similar."

The phrase "percent identity" as applied to polynucleotide or polypeptide sequences refers to the percentage of residue matches between at least two sequences aligned using a standardized algorithm such as any of the BLAST suite of programs (e.g., blast, blastp, blastx, nucleotide blast and protein blast) using, for example, default parameters. BLAST tools are very commonly used and are available on the NCBI web site.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool set at default parameters. Such a pair of polypeptides may show, for example, at least 50%, at least 60%, at least 70%, at least 80%, at least 86%, at least 90%, at least 95%, or at least 98% or greater sequence identity over a certain defined length of one of the polypeptides.

Detailed Description of the Invention (SC2009-449 PCT)

Described is a new way to identify mutations that effect sensitivity and resistance to virus neutralization by anti-HIV antisera. Some of these mutations occur in previously undescribed sites critical for preservation of the structure and function of HIV. One of these sites appears to affect a previously overlooked hydrogen bonded ring structure in the trimeric form of the HIV envelope protein, gp41. This novel structure is formed by oligomeric interactions between the C34 and N-36 helices of gp41 and is located close to the C-terminus of the domains that undergo massive rearrangement to form the 6 helix bundle required for virus entry and fusion. Disruption of this structure by naturally occurring or experimental mutations renders the virus much more sensitive to neutralization by antibodies. Disclosed is the development of and the use of small molecule drugs that target this site which interfere with virus fusion in such a way as to prevent, or lower the efficiency of fusion and therefore virus infection.

A mutation mapped and herein disclosed is located in the middle of a sequence that forms the basis of a commercially marketed HIV antiviral drug, FUZEON. The structure identified allows for the rational design of new compounds targeting the same area as FUZEON, but which work by a different mechanism.

The molecular structures responsible for HIV fusion have been conserved through evolution, and homologous structures are present in other viruses, such as influenza, and vesicle proteins required for the export and secretion of a number of important molecules (e.g. hormones, cytokines, an neurotransmitters). Targeting weak, hydrogen bonded interactions of the type that we have identified may provide a new approach to the development of small molecule therapeutics that disrupt such structures.

Disclosed is a new method ("swarm analysis") used to identify mutations that confer sensitivity and resistance to neutralization by bNAbs (broadly neutralizing antibodies) in polyclonal HIV+ sera with broad neutralizing activity. The method takes advantage of the swarm of closely related virus variants that occur in each HIV-infected individual to establish panels of envelope proteins that differ from each other by a limited number of mutations causing amino acid substitutions (1-3%). By studying the effect of these mutations in swarms of viruses from the same individual, we can identify specific amino acids that affect sensitivity and resistance to neutralization by HIV+ sera. We have used this method to identify a novel structural element in the gp41 fragment of the HIV envelope glycoprotein that appears to stabilize the oligomeric 6 helix bundle in the HIV-1 fusion apparatus. This oligomeric 6 helix structure is important in promoting fusion of the viral membrane to membrane of the host cell being infected. Mutations that affect this structure confer sensitivity or resistance to virus neutralization, i.e., they make the virus more or less sensitive to neutralizing Abs such as broadly neutralizing antibodies.

The studies described made use of a large collection of clinical specimens from new and recent HIV infection collected in the course of a Phase 3 clinical trial (VAX004) of a candidate HIV-1 vaccine, AIDSVAX B/B (Flynn N M, Forthal D N, Harro C D, Judson F N, Mayer K H, Para M F; "Placebo-controlled phase 3 trial of a recombinant glycoprotein 120 vaccine to prevent HIV-1 infection." The Journal of infectious diseases 2005; 191:654-65). This collection of specimens is unique in that they were obtained within six months of infection and are representative of viruses currently circulating in North America. Transmission of HIV-1 involves a genetic bottleneck where, out of the myriad of genetic variants in each HIV infected donor, only a single homogeneous variant of HIV-1 successfully replicates in the recipient. This variant replicates to very high titers in the first days and weeks after HIV-1 infection and eventually starts to mutate in response to error-prone reverse transcription to generate a swarm of closely related variants (Richman et al., 2003; Wei et al., 2003). The swarm of viruses further diversifies in response to selective pressures imposed by both cellular and humoral antiviral immune responses and in response to drug therapy. Virus variation, driven by the relentless error-prone reverse transcription and selection by the immune system, occurs throughout the course of HIV infection, and is perhaps the greatest challenge in the development of vaccine and therapeutic products. The applicants reasoned that by studying viruses from early infections, sequence variation would be limited compared to sequences collected at later times. The analysis described is made possible by high throughput, automated methods for virus infectivity and neutralization assays as well as systems for the construction and analysis of pseudotype viruses (Schweighardt et al., 2007, J Acquir Immune Defic Syndr 46:1-11 and Whitcomb et al., 2007, Antimicrob Agents Chemother 51:566-75) with defined amino acid sequences. This technology allows for the accurate and efficient analysis of thousands of individual envelope glycoproteins for sensitivity/resistance to neutralization by panels of HIV+ sera. These analyses provide particular insight into the strategies employed by HIV to evade the immune response and can guide the development of a new generation of HIV vaccine antigens, one or more of which are described herein.

Experimental Methods and Results

Figure 2:
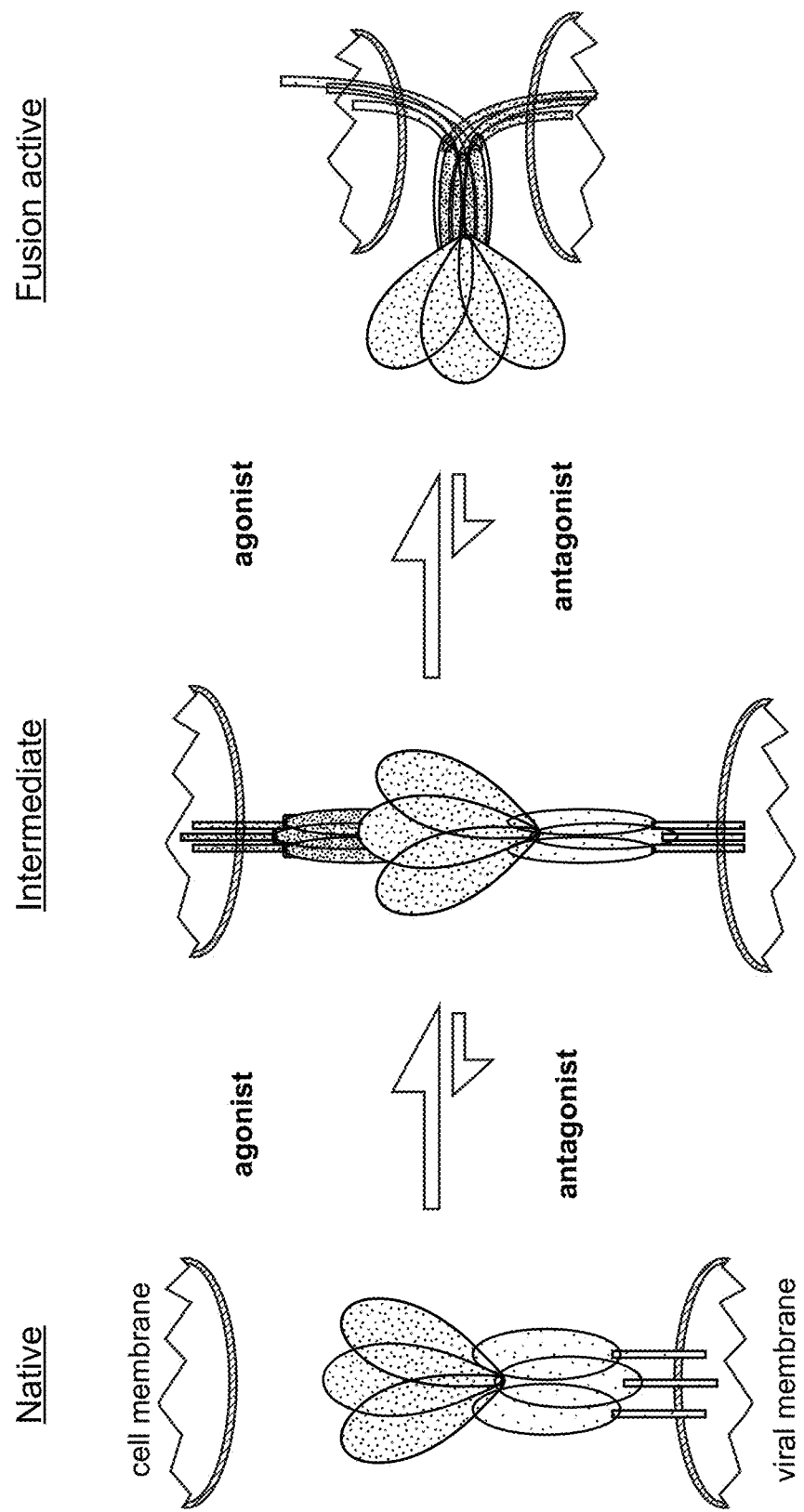
FIG. 2. Conformational transitions involved formation of the fusion active 6 helix bundle in gp41. Binding of the HIV envelope protein gp120 by CD4 and either of the CXCR4 or CCR5 chemokine receptors (agonists) triggers the formation of the pre-hairpin intermediate structure. This transition is inhibited by antagonists such as CD4 blocking antibodies found in HIV+ sera and the CD4 blocking MAb, b12. The transition from the pre-hairpin intermediate to the fusion active 6 helix bundle structure is facilitated by cooperative interactions between the N-36 and C34 helices and the hydrogen bonded ring structure involving Q655. This transition is antagonized by bNAbs in HIV+ sera, MAbs such as 2F5 and 4E10, the antiviral drug, FUZEON, and mutations such as Q655R, Q655K, Q655S, and Q655E that destabilize the hydrogen bonded ring structure of the 6 helix bundle.
Figure 3:
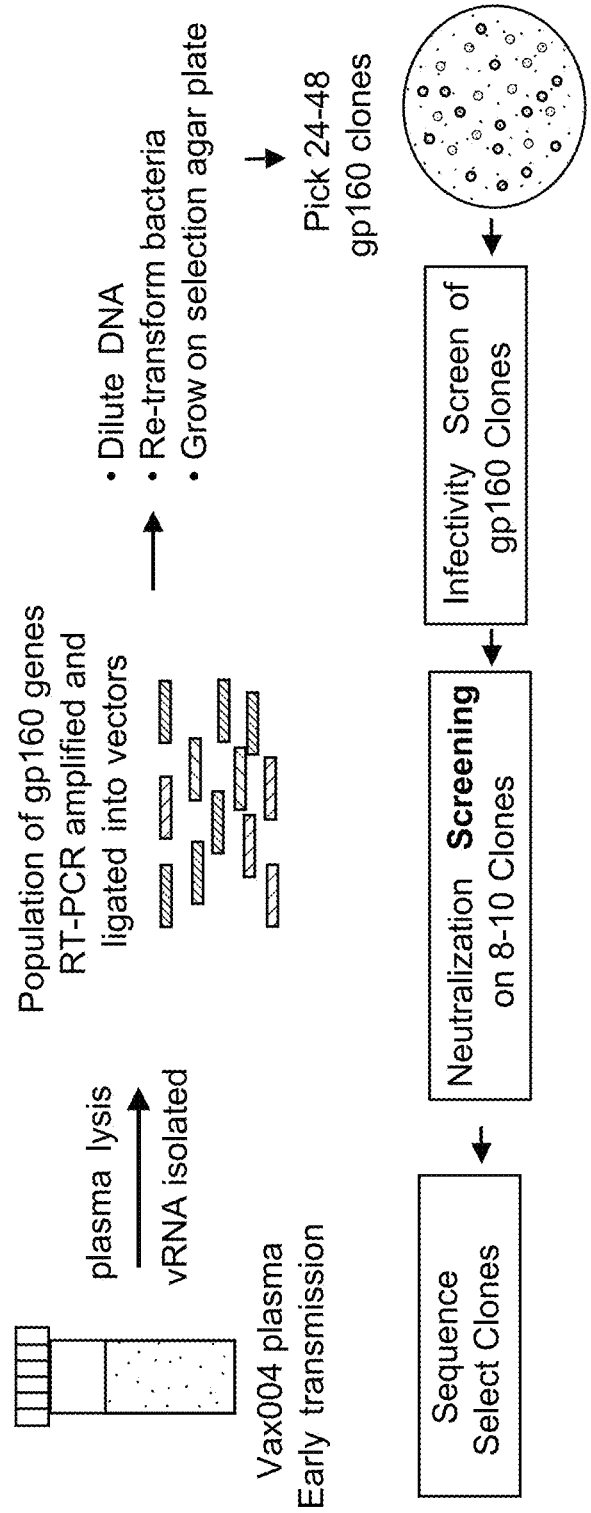
FIG. 3. shows the method of swarm analysis. Swarm analysis of quasi-species from one individual infected with HIV, for the identification of mutations that confer sensitivity and resistance to broadly neutralizing antibodies.
Figure 4:
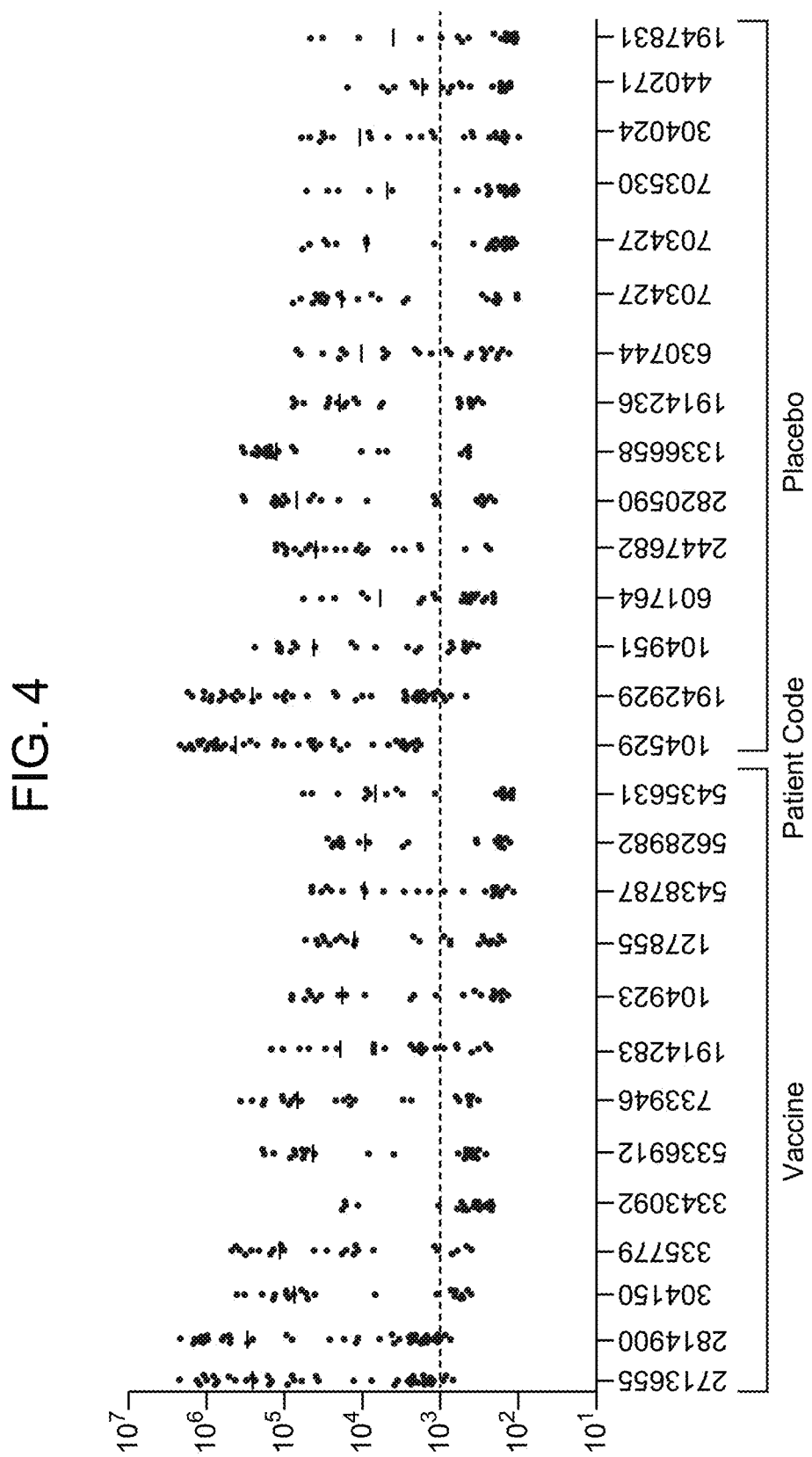
FIG. 4. shows the results of the infectivity screen used to identify env clones used in the neutralization assay. Infectivity screen to identify envelope clones for use in neutralization assay. 24-48 envelope genes are isolated from each subject and used to construct pseudoviruses. Viruses are screened for infectivity on CD4+ cell lines expressing either the CCR5 or CXCR4 chemokine receptors to determine the tropism of each envelope clone.

Cryopreserved plasma was obtained from 28 randomly selected individuals who became infected with HIV during the course of the VAX004 clinical trial. The specimens were all collected from the first post-diagnosis blood draw, with a mean estimated time post infection of 109+/−58 days. Populations of gp160 genes were amplified from each patient plasma by RT-PCR and ligated into a plasmid expression vector to create libraries of envelope genes (Schweighardt et al., 2007). A diagram that describes the swarm analysis strategy is provided in FIG. 3. The plasmid libraries from each individual were then used to create pseudoviruses for neutralization assays. Because HIV infection is known to result in a high frequency of defective envelope genes, it was necessary to screen individual clones for infectivity prior to performing virus neutralization assays. For this purpose 24-48 individual colonies were selected from each library, and the plasmids from each used to construct pseudotype viruses for initial screening in infectivity and receptor tropism assays. Data from these infectivity studies on a cell line (CCR5/CD4/U89) expressing CD4 and CCR5 are provided in the supplemental information (FIG. 4). Based on the results of this assay, sets of 10 pseudotype viruses with robust infectivity were selected from each individual for use in a pseudotype virus neutralization assay. These 280 pseudotype viruses were then tested for sensitivity/resistance to neutralization by a panel of four standard HIV+ sera (Z23, Z1679, Z1684, and N16) known from previous studies to possess bNAbs. The results of these studies provided insights into both virus variation and variation in the specificity of bNAbs in different HIV+ sera. Overall three different neutralization phenotypes were observed in the viruses. We found that one individual (1/28) possessed viruses that were extremely resistant to neutralization, such that none of the 10 clones were sensitive to neutralization by any of the HIV+ sera. Conversely we found that some individuals (3/28) possessed viruses that were extremely sensitive to neutralization, such that almost all of the clones were sensitive to neutralization by all four HIV+ sera. However, in the majority of the individuals (24/28), we found a mixture of neutralization sensitive and resistant clones.

When the activities of the four HIV+ sera were compared, differences in the apparent potency and specificity of the bNAbs were observed. For example in some cases (e.g. 108059) only one of the four sera was able to neutralize the clones from a particular individual (Table 1A). This result suggested that serum Z23 possessed at least one population of neutralizing antibodies that was missing or under-represented in the antibodies from the other HIV+ sera. One particularly interesting pattern of neutralization was found in subject 108060 (Table 1B) where all four HIV+ sera neutralized three of the ten clones. These results raised the possibility of a mutational difference between clones that affected a population of neutralizing antibodies common to all four HIV+ sera. Because we expected sequence variation between clones from the same individual to be minimal, we reasoned that comparison of the sequences between the neutralization sensitive and resistant variants would allow us to identify the mutation that conferred neutralization sensitivity.

Further examination of the dataset revealed that 7/28 individuals exhibited a similar pattern of neutralization sensitivity, where at least one clone was sensitive to neutralization by all four HIV+ sera and at least one clone was resistant to all four HIV+ sera. Based on this observation, we selected pairs of viruses (one neutralization sensitive, and the other neutralization resistant) from seven of the 28 individuals with the largest differences in neutralization titers for further analysis.

Figure 5:
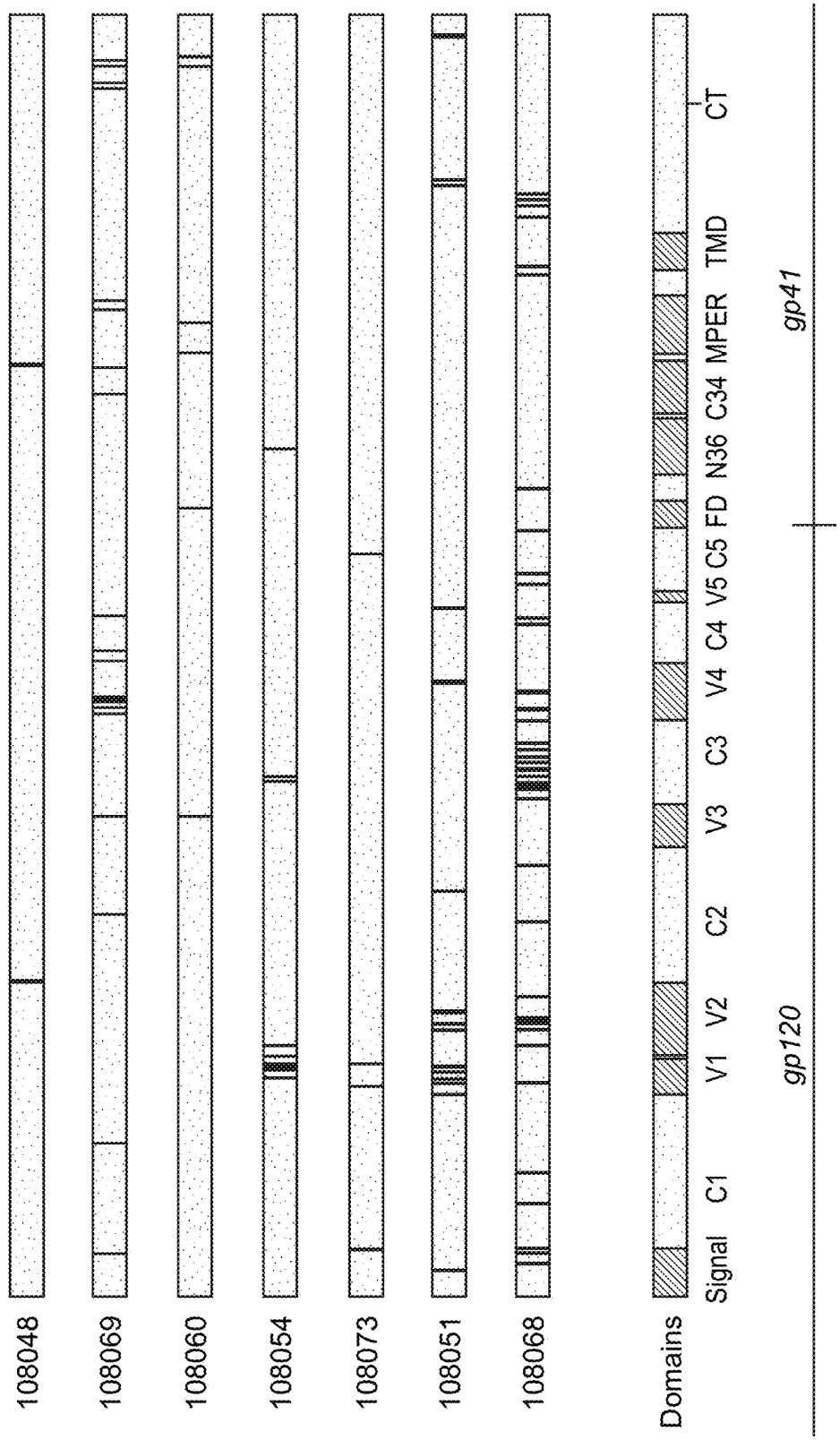
FIG. 5. shows the location of amino acid differences between neutralization sensitive and resistant clones.

We next sequenced the envelope glycoproteins from each neutralization sensitive/resistant pair and compared the sequences. In some cases we found that sequence variation was minimal between the two clones from the same individual, whereas in other cases there were a large number of amino acid differences between neutralization sensitive and resistant clones (FIG. 5). In one case (subject 108048), there were only two amino acid differences between the neutralization sensitive and resistant clones. In contrast, other viruses (e.g. 108068) showed a large number of amino acid differences (48) between neutralization sensitive and resistant viruses. Pairs with limited sequence variation allowed for the possibility of in vitro mutagenesis to localize the amino acids responsible for conferring sensitivity or resistance to neutralization by HIV+ sera. To explore this possibility, we initially selected the viruses from subject 108060 for further analysis.

Identification of a mutation in gp160 from subject 108060 that confers sensitivity to neutralization by HIV+ sera. It can be seen (Table 1A) that three of the ten clones from subject 108060 (clones 002, 018, and 024) were sensitive to neutralization by all four HIV+ sera, and of the remaining seven clones, most were resistant to neutralization by HIV+ sera Z1679, Z1684, and N16, but somewhat sensitive to HIV+ sera from Z23. Based on the fact that there was at least a 10-fold difference in neutralization sensitivity with all four HIV+ sera, clones 022 and 024 were selected for further study. When the gp160 sequences of the neutralization resistant variant (clone 022 wtR) and a neutralization sensitive variant (clone 024 wtS) were compared (FIG. 5), it was found that they differed at only seven positions. Two of the amino acid differences were in gp120, two amino acid differences were in the gp41 ectodomain, and the remaining three differences were in the cytoplasmic tail of gp41. To determine which amino acids were responsible for the difference in sensitivity to neutralization between clone 022 and clone 024, a series of mutant envelope proteins were constructed and used to create pseudovirions where polymorphisms from the neutralization sensitive variant (clone 024) were introduced into the neutralization resistant (clone 022) background (FIG. 1A).

We found (Table 2A) that the replacement of asparagine (N) for serine (S) at position 323 (N323S) in the V3 domain of gp120 had no effect on sensitivity to neutralization. Similarly, the substitution of N for glycine (G) at position 530 in the C5 domain (N530G) of gp120 had no effect. Replacement of lysine (K) at position 634 of the second heptad repeat domain (C34 helix) of gp41 with glutamic acid (E) in the mutant K634E also failed to show a significant difference in neutralization sensitivity.

However, the replacement of glutamine (Q) for arginine (R) at position 655 (Q655R) resulted in a remarkable increase (>30 fold) in neutralization sensitivity by all four of the HIV+ sera.

Figure 6:
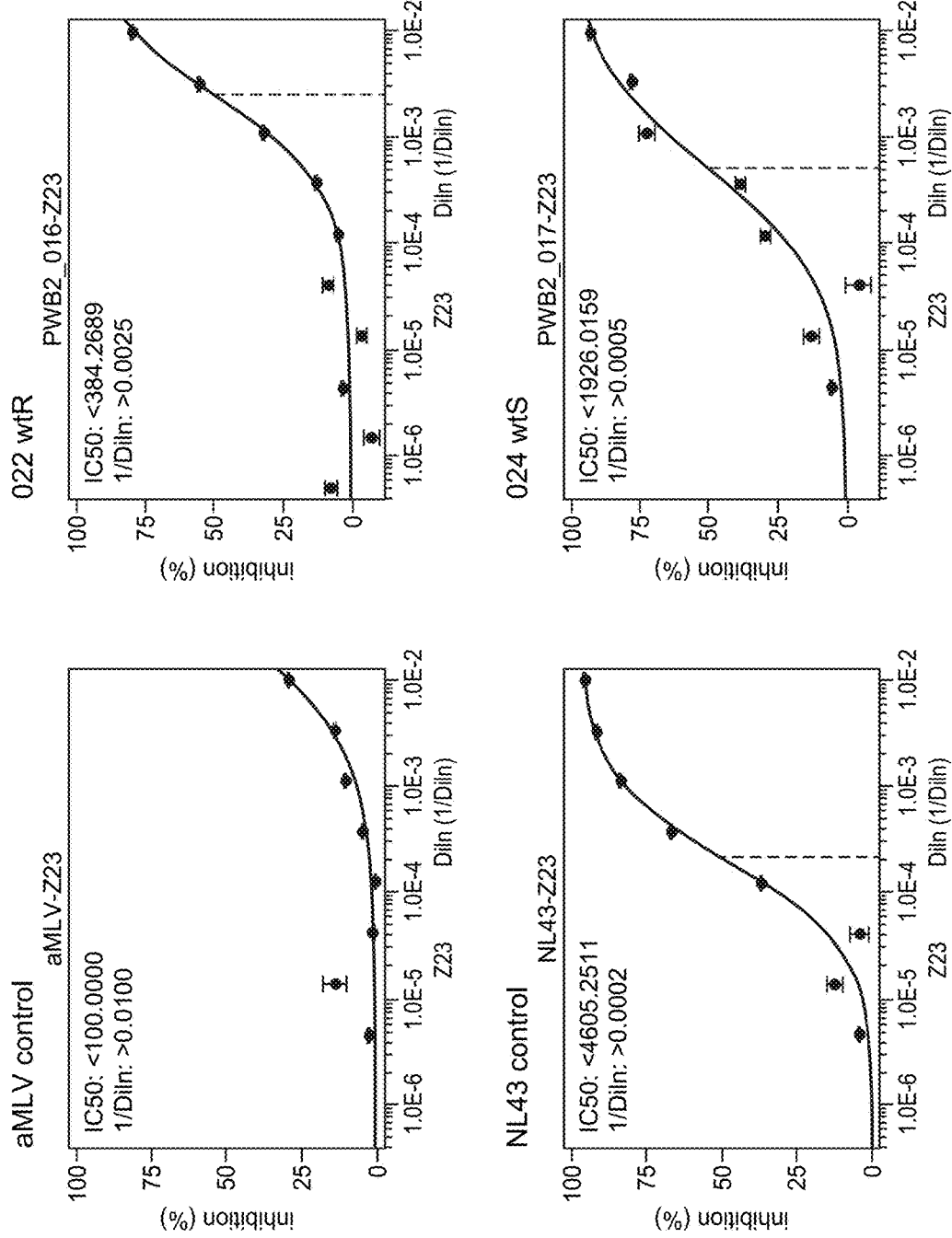
FIG. 6. shows graphs of neutralization for various clones. Neutralization of mutants from clone 022 of subject 108060. The mutant envelope genes described in FIG. 1 were used to construct pseudo-viruses which were evaluated for sensitivity to neutralization by HIV+ serum. Curves for the Z23 serum are shown. The ordinate indicates percentage neutralization and the abscissa indicates the log of the serum dilution. The dotted line indicates the 50% neutralization titer. For brevity, the cytoplasmic tail mutants are not shown, but all had well behaved neutralization curves.
Figure 6:
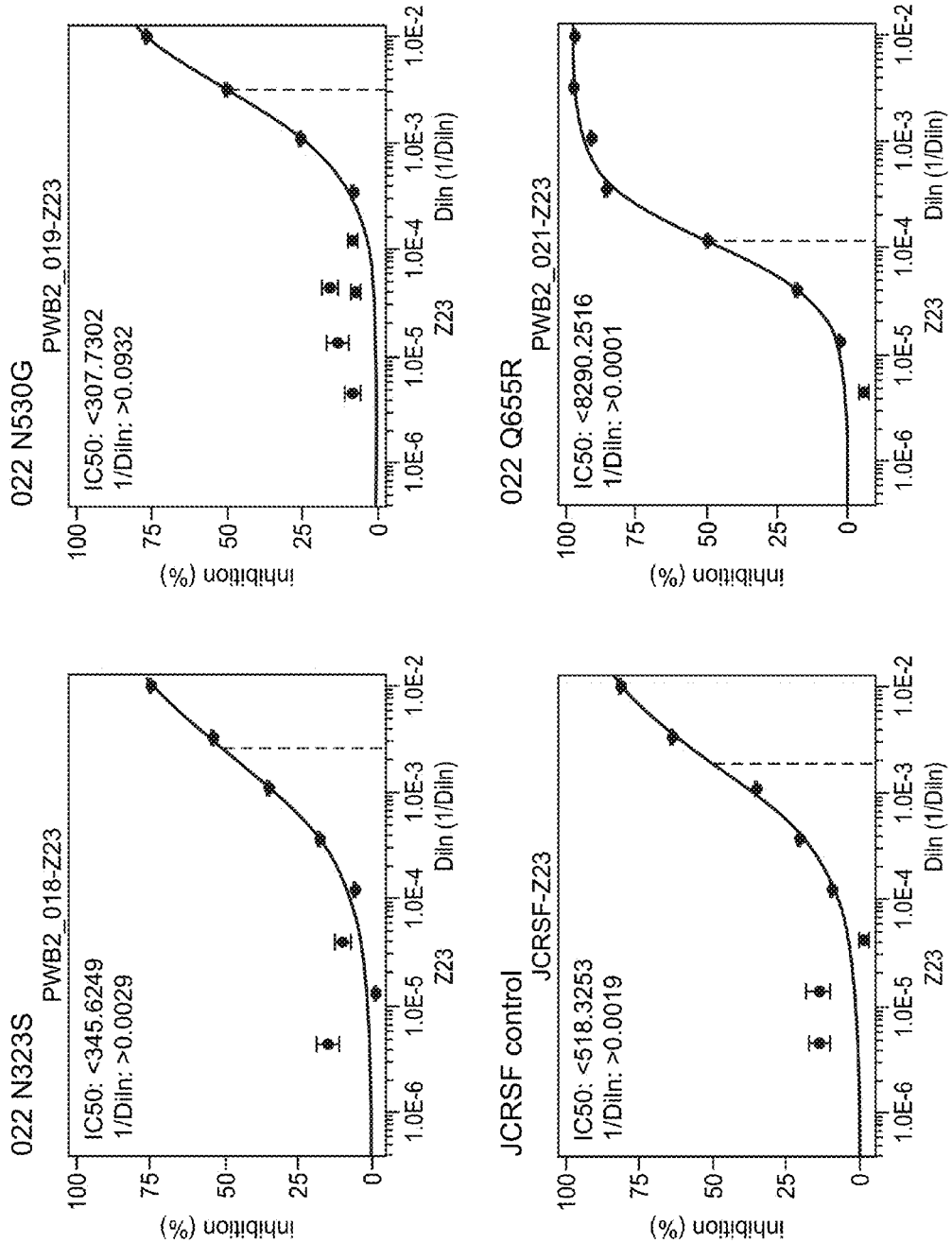
Figure 6:
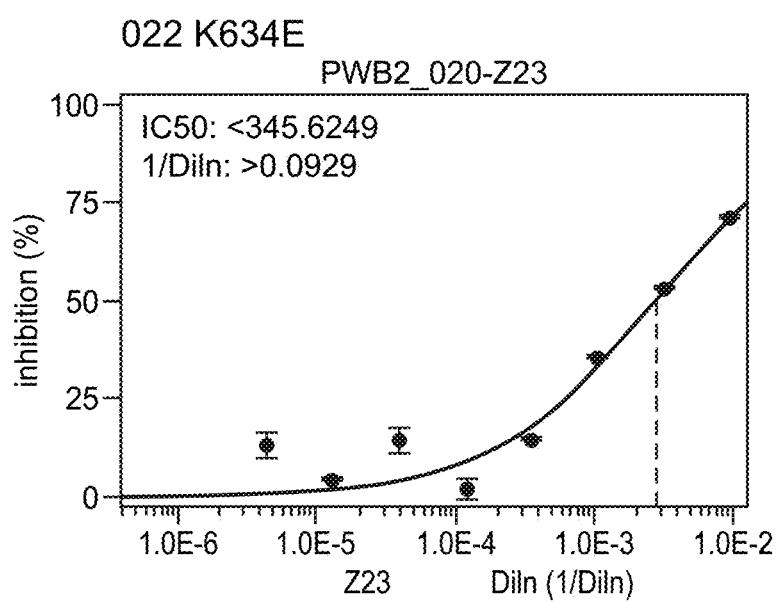

Mutations in the cytoplasmic tail region (832/833 and 827/832/833) were also examined and had no significant effect. The primary data used to calculate 50% neutralization titers with HIV+ serum Z23 are presented in supplemental information (FIG. 6). It can be seen that the neutralization curves were well behaved for all of the mutants.

Localization of residue 655 on linear sequence and 3-D structure of gp41. To better understand the impact of this mutation on the structure and function of the 108060 envelope glycoprotein, we located residue 655 on the linear sequence and 3-dimensional structure of gp41. Examination of the linear sequence (FIG. 1B) revealed that position 655 was located in the conserved second heptad repeat (HR2) of gp41 in a region also known as the C34 helix. This part of the molecule is known to play an integral role in virus fusion and indeed forms an essential component of the 6 helix bundle in the trimeric structure of gp41 that mediates fusion of the viral membranes with cellular membranes in the course of HIV infection. Position 655 is also located within in the T20 peptide that serves as the basis for the antiviral drug, FUZEON, that inhibits HIV infectivity by inhibiting virus fusion and entry. Finally the location of this mutation is only eight amino acids from a distinct structural region of gp41, termed the Membrane Proximal External Region (MPER), that is known to contain distinct epitopes recognized by the broadly neutralizing monoclonal antibodies 2F5, 4E10 and Z13. Taken together, these results suggest that this mutation occurs in a region that is important for virus fusion, and is close to—but structurally distinct from—a region known to contain other epitopes recognized by bNAbs. Interestingly, while the Q655R mutation in the C34 helix of gp41 had a marked effect on virus neutralization, the K634E mutation also in the C34 helix had no significant effect. These results demonstrated that some amino acid substitutions in the C34 helix, but not others, can cause a significant change in sensitivity and/or resistance to neutralization by antibodies in HIV+ sera.

The availability of the PDB (Protein Data Bank) co-ordinates of the gp41 fusion domain allowed us to evaluate the impact of the substitution of R for Q at position 655 upon the structure and function of gp41. Using the structure of Chan and Kim, we were able to determine that in the fusion activated form of the gp41 trimer, Q at position 655 is located two turns from the terminus of the C34 helix and is subject to both intra-molecular interactions with the N36 helix of the same monomer and inter-molecular interactions with the N-36 helix of adjacent monomers. The N36 and C34 helices within a gp41 monomer pack together in a fairly standard anti-parallel coiled-coil hair-pin structure. The 3-fold symmetric packing interface of the gp41 trimer is mediated almost exclusively by a set of parallel three-helical bundle contacts between the N36 helices of each gp41 monomer. One of the few exceptions to this is the set of contacts mediated by Q655. Although Q655 resides in the C34 helix, its side chain accepts an intramolecular hydrogen bond from Q553 of the N36 helix within the gp41 monomer, and it donates an inter-molecular hydrogen bond to the backbone carbonyl oxygen of V551 in the N36 helix of an adjacent gp41 monomer. The gp41 trimeric structure is thus stabilized by a "ring" of amino acids Q655-Q553-V551 in a 3-fold symmetric repeat. Hence the three copies of Q655 contribute six hydrogen bonds that specifically stabilize the trimeric structure through intra-molecular as well as inter-molecular hydrogen bonding contacts. Mutations of Q655 clearly possess a significant potential to disrupt the stability of the tertiary gp41 structure as well as the quaternary structure of the gp41 trimer. Molecular modeling suggested that replacement of Q with R might impact the structure of the 6 coiled-coil bundle in two ways. First, the longer R side chain may have a steric effect that disrupts the close packing of the C34 helix with the N36 helix on the adjacent monomers. A second mechanism by which this substitution at position 655 could confer neutralization sensitivity is by disruption of the intra-molecular hydrogen bond with position 553, as there is no longer a keto oxygen to act as a hydrogen bond acceptor. Hence the effect of the mutation is predicted to destabilize each of the gp41 monomers in the trimeric structure. However, the potential to form the inter-molecular hydrogen bond with V551 remains, so that if the gp41 monomer can still fold correctly, a partially stable trimer should be able to form.

Role of Inter- and Intra-Molecular Hydrogen Bonds.

To further investigate the role of R655 in conferring sensitivity to virus neutralization, we used in vitro mutagenesis to replace Q at position 655 with other residues predicted to affect inter- and intra-molecular interactions in the hydrogen bonded ring structure and examined their affect on neutralization sensitivity (Table 2B). Some of the replacements, such as threonine (T), failed to yield infectious viruses. We found that the conservative replacement of Q for asparagine (N) at position 655 resulted in a small but significant increase in neutralization sensitivity. Glutamine and asparagine share the same side chain amide functionality, but asparagine has one fewer side chain carbon atoms than does glutamine. Hence, the Q655N mutation is unique in that it retains the potential to form both the intra-molecular hydrogen bond and the inter-molecular hydrogen bond, providing that a local distortion of the helical backbone can compensate for the shortening of the side chain by one carbon atom. This observation explains the relative insensitivity of HIV-1 to the Q655N mutation.

We next examined the replacement of Q at position 655 with lysine (K). The side chain of lysine is shorter than that of arginine and has reduced potential to interfere with the inter-helix packing structure than arginine. Modeling suggested that Q655K mutation, like the Q655R mutation, was unable to form the intra-molecular hydrogen bond with Q553, but preserved the inter-molecular hydrogen bond with V551. We found the Q655K mutation resulted in a highly neutralization sensitive phenotype. This result suggested that the destruction of the hydrogen bond was a more important factor in conferring neutralization sensitivity than the steric hindrance provided by the longer side chain of arginine. This conclusion was confirmed in the next two mutants examined (Q655S) where serine (S) replaced glutamine at position 655, and Q655E where glutamic acid (E) replaces glutamine. We found that these substitutions also resulted in a significant increase in neutralization sensitivity (Table 2B), albeit not as high as the Q655K mutation. The effect of S or E at position 655 is predicted to differ from that of the Q655R mutation in that they preserve the intra-molecular hydrogen bond, but are unable to form the inter-molecular hydrogen bonds. Together these results suggest that both the inter-molecular and intra-molecular hydrogen bonds are important for stabilizing the ring structure, and that disruption of either the set of three intra-molecular hydrogen bonds or the set of three inter-molecular hydrogen bonds results in increased sensitivity to neutralization.

Monoclonal Antibody Sensitivity and Envelope Transfer—Sensitivity to Neutralization by MAbs and Fusion Inhibitors.

While the structural analysis provided insight into the functional consequences of mutations at position 655, two alternate hypotheses can account for a mechanism by which this mutation increases sensitivity to antibody-mediated neutralization. One possibility is that this mutation is located at or near an antibody binding site and that the Q655R mutation restores an epitope recognized by a population of neutralizing antibodies present in all four HIV-positive sera. Alternatively, it is possible that this mutation results in a significant conformational change that is transmitted to other parts of gp41 such as the adjacent MPER or the gp120/gp41 trimer complex in such a way as to increase exposure or access to antibodies at other locations on the molecule.

To explore these possibilities, antibody neutralization studies were carried out with a panel of neutralizing MAbs to epitopes in gp120 and gp41 as well as fusion inhibitors targeting either the gp120 or the gp41 portion of the HIV envelope glycoprotein. In these studies, we examined two broadly gp41-neutralizing MAbs, 2F5 and 4E10; the broadly neutralizing b12 antibody able to block CD4 binding to gp120; and 2G12, an antibody that binds to a carbohydrate epitope in gp120. In addition, we tested the antiviral entry inhibitor CD4-IgG, which binds to sequences in gp120 and is able to neutralize lab-adapted CXCR4-dependent clinical isolates at low concentrations (0.01 to 0.1 µg/ml), and primary clinical isolates of HIV at high concentrations (10 to 100 µg/ml). We also examined the sensitivity of envelope mutants to enfuvirtide, a peptide virus entry inhibitor that consists of a gp41-derived peptide that includes sequences from the C34 helix containing Q655.

The results of these studies are shown in Table 4, in which the sensitivities of clone 022 and clone 024 from subject 108060 to neutralizing MAbs were compared. It can be seen that the neutralization-resistant clone 022 is moderately sensitive to the 2F5 and 4E10 MAbs specific for the MPER of gp41 but resistant to neutralization by the b12 and 2G12 MAbs reactive with gp120. This virus was also sensitive to enfuvirtide and resistant to CD4-IgG. The high CD4-IgG concentration required for the neutralization of this virus is consistent with the concentration required to neutralize other primary, CCR5-dependent viruses.

We next examined the neutralization-sensitive clone 024 that differs from the neutralization-resistant clone 022 at only seven amino acid positions. We found that this clone was 15- to 20-fold more sensitive to the MPER-specific MAbs (2F5 and 4E10) than the 022 clone. Similarly, the neutralization-sensitive clone 024 was more than 20-fold more sensitive to CD4-IgG and 3.5-fold more sensitive to neutralization by enfuvirtide (Table B). Thus, clone 024 exhibited significantly increased sensitivity to neutralization by MAbs and antiviral entry inhibitors as well as antibodies in HIV-positive sera.

We then mutated the neutralization-sensitive clone 024 so as to replace R with Q at position 655. We found that the resulting mutant (108060_024 R655Q) became resistant to neutralization and showed a pattern of neutralization sensitivity closely resembling that of the neutralization-resistant clone 022. Conversely, when we mutated the neutralization-resistant clone 022 to replace Q at position 655 with R, the resulting mutant (108060_022 Q655R), which differed from the parental neutralization-resistant clone by a single amino acid, exhibited an extraordinary increase in neutralization sensitivity (Table 3). We observed a >125-fold increase in sensitivity to CD4-IgG compared to that of the wild-type clone 022 and a 30- to 35-fold increase in sensitivity to the MPER-reactive antibodies 2F5 and 4E10. We also noted a 17-fold increase in sensitivity to the antiviral drug enfuvirtide.

These results highlight the importance of glutamine at position 655 and suggest that epistatic mutations at other sites in clone 024 moderate sensitivity to neutralization. The results of these studies are remarkable in that they show that a single amino acid substitution in gp41 not only confers sensitivity to neutralization by MAbs and entry inhibitors directed to gp41 but also increases sensitivity to CD4-IgG, a molecule that binds to gp120, an entirely different protein. Thus, the Q655R mutation appears to cause a conformational change in gp41 that affects not only the binding of antibodies and entry inhibitors (2F5, 4E10, and enfuvirtide) that bind close to the site of the mutation but also the binding of another inhibitor (CD4-IgG) that binds to a site on gp120 located a considerable distance from the mutation.

Transfer of the Q655R Mutation to Related and Unrelated Viruses.

In order to determine whether the Q655R mutation could confer neutralization sensitivity and resistance to other viruses, this mutation was introduced into two unrelated viruses highly resistant to neutralization (from subjects 108069 and 108051) that normally possessed a Q at a position corresponding to 655 of the virus from subject 108060 (the 108060 virus). The results of these experiments are shown in Table 3. Interestingly, we found that the replacement of Q655 with R had little or no effect on neutralization by any of the HIV-positive sera. However, these mutations significantly increased the sensitivity to neutralization by the 2F5 and 4E10 MAbs (25- to 35-fold). These mutations also increased the sensitivities to neutralization by the entry inhibitors enfuvirtide and CD4-IgG. Thus, the mutation of Q to R at a position corresponding to 655 in the 108069 virus increased the sensitivity to enfuvirtide by more than 17-fold and increased the sensitivity to CD4-IgG by more than 20-fold. The 108069 mutant with the Q655R mutation seemed to be somewhat more sensitive to enfuvirtide and possibly CD4-IgG than the corresponding mutant of the 108051 virus.

Together, these results demonstrate that the mutation of Q to R at positions corresponding to 655 of the 108060 virus confers sensitivity to neutralizing MAbs to the MPER and antiviral compounds targeted to the C34 helix and the MPER of gp41. However, it was interesting that these mutations failed to increase the sensitivity to bNAbs in HIV-positive sera. We do not know whether neutralizing activity in HIV-positive sera is attributable to antibodies binding to the C34 region, the MPER, or other parts of the molecule. It has been recently reported that antibodies with specificities similar to 2F5 and 4E10 are rare in HIV-positive sera, which might account for the lack of effect. Alternatively, the failure of the Q655R mutation to increase neutralization sensitivity by HIV-positive sera might be attributable to polymorphisms outside of the MPER and the C34 region that preclude the binding of otherwise bNAbs. This may well be the case since the 108069 and 108051 viruses were selected because of their resistance to neutralization by the HIV-positive sera selected for use in these studies.

Transfer of Q655R mutation to related and unrelated viruses. In order to determine whether the Q655R mutation could confer neutralization sensitivity and resistance to other viruses, this mutation was introduced into two unrelated viruses (108069 and 108051) that normally possessed a Q at a position corresponding to 655 of the 108060 virus. The results of these experiments are shown in Table 3. Interestingly, we found that replacement of Q655 with R had little or no effect on neutralization by any of the HIV+ sera (supplementary information S4). However, these mutations significantly increased the sensitivity to neutralization by the 2F5 and 4E10 MAbs (25- to 35-fold). These mutations also increased sensitivity to neutralization by the entry inhibitors FUZEON and CD4-IgG. Thus the mutation of Q to R at a position corresponding to 655 in 108069 increased the sensitivity to FUZEON by more than 17-fold and increased the sensitivity to CD4-IgG by more than 20-fold. The 108069 mutant with the Q655R mutation seemed to be somewhat more sensitive to FUZEON and possibly CD4-IgG than the corresponding mutant in the 108051 virus. Together these results demonstrate that the mutation of Q to R at positions corresponding to 655 of 108060 confers sensitivity to neutralizing MAbs and anti-viral compounds targeted to the C34 and MPER regions of gp41 and to the CD4 binding site in gp120. However, this mutation is not able to confer sensitivity to neutralization by bNAbs in HIV+ sera to all viruses.

Discussion

These studies utilized a novel method for the identification and mapping of mutations that affect the sensitivity/resistance of viruses to neutralization by HIV+ sera and anti-viral entry inhibitors. This approach differs from previously described methods of mutational analysis used to study HIV in that it relies on naturally occurring mutations in the swarm of closely-related viruses that evolve during the course of HIV infection.

Identification of a mutation at position 655 in gp41 that confers sensitivity to neutralization by bNAbs. In this study we identified a naturally occurring mutation (Q655R) that affects sensitivity/resistance of viruses to neutralization by bNAbs. X-ray crystallography studies showed that glutamine at position 655 is located close to the C-terminus of the C34 helix and contributes to two hydrogen bonds: one mediating an intra-molecular interaction with the N36 helix on the same monomer, and the other mediating an inter-molecular interaction with the N36 helix on an adjacent monomer. These two hydrogen bonds appear to stabilize the fusion active conformation of the 6 helix bundle in trimeric gp41 in such a way as to increase infectivity and confer resistance to neutralization. Our data suggest that naturally occurring mutations (e.g. Q655R) and experimental mutations (e.g. Q655K, Q655S or Q655E) that interfere with either the intra-molecular or inter-molecular hydrogen bonds normally provided by Q655 confer sensitivity to neutralization by interfering with the formation of the hydrogen bonded ring. In this regard, the function of this ring structure appears to be twofold: 1) to stabilize interactions between the backbones of adjacent N-36 helices in the core of the 6 helix bundle and 2) to stabilize the ends of the coiled-coil hairpin structures in each gp41 monomer. This latter interaction may serve a function analogous to the fibular clasp on brooch or badge.

The mechanism by which the Q655R mutation confers sensitivity and resistance to neutralization. HIV fusion is thought to be a step-wise process that begins with the binding of CD4 and a suitable chemokine receptor (CXCR4 or CCR5) to gp120. This triggers a conformational change resulting in the formation of the "pre-hairpin" fusion intermediate complex via rearrangement of the amphipathic helices in the external domains of gp41. The N36 helices pack in a parallel three-helical bundle. The pre-hairpin is characterized by the exposure of the N-terminal hydrophobic fusion domain and the C-terminal MPER of gp41 which are normally folded inside the gp41 trimer and not exposed to circulating antibodies. Further molecular rearrangements result in closure of the hairpin structure, resulting in anti-parallel packing of each C34 helix into the grooves on the outside of each N-helix in the gp41 trimer. Ultimately, a highly thermostable 6 helix bundle is formed, which is thought to provide the energy required to fuse viral with cellular membranes. We hypothesize that the Q655R mutation alters the conformational equilibria so as to favor the pre-hairpin fusion intermediate structure where both the N terminal fusion domain and MPER are exposed. This would explain the increased sensitivity to the 2F5 and 4E10 MAbs, which recognize the exposed MPER as well as the increased sensitivity to neutralization by CD4-IgG. Previous studies have suggested that transition of the fusion intermediate to the fusion-active conformation is the rate limiting step in virus infection, and is estimated to be in the range of 15 minutes based on T-20 (FUZEON) sensitivity. An interesting possibility is that HIV envelope glycoproteins that are "trapped" into the fusion intermediate conformation might represent superior HIV vaccine antigens, since they would expose epitopes normally hidden, and only exposed during virus fusion. The results obtained with swarm analysis are consistent with the possibility that mutations at 655 in the 108060 virus, such as Q655R and Q655K, alter the conformational equilibria to favor the gp41 trimer in the fusion intermediate conformation.

Sera from early infections may represent an opportunity to identify rare mutations that confer sensitivity to bNAbs. Based on the examination of sequence data in the Los Alamos HIV Sequence database, it appears that the mutation of arginine for glutamine at position 655 is extremely rare and occurs with an observed frequency of 8/1242 (0.64%). How is it then that we were able to find such a rare mutation within the first seven viruses examined? One possible explanation relates to the fact that the viruses analyzed in this study were all collected close to the time of infection, and may possess antigenic structures that are uncommon in viruses recovered from later infections due to kinetics of the development of the neutralizing antibody response. Several studies have shown that bNAbs do not occur until 6-12 months after infection. It could well be the case that viruses recovered from early infections possess a broader range of antigenic features because they are being selected primarily for infectivity rather than neutralization resistance. Once effective neutralizing antibodies are present, neutralization sensitive variants, such as Q655R, would be selected against, and rapidly disappear from plasma. The possibility that viruses from early infections may contain mutations resulting in unusual structures is consistent with a previous study where viruses recovered from the same clinical cohort as 108060 had an unexpectedly high frequency of mutations that affected the disulfide structure of gp120.

Envelope proteins from early infections with rare mutations such as Q655R may represent a new source of vaccine antigens. How are mutations that occur with such low frequencies useful for HIV vaccine development? The results obtained for the Q655R mutation suggest that mutations of this type significantly alter the antigenic structure of the envelope protein in such a way as to expose important epitopes that are normally shielded from contact with the immune system. Frey et al. have hypothesized that immunization with a gp41 trimer locked into the pre-hairpin fusion intermediate conformation might be an effective way to elicit bNAbs to the MPER with activities similar to 2F5 and 4E10. We believe that the Q655R and other mutations that we have described may have "trapped" the gp41 trimer into this pre-hairpin intermediate conformation and might be effective in inducing bNAbs. The immunogenicity of such variants has not yet been explored; however, studies are underway to examine their immunogenic potential.

Virus fusion is a delicately balanced process that involves major conformational transitions triggered by ligand binding. These transitions are no doubt aided, and stabilized, by a variety of cooperative interactions. The studies described highlight a set of novel interactions mediated by hydrogen bonds that appear to facilitate fusion of viruses with cellular membranes. The 6 helix bundle structure and fusion mechanism is conserved throughout evolution and is essential for the infectivity of most enveloped viruses. A homologous 4 helix bundle plays a similar role in cellular vesicles mediating intracellular transport and secretion. It may well be that the infectivity of other enveloped viruses (e.g. influenza) as well as membrane fusion processes (e.g. intracellular transport and secretion) might also depend on stabilizing interactions from hydrogen bonded structures of the type that we have observed in gp41. Knowledge of these stabilizing interactions may be useful in understanding the details of the fusion process and may provide a new approach to the development of vaccine and therapeutic products, where alteration of these interactions may provide a functional benefit.

Materials and Methods

Sera and Plasma. Cryopreserved plasma used to clone full length envelope glycoproteins were collected in the course of a Phase 3 clinical trial of a candidate HIV vaccine (AIDSVAX B/B) sponsored by VaxGen, Inc. (S. San Francisco, Calif.). Deidentified specimens and data required for these studies were provided by Global Solutions for Infectious Diseases (S. San Francisco, Calif.). All of the viruses used in this study were obtained from patient plasma collected within six months of initial infection. HIV+ sera containing broadly neutralizing antibodies (Z23, Z1679, Z1684, and N16) were provided by Monogram Biosciences, Inc. (S. San Francisco, Calif.) and are known from previous studies to neutralize a variety of primary clinical isolates of HIV. The monoclonal antibodies used in these studies were obtained from two different sources. The broadly neutralizing monoclonal antibodies b12, 2F5, and 4E10 were obtained from the NIH AIDS Reagent Repository and Polymun A.G. (Vienna, Austria). The antiviral compound CD4-IgG was described previously and provided by GSID (S. San Francisco, Calif.).

Construction of envelope gene libraries and pseudoviruses. Libraries of envelope glycoprotein were created from each subject by PCR amplification of full length envelope genes from cryopreserved plasma using the method described previously. The swarm of PCR products was cloned into a plasmid expression vector useful for the construction of pseudoviruses. The vector was specifically designed to permit the construction of pseudovirus libraries for use in a well-established and validated virus neutralization assay. However, instead of pooling all of the clones together and carrying out neutralization assays or drug sensitivity assays with an entire library of cloned genes from each infected individual as had been done previously, we plated out the plasmid library on agar plates and picked 24-48 clones from each individual for infectivity studies. The plasmid DNA was isolated from each clone and used to create a stock of pseudovirus particles that were then screened for infectivity, and chemokine receptor usage. After verifying infectivity and receptor usage, we then selected approximately ten CCR5-dependent pseudotype viruses with good infectivity for virus neutralization assays. The virus neutralization assays were carried out as described by Schweighardt et al.

Sequencing and mutagenesis. Plasmids containing cloned envelope glycoproteins were sequenced using fluorescently labeled dideoxynucleotides at either Monogram Biosciences or the University of California Sequencing Facility (Berkeley, Calif.) using capillary electrophoresis sequencing devices (Applied Biosystems, Foster City, Calif.). HIV envelope glycoprotein sequences were mutagenized by a mismatched primer method using the QuikChange Mutagenesis kit (Stratagene, San Diego). All mutations were confirmed by DNA sequencing. The numbering of amino acids is made with reference to the sequence of gp160 from clone 022 of from subject 108060. Position 655 corresponds to position 653 of the HXB2 reference strain of HIV-1.

Virus neutralization assay. The automated virus neutralization assay described in this study has been described previously. The neutralization data reported represent IC50 values calculated from serum dilution curves. This assay employs multiple assay controls, including a positive pseudotype virus control panel and a negative pseudotype virus control panel. Assay acceptability criteria have been established to minimize interassay variability and assure comparability of data from different experiments. The positive virus control panel includes the pseudotypes from the neutralization sensitive isolate, NL43, and the less neutralization sensitive primary isolate JRcsf. The negative virus (specificity) control consists of pseudotype viruses prepared from the envelope of the amphitropic murine leukemia virus. Previous studies (Wrinn, Montefiore, and Sinangil, manuscript in preparation) have shown that the Monogram virus neutralization assay yields comparable results to the TZM-BL pseudotype virus neutralization assay when tested on standard panels of HIV-1 isolates distributed by the NIH.

Molecular modeling. Although the complete gp41 HIV-1 glycoprotein structure is currently unavailable, a crystal structure comprising the N36 and C34 helices of gp41 (PDB accession code 1AIK) anti-parallel helical core duplicates the essential intra-molecular as well as inter-molecular packing interactions in which the crystallographic three-fold axis corresponds to the natural gp41 trimer three-fold axis. The intra-molecular and inter-molecular hydrogen bonding contacts involving Q655 were identified in the context of the gp41 trimeric structure in the PyMOL molecular visualization software package. The potential effects of the various Q655 mutations upon both sets of packing interactions were then analyzed by in silico mutagenesis in PyMOL combined with crystallographic symmetry-constrained energy minimization molecular modeling (using the crystallographic software package Phenix to enforce the gp41 trimeric symmetry. The results of the crystal-structure-based molecular modelling data were subsequently analyzed in PyMOL.

Detailed Description of the Embodiments Related to Selection of HIV Vaccine Antigens by Use of Intrapatient Sequence Variation to Identify Mutations in the HIV Envelope Glycoprotein that Affect the Binding of Broadly Neutralizing Antibodies (See U.S. Provisional Application 61/195,112 Filed 4 Oct. 2008 and International Application No. PCT/US09/59583 Filed 5 Oct. 2009).

Disclosed is a new method for identifying mutations in envelope proteins, which methods comprise analyzing intrapatient HIV-1 virus variation to identify specific amino acid residues of the HIV-1 envelope glycoproteins, gp160, gp120, and gp41 that affect sensitivity or resistance to broadly neutralizing HIV-1 antibodies. The mutations identified by the methods of the invention provide enhanced sensitivity (or resistance) to neutralization of a virus by anti-viral antisera; in particular neutralization of an HIV virus by anti-HIV antibodies, such as in antisera. The methods described identify epitopes recognized by broadly neutralizing antibodies. Such epitopes and the proteins of which they are a part may provide a powerfully immunogenic, protective vaccine against HIV. To identify polymorphisms and sequences that effect sensitivity or resistance to broadly neutralizing antibodies, viral envelope sequences (such as gp160, gp120, and gp41) from sensitive and resistant viruses were identified and compared and the differences were noted. Mutagenesis was carried out to identify specific residues that correlated with sensitivity or resistance to virus neutralization.

Essentially, the method consists of carrying out the following steps: (i) Providing a plurality of individual subjects who are seropositive for HIV antibodies and taking a biological sample such as blood or plasma from each subject, wherein the sample contains a multiplicity of HIV viruses with closely related genomes, wherein all subjects had been infected with HIV no more than one year before, and no less than one month before sample collection. (ii) Amplifying the env genes by the polymerase chain reaction (PCR) of the multiplicity of viruses to produce a library of different env genes. (iii) Cloning the amplified env genes into a plasmid shuttle vector allowing the plasmid to replicate in both bacteria (such as E. coli) and mammalian cells. Such vectors contain: a bacterial origin of replication, an origin of replication from a mammalian cell virus such as SV-40 or adenovirus, and a functional transcription unit that enables expression of a suitable drug resistance gene such as ampicillin, tetracycline, or kanamycin in order to allow selective growth of bacteria transformed with the shuttle vector. The shuttle vector must also contain the elements of a functional mammalian cell transcription unit. Beginning at the 5' end of the sense DNA strand, the transcription unit should contain a promoter sequence from a mammalian gene or virus, a splice donor/acceptor site, a segment of synthetic DNA containing either multiple restriction enzyme recognition sites or other sequences to allow directional cloning of PCR amplified envelope genes, a transcription termination codon, and a polyadenylation site. The transcription unit should also contain transcription enhancer sequences at either locater either 5' to the promoter or 3' of the polyadenylation site. Once PCR amplified HIV genes are ligated into the shuttle vector, the collection of plasmids containing the cloned envelope genes are transformed into E. coli by standard techniques, grown in a small volume of bacterial culture media and then plated onto agar plates containing the appropriate antibiotic so that only bacterial containing the shuttle vector plasmid containing the cloned envelope genes are able to form colonies. Individual colonies are then selected at random and plasmid DNA from each colony is prepared and analyzed by restriction digestion, and only those containing an insert of the proper size of the full length HIV envelope gene are retained and used for the preparation of pseudoviruses as described below. (iv) Co-transfecting mammalian cells (e.g. 293HEK) with the env-containing vector and simultaneously with a plasmid containing a defective HIV provirus virus where the coding sequence of the env gene was replaced with the coding sequence of a marker gene such as one capable of emitting light, e.g. Luciferase) to produce pseudovirions containing the amplified env genes. (v) The pseudovirions are placed in contact with cells capable of being infected by HIV so as to produce colonies of infected cells. Such cells express the genes for CD4 and at least one chemokine receptor gene (either CCR5 or CXCR4). The cells can also express CD4 and both the CCR5 and CXCR4 chemokine receptor genes. Cell culture supernatants containing pseudoviruses are harvested from the transfected cells and individual stocks of pseudoviruses resulting from single purified expression plasmids represent virus stocks. (vi) The pseudotype virus colonies thus created are tested to determine infectivity; 20-50 pseudo virus stock are prepared from each individual and only those exhibiting good infectivity as measured by a significant higher level of relative light units relative to control pseudoviruses containing only defective envelope genes are advanced to neutralization assays. (vii) Then each infective pseudotype virus is tested for sensitivity or resistance to neutralization by one or more broad neutralizing antibodies. In neutralization assays two or more pseudovirions from the same individual are tested. Each pseudovirus stock is incubated with serially diluted plasma or sera from HIV infected individuals or purified polyclonal or monoclonal antibodies. A significant decrease in the emission of light relative to pseudoviruses incubated with a negative control specimen that does not contain antibodies to HIV envelope proteins. (viii) Then selection is done of pairs of plasmids containing specific env proteins which were used to prepare the pseudoviruses described above, wherein each pair contains one env gene that yielded a neutralization resistant pseudovirus and one env gene that yielded neutralization sensitive pseudovirion. (ix) The envelope genes from sensitive and resistant pseudoviruses are then sequenced and comparison was done to thus to identify amino acid sequence differences between the neutralization sensitive and neutralization resistant envelope genes. Only pairs of sequences with a minimal number of sequence differences (no more than for example 10%, 8%, 6%, 5% or 4% sequence difference over the entire coding region of the env sequence in question) are then selected for further analysis. (x) In vitro mutagenesis may then be performed to create envelope genes where the effect of each amino acid difference between the neutralization sensitive and neutralization resistant pairs can be determined when such mutant genes are incorporated into pseudovirions and tested for sensitivity and resistance to neutralization. In this step, amino acids at corresponding positions of neutralization sensitive member of the pair is introduced into the neutralization resistant member of the pair to see if it confers the neutralization sensitive phenotype. Conversely, specific amino acids from the neutralization resistant sequence can be introduced into the neutralization sensitive envelope gene by in vitro mutagenesis to identification of the specific amino acid responsible for the neutralization resistant phenotype.

It should be noted that it is an important feature of the invention that the samples be taken from individuals within a certain window. For various reasons more thoroughly explained elsewhere in this disclosure, the HIV virus population changes dramatically during the course of infection, and the inventors have reasoned that in order to successfully identify the polymorphisms of the invention, samples need to be taken within a certain window of time. In the present invention samples need to be taken from subjects who had been infected with HIV no more than one year before, and no less than one month before sample collection. In various embodiments a wider window may be used and samples may be taken no more than 18 months before, and no less than two weeks before sample collection. In other embodiments a narrower window may be used and the earliest and latest times that bracket the sample window may be, for example, 14 months and 1 month, 12 months and 1 month, 10 months and 6 weeks, 8 months and 6 weeks, 6 months and 6 weeks, or any combination of these times from the date of infection. Obviously the date of infection is not always precisely known, and the dates that comprise the earliest and latest times since infection may vary, for example +/−14 days or +/−24 days. In one specific embodiment used to produce the current experimental results, all subjects had been infected with HIV 109 days+/−58 days before specimen collection.

Although most of the viruses from an individual exhibited a predominant "neutralization sensitive" or "neutralization resistant" phenotype, variants were identified that differed in sensitivity from predominant forms. Because all of the samples compared were from recent infections the amount of intra-patient sequence variation in the envelope glycoprotein was minimal. Site directed mutagenesis enabled us to identify amino acids residues responsible for neutralization sensitivity or resistance. Mutations affecting virus neutralization were found in both gp120 and gp41.

The methods disclosed provide a novel strategy to enable quick and efficient identification of the epitopes recognized by bNAbs in HIV+ patient sera. Characterization of polymorphism at these sites will provide information to guide the formulation of multivalent vaccines. In one aspect, the invention discloses methods for identification of certain immunogenic epitopes, and further discloses the epitopes themselves. Broadly neutralizing antibodies recognize the specific epitopes of the HIV-1 envelope glycoproteins, including gp120, and gp41 and any gp160-derived protein, whether monomeric or oligomeric. Thus, aspects of the present invention include these HIV-1 envelope glycoproteins, nucleic acids encoding the polypeptides and vaccines comprising the polypeptides or nucleic acids.

Also described are methods for the identification of specific polymorphisms within, or having an effect upon, neutralizing epitopes that are suitable for inclusion in a protein or polypeptide that may be included in the formulation of a multivalent HIV vaccine cocktail. It should be noted that the polymorphisms of the invention need not be within or even close to the epitopes affected. The polymorphisms of the invention alter the conformation of the epitopes so as to reveal (or hide) a portion of the epitope in such a way that it becomes available to bind with (or hidden from) a corresponding antibody, such as a broadly neutralizing antibody. Further described is a method for identifying and purifying broadly neutralizing antibodies from HIV patient serum or plasma. HIV envelope genes were amplified from HIV+ plasma obtained in the VAX004 Phase 3 trial. See Flynn, N. M., D. N. Forthal, C. D. Harro, F. N. Judson, K. H. Mayer, and M. F. Para. 2005. Placebo-controlled phase 3 trial of a recombinant glycoprotein 120 vaccine to prevent HIV-1 infection. J Infect Dis 191:654-65.

Also disclosed are vectors, pseudoviruses and other constructs that comprise specific polynucleotide sequences and mutations that encode antigens and epitopes described. Also disclosed are generic and specific sequences, polymorphisms, mutations, antigens and epitopes that may be used for the treatment and/or prevention of viral infection such as HIV infection.

Also disclosed are medicaments and therapeutic formulations such as vaccines that comprise antigens and epitopes of the invention or that comprise polynucleotide sequences or vectors encoding antigens and epitopes of the invention. Vaccines of the invention may be used both to treat an infection once the infection has occurred, so as to prevent or cure a disease, and more commonly, to prevent an infection. Also disclosed are therapeutic methods that comprise delivering a vaccine to a subject wherein the vaccine may comprise one or more antigens or epitopes of the invention, or polynucleotide sequences or vectors encoding antigens and epitopes of the invention. Also described are specific glycoproteins, polypeptides, proteins and epitopes which may be formulated as part of an effective vaccine. Also described are polyclonal and/or monoclonal antibodies that may be used as therapeutic agents for passive immunization. The vaccines of the invention may be protein/polypeptide antigen vaccines, or may be polynucleotide vaccines wherein the polynucleotides express antigenic proteins that provoke a protective immune response.

Also disclosed are therapeutic methods that employ compositions such as drugs and small molecules or antibodies that interact with specific antigens or epitopes or regions of the glycoproteins or polypeptides described, thereby (i) exposing a previously unexposed epitope which epitope can bind specifically with a neutralizing antibody and/or (ii) limiting, inhibiting or preventing fusion of a viral membrane with a cell membrane, thereby inhibiting infection of a call by a virus. Also disclosed are the therapeutic compositions, drugs, small molecules or antibodies used in the above method.

Also described are compositions containing specific sequences and amino acid substitutions, deletions and additions that affect the confirmation of a protein or a polypeptide so as to hide or expose one or more particular epitope. Also described are methods of contacting a virus with such a composition to affect the confirmation of a protein or a polypeptide so as to hide or expose one or more particular epitope so as to expose a previously unexposed epitope which epitope can bind specifically with a neutralizing antibody and/or to limit, inhibit or prevent fusion of a viral membrane with a cell membrane.

Also described are polypeptides containing the epitopes of the invention, nucleic acids encoding the polypeptides, vaccines comprising the polypeptides or nucleic acids, and methods of attenuating or preventing HIV infection via administration of the vaccines.

Also described are nucleic acids encoding the polypeptides of the invention and vectors that comprise nucleic acids encoding the polypeptides of the invention, which vectors may be used for therapeutic and/or vaccination purposes.

Further, the invention isolated polynucleotides encoding the polypeptides of the invention, a polypeptide comprising a) an amino acid sequence selected from any sequence described herein, b) an amino acid sequence having at least 90% sequence identity to an amino acid sequence described herein, c) a biologically active or immunogenic fragment of an amino acid sequence described herein. The invention further provides an isolated polynucleotide comprising a polynucleotide sequence having at least 90% sequence identity to a polynucleotide described, or a polynucleotide sequence complementary to the foregoing. In one alternative, the polynucleotide comprises at least 60 contiguous nucleotides. The invention also includes any of the polypeptides encoded by such polynucleotides. Additionally, the invention provides an isolated antibody which specifically binds to an amino acid sequence described herein.

The investigators have identified various specific polynucleotide and polypeptide envelope sequences that contain specific polymorphisms such as a substitution of arginine for glutamine at position 655 in gp41 ("Q655R"). The invention includes these sequences and also encompasses other similar and related sequences that display the same specific polymorphism at a location identifiable as being homologous to Q655R in the HIV env gene as disclosed in SEQ ID NO:16.

To say that a first particular sequence of amino acids, or a particular single amino acid residue or polymorphism "corresponds to" a particular (second) sequence, site or position on a known sequence means that the first sequence, residue or polymorphism is located at a position that is readily identifiable by virtue of sequence homology as being equivalent to a known sequence, site or position on a known sequence on the second, known sequence. The same reasoning may be applied to polynucleotides.

To say that a first particular sequence or specific polymorphism is "identifiable as being homologous to" a second particular sequence or polymorphism means that the sequences shows homology or sequence identity with each other so as to be identifiable as being homologues (and quite possibly, paralogs) of the same gene. Such homology is usually evident to one of skill in the art and can be determined by eye. Additionally various algorithms such as BLAST may be used.

In the present case, the region in which the polymorphism is found is highly conserved between variants, and the recognition of sequences or polymorphisms as being located at a site "identifiable as being homologous to" amino acid 655 in SEQ ID NO:16 is clear and easily understood. In the present case the invention includes a substitution of Q to another residue such as R at a site identifiable as being homologous to amino acid 655 in SEQ ID NO:16.

The env polypeptide may be selected from any of the known env sequences, or may be a previously unpublished sequence having a certain degree of sequence similarity to one of the known env sequences.

For example, the env polypeptide of the invention may comprise a sequence with a substitution of arginine for glutamine at position identifiable as homologous to position 655 within in a gp41, wherein the env polypeptide has at least 60% identity (or, in other embodiments, at least 70%, at least 80%, or at least 87% or at least 90% or at least 95% or at least 98% or at least 99% identity) using BLASTP 2.2.21 with default settings (see Altschul et al., (1997), "Gapped BLAST and PSI-BLAST: a new generation of protein database search programs", Nucleic Acids Res. 25:3389-3402) to one of the following sequences: SEQ ID NO:16, SEQ ID NO:17, SEQ ID NO:18, SEQ ID NO:19, SEQ ID NO:20.

Alternatively, for example, the env polypeptide of the invention may comprise a sequence with a substitution of arginine for glutamine at position identifiable as homologous to position 655 within in a gp41, wherein the env polypeptide has at least 65% identity (or at least 70%, 80%, 87%, 90%, 95%, 98% or at least 99% identity) using BLASTP 2.2.21 with default settings to one of the following sequences described in this application as: p1.10848_c2 Resistant, p1.10848_c11 Sensitive, 108051_c6 Sensitive, p1.108051_c5 Resistant, p1.108060_c22 Resistant, or p1.108060_c24 Sensitive.

Any of the above sequences may additionally include signal sequences of variable length or sequences that assist trimer at either the 5' or 3' ends. Any of the above sequences may be truncated by deletion of sequences encoding the transmembrane domain and cytoplasmic tail of the gp41 region of the gp160 gene.

Any of the above sequences may also be expressed as a fusion protein where nucleotides encoding the signal sequence and 0-12 N-terminal residues of the mature HIV envelope protein are deleted from the HIV envelope gene and replaced by nucleotide sequences encoding the signal sequence from another highly expressed protein to facilitate expression in mammalian cells. Examples of suitable signal sequence include those of herpes simplex virus 1 glycoprotein D or the prepro signal sequence of human tissue plasminogen activator. It is also sometimes desirable to include nucleotide sequences encoding a flag epitope immediately adjacent to the signal peptidase cleavage site at the N-terminus of the mature gp140 protein, or a flag epitope adjacent to the C-terminal sequence of the gp140 protein to facilitate purification. The flag epitope can be any 4-30 amino acid sequence recognized by a monoclonal antibody suitable for immunoaffinity chromatography, or can be a cluster of amino acids such as a poly-histidine (his-tag) sequence that can mediate adherence to an insoluble matrix for affinity purification. In this regard it is important that a simple, non-denaturing process is available to elute the poly-histidine fusion containing fusion protein form the insoluble matrix. In some cases (e.g. herpes simplex virus glycoprotein D) the flag epitope can be derived from the same protein as the heterologous signal sequence. The flag epitope can be attached to any amino acid within the first 20 amino acids of the gp120 portion of the molecule. An example of this is fusion adjacent to the conserved V at position 41 within the full length gp160 sequence and located at the sequence beginning VPVWKEA (SEQ ID NO:21). Amino acid residues corresponding to a heterologous flag epitopes can be located either at the amino terminus of the mature protein.

Glycoprotein gp140 may be expressed as a fusion protein lacking the furin cleavage site. In another embodiment, it may be necessary to mutagenize the highly conserved furin cleavage site that occurs at the junction between gp120 and gp41 in order to insure that the gp41 domain is covalently attached to the gp120 domain during purification and possibly during immunization.

Glycoprotein gp140 may include sequences attached at the C-terminus of gp140 to facilitate oligomerization into gp140 trimers. In order to create an antigen that replicates the structure of the HIV envelope protein on the surface of virions, it is often desirable to produce gp140 trimers. To accomplish this goal, one can use one of the several strategies such as the addition of a GCN4 coiled coil domain or the T4 fibrin tag that have been described and successfully used by other investigators to produce stable gp140 trimers. Locations where sequences could be attached are within 7 amino acids of the C terminus of gp140 as indicated. Thus, for example, the invention includes a composition comprising a purified HIV env polypeptide, the polypeptide having a Q655R substitution, and having at least 90% amino acid sequence identity to one of the following sequences: SEQ ID NO:16, SEQ ID NO:17, SEQ ID NO:18, SEQ ID NO:19, SEQ ID NO:20. Such compositions include vaccines. Additionally, the invention encompasses an isolated antibody which specifically binds to a purified HIV env polypeptide, the polypeptide having a Q655R substitution, and having at least 90% amino acid sequence identity to one of the following sequences: SEQ ID NO:16, SEQ ID NO:17, SEQ ID NO:18, SEQ ID NO:19, SEQ ID NO:20. Vaccines of the present invention can be used in a prophylactic manner to prevent HIV infection or in a passive therapeutic manner to attenuate existing HIV infection. Vaccines of the present invention may be multivalent, i.e., contain multiple HIV antigens, for example, containing two more HIV-1 envelope glycoproteins, gp160, gp120, and gp41 which present one of more epitopes that bind specifically to broadly neutralizing antibodies. Vaccines of this invention may be administered alone or in combination with other HIV antigens and/or adjuvants, cofactors or carriers. The HIV-1 envelope protein or nucleic acid may be administered in combination with other antigens in a single inoculation "cocktail". Adequacy of the vaccination is determined by assaying antibody titers or the presence of T cells and/or the viral load may be monitored. The polypeptides of this invention may optionally be administered along with other pharmacologic agents used to treat AIDS or ARC or other HIV-related diseases and infections, such as AZT, CD4, antibiotics, immunomodulators such as interferon, anti-inflammatory agents, and anti-tumor agents.

The invention also encompasses constructs containing the sequence of gp160, gp140 or gp41 from neutralization resistant clone 22 from subject 108060 in which a mutation is present, the mutation (Q655R) created by replacement of glutamine with arginine at position 655. The mutation may be introduced by standard in vitro mutagenesis techniques. Note that the basic gp160 sequence (prior to the Q655R mutation) is that from a neutralization resistant clone, and not the neutralization sensitive clone. The Q665R neutralization resistant sequence appears to be more immunogenic than the Q665R neutralization sensitive sequence and confers a stronger neutralizing and protective antibody response. This is not what would have been predicted. Possible preferred embodiments include constructs containing the sequences of SEQ ID NO:16, SEQ ID NO:17, SEQ ID NO:18, SEQ ID NO:19, and SEQ ID NO:20 described herein.

SEQ ID NO:16 is the full length gp160 854 residue sequence (from p1.108060_c22) with the Q655R mutation.

SEQ ID NO:17 is a truncated form of the envelope protein lacking the gp41 transmembrane domain and cytoplasmic tail, termed gp140. In this embodiment the gp160 gene is truncated by deletion of sequences encoding the transmembrane domain and cytoplasmic tail of the gp41 region of the gp160 gene. This is accomplished by introduction of a stop codon (e.g. TAA) after any of the amino acids in the following sequence located adjacent to the start of the gp41 transmembrane domain: SWLWYIK (SEQ ID NO:39).

SEQ ID NO:18 is a fusion protein where the signal sequence of HIV has been deleted and replaced with the signal sequence of another highly expressed protein. The fusion protein is designed to facilitate expression in mammalian cells, and is termed gp140-FP. This embodiment includes at least 95% of gp120 and the extracellular domain of gp41. It specifically lacks the transmembrane domain and cytoplasmic tail of gp41. The molecule is best expressed as a fusion protein where nucleotides encoding the signal sequence and 0-12 N-terminal residues of the mature HIV envelope protein are deleted from the HIV envelope gene and replaced by nucleotide sequences encoding the signal sequence from another highly expressed protein to facilitate expression in mammalian cells. Examples of suitable signal sequence include those of herpes simplex virus 1 glycoprotein D or the prepro signal sequence of human tissue plasminogen activator. It is also desirable to include nucleotide sequences encoding a flag epitope immediately adjacent to the signal peptidase cleavage site at the N-terminus of the mature gp140 protein, or a flag epitope adjacent to the C-terminal sequence of the gp140 protein to facilitate purification. The flag epitope can be any 4-30 amino acid sequence recognized by a monoclonal antibody suitable for immunoaffinity chromatography, or can be a cluster of amino acids such as a poly-histidine (his-tag) sequence that can mediate adherence to an insoluble matrix for affinity purification. In this regard it is important that a simple, non-denaturing process is available to elute the poly-histidine fusion containing fusion protein form the insoluble matrix. In some cases (e.g. herpes simplex virus glycoprotein D) the flag epitope can be derived from the same protein as the heterologous signal sequence. The flag epitope can be attached to any amino acid within the first 20 amino acids of the gp120 portion of the molecule. An example of this is fusion adjacent to the conserved V at position 41 within the full length gp160 sequence and located at the sequence beginning VPVWKEA (SEQ ID NO:21) Amino acid residues corresponding to a heterologous flag epitopes can be located either at the amino terminus of the mature protein.

(SEQ ID NO:19) is a gp140 from 108060_c22 Q655R containing gp120 and the extracellular domain of gp41 with Q655R mutation expressed as a fusion protein and lacking the furin cleavage site.

(SEQ ID NO:20) is a gp140 from 108060_c22 Q655R containing gp120 and the extracellular domain of gp41 with Q655R mutation expressed as a fusion protein and containing sequences to facilitate or stabilize trimer formation.

Experimental Procedures, Materials, Methods and Results

Described is a new method to identify the epitopes recognized by broadly neutralizing antibodies by taking advantage of the naturally occurring amino acid sequence variation (intra-patient variation) that evolves within every HIV-infected individual. This method also allows one to define molecular determinants of sensitivity and resistance to antibody mediated neutralization, and allows for the design of a new class of antiviral drugs. We have used this method to identify a mutation in the HIV fusion protein, gp41, that markedly affects sensitivity and resistance of primary HIV-1 isolates to neutralization by HIV+ sera. The new approach that we describe provides a powerful and convenient method to identify epitopes recognized by bNAbs in HIV+ sera and will enable the development of new immunogens that target these sites.

Studies of the early events in infection have shown that transmission of HIV-1 involves a genetic bottleneck where, out of the myriad of genetic variants in each HIV infected donor, only a single homogeneous variant of HIV-1 successfully replicates in the recipient. This variant replicates to very high titers for the first days and weeks after HIV-1 infection and eventually starts to mutate in response to error-prone reverse transcription to generate a swarm of closely related variants. The swarm further diversifies in response to selective pressures imposed by both cellular and humoral antiviral immune responses. Virus variation, driven by the relentless error-prone reverse transcription and selection by immune responses, occurs throughout the course of HIV infection and is perhaps the greatest challenge in the development of vaccine and therapeutic products. In the present studies we have taken advantage of mutations occurring early in the course of HIV-1 infections to identify specific amino acid substitutions in the HIV-1 envelope glycoproteins gp120 and gp41 to address the problem of susceptibility and resistance to neutralization by bNAbs. For this purpose we have made use of a large collection of clinical specimens from new HIV infections collected in the course of a clinical trial (VAX004) of a candidate HIV-1 vaccine, AIDSVAX. See: Flynn N M, Forthal D N, Harro C D, Judson F N, Mayer K H, Para M F; "Placebo-controlled phase 3 trial of a recombinant glycoprotein 120 vaccine to prevent HIV-1 infection." The Journal of infectious diseases 2005; 191:654-65.

This collection of specimens is unique in that they were obtained within 6 months of infection (mean 109+/−58 days) from multiple sites throughout North America. We reasoned that by studying viruses from early infections, sequence variation would be limited compared to sequences collected at later times after infection, and that subsequent mutational analysis would be simpler than that which would be required if we used specimens collected from later time points.

Results and Analysis

In initial experiments, we PCR amplified full length envelope genes from cryopreserved plasma using nested primers of the type described by Li et al. and cloned the swarm of PCR products into a plasmid expression vector. The vector was specifically designed to permit the construction of pseudoviruses for use in a well established and validated virus neutralization assay (Monogram Biosciences, Inc—see Schweighardt et al., 2007, J Acquir Immune Defic Syndr 46:1-11 and Whitcomb et al., 2007, Antimicrob Agents Chemother 51:566-75). However, instead of pooling all of the clones together and carrying out neutralization assays with a library of cloned genes from each infected individual for neutralization studies as had been done previously, we selected 24-48 clones from each individual and screened each for infectivity and chemokine receptor usage. We then selected approximately 10 CCR5-dependent pseudotype viruses with high infectivity for virus neutralization assays. Overall, viruses were prepared from each of 28 individuals and screened for sensitivity and resistance to neutralization (Table 1). In some cases (e.g. subject 108045) all 10 viruses were resistant to neutralization by a panel of four HIV+ sera known to contain broadly neutralizing antibodies (Table 2A). In other cases (e.g. subject 108073) most of the clones were sensitive to neutralization (Table 2B). However in approximately 85% of the specimens (e.g. subjects 108048 and 108051) we found a mixture of neutralization sensitive and resistant clones that showed differences in sensitivity or resistance to neutralization (Tables 3A and 3B).

After examining the results, 7 clones showing the greatest disparity in sensitivity and resistance to neutralization within the same individual were selected for oligonucleotide sequencing and further analysis. As we hypothesized, sequence variation in several of the sets of neutralization sensitive and resistant clones was limited and allowed for the possibility of in vitro mutagenesis to localize the amino acids responsible for conferring sensitivity and resistance to neutralization by HIV+ sera. To explore this possibility, we selected the viruses from subject 108060 for further analysis. It can be seen (Table 4A) that 3 of the 10 clones analyzed (clones 2, 18, and 24) were relatively sensitive to neutralization by all 4 HIV+ sera; and of the remaining 7 clones, most were resistant to neutralization by HIV+ sera Z1679, Z1684, and N16) and somewhat sensitive to HIV+ sera from Z23. When the gp160 sequences of the neutralization resistant variant (clone 22) and a neutralization sensitive variant (clone 24) were compared (FIG. 1), it was found that they differed at only seven positions. There were 2 amino acid differences in gp120, two amino acid differences in the gp41 ectodomain, and 3 differences in the cytoplasmic tail of gp41.

To determine which amino acids were responsible for the difference in sensitivity to neutralization between clone 22 and clone 24, a series of mutants were introduced onto the backbone of the neutralization resistant clone 22 (FIG. 1B). We found (Table 5) that the replacement of asparagine for serine at position 323 (N323S) in the V3 domain of gp120 had no effect on sensitivity to neutralization. Similarly, the substitution of asparagine for glycine at position 530 in the C5 domain (N530G) of gp120 had no effect. Replacement of lysine at position 634 of the second heptad repeat domain (C34 helix) of gp41 with glutamic acid (K634E) also failed to show a significant difference in neutralization sensitivity. However the replacement of glutamine for arginine at position 655 (Q655R) resulted in a remarkable increase in neutralization sensitivity by all 4 of the HIV+ sera. The difference in neutralization sensitivity was seen with all four HIV+ sera tested, and titration data from the experiments carried out with HIV+ sera Z23 are presented in FIG. 6. This result demonstrated that amino acid substitutions at some locations in the 34 helix, but not others, can cause a significant change in sensitivity and/or resistance to neutralization by antibodies in HIV+ sera.

To understand the impact of this mutation on the structure and function of the 108060 envelope glycoprotein, we examined the linear and 3 dimensional structures of gp41. Examination of the linear structure (FIG. 12) revealed that position 655 was located in the conserved second heptad repeat of gp41 in a region also known as the C34 helix. This part of the molecule is known to play an integral role in virus fusion and indeed forms an essential component of the 6 coil bundle structure that is thought to mediate fusion of the viral membrane with T cell membrane in the course of HIV infection. Position 655 is also located in the T-20 peptide (FIG. 12) that provides the basis for the antiviral drug, FUZEON, that inhibits HIV infectivity by inhibiting virus fusion and entry. Finally the location of this mutation is only eight amino acids from the Membrane Proximal External Region (MPER) of gp41 that is known to contain two distinct epitopes recognized by the broadly neutralizing monoclonal antibodies 2F5 and 4E10. Taken together these results suggest that this mutation occurs in a region that is essential for virus fusion and is in close proximity to a region known to contain other epitopes recognized by other broadly neutralizing antibodies.

The availability of a 3-D structure of the activated 6 coil structure of the gp41 fusion domain allowed us to evaluate the impact of the substitution of arginine for glutamine at position 655 on the structure and function of gp41. Using the structure of Chan and Kim we were able to determine that glutamine at position 655 is located at an internal position facing the interface with the adjacent between two adjacent gp41 monomers, two turns from the terminus of the C34 helix. The glutamine 655 side chain contributes two hydrogen bonds that support both intra-molecular and inter-molecular interactions. One hydrogen bond is formed by association with glutamine at position 553 of the N-terminal heptad repeat 1 (N36 helix) and the second hydrogen bond involves an inter-molecular interaction with the backbone of valine at position 551 of an adjacent C34 monomer in the 6 coil bundle. When viewed in the context of the 6 coiled bundle, the hydrogen bonds contributed by glutamine 655, glutamine 551, and valine 551 form an inter-molecular ring structure that appears to stabilize the 6 coil oligomeric structure. Molecular modeling suggested that replacement of glutamine with arginine impacts the structure of the 6 coil bundle in two ways. First the longer arginine side chain disrupts the close packing of the C34 helix with the N36 helix on the adjacent monomers and precludes the possibility of a hydrogen bond between the arginine side chain with valine 551. Although replacement of arginine for glutamine at 655 does permit an intra-molecular hydrogen bond between arginine with glutamine 553, this mutation precludes the possibility of the inter-molecular ring of hydrogen bonds that appears to stabilize the quaternary interactions involved in the 6 coil assembly.

Monoclonal Antibody Sensitivity and Envelope Transfer—Sensitivity to neutralization by MAbs and fusion inhibitors. While the structural analysis provided insight into the functional consequences of mutations at position 655, two alternate hypotheses can account for a mechanism by which this mutation increases sensitivity to antibody-mediated neutralization. One possibility is that this mutation is located at or near an antibody binding site and that the Q655R mutation restores an epitope recognized by a population of neutralizing antibodies present in all four HIV-positive sera. Alternatively, it is possible that this mutation results in a significant conformational change that is transmitted to other parts of gp41 such as the adjacent MPER or the gp120/gp41 trimer complex in such a way as to increase exposure or access to antibodies at other locations on the molecule.

To explore these possibilities, antibody neutralization studies were carried out with a panel of neutralizing MAbs to epitopes in gp120 and gp41 as well as fusion inhibitors targeting either the gp120 or the gp41 portion of the HIV envelope glycoprotein. In these studies, we examined two broadly gp41-neutralizing MAbs, 2F5 and 4E10; the broadly neutralizing b12 antibody able to block CD4 binding to gp120; and 2G12, an antibody that binds to a carbohydrate epitope in gp120. In addition, we tested the antiviral entry inhibitor CD4-IgG, which binds to sequences in gp120 and is able to neutralize lab-adapted CXCR4-dependent clinical isolates at low concentrations (0.01 to 0.1 µg/ml), and primary clinical isolates of HIV at high concentrations (10 to 100 µg/ml). We also examined the sensitivity of envelope mutants to enfuvirtide, a peptide virus entry inhibitor that consists of a gp41-derived peptide that includes sequences from the C34 helix containing Q655. The results of these studies are shown in Table 6, in which the sensitivities of clone 022 and clone 024 from subject 108060 to neutralizing MAbs were compared. It can be seen that the neutralization-resistant clone 022 is moderately sensitive to the 2F5 and 4E10 MAbs specific for the MPER of gp41 but resistant to neutralization by the b12 and 2G12 MAbs reactive with gp120. This virus was also sensitive to enfuvirtide and resistant to CD4-IgG. The high CD4-IgG concentration required for the neutralization of this virus is consistent with the concentration required to neutralize other primary, CCR5-dependent viruses. We next examined the neutralization-sensitive clone 024 that differs from the neutralization-resistant clone 022 at only seven amino acid positions. We found that this clone was 15- to 20-fold more sensitive to the MPER-specific MAbs (2F5 and 4E10) than the 022 clone. Similarly, the neutralization-sensitive clone 024 was more than 20-fold more sensitive to CD4-IgG and 3.5-fold more sensitive to neutralization by enfuvirtide (Table 6). Thus, clone 024 exhibited significantly increased sensitivity to neutralization by MAbs and antiviral entry inhibitors as well as antibodies in HIV-positive sera. We then mutated the neutralization-sensitive clone 024 so as to replace R with Q at position 655. We found that the resulting mutant (108060_024 R655Q) became resistant to neutralization and showed a pattern of neutralization sensitivity closely resembling that of the neutralization-resistant clone 022. Conversely, when we mutated the neutralization-resistant clone 022 to replace Q at position 655 with R, the resulting mutant (108060_022 Q655R), which differed from the parental neutralization-resistant clone by a single amino acid, exhibited an extraordinary increase in neutralization sensitivity (Table 5). We observed a >125-fold increase in sensitivity to CD4-IgG compared to that of the wild-type clone 022 and a 30- to 35-fold increase in sensitivity to the MPER-reactive antibodies 2F5 and 4E10. We also noted a 17-fold increase in sensitivity to the antiviral drug enfuvirtide. These results highlight the importance of glutamine at position 655 and suggest that epistatic mutations at other sites in clone 024 moderate sensitivity to neutralization. The results of these studies are remarkable in that they show that a single amino acid substitution in gp41 not only confers sensitivity to neutralization by MAbs and entry inhibitors directed to gp41 but also increases sensitivity to CD4-IgG, a molecule that binds to gp120, an entirely different protein. Thus, the Q655R mutation appears to cause a conformational change in gp41 that affects not only the binding of antibodies and entry inhibitors (2F5, 4E10, and enfuvirtide) that bind close to the site of the mutation but also the binding of another inhibitor (CD4-IgG) that binds to a site on gp120 located a considerable distance from the mutation. Transfer of the Q655R mutation to related and unrelated viruses. In order to determine whether the Q655R mutation could confer neutralization sensitivity and resistance to other viruses, this mutation was introduced into two unrelated viruses highly resistant to neutralization (from subjects 108069 and 108051) that normally possessed a Q at a position corresponding to 655 of the virus from subject 108060 (the 108060 virus). The results of these experiments are shown in Table 6. Interestingly, we found that the replacement of Q655 with R had little or no effect on neutralization by any of the HIV-positive sera. However, these mutations significantly increased the sensitivity to neutralization by the 2F5 and 4E10 MAbs (25- to 35-fold). These mutations also increased the sensitivity to neutralization by the entry inhibitors enfuvirtide and CD4-IgG. Thus, the mutation of Q to R at a position corresponding to 655 in the 108069 virus increased the sensitivity to enfuvirtide by more than 17-fold and increased the sensitivity to CD4-IgG by more than 20-fold. The 108069 mutant with the Q655R mutation seemed to be somewhat more sensitive to enfuvirtide and possibly CD4-IgG than the corresponding mutant of the 108051 virus. Together, these results demonstrate that the mutation of Q to R at positions corresponding to 655 of the 108060 virus confers sensitivity to neutralizing MAbs to the MPER and antiviral compounds targeted to the C34 helix and the MPER of gp41. However, it was interesting that these mutations failed to increase the sensitivity to bNAbs in HIV-positive sera. We do not know whether neutralizing activity in HIV-positive sera is attributable to antibodies binding to the C34 region, the MPER, or other parts of the molecule. It has been recently reported that antibodies with specificities similar to 2F5 and 4E10 are rare in HIV-positive sera, which might account for the lack of effect. Alternatively, the failure of the Q655R mutation to increase neutralization sensitivity by HIV-positive sera might be attributable to polymorphisms outside of the MPER and the C34 region that preclude the binding of otherwise bNAbs. This may well be the case since the 108069 and 108051 viruses were selected because of their resistance to neutralization by the HIV-positive sera selected for use in these studies.

Expression of envelope proteins derived from the 108060 clone 22 with the Q655R mutation. In certain embodiments it is desirable to express the protein as a fusion protein that includes a non-HIV signal sequence and a flag epitope for purification. In certain embodiments it is considered desirable to delete the furin cleavage site that is responsible for maturational cleavage of the gp160 precursor into the mature gp120 and gp41 proteins.

FIG. 14 shows three pairs of sequences from neutralization sensitive and neutralization resistant viruses. Swam analysis was used to map the mutations conferring sensitivity and resistance to broadly neutralizing antibodies in HIV+ sera. Included are sequences from subject 108060 as well as sequences from subject 108051 and 108048. The preferred sequences for vaccines can be (1) the neutralization sensitive variant envelope proteins, or (2) the envelope proteins of the resistant viruses where a single amino acid substitution (e.g., Q655R) conferring neutralization sensitivity has been created by in vitro mutagenesis, or (3) any sequence derived from of such sequences. This second type of envelope protein construct appears to provide very strong immunogenicity. Insertion of the single amino acid substitution in a neutralization resistant variant envelope protein often results in a virus that is much more sensitive to neutralization than the original neutralization sensitive variant where there are multiple amino acid differences between the neutralization sensitive and resistant variants. An example of this can be seen in Table 5 where clone 22 with the Q655R mutation is much more sensitive to neutralization than the neutralization sensitive clone 24 variant.

FIG. 14 shows the sequences from subjects 108060, 108051, 108048 corresponding to neutralization sensitive and neutralization resistant variants.

It is interesting to note that the resistant sequence from 108069, when altered to include the Q655R substitution, and analyzed using protein-blast, identified the following top three most similar sequence alignments:

gb|ABG67916.1| optimized HIV-1 subtype B consensus env gp [synthetic construct] Length=850
Score=1482 bits (3836), Expect=0.0, Method: Compositional matrix adjust.
Identities=736/863 (85%), Positives=788/863 (91%), Gaps=22/863 (2%)

gb|AAB64170.1| env polyprotein [HIV-1] Length=854
Score=1461 bits (3783), Expect=0.0, Method: Compositional matrix adjust.
Identities=723/864 (83%), Positives=770/864 (89%), Gaps=20/864 (2%)

gb|ACD41904.1| envelope glycoprotein [HIV 1] Length=855
Score=1459 bits (3777), Expect=0.0, Method: Compositional matrix adjust.
Identities=715/862 (82%), Positives=775/862 (89%), Gaps=15/862 (1%)

Clearly none of these have greater than 85% amino acid identity.

Discussion

In the present studies we describe a novel method useful for mapping epitopes recognized by bNAbs in HIV+ sera as well as mapping mutations that confer sensitivity and resistance to virus neutralizing antibodies. The method relies on naturally occurring mutations in the swarm of closely related viruses that evolve during the course of HIV infection. Some of these mutations occur at epitopes or contact residues recognized by broadly neutralizing antibodies, and some of these appear to effect a conformational change that alters the binding of bNAbs at sites that are distinct from the site of mutation. In previous studies we noted a difference in the binding of a monoclonal antibody between two clones of the HIV-1 gp120 envelope protein obtained from a high risk volunteer that participated in a phase I trial of a candidate HIV vaccine. However, at the time the study was carried out it was not possible to study the effect of this mutation in a virus neutralization assay because technology was not yet available to re-introduce the mutant envelope protein back into the virus with assurance that the sequences were stable and wouldn't change as a consequence of errors in reverse transcription or selection induced by in vitro culture. However, the advent of pseudotype virus neutralization assays utilizing HIV envelope genes incorporated into a stable DNA plasmid vector as opposed to retroviruses with RNA genomes provided the opportunity to take advantage of naturally occurring mutations in HIV envelope genes without the fear of reversion or further mutations. Moreover high throughput sequencing strategies have since been developed that have allowed us to quickly and conveniently sequence multiple variants from the same individual.

Previous attempts to characterized bNAbs in HIV patient sera have relied primarily on immunoadsorbtion studies or on the production of bNAbs from human or mouse B-cells Immunoadsorbtion studies of HIV+ sera with recombinant gp120 has shown that some bNAbs appear to recognize conformation dependent epitopes, some of which are able to block the binding of gp120 to its cellular receptor, CD4. Studies with monoclonal antibodies prepared from HIV+ individuals have shown that broadly neutralizing antibodies recognize carbohydrate residues in gp120 (e.g. 2G12) or epitopes in the membrane proximal domain of gp41 (e.g. 2F5 or 4E10). The best characterized bNAb, 1B12, was isolated from mice immunized with gp120 and optimized for neutralizing activity by genetic engineering. This antibody binds to a complex conformational epitope and is able to block CD4 binding. However it is not clear whether any of these monoclonal antibodies are representative of antibodies found in HIV+ sera, and attempts investigate this possibility remain inconclusive.

In this study we validate the method of using intra-patient variation in the HIV envelope protein in the context of a pseudotype virus neutralization assay to identify mutations that sensitivity and resistance of viruses to neutralization by broadly neutralizing antibodies. Using this method we expect to be able to identify specific epitopes recognized by bNAbs as well as amino acid mutations that alter the sensitivity and resistance of viruses to neutralization by antibodies. In the present studies we have identified a single amino acid substitution (Q655R) in the C34 helix of gp41 that appears to play an important and previously unrecognized role in maintaining the integrity of the 6 coil bundle in the viral membrane fusion apparatus of HIV-1. X-ray crystallography studies demonstrate that this residue contributes two hydrogen bonds: one mediating an intra-molecular interaction with the N36 helix on the same monomer and the other mediating an inter-molecular interaction with the N36 helix on an adjacent monomer. This mutation appears to affect sensitivity to neutralization by bNAbs by altering 4 distinct interactions. First the Q655R mutation breaks a hydrogen bond that mediates an intra-molecular interaction (Q at position 655 of the C34 helix with valine at position 551 of the N36 helix). Second, the Q655R mutation disrupts an inter-molecular interaction (Q at position 655 with valine at position 553 in the N36 helix) with an adjacent monomer. Third, the longer arginine side chain in the Q655R mutation appears to alter the inter-helix packing interface between adjacent monomers by sterically hindering the close association between the C34 helix and the N36 helix on adjacent monomers. Finally, the Q655R mutation appears to prevent the formation of a ring structure involving 12 hydrogen bonds in the 6 coil bundle that occurs upon formation of the gp41 fusion complex. Although it is possible that R655 is able to form an intra-molecular hydrogen bond with position 551, it does not appear likely that this mutation allows for replacement of the inter-molecular hydrogen bond with a residue on the adjacent N36 helix essential for the formation of an inter-molecular hydrogen bonded ring structure.

The location and structural impact of the 655 mutation described in this paper appears to be fundamentally different from another recently described gp41 variant that that affects sensitivity and resistance to neutralization by bNAbs. First, the neutralization sensitive phenotype in this study requires two mutations: an isoleucine to valine substitution at position 675 (I675V) in the MPER and a threonine for alanine substitution at position 569 (T569A) in the first heptad repeat domain (N36 helix) of gp41. The MPER is a well known target of virus neutralizing monoclonal antibodies and is structurally distinct from the C34 helix. The T569A mutation does appear to occur at the interface of the intra-molecular interaction between the N36 and C34 helices. In this case, the substitution of the longer threonine for alanine at position 569 appears to preclude a classical "knob in hole" interaction between adjacent helices and does not appear to affect inter-molecular interactions.

Since the 6 helix coil structure appears to be a conserved structural element fundamental to many biologic processes involving membrane fusion, it may well be the case that hydrogen bond ring structures of the type we have identified for HIV-1 are present and essential for maintaining the functional integrity of coiled-coil bundles required for membrane fusion in other viruses such as influenza, Moloney leukemia virus, Ebola virus, and Visna virus.

If hydrogen bonded ring structures of the type we have identified for HIV are found to be present in other coiled-coil bundles involved in membrane fusion, they may provide a novel rationale for the development of vaccines for the prevention and treatment of other virus infections. Many viruses are thought to use homologous 6 coil bundles to mediate membrane fusion and virus entry, see: Flint S J, Enquist L W, Krug R M, Racaniello V R, Skalka A M. Principles of Virology. 2nd ed.: ASM Press; 2004. We would expect that viruses with similar mutations that affect hydrogen bonded ring structures that stabilize 6 coil bundles may alter the structure of the virus in such a way as to expose important neutralizing sites and facilitate recognition by the immune system. We suggest that HIV envelope glycoproteins with mutations in gp41 that destabilize the 6 coil bundle structure such as that seen in clone 24 from subject 108060 may prove to be superior vaccine immunogens by providing better exposure of epitopes to B-cell receptors or T-cells required for the formation of broadly neutralizing antibody responses.

Detailed Description of the Invention (SC2010-117) Relating to Method to Improve the Immunogenicity of Vaccine Antigens by Modification of Cleavage Sites in HIV-1 gp120

A major goal in HIV vaccine research is the identification of vaccine immunogens able to elicit broadly neutralizing antibodies (bNAbs) and protective cellular immune responses. After more than 25 years of research, antigens with these properties have yet to be described. However, several studies have demonstrated that recombinant envelope glycoproteins are able to adsorb broadly neutralizing antibodies from HIV+ sera. Thus the epitopes recognized by bNAbs are present on recombinant proteins, but they are not immunogenic. These results raised the possibility that alteration of the pattern of antigen processing might refocus the immune response to regions of the envelope glycoprotein that are better able to elicit protective immunity.

The inventors have discovered various protease cleavage sites on HIV gp120 recognized by three major human proteases (cathepsins L, S, and D) important for antigen processing and presentation. Remarkably, six of the eight sites identified were highly conserved and clustered in regions of the molecule associated with receptor binding and/or the binding of neutralizing antibodies. These results suggested that HIV may have evolved a novel mechanism of immune escape by taking advantage of antigen processing enzymes in order to insure that epitopes recognized by neutralizing antibodies are labile and destroyed by proteolysis before they can stimulate protective immune responses. The results from these suggest the possibility that HIV regulates the immunodominance of MHC class II restricted immune responses by limiting the number and location of protease cleavage sites.

The invention encompasses improved vaccine antigens that may be produced by mutation of conserved protease cleavage sites in various viral envelope glycoproteins. The invention details a method of improving the immunogenicity of vaccine antigens by preserving the structure of epitopes recognized by virus neutralizing antibodies that are otherwise inactivated in vivo by exposure to cell associated or secreted proteases. The method entails: 1) determination of the location of protease cleavage sites on virus envelope proteins by in vitro analysis where purified envelope proteins are treated with serum or cellular proteases in vitro, and determination of the identity/location of the protease cleavage sites by standard techniques such as Edmund sequence degradation or mass spectroscopy. 2) Bioinformatic analysis to align the sequences of one virus envelope protein with envelop proteins from different strains of the same virus to determine which protease cleavage sites are conserved and to determine which cleavage sites are located at previously described neutralizing epitopes or receptor binding sites. 3) In vitro mutagenesis to inactivate conserved protease cleavage sites in such a way as to preserve the binding of neutralizing antibodies and/or receptor binding. 4) Screening mutagenized envelope proteins for improved immunogenicity relative to the wild type virus protein by comparing the neutralizing activity of experimental antisera produced in small animal (e.g. rabbits, rat, mice, guinea pigs) immunogenicity studies.

Certain embodiments of the invention include:

A virus envelope protein [such as gp120 from the MN strain of HIV where conserved protease cleavage sites in regions important for receptor binding or the binding of neutralizing antibodies sites are mutated by amino acid replacement to prevent protease cleavage while at the same time preserving the antigenic structure of the molecule as defined by the ability to stimulate the formation of neutralizing antibodies (when used as an immunogen) or be recognized by neutralizing antibodies (when used as an antigen).

A virus envelope protein where protease cleavage sites recognized by serum or cellular proteases are deleted or inactivated or otherwise protected from protease cleavage by in vitro mutagenesis.

A virus envelope protein used as a vaccine antigen where in vitro mutagenesis of conserved cleavage sites protects the neutralizing epitopes from proteolytic degradation in an in vivo environment.

A virus envelope protein where conserved protease cleavage sites located within epitopes recognized by neutralizing antibodies are deleted or inactivated or otherwise protected from protease cleavage by in vitro mutagenesis in such a way as to preserve the ability of the epitope to bind specifically to neutralizing antibodies.

A virus envelope protein described above where the protease cleavage sites are specific for the antigen processing enzymes cathepsin L, cathepsin S, or cathepsin D.

A virus envelope protein described above where the protease cleavage sites are specific for the serum protease thrombin, or the cell associated protease, tryptase, or the inflammation associated proteases such as elastase.

A virus envelope protein described above where the protease cleavage sites are specific for other members of the cathepsin family such as cathepsin B, K, N.

A virus envelope protein as described above where the protein consists of monomeric or oligomeric fragments of the HIV envelope protein gp160 such as gp120, gp140, or gp41.

A virus envelope protein as described above where the protein consists of monomeric or oligomeric fragments of the influenza virus haemagglutinin (HA1/HA2) any strain of influenza (e.g. H1N1).

A virus envelope protein as described above where the protein consists of monomeric or oligomeric fragments of glycoprotein D from Herpes Simplex virus type 1 or type 2.

A virus envelope protein as described above where the protein consists of monomeric or oligomeric fragments of any virus envelope protein for cellular receptor binding.

A virus envelope protein wherein one or more conserved cleavage sites are protected from protease cleavage by in vitro mutagenesis, and wherein said cleavage sites are selected from the cathepsin cleavage sites on MN-rgp120 shown in Table 1.

Other embodiments include the following:

1. A virus envelope protein wherein one or more conserved cleavage sites are protected from protease cleavage by in vitro mutagenesis.

2. The virus envelope protein of claim 1 wherein said cleavage sites are selected from the cathepsin cleavage sites of MN-rgp120 as shown in Table 1, and homologues thereof.

3. The virus envelope protein of claim 1 wherein said cleavage sites the protected from protease cleavage by deletion, mutation, chemical modification (e.g. methylation, acetylation, glycosylation, etc).

4. The virus envelope protein of claim 1 formulated with an excipient, carrier or adjuvant for use as a vaccine.

5. A vaccine formulation comprising an HIV envelope glycoprotein and a protease inhibitor.

6. The vaccine formulation of claim 5 wherein the protease inhibitor is a cathepsin.

7. The vaccine formulation of claim 6 wherein the cathepsin is human cathepsin L, S or D.

8. A vaccine formulation comprising an HIV envelope glycoprotein wherein one or more conserved cleavage sites of the HIV envelope glycoprotein is protected from protease cleavage by in vitro mutagenesis, and wherein the one or more conserved cleavage sites is selected from the cathepsin cleavage sites of MN-rgp120 as shown in Table 1, and homologues thereof.

9. The vaccine formulation of claim 8 wherein the cleavage sites are protected from protease cleavage by deletion, mutation, methylation or acetylation.

10. A method for treatment or prevention of a viral infection, the method comprising administering to a subject the vaccine formulation of claim 5.

11. A method for treatment or prevention of a viral infection, the method comprising administering to a subject the vaccine formulation of claim 8. 12. A method for treatment or prevention of a viral infection, the method comprising contemporaneously administering to a subject a composition comprising an HIV envelope glycoprotein and a protease inhibitor.

13. The method of claim 12 wherein the protease inhibitor is an inhibitor of a cathepsin.

Additional embodiments include the following: 1. A virus envelope protein where conserved protease cleavage sites serve to inactivate epitopes recognized by neutralizing antibodies and are responsible for the lack of protective immune responses when used as a vaccine antigen. 2. A virus envelope protein where conserved cleavage sites recognized by serum or cellular proteases are deleted or inactivated by in vitro mutagenesis. 3. A virus envelope protein used as a vaccine antigen where in vitro mutagenesis of conserved cleavage sites protects the neutralizing epitopes from proteolytic degradation after parenteral injection 4. A virus envelope protein where conserved protease cleavage sites located within epitopes recognized by neutralizing antibodies are deleted or inactivated by in vitro mutagenesis in such a way as to preserve the ability to bind neutralizing antibodies. 5. A virus envelope protein described in claim 2 where the protease cleavage sites are specific for the antigen processing enzymes: cathepsin L, cathepsin S, or cathepsin D. 6. A virus envelope protein described in claim 2 where the protease cleavage sites are specific for the serum protease thrombin, or the cell associated protease, tryptase, or the inflammation associated proteases such as elastase. 7. A virus envelope protein described in claim 2 where the protease cleavage sites are specific for other members of the cathepsin family such as cathepsin B, K, N. 8. A virus envelope protein as described in claim 2 where the protein consists of monomeric or oligomeric fragments of the HIV envelope protein gp160 such as gp120, gp140, or gp41. 9. A virus envelope protein as described in claim 2 where the protein consists of monomeric or oligomeric fragments of the influenza virus haemagglutinin (HA1/HA2) of any strain of influenza (e.g. H1N1). 10. A virus envelope protein as described in claim 2 where the protein consists of monomeric or oligomeric fragments of glycoprotein D from Herpes Simplex virus type 1 or type 2. 11. A virus envelope protein as described in claim 2 where the protein consists of monomeric or oligomeric fragments of any virus envelope protein for cellular receptor binding.

After many years of research, vaccine immunogens able to elicit protective immunity in humans have yet to be described. Although it has been possible to produce recombinant proteins that accurately replicate the complex structure of HIV envelope glycoproteins, these antigens have not been able to elicit broadly neutralizing antibodies or protective immune responses. The fact that recombinant proteins can bind with high affinity to the CD4 and chemokine receptors used by HIV-1 for attachment and entry, and can adsorb virus broadly neutralizing antibodies from HIV-1+ sera suggests that while the neutralizing epitopes of recombinant immunogens possess the proper antigenic structures, these structures are immuno-recessive and simply not immunogenic. Over the last decade, several different approaches have been employed in order to create immunogens able to elicit broadly neutralizing antibodies. These strategies have included 1) efforts to duplicate and/or stabilize the oligomeric structure of HIV envelope proteins 2) the creation of minimal antigenic structures lacking epitopes that conceal important neutralizing sites, and 3) prime/boost strategies combining protein immunization with DNA immunization or infection with recombinant viruses in order to stimulate the endogenous synthesis and presentation of HIV immunogens (13, 26, 27, 69). However, none of these approaches has resulted in a clinically significant improvement in antiviral immunity or HIV vaccine efficacy. Efforts to elicit protective cellular immune responses (e.g. cytotoxic lymphocytes) using recombinant virus vaccines have likewise been disappointing. In fact such vaccines may have promoted HIV infection rather than inhibiting it.

The inventors describe a new approach to re-engineering the immunogenicity of HIV envelope proteins in order to improve the potency and specificity of humoral and cellular immune responses. The approach is based on defining the sites recognized by proteases important for antigen processing as well as other plasma and cell associated proteases. The inventors reasoned that mutation of the sites recognized by proteases essential for antigen processing and presentation might increase the level of helper T cells and refocus the specificity of the antiviral immune response to favor the development of protective immunity. Both humoral and cellular immune responses depend on proteolytic degradation in connection with antigen processing and presentation mediated by professional antigen presenting cells (macrophages, dendritic cells, and B-cells). Normally, proteins of intracellular origin are processed by the proteosome, a 14-17 subunit protein complex located in the cytosol. Proteins of extracellular origin are processed in lysosomes or late endosomes of antigen presenting cells (APCs). The resulting peptide epitopes are then loaded into MHC class I molecules and presented to CD8 or CD4 T-cells on the surface of APC. Within the endosomes and lysosomes of APCs, there are cathepsins, acid thiol reductase, and aspartyl endopeptidase. The enzymes perform two activities: degrading endocytosed protein antigens to liberate peptides for MHC Class II binding, and removal of the invariant chain chaperone (4). Although all cathepsins can liberate epitopes from a diverse range of antigens (14), only cathepsins S and L have nonredundant roles in antigen processing in vivo (reviewed in Hsing and Rudensky 2005). Cathepsin L is expressed in thymic cortical epithelial cells but not in B cells or dendritic cells, while the distribution of cathepsin S is in both types of antigen presenting cells. Unlike cathepsins L and S, which are cysteine proteases and active at neutral pH, cathepsin D is an aspartic protease, active at acidic pH, and participates in proteolysis and antigen presentation in connection with MHC class I and class II antigen presentation pathways established for CD4 and CD8 T-cells. When considering the use of envelope proteins as potential vaccines, the route of immunization, formulation (e.g. adjuvants), protein folding, disulfide bonding, and glycosylation pattern all determine which peptides are available for MHC restricted presentation. Previous studies provided evidence that cathepsins B, D, and L are involved in antigen processing of gp120, but the specific cleavage sites were not defined (Chien, P. C. 2004. Human immunodeficiency virus type 1 evades T-helper responses by exploiting antibodies that suppress antigen processing. J Virol 78:7645-52.). In the present studies, we: 1) describe the location of eight protease cleavage sites on HIV-1 gp120 recognized by cathepsins L, S, and D involved in antigen processing, 2) determine the extent to which they are conserved, and 3) evaluate the effect of cathepsin cleavage on the binding of gp120 to CD4-IgG and neutralizing antibodies. The results obtained provide new insights into the basis of envelope immunogenicity that may prove useful in the development of HIV vaccine antigens.

Materials and Methods.

Proteins, Enzymes and Enzyme Inhibitors.

Recombinant gp120 from the MN strain of HIV-1 (MN-rgp120) was produced in Chinese hamster ovary (CHO) cells by Genentech, Inc. (South San Francisco, Calif.). MN-rgp120 was a major component of the candidate HIV vaccine, AIDSVAX, B/B (29). Purified human cathepsins L, S and D as well as the cathepsin L and D inhibitors N-Acetyl-Leu-Leu-Methional calpain Inhibitor II (ALLM) and Pepstatin A were obtained from Biomol (Philadelphia, Pa.).

Monoclonal Antibodies.

The broadly neutralizing, CD4 blocking monoclonal antibody (MAb) b12 (10, 57) was obtained from Polymun (Vienna, Aus). The virus entry inhibitor, CD4-IgG (11) and MAbs able to neutralize the MN strain of HIV reactive with the V3 domain (1026), and the C4 domain (13H8) were obtained from Genentech, Inc. (S. San Francisco, Calif.) and have been described previously (54, 55). Polyclonal antibody D7324 was purchased from Aalto Bio Reagents Ltd. (Dublin, Ireland). HRPlabeled goat anti-human IgG and goat anti-mouse IgG+M were obtained from American Qualex Antibodies (San Diego, Calif.).

Cathepsin Digestions for Cleavage Site Analysis.

Fifty μg of MN-rgp120 in 25 μl of 100 mM sodium acetate, pH 5.5 digestion buffer was mixed with 0.5 μg cathepsin L (protease to protein ratio 1:100). The reaction was performed at 37° C. Aliquots of 3 μl were taken at 15 min, 30 min, 60 min, 120 min, 240 min, 420 min and the digestion was stopped by rapid cooling in liquid nitrogen. An additional 3 μl aliquot was taken after overnight incubation at room temperature. The aliquots of cathepsin L digestion were mixed with 3 μl of 3× reducing polyacrylamide gel electrophoresis (PAGE) sample buffer (5% SDS, 5% β-mercaptoethanol, 40% glycerol and 200 mM Tris, pH 6.8) and boiled for 2 min. The collected samples were run in two 4-12% Bis-Tris pre-cast gels (Invitrogen, Carlsbad, Calif.). Digested fragments were visualized either by direct Coomassie blue staining or on immunoblots after transferred to a PVDF membrane (Millipore Immobilon PSQ). For sequencing peptides on PVDF membranes, bands were cut out and transferred to the Molecular Structure Facility at the University of California, Davis for N-terminal protein sequencing by Edman degradation. The same experimental procedure was carried out for cathepsin S and D digestion except for the digestion buffer, which was 50 mM sodium phosphate, pH 6.5, with 50 mM sodium chloride for cathepsin S, and 100 mM sodium acetate, pH 3.3 for cathepsin D.

Cathepsin Digestions for ELISA Experiments.

To prepare cathepsin L digested MN-rgp120 for ELISA experiments, 25 µg MN-rgp120 in 50 µl of 100 mM sodium acetate, pH 5.5 digestion buffer was mixed with 1 µg cathepsin L (protease to protein ratio 1:25) at 37° C. for overnight incubation and followed by 1 µl ALLM (25 mg/mL in DMSO) solution to stop the digestion reaction. For cathepsin D treated MN-rgp120, 25 µg of MN-rgp120 was mixed with 1 µg of cathepsin D in 50 µL buffer (100 mM sodium acetate, pH 3.3) at 37° C. for 1 h. Pepstatin A (1 µl at 25 mg/mL in DMSO) solution was added to stop cathepsin D activity.

ELISA of Monoclonal Antibodies and CD4-IgG Binding to Cathepsin Digested MN-Rgp120.

Wells of microtiter plates (Immunosorb II, Becton-Dickenson, Mountain View, Calif.) were coated with 100 µL of the polyclonal antibody D7324 solution (2 µg/mL in PBS buffer) overnight at 4° C. The wells were blocked with 200 µL of blocking buffer (1% BSA in PBS) and incubated at 37° C. for 1 h. After rinsing with washing buffer (0.05% Tween 20 in PBS), 100 µL of cathepsin L treated, cathepsin D treated or undigested MN-rgp120 solution was added to each well (2 µg/mL in blocking buffer) and incubated for 1 h at 37° C. Then, after washing, MAbs were added and five-fold serial dilutions were carried out, starting with 25 ug/mL of MAb b12 and 5 µg/mL of all of the other MAbs, and incubated for 1 h at 37° C. After washing three times with blocking buffer, 100 µL of HRP labeled goat anti-human IgG or goat anti-mouse IgG+M solution (1:10000 in blocking buffer) was added and incubated for 1 h at 37° C. Finally, after washing, 100 µL of 0.4 mg/mL o-phenylenediamine dihydrochloride (Sigma Aldrich Chemicals, St. Louis Mo.) solution was added and incubated at room temperature for 10 min, followed by 100 µL of 3M sulfuric acid to stop the reaction. The O.D. was measured by SpectraMax 190 (Molecular Devices) at 490 nm.

Prediction of Cleavage Sites by Computational Methods.

Envelope glycoprotein sequences were obtained from the Los Alamos HIV sequence database and aligned using MAFFT. The sequence for gp120 from the MN strain of HIV-1 used in these studies, MNGNE, differs from the sequence of Gurgo et al. and has been published previously. To determine the location of predicted cathepsin cleavage sites in MNrgp120, we used the PoPs program developed by Boyd et al., and cleavage specificity algorithms for cathepsins L, S and B generated by Choe and the cathepsin D recognition sequence of Dunn et al.

Conservation Study of Identified Cleavage Sites.

Three datasets were used to investigate the sequence conservation of cathepsin cleavage sites. The VAX004 dataset was obtained from the GSID HIV data browser ("hap:" followed by "//www.gsid" followed by ".org"), which includes 1047 Glade B envelope glycoprotein sequences from 349 individuals with recent HIV infections. A dataset of acute and recent Glade B infections containing 2908 envelope glycoprotein sequences from 102 infected individuals was obtained from the studies of Keele et al. Finally a listing of Glade specific reference sequences as well as a dataset containing 1766 envelope glycoprotein sequences from isolates collected world-wide at various undefined times after HIV infection was obtained from the Los Alamos HIV Sequence Database ("http:" followed by "//www.hiv-.lanl" followed by ".gov/"). The sequences from all three databases were aligned using MAFFT.

Results.

Computational Methods to Locate Protease Cleavage Sites.

Cathepsins L, S, and D are known to play an important role in antigen processing and presentation. In initial studies we used computational methods (see Materials and Methods) to determine whether gp120 was likely to possess cleavage sites recognized by cathepsins known to be important for antigen processing. For these studies we examined sequences with the prediction algorithm (6) set for maximum stringency. The results of these studies (FIG. 13) suggested that MN-rgp120 was likely to possess multiple cathepsin cleavage sites. However, because cathepsin cleavage sites are difficult to predict, and limited information is available (17); MEROPS Peptidase Database ("www-.merops." followed by "sanger.ac" followed by ".uk"), we reasoned that actual protease digestion studies would be required to reliably identify the number and location of these sites.

Mapping Cathepsin L Cleavage Sites.

Initially we examined sensitivity of MNrgp120 to digestion by cathepsin L. A time-course experiment is shown in FIG. 7, Panel A. We found that cathepsin L digestion resulted in six proteolytic fragments. Because of their size, these fragments could not be analyzed by mass spectrometry but rather required analysis by Edman sequence degradation. The size, location, and experimentally determined N-terminal sequence of the peptides isolated is shown in Table 1. The cleavage site shown in this table represents the P1 and P1' residues located on either side of the cleavage site according to standard protease substrate nomenclature. A listing of flanking residues ranging from P4 to P4' is provided in supplemental table S1. We found that digestion with cathepsin L resulted in a 70 kD fragment and a 50 kD fragment appeared within fifteen minutes of treatment. Edman degradation showed the first five amino acids in the N-terminal of the 50 kD fragment are GTIRQ, which revealed that the cleavage site is located between the K327-G328 bond in the V3 domain. The N terminus of the 70 kD fragment is derived from cleavage between the A28-L29 bond in the glycoprotein D flag epitope at the N-terminus of MN-rgp120, resulting in the L29-A30-N31 N-terminal sequence. The kinetics of the appearance of these two fragments indicates the MN-rgp120 was first attacked at the V3 domain cleavage site K327-G328 resulting in two fragments, the 70 kD fragment and the 50 kD fragment. The 50 kD fragment was subsequently degraded at longer digestion times to yield additional fragments (FIGS. 7, Panel A and 8). The Edman degradation confirmed that the resulting 45 kD and the 35 kD fragments are originally from the 50 kD fragment because both include the same N-terminal sequence GTIRQ as the 50 kD fragment. Although the C-terminal sequences of the 50 kD, 45 kD and 35 kD fragments are not known, at least two cathepsin L cleavage sites in the 50 kD fragment are indicated, which result in the 45 kD and 35 kD fragments. The N-terminal amino acid sequence of the resulting 20 kD fragment and the 14 kD fragment proved that there are two cathepsin cleavage sites within the C4 domain. The first four amino acids of the N-terminal of the 20 kD fragment and the 14 kD fragment are KAMY and APPI respectively. Thus, two cathepsin L cleavage sites located between the G431-K432 and Y435-A436 bonds were identified. However, because the molecular weight difference between 20 kD and 14 kD is about 6 kD while the N-terminal sequence difference between the 20 kD and 14 kD is only four amino acids, we deduced that another cathepsin L cleavage site must be present within the C-terminus of MN-rgp120.

Mapping Cathepsin S Cleavage Sites.

We next examined the ability of cathepsin S to digest gp120 using the same methods. The result of a time-course experiment is shown in FIG. 7, Panel B. It can be seen that six degradation products were visible on SDSPAGE gels. The size of the peptides isolated, the N-terminal sequence and the location within gp120 is shown in Table 1. Compared to the cathepsin L digestion, the kinetics of the cathepsin S digestion were much more rapid and indicated significantly increased sensitivity to cathepsin S. Six major digestion fragments appeared on the SDS-PAGE gel within fifteen minutes of cathepsin S digestion, indicating greater exposure or accessibility of cathepsin S cleavage sites compared to cathepsin L. Because of the rapid digestion by cathepsin S, it wasn't possible to determine whether there was a kinetically distinct, ordered degradation of gp120 as seems to be the case with cathepsin L. Rather, cathepsin S appears to follow a different digestion pathway where the protease generates multiple fragments in a very short time frame. Analysis of five cathepsin S digest fragments (e.g. 60 kD, 50 kD, 38 kD, 18 kD and 12 kD) identified four distinct cathepsin S cleavage sites (FIG. 8). Two of these were located in the C2 domain and occurred between Q208-A209 (60 kD) and S261-T262 (50 kD). The third cathepsin S cleavage site occurred in the V3 domain and involved the bond joining T322-T323 (38 kD). Finally an additional cleavage site was located in the C4 domain and occurred between Y435-A436 (18 kD and 12 kD) which is also a cathepsin L cleavage site. Fragments located Nterminal to the C2 domain were not recovered, suggesting that this region of the molecule contains multiple yet undefined cathepsin S cleavage sites. It is possible that some of these yield 3.5 kD fragments, since the final 3.5 kD band on the PAGE gels appeared to be heterogeneous, with multiple fragments migrating at the same position.

Mapping Cathepsin D Cleavage Sites.

A complicated digestion pattern was observed in the digestion of MN-rgp120 with cathepsin D (FIG. 7, Panel C). Eleven digestion fragments were visualized on the SDS-PAGE gel, but only eight fragments were able to be characterized by Edman degradation due to heterogeneity in bands and/or low abundance. Four fragments (55 kD, 52 kD, 30 kD and 12 kD) share a common N-terminal sequence VVIRS (SEQ ID NO:14), which is located in the C2 domain, suggesting a cleavage site E274-V275. Based on differences in molecular weights, we have deduced that additional cathepsin D cleavage sites occur in the V3, C3, V4 and C4 domains (FIG. 8). The Nterminal sequencing of the 20 kD and 70 kD fragment indicated another cathepsin D cleavage site in the V2 domain at the bond between residues L181-Y182. A third cathepsin D cleavage site Gly25-Lys26 occurred close to the N-terminus and produced a 4 kD and a 5 kD fragment. The location of cleavage sites relative to conserved and variable domains as well as disulfide bonds was mapped onto the 2-dimensional structure of Leonard et al. (49) and is shown in FIG. 9. In total, nine cathepsin cleavage sites were identified, one in the N-terminal flag sequence, one in the V2 domain, three in the C2 domain, two in the V3 domain and two in the C4 domain.

Localization of Cathepsin Cleavage Sites on the 3-Dimensional Structure of Gp120.

The cathepsin L, S and D cleavage sites identified in these experiments were mapped onto the 3-dimensional structure gp120 (FIG. 10) of Huang et al. (41). It was clear from these studies that the cathepsin cleavage sites are not randomly distributed throughout the 3-dimensional structure. Remarkably, they appeared to cluster in regions of functional significance, often in close proximity to the binding sites for the CD4 and chemokine co-receptors and/or epitopes recognized by neutralizing antibodies (Table 1). For example, the cathepsin S cleavage sites in the C2 (Q208-A209) and the C4 domains (Y435-A436) and the cathepsin L sites at G431-K432 and Y435-A436 are located in close proximity in the 3 dimensional structure of gp120. The K432 residue and the Y435 residues are known to be contact residues for chemokine receptor binding, and the Q208 residue is one amino acid away from K207 that is also known to be a chemokine receptor contact residue (22, 64, 65). Additionally, the G431 residue is located 2 amino acids away from a string of six amino acid residues 424-429 known to be contact residues for CD4 binding (46). V429 which is at the P2 position for the cathepsin L recognition site is known to be a contact residue for both CD4 and the broadly neutralizing b12 MAb (88). Finally the Q208-A209 cathepsin S cleavage site is 3 amino acids away from K212 also known to be a CD4 contact residue. Two additional cathepsin cleavage sites occur in the C2 domain. Of these, position T262 in the S261-T262 cathepsin L cleavage site is known to be a contact residue for the broadly neutralizing b12 MAb (88); whereas the cathepsin D cleavage site (E274-V275) was the only cathepsin cleavage site that was not part of, or adjacent to, a receptor or neutralizing antibody binding site. Two cathepsin cleavage sites were identified in the V3 domain. The V3 domain is known to be an important determinant of chemokine receptor usage (18, 85) and is known to possess epitopes recognized by a variety of neutralizing antibodies. The cathepsin S site (T322-T323) is located one amino acid away from the crown of the V3 loop containing the GPGRAF (SEQ ID NO:40) sequence important for the binding of multiple neutralizing antibodies (21, 54, 67). The cathepsin L cleavage site at K327-G328 is four amino acids from the cathepsin S site between the stem and the crown of the V3 loop. Finally, a single cathepsin D site involving residues L181-Y182 was located in the V2 domain. The V2 domain is known to possess multiple epitopes for neutralizing antibodies (52, 59) and contains the newly described receptor binding site for the alpha-4-beta-7 integrin (2). Interestingly, position L181-Y182 cleavage site is located one amino acid away from the LDI/LDV recognition sequence required for alpha-4-beta-7 binding to gp120.

Conservation of Cathepsin Cleavage Sites.

An important question in these studies was to determine which if any of the cathepsin protease sites was conserved. A conserved pattern of cathepsin cleavage sites would suggest conservation of the MHC class II restricted immune response. In view of the high degree of sequence variation within the HIV virus, and the fact that the envelope protein is the most variable of all of the HIV proteins, it was uncertain whether any of the sites would be conserved. In initial studies, we aligned the MN-rgp120 and HXB2 gp120 sequences with twelve reference sequences: two from each of four major group clades: A, C, D, E (crf A/E), plus two from the chimpanzee isolate, HIVcpz, and two simian immunodeficiency virus (SIV) sequences (SIVMac 251 and SIVMac239). The results of this analysis are shown in Table 2 where both the location and conservation of the sites recognized by cathepsins L, S, and D can be seen along with the locations of predicted cathepsin cleavage sites. This analysis of the residues occurring at the P1 and P1' positions showed a high level of conservation at 6 of the 8 cathepsin cleavage sites. Remarkably, two sites, including the cathepsin S sites 5261-T262 site in the C2 domain and the cathepsin L site at position G431-K432 in the C4 domain, were conserved in the reference strains of the major group HIV clades, the HIV cpz strains, and the SIV strains. A high level of conservation (~98%) was also noted at the Q208-A209 cleavage site in the C2 domain, and the Y435-A436 site in the C4 domain. A somewhat lower (81-92%) level of conservation was also noted at the L181-Y182 site in the V2 domain; however, in this case the MN strain is unusual in that L replaces F at position 181. The highly conserved nature of these sites suggests that they are important for virus function or survival and have been preserved by positive selection across species and time.

To further explore the conservation of cathepsin cleavage sites, we examined the three independent HIV sequence datasets. One dataset (GSID HIV Sequence Database) included 1047 gp120 sequences from 349 individuals with new and recent HIV infections (less than 6 months post infection) from different cities throughout North America (29). A second dataset was obtained from the studies of Keele et al. (44) consisting of 2908 sequences from 102 new and acute infections collected in the United States. The third HIV dataset examined was the Los Alamos HIV Sequence database, comprising 1766 gp120 sequences collected from world-wide isolates that included sequences from the 1980s through the present time. Most of these sequences were from chronic HIV infections. The results of this analysis are presented in Table 2.

We found a very high level of conservation (i.e. >96%) in the Q208-A209 and S261-T262 cathepsin cleavage sites in the C2 domain, and the G431-K432 and Y435-A436 cleavage sites in the C4 domain of gp120. In the case of the 431-432 cleavage site, a significant discrepancy was noted between the Los Alamos dataset and the VAX004 and Keele datasets. Further analysis indicated that this result could be attributed to clade-specific polymorphism, where Glade B viruses typically possessed K at position 432, while other clades typically possessed R at this position. The F181-Y182 cleavage site in the V2 domain was also highly conserved (i.e., >80%); however the sequence of HIVMN was unusual in that K replaced F at position 181.

Effect of Cathepsin Cleavage on the Binding of CD4-IgG and Neutralizing Antibodies.

Based on the location of cathepsin cleavage sites at or near receptor binding sites and epitopes recognized by neutralizing antibodies, it was of interest to determine whether cathepsin cleavage actually affected the binding of antibodies to these sites. The binding of monoclonal antibodies to cathepsin treated and untreated MN-rgp120 was investigated by ELISA (FIG. 11). One concern in performing this assay was the possibility that enzyme cleavage would release small peptide fragments that would not be captured onto the microtiter plate. Examination of the proteases cleavage sites in relation to the disulfide structure showed that proteolysis of the peptide backbone would not necessarily release multiple peptide fragments since most would remain associated by virtue of disulfide bonds. Thus, treatment with cathepsin L should only release a small 4 amino acid peptide, K432-Y435, from the C4 domain Treatment with cathepsin D might split the molecule into two large fragments by virtue of the cleavage site located at position 274 in the C2 domain and might also result in the release of an undefined 4-5 kD fragment from the C1 domain. Treatment with cathepsin S should have the largest effect and should result in the loss of the C1, V1, V2, and C2 domains. For this reason, we studied antibody binding to only cathepsin L and cathepsin D treated molecules. The panel of MAbs used for this study included two that were made against MN-rgp120, 1026 and 13H8, which were sequence dependent and recognized the V3 and C4 domains respectively (54, 55). In addition, we included the broadly neutralizing, CD4 blocking MAb b12 (10, 57), as well as CD4-IgG (11), both of which bind to conformation dependent sites involving several regions of the molecule.

Using a standard ELISA, we compared antibody binding to cathepsin L treated and untreated MN-rgp120. The digestions ran to completion as judged by the absence of intact gp120 when resolved by polyacrylamide gel electrophoresis. We found that cathepsin L digestion of gp120 destroyed the ability to bind both the V3 domain specific, virus neutralizing 1026 MAb, and the C4 domain specific, CD4-blocking 13H8 MAb. Much of the binding to b12 and CD4 IgG was preserved by cathepsin L digestion; however, there was a significant reduction in binding affinity. This result can be explained by the fact that the two C4 sites, G431-K432 and Y435-A436, and one V3 site, K327-G328, are located in close proximity to the epitopes recognized by the 13H8 and 1026 MAbs. A different pattern of binding was observed with cathepsin D treated gp120. In these experiments, the binding to 13H8 and 1026 was preserved, although there appeared to be some reduction in binding affinity of the 1026 MAb. In addition, there was a large reduction in binding to b12 as well as to CD4-IgG. The inability of cathepsin D treatment to inhibit the binding of the 13H8 MAb can be attributed to the fact that the cathepsin D cleavage sites are located in the V2 and C2 domains, and remote from the conformation independent 13H8 epitope in the C4 domain. The large decrease in binding affinity of the b12 MAb and CD4-IgG to cathepsin D treated gp120 might be explained by the fact that sequences in the C2 domain are known to be important for maintaining the structure of the CD4 binding site, and that binding of the b12 MAb is dependent on contact sites in this region (46, 88). Together these results demonstrate that cathepsin cleavage sites are located in regions of gp120 recognized by neutralizing MAbs and CD4-IgG, and that cleavage by cathepsins L and D differentially alters antibody and CD4 binding to these sites.

Discussion.

In these studies we have identified the location of cleavage sites on MN-rgp120 recognized by three proteases (cathepsin L, cathepsin S and cathepsin D) thought to be important in antigen processing and presentation. We found that these sites are not randomly distributed, but rather occurred in regions of the envelope glycoprotein known to possess receptor binding and attachment sites and epitopes recognized by neutralizing antibodies. Comparative sequence analysis showed that many of these sites are highly conserved in the major clades of HIV with some being conserved in both the chimpanzee form of HIV as well as SIV. Finally we showed that cleavage by cathepsins L and D diminished the binding of neutralizing antibodies and CD4-IgG. We found that none of the experimentally determined cathepsin cleavage sites matched the cathepsin cleavage sites predicted by enzyme cleavage site prediction programs (Table 1).

To some extent, the ability to predict cathepsin cleavage sites has been limited by the availability of experimental data as indicated in the MEROPS Peptidase Database (Rawlings et al. 2008). Moreover there is uncertainty as to the extent to which cathepsin recognition sequences extend upstream and downstream of the cleavage site. The listing of N-terminal and C-terminal flanking sequences for the sites defined in this study is provided in supplemental information Tables S1 and S2 and will contribute to our knowledge of cathepsin recognition motifs.

Remarkably seven of the cathepsin cleavage sites identified in this study were located in regions of the envelope protein known to be associated with receptor binding or the binding of neutralizing monoclonal antibodies. For example, the V2 domain is known to contain epitopes recognized by virus neutralizing antibodies and has been termed the global regulator of virus neutralization. Moreover the L181-Y182 cathepsin D cleavage sites are located just one amino acid away from the alpha-4-beta-7 receptor binding site (LDI/V) recently reported by Arthos et al. The V3 domain is known as the principal neutralizing determinant and contains epitopes recognized by a variety of neutralizing antibodies and is a key determinant of chemokine receptor tropism. The C4 domain is known to possess multiple contact residues for CD4 binding, chemokine receptor binding, and the binding of CD4 blocking, neutralizing antibodies. The importance of the CD4 binding site in antigen processing was noted by Tuen et al. (2005) who reported that antibodies to the CD4 binding site inhibited cleavage by antigen processing enzymes and subsequent MHC class II antigen presentation. Sequences in the C2 domain have been reported to be important for both CD4 binding and chemokine receptor binding, and it is remarkable that one of the cathepsin S sites identified in the C2 domain is located at a CD4 contact residue and the other is located at a chemokine receptor contact residue. It is difficult to understand how this remarkable correspondence between receptor binding sites and cathepsin cleavage sites could occur by chance. This is particularly significant in view of the fact that there are several domains in gp120 that appear to be devoid of cathepsin cleavage sites. These include the C1, V1, V4, and V5 domains which lack cathepsin L cleavage sites. However our data suggest that one or more cathepsin S and cathepsin D cleavage sites remain to be located between the N-terminus and the V2 domain.

The functional importance of the cathepsin cleavage sites identified above was further supported by the observation that six of the eight cathepsin cleavage sites were highly conserved in HIV, with one, G431-K432 in the C4 domain, being conserved in HIVcpz as well as SIV. Previous studies have suggested that many viruses, including, HIV, have evolved mechanisms to alter antigen processing as a way to escape or direct the immune response to their advantage, see Wolf, P. 1995 Annu Rev Cell Dev Biol 11:267-306. Most of these mechanisms affect MHC class I restricted cellular immune responses; however, mechanisms that alter MHC class II antigen presentation have also been reported (Keele, B. F. 2008. Proc Natl Acad Sci USA 105:7552-7.). HIV has developed a variety of mechanisms to evade the immune response. HIV directly destroys CD4+ helper T cells required for effective control of virus replication, and a lack of effective T-cell help is thought to limit the antiviral immune response. Other mechanisms to evade the immune response include the high level of sequence variation that is evident in all HIV proteins, but particularly evident in the envelope protein that incorporates many insertions and deletions. The virus also appears to have evolved epitope concealment mechanisms in the envelope protein that restrict access to antibody binding at neutralizing sites in the V3 domain, CD4 binding site, and membrane proximal external region (MPER) Finally, the large number of N-linked glycosylation sites on gp120 which are thought to form a protective "glycan shield" that provides yet another level of protection from the binding of neutralizing antibodies.

The results of our studies suggest that HIV may have evolved another mechanism of immune escape involving incorporation of protease cleavage sites in regions important for receptor binding and the binding of neutralizing antibodies. Cleavage at these sites may direct or modulate the immune response in such a way as to prevent the formation of neutralizing antibodies or prevent recognition of existing neutralizing antibodies. Our results suggest that the cleavage sites recognized by enzymes important for MHC class II antigen processing are highly conserved and localized to functionally specific regions of the envelope glycoprotein. Because of the extraordinarily high level of sequence variation in HIV-1, resulting from high mutation and replication rates as well as immune selection, it is unlikely that these sites could be preserved unless they provided a significant fitness advantage for the virus.

Recent studies by Tenzer et al. (Virology 372:273-90) suggested that the immunodominance of CTL epitopes is determined by proteosome digestion profiles and trimming by endoplasmic reticulum aminopeptidases. They further showed that CTL escape mutations involved amino acid substitutions that affected proteosome cleavages directly or sequences flanking cleavage sites in p17 and p24. The results from the present studies are consistent with the possibility that HIV might similarly regulate the immunodominance of MHC class II restricted immune responses by tightly controlling proteolysis by the enzymes required for MHC class II antigen processing. The observation that the antigen processing sites are highly conserved is itself remarkable and consistent with this hypothesis. The additional observation that these sites are located in regions associated with receptor binding and neutralizing antibodies binding is especially noteworthy and suggests important functional significance. It should be emphasized that while Tenzer at al. suggests that protease cleavage affects the immunogenicity of the cytotoxic lymphocyte immune response to HIV core proteins, the present work is significantly novel in that we have discovered that protease cleavage affects the immunogenicity of antibody mediated immune response.

One potential explanation for the conservation of cathepsin cleavage sites at receptor binding sites is the fact that the receptor binding sites are among the few sites on the virion associated envelope proteins that are not protected by the protective glycan shield and thus may be the only sites accessible to proteases. However, it is unlikely that this can explain the data since gp120 is readily shed from viruses and monomeric gp120 has multiple exposed regions that are not glycosylated. An alternative explanation may relate to an additional immune escape mechanism first described for poliovirus.

Studies with poliovirus type 3 have shown that a major neutralizing epitope (antigenic site 1) contains a protease cleavage site, and that cleavage at this site prevents the binding of neutralizing antibodies. The authors suggested that this protease site may have evolved as a means by which the virus could escape from neutralizing antibodies directed to this site. The incorporation of protease cleavage sites at neutralizing epitopes, in effect, causes neutralizing epitopes to "self destruct" after coming into contact with serum or cellular proteases. The possibility that epitopes recognized by neutralizing antibodies are labile and subject to destruction by extracellular proteases before they can stimulate antigen receptors on B cells is intriguing and could explain why it has been so difficult to elicit neutralizing antibodies with recombinant envelope proteins, despite the fact that they clearly possess the capacity to absorb broadly neutralizing antibodies from HIV+ sera. The effect of such cleavage could be to prevent the formation of neutralizing antibodies to the intact virus envelope protein or the prevention of existing neutralizing antibodies to important neutralizing epitopes. For this type of mechanism to be operative, one would need to show that cathepsin proteolysis is able to destroy the epitopes recognized by neutralizing antibodies, and that cleavage would need to occur prior to exposure of gp120 to antigen receptors on B cells. The antibody binding studies described in this paper showed that the binding of neutralizing antibodies and CD4-IgG was significantly reduced, and in some cases completely prevented, by cathepsin cleavage. These results in part fulfill the first requirement of this epitope "self-destruct" hypothesis. However, these cathepsins are best known as lysosomal and endosomal enzymes and therefore, would not be expected to come in direct contact with HIV virions. Examination\ of the literature revealed that several cathepsins (e.g. cathepsins L, B, S, and K) can be secreted and are known to play an important role in cancer biology, tissue remodeling, and inflammatory diseases (15, 48, 56, 86). The release of these enzymes has not been studied in the course of HIV infection; however, cathepsin S has been reported to be secreted from activated macrophages (63). While proteolysis of virion-associated envelope proteins would be expected to inhibit virus infectivity, it is doubtful that this cleavage would be 100% effective. The high levels of plasma viremia and integrated provirus that occur in HIV infection would likely insure that infection is sustained even if a large percentage of virus is inactivated by protease cleavage. Since our studies show that gp120 is highly sensitive to cathepsin S, and because cathepsin S is unique in being highly active at neutral pH, and because cathepsin S sites are located in close proximity to neutralizing sites in the C2, V3, and C4 domains, this enzyme is a logical candidate to mediate epitope destruction in vivo.

While the role of cathepsins on the MHC class II immune responses is undisputed, they may also play an important role in MHC class I responses to HIV. A variety of MHC class I restricted CTL epitopes occur at or in close proximity to the cathepsin cleavage sites identified in this paper. These include the cathepsin S site in the C2 domain, the cathepsin S and L sites in the V3 domain, and the cathepsin L sites in the C4 domain. The co-location of these CTL epitopes with the cathepsin cleavage sites identified in this paper may result from the TAP independent "crosspresentation" pathway that has been documented for dendritic cells and macrophages and known to require cathepsin S. This pathway enables proteosome independent MHC class I restricted presentation of peptides generated by cathepsin S cleavage. Identification of antigen processing sites promises to provide a new understanding of the molecular basis of the specificity of the immune response to HIV envelope glycoprotein. Insertion or deletion of cathepsin cleavage sites may provide a new approach to refocus both humoral and cellular antiviral immune responses. Studies to explore this possibility are in progress. Proteases are estimated to represent ~2% of the genes in the human genome (62) and it would not be surprising that HIV has evolved additional strategies to use proteases to its advantage. The studies described will contribute to our understanding of the specificity of antiviral immune responses and will add to our knowledge of the role of proteases in HIV biology.

TABLES from SC-2010-117

| Sequence ID number | Protein or protein segment | Species * |
|---|---|---|
| SEQ ID NO: 7 | GlyThrIleArgGln | HIV 1 |
| SEQ ID NO: 8 | LysAlaMetTyr | HIV-1 |
| SEQ ID NO: 9 | AlaProProIle | HIV-1 |
| SEQ ID NO: 10 | AlaCysProLys | HIV-1 |
| SEQ ID NO: 11 | ThrGlnLeuLeu | HIV-1 |
| SEQ ID NO: 12 | ThrLysAsnIle | HIV-1 |
| SEQ ID NO: 13 | TyrLysLeuAsp | HIV-1 |
| SEQ ID NO: 14 | ValValIleArgSer | HIV-1 |
| SEQ ID NO: 15 | LysTyrAlaLeu | HIV-1 |
| SEQ ID NO: 22 | MN | HIV-1 |
| SEQ ID NO: 23 | HXB2 | HIV-1 |
| SEQ ID NO: 24 | A1.KE.94.Q23_17 | HIV-1 |
| SEQ ID NO: 25 | A1.UG.92.92UG037 | HIV-1 |
| SEQ ID NO: 26 | C.ET.86.ETH2220 | HIV-1 |
| SEQ ID NO: 27 | C.IN.93.93IN101 | HIV-1 |
| SEQ ID NO: 28 | D.TZ.01. A280 | HIV-1 |
| SEQ ID NO: 29 | D.UG.94.94UG114 | HIV-1 |
| SEQ ID NO: 30 | AE.TH.93.93TH051 | HIV-1 |
| SEQ ID NO: 31 | AE.TH.90.CM240 | HIV-1 |
| SEQ ID NO: 32 | CPZ.CM.05.SIVcpzMT145 | SIV |
| SEQ ID NO: 33 | CPZ.US.85.CPZUS | SIV |
| SEQ ID NO: 34 | SIV.US.MAC251 | SIV |
| SEQ ID NO: 35 | SIV.US.MAC239 | SIV |

* HIV-1: Viruses; Retro-transcribing viruses; Retroviridae; Orthoretrovirinae; Lentivirus; Primate lentivirus group
SIV: Viruses; Retro-transcribing viruses; Retroviridae; Orthoretrovirinae; Lentivirus; Primate lentivirus group

TABLE 1

Identification of cathepsin cleavage sites on MN-rgp120 identified by N-terminal sequencing

| Proteases | Size | Cleavage site | N-terminal sequence | Domain | Associated function* | Sequence No. |
|---|---|---|---|---|---|---|
| Cathepsin L | 70k | $A_3$-$L_4$ | LAD | HSV-1 gD | Flag | |
| | 50k | $K_{327}$-$G_{328}$ | GTIRQ | V3 | 3 | SEQ ID NO: 7 |
| | 45k | $K_{327}$-$G_{328}$ | GTIRQ | V3 | 3 | SEQ ID NO: 7 |
| | 35k | $K_{327}$-$G_{328}$ | GTIRQ | V3 | 3 | SEQ ID NO: 7 |
| | 20k | $G_{431}$-$K_{432}$ | KAMY | C4 | 1, 2, 4 | SEQ ID NO: 8 |
| | 14k | $Y_{435}$-$A_{436}$ | APPI | C4 | 2, 4 | SEQ ID NO: 9 |
| Cathepsin S | 60k | $Q_{208}$-$A_{209}$ | ACPK | C2 | 1, 2 | SEQ ID NO: 10 |
| | 50k | $S_{261}$-$T_{262}$ | TQLL | C2 | 3 | SEQ ID NO: 11 |
| | 38k | $T_{322}$-$T_{323}$ | TKNI | V3 | 3 | SEQ ID NO: 12 |

TABLE 1-continued

Identification of cathepsin cleavage sites on
MN-rgp120 identified by N-terminal sequencing

| Proteases | Size | Cleavage site | N-terminal sequence | Domain | Associated function* | Sequence No. |
|---|---|---|---|---|---|---|
| | 18k | $Y_{435}$-$A_{436}$ | APPI | C4 | 2, 4 | SEQ ID NO: 9 |
| | 12k | $Y_{435}$-$A_{436}$ | APPI | C4 | 2, 4 | SEQ ID NO: 9 |
| | 3.5k | — | — | — | | |
| Cathepsin D | 70k | $L_{181}$-$Y_{182}$ | YKLD | V2 | 3, 5 | SEQ ID NO: 13 |
| | 55k | $E_{274}$-$V_{275}$ | VVIRS | C2 | N/A | SEQ ID NO: 14 |
| | 52k | $E_{274}$-$V_{275}$ | VVIRS | C2 | N/A | SEQ ID NO: 14 |
| | 45k | — | — | — | | |
| | 30k | $E_{274}$-$V_{275}$ | VVIRS | C2 | N/A | SEQ ID NO: 14 |
| | 20k | $L_{181}$-$Y_{182}$ | YKLD | V2 | 4, 5 | SEQ ID NO: 13 |
| | 12k | $E_{274}$-$V_{275}$ | VVIRS | C2 | N/A | SEQ ID NO: 14 |
| | 10k | — | — | — | | |
| | 6k | — | — | — | | |
| | 5k | — | KYAL | HSV-1 gD | Flag | SEQ ID NO: 15 |
| | 4k | — | KYAL | HSV-1 gD | Flag | SEQ ID NO: 15 |

*1, indicates CD4 binding site; 2, indicates chemokine receptor binding site; 3, indicates V3 domain neutralizing antibody binding site; 4, indicates b12 antibody binding site; 5, indicates α4β7 binding site; N/A, indicates data not available; and Flag, indicates sequence from herpes simplex virus glycoprotein D used as a flag epitope to facilitate purification.

TABLE 2

Conservation of cathepsin cleavage sites in HIV sequence datasets*

| Observed cleavage sites for MN | | | | Polymorphism prevalence in HIV cohorts (%) | | | | | |
|---|---|---|---|---|---|---|---|---|---|
| | | | | VAX004 n = 1047 | | Keele n = 2908 | | Los Alamos n = 1766 | |
| Domain | Cathepsin | Location | Site | | | | | | |
| V2 | D | 181-182 | LY | FY | (81.4) | FY | (81.0) | FY | (92.2) |
| C2 | S | 208-209 | QA | QA | (97.6) | QA | (96.8) | QA | (97.3) |
| C2 | S | 261-262 | ST | ST | (97.4) | ST | (99.3) | ST | (97.9) |
| C2 | D | 274-275 | EV | EV | (61.3) | EV | (60.6) | EI | (39.8) |
| V3 | S | 322-323 | TT | AT | (59.4) | AT | (49.5) | AT | (58.0) |
| V3 | L | 327-328 | KG | IG | (87.1) | IG | (91.6) | IG | (83.2) |
| C4 | L | 431-432 | GK | GK | (91.5) | GK | (96.3) | GK | (36.6) |
| C4 | S, L | 435-436 | YA | YA | (98.9) | YA | (97.7) | YA | (97.7) |

*The VAX004 dataset of clade B viruses from the US was obtained from the GSID HIV Sequence database (www.gsid.org); a dataset of clade B viruses from acute infections (Keele et al., 2008) and a dataset of world-wide isolates of HIV were obtained from the Los Alamos HIV Sequence database (www.lanl.hiv.gov).

SUPPLEMENTAL TABLE S1

Predicted cathepsin cleavage sites in MN-rgp120

| Cathepsin | Cleavage Site | P4 | P3 | P2 | P1 | P1' | P2' | P3' | P4' |
|---|---|---|---|---|---|---|---|---|---|
| L | 45-46 | P | V | W | K | E | A | T | T |
| | 96-97 | N | M | W | K | N | N | M | V |
| | 183-184 | L | L | Y | K | L | D | I | E |
| | 197-198 | T | S | Y | R | L | I | S | C |
| | 471-472 | E | I | F | R | P | G | G | G |
| | 482-483 | D | N | W | R | S | E | L | Y |
| | 487-488 | E | L | Y | K | Y | K | V | V |
| | 489-490 | Y | K | Y | K | V | V | T | I |
| S | 354-355 | S | K | L | K | E | Q | F | K |
| | 421-422 | C | K | I | K | Q | I | I | N |
| | 440-441 | P | P | I | E | G | Q | I | R |
| D | 215-216 | K | I | S | F | E | P | I | P |

Predicted cathepsin L, S and D cleavage sites in MN-rgp120. The location of cathepsin cleavage sites and flanking sequences was predicted using the method of Boyd et al. (6) and cleavage specificity algorithms for cathepsin L and S from Choe et al. (17) and cathepsin D from Scarborough et al. (73). The scissile bond, located between the P1 and P1' residues, and the flanking residues are listed according to the nomenclature of Schechter and Berger (74).

SUPPLEMENTAL TABLE S2

Observed cathepsin cleavage sites in MN-rgp120

| Cathepsin | Site | P4 | P3 | P2 | P1 | P1' | P2' | P3' | P4' |
|---|---|---|---|---|---|---|---|---|---|
| L | 327-328 | K | N | I | K | G | T | I | R |
| | 431-432 | Q | K | V | G | K | A | M | Y |
| | 435-436 | K | A | M | Y | A | P | P | I |
| S | 208-209 | V | I | T | Q | A | C | P | K |
| | 261-262 | P | V | V | S | T | Q | L | L |
| | 322-323 | A | F | Y | T | T | K | N | I |
| | 435-436 | K | A | M | Y | A | P | P | I |
| D | 181-182 | Y | A | L | L | Y | K | L | D |
| | 274-275 | A | E | E | E | V | V | I | R |

Experimentally determined cathepsin L, S and D cleavage sites in MN-rgp120. The location of cathepsin cleavage sites and flanking sequences was determined for MN-rgp120 by Edman sequence degradation of peptides recovered after protease digestion (see Material and Methods). The scissile bond, located between the P1 and P1' residues, and the flanking residues are listed according to the nomenclature of Schechter and Berger (74).

Tables from SC2009-449

TABLE 1

Neutralization in 108059 and 108060

| A Clone | 108059 Wild Type Viruses Sera/Neutralization Titers* | | | | B Clone | 108060 Wild Type Viruses Sera/Neutralization Titers | | | |
|---|---|---|---|---|---|---|---|---|---|
| | Z1679 | Z1684 | N16 | Z23 | | Z1679 | Z1684 | N16 | Z23 |
| 002 | <40 | <40 | <40 | 251 | 022 | 53 | 58 | 51 | 117 |
| 005 | <40 | <40 | <40 | 234 | 024 | 804 | 609 | 612 | 1667 |
| 008 | <40 | <40 | <40 | 244 | 002 | 303 | 160 | 195 | 379 |
| 010 | <40 | <40 | <40 | 238 | 003 | 69 | 57 | 67 | 151 |
| 013 | <40 | <40 | <40 | 196 | 011 | 136 | 130 | 177 | 222 |
| 014 | <40 | <40 | <40 | 436 | 012 | 62 | 57 | 70 | 241 |
| 016 | 44 | 50 | 49 | 490 | 013 | 53 | 50 | 58 | 158 |
| 018 | <40 | <40 | <40 | 167 | 018 | 428 | 243 | 388 | 1378 |
| 021 | <40 | <40 | <40 | 278 | 019 | 44 | <40 | 40 | 145 |
| 023 | <40 | <40 | <40 | 258 | 021 | 47 | 47 | 70 | 157 |

The neutralizing antibody titer (IC50) is defined as the reciprocal of the plasma dilution that produces a 50% inhibition in target cell infection. Values in bold represent neutralization titers that are at least 3 times greater than those observed against the negative control (aMLV). All clones tested were CCR5 tropic. Clone indicates gp160 envelope genes.

TABLE 2

Neutralization of Wild Type (WT) and Mutated Clones from Subject 108060 by HIV + sera possessing broadly neutralizing antibodies

| A Clone/ Mutants | Mutation of Clone 022 wtR from 108060 Sera/Neutralization Titers* | | | | B Clone mutant | Mutation at Position 655 Sera/Neutralization Titers* | | | |
|---|---|---|---|---|---|---|---|---|---|
| | Z1679 | Z1684 | N16 | Z23 | | Z1679 | Z1684 | N16 | Z23 |
| 022 wtR | 75 | 104 | 76 | 384 | 022 wtR | 40 | <20 | 36 | 281 |
| 024 wtS | 728 | 1086 | 982 | 1926 | 024 wtS | 1099 | 1193 | 545 | 4167 |
| N323S | 73 | 95 | 54 | 382 | 022 Q655R | 14276 | 2876 | 2610 | 8422 |
| N530G | 37 | 42 | 41 | 308 | 022 Q655K | 5486 | 8590 | 4276 | 19476 |
| K634E | 67 | 73 | 72 | 346 | 022 Q655E | 564 | 132 | 366 | 2424 |
| Q655R | 2165 | 2562 | 4472 | 8290 | 022 Q655S | 1565 | 472 | 674 | 2650 |
| I827T | 39 | <20 | 113 | <100 | 022 Q655N | 148 | 24 | 57 | 820 |
| 832/833 | 104 | 50 | 63 | 404 | 022 I827T | 49 | <20 | <20 | 277 |
| 827/832/833 | 72 | 53 | 81 | 279 | 024 R655Q | 50 | <20 | 39 | 372 |

The neutralizing antibody titer (IC50) is defined as the reciprocal of the plasma dilution that produces a 50% inhibition in target cell infection. Values in bold represent neutralization titers that are significantly above the background (Experimental Procedures). All clones tested were CCR5 tropic. Clone indicates gp160 envelope genes. wtR and wtS indicate wild type neutralization-resistant and -sensitive clones respectively.

TABLE 3

Transfer of Q655R Mutation to Unrelated Viruses: Sensitivity to Neutralizing Monoclonal Antibodies and Entry Inhibitors

| Clone | Mutation | IC50 MAbs and Fusion Inhibitors (µg/ml) | | | | | |
|---|---|---|---|---|---|---|---|
| | | 2F5 | 4E10 | b12 | 2G12 | FUZEON | CD4 IgG |
| 108060_022 | wtR | 3.250 | 5.201 | >20 | >20 | 0.068 | >20 |
| 108060_022 | Q655R | 0.093 | 0.156 | >20 | >20 | 0.004 | 0.161 |
| 108060_024 | wtS | 0.151 | 0.333 | >20 | >20 | 0.019 | 0.798 |
| 108060_024 | R655Q | 3.434 | 6.546 | >20 | >20 | 0.130 | >20 |
| 108069_005 | wtR | 1.129 | 3.556 | >20 | >20 | 0.071 | >20 |
| 108069_011 | wtS | 0.043 | 0.040 | >20 | >20 | 0.145 | >20 |
| 108069_005 | Q655R* | 0.052 | 0.044 | >20 | >20 | 0.011 | 1.080 |
| 108051_005 | wtR | >20 | >20 | >20 | >20 | 0.088 | >20 |
| 108051_006 | wtS | 1.176 | 1.369 | >20 | >20 | 0.008 | 0.231 |
| 108051_005 | Q655R* | 0.343 | 1.314 | >20 | >20 | 0.036 | 5.209 |

*Numbering with reference to 108060 protein.

The neutralizing antibody titer (IC50) is defined as the concentration (µg/ml) of mAB or entry inhibitor that produces a 50% inhibition in target cell infection. Values in bold represent neutralization titers that are significantly above the background (Experimental Procedures). All clones tested were CCR5 tropic. Clone indicates gp160 envelope genes. wtR and wtS indicate wild type neutralization-resistant and -sensitive clones respectively.

TABLE 4

Sensitivity to neutralizing monoclonal antibodies and entry inhibitors in 108060 clones and unrelated viruses[a]

| Clone | Mutation | IC$_{50}$ (µg/ml) of indicated MAb or fusion inhibitor | | | | | |
|---|---|---|---|---|---|---|---|
| | | 2F5 | 4E10 | b12 | 2G12 | Enfuvirtide | CD4-IgG |
| 108060_022 | wtR | 3.250 | 5.201 | >20 | >20 | 0.068 | >20 |
| 108060_022 | Q655R | 0.093 | 0.156 | >20 | >20 | 0.004 | 0.161 |
| 108060_024 | wtS | 0.151 | 0.333 | >20 | >20 | 0.019 | 0.798 |
| 108060_024 | R655Q | 3.434 | 6.546 | >20 | >20 | 0.130 | >20 |
| 108069_005 | wtR | 1.129 | 3.556 | >20 | >20 | 0.071 | >20 |
| 108069_011 | wtS | 0.043 | 0.040 | >20 | >20 | 0.145 | >20 |
| 108069_005 | Q655R[b] | 0.052 | 0.044 | >20 | >20 | 0.011 | 1.080 |
| 108051_005 | wtR | >20 | >20 | >20 | >20 | 0.088 | >20 |
| 108051_006 | wtS | 1.176 | 1.369 | >20 | >20 | 0.008 | 0.231 |
| 108051_005 | Q655R[b] | 0.343 | 1.314 | >20 | >20 | 0.036 | 5.209 |

[a]The neutralizing antibody titer (IC$_{50}$) is defined as the concentration (µg/ml) of an MAb or entry inhibitor that produces a 50% inhibition in target cell infection. Values in bold represent neutralization titers that are significantly above the background (see Materials and Methods). All clones tested were CCR5 tropic. Clones indicate gp160 envelope proteins, wtR and wtS indicate wild-type neutralization-resistant and -sensitive clones, respectively.
[b]Numbering with reference to subject 108060 protein.

---

The invention claimed is:

1. A composition comprising:
a HIV-1 gp120/gp41 trimer complex comprising a single amino acid substitution in a helix of gp41,
wherein the helix is selected from the group consisting of N36 helix and C34 helix,
wherein the single amino acid substitution is introduced at V551, Q553, or Q655, where the substituting amino acid at Q655 and Q553 is not N and the substituting amino acid at V551 is not Q or N, and
wherein the numbering of the substituted amino acid is with reference to the amino acid sequence set forth in SEQ ID NO:16.

2. The composition of claim 1, comprising an adjuvant.

3. The composition of claim 1, comprising an excipient.

4. The composition of claim 1, wherein the single amino acid substitution is Q655R.

5. A method of inducing an immune response to HIV-1 in a subject, the method comprising administering the composition of claim 1 to the subject.

6. A method of inducing an immune response to HIV-1, the method comprising administering a formulation comprising an HIV envelope glycoprotein polypeptide comprising a single amino acid substitution in a helix of the HIV envelope glycoprotein polypeptide, wherein the helix is selected from the group consisting of the N36 helix and the C34 helix, wherein said single amino acid substitution increases the ability of said polypeptide to bind neutralizing antibodies, wherein the single amino acid substitution is selected from the group consisting of V551[*], Q553[*], and Q655[*], where [*] represents any amino acid other than Q or N, and wherein the numbering of the substituted amino acid is with reference to the amino acid sequence set forth in SEQ ID NO: 16.

7. The method of claim 6, wherein the formulation comprises an excipient.

8. The method of claim 6, wherein the formulation comprises a carrier or an adjuvant.

9. The method of claim 6, wherein the single amino acid substitution is Q655[*], where [*] represents any amino acid other than Q or N.

10. The method of claim 6, wherein the single amino acid substitution is Q655R.

* * * * *

UNITED STATES PATENT AND TRADEMARK OFFICE
CERTIFICATE OF CORRECTION

PATENT NO. : 10,201,603 B2
APPLICATION NO. : 15/694388
DATED : February 12, 2019
INVENTOR(S) : Phillip Berman et al.

It is certified that error appears in the above-identified patent and that said Letters Patent is hereby corrected as shown below:

In the Specification

Column 13, Line 14:
Replace "Glade" with --clade--.

Column 46, Lines 1, 3 and 6:
Replace "Glade" with --clade--.

Column 49, Line 12:
Replace "5261" with --S261--.

Column 49, Line 47:
Replace "Glade" with --clade--.

Signed and Sealed this
Twenty-first Day of January, 2020

Andrei Iancu
*Director of the United States Patent and Trademark Office*